US009598447B2

(12) United States Patent
Tadesse et al.

(10) Patent No.: US 9,598,447 B2
(45) Date of Patent: Mar. 21, 2017

(54) PHOSPHORUS-SUBSTITUTED QUINOXALINE-TYPE PIPERIDINE COMPOUNDS AND USES THEREOF

(75) Inventors: Dawit Tadesse, Parlin, NJ (US); Laykea Tafesse, Robbinsville, NJ (US); Xiaoming Zhou, Plainsboro, NJ (US)

(73) Assignee: Purdue Pharma L.P., Stamford, CT (US)

( * ) Notice: Subject to any disclaimer, the term of this patent is extended or adjusted under 35 U.S.C. 154(b) by 274 days.

(21) Appl. No.: 13/996,440

(22) PCT Filed: Dec. 21, 2011

(86) PCT No.: PCT/IB2011/003132
§ 371 (c)(1),
(2), (4) Date: Jan. 21, 2014

(87) PCT Pub. No.: WO2012/085648
PCT Pub. Date: Jun. 28, 2012

(65) Prior Publication Data
US 2014/0128346 A1 May 8, 2014

Related U.S. Application Data

(60) Provisional application No. 61/553,699, filed on Oct. 31, 2011, provisional application No. 61/426,447, filed on Dec. 22, 2010.

(51) Int. Cl.
*C07F 9/6561* (2006.01)
*C07F 9/6558* (2006.01)

(52) U.S. Cl.
CPC ........ *C07F 9/6561* (2013.01); *C07F 9/65583* (2013.01)

(58) Field of Classification Search
None
See application file for complete search history.

(56) References Cited

U.S. PATENT DOCUMENTS

| 3,536,809 | A | 10/1970 | Applezweig |
| 3,598,123 | A | 8/1971 | Zaffaroni |
| 3,845,770 | A | 11/1974 | Theeuwes et al. |
| 3,916,899 | A | 11/1975 | Theeuwes et al. |
| 4,008,719 | A | 2/1977 | Theeuwes et al. |
| 5,059,595 | A | 10/1991 | Le Grazie |
| 5,073,543 | A | 12/1991 | Marshall et al. |
| 5,120,548 | A | 6/1992 | McClelland et al. |
| 5,354,556 | A | 10/1994 | Sparks et al. |
| 5,591,767 | A | 1/1997 | Mohr et al. |
| 5,639,476 | A | 6/1997 | Oshlack et al. |
| 5,674,533 | A | 10/1997 | Santus et al. |
| 5,698,155 | A | 12/1997 | Grosswald et al. |
| 5,733,566 | A | 3/1998 | Lewis et al. |
| 6,562,319 | B2 | 5/2003 | Mishani et al. |
| 6,635,653 | B2 | 10/2003 | Goehring et al. |
| 6,861,421 | B2 | 3/2005 | Goehring et al. |
| 7,355,045 | B2 | 4/2008 | Dey et al. |
| 7,432,275 | B2 | 10/2008 | Bakthavatchalam et al. |

(Continued)

FOREIGN PATENT DOCUMENTS

WO    WO 99/46260    9/1999
WO    WO 99/50254    10/1999

(Continued)

OTHER PUBLICATIONS

Danziger et al., Automated Site-directed Drug Design: A General Algorithm for Knowledge Acquisition about Hydrogen-Bonding Regions at Protein Surfaces, Mar. 22, 1989, The Royal Society, Proceedings of the Royal Society of London.Series B, Biological Sciences, vol. 236, No. 1283, p. 101-113.*
Bartho et al. (1990), "Involvement of capsaicin-sensitive neurons in hyperalgesia and enhanced opioid antinociception in inflammation," *Naunyn-Schmiedeberg's Archives of Pharmacol.* 342:666-670.
Baudy et al. (2009), "Prodrugs of Perzinfotel with Improved Oral Bioavailability," *J Med Chem.* 52:771-778.
Berdini et al. (2002), "A modified palladium catalysed reductive amination procedure," *Tetrahedron* 58:5669-5674.
Bignan (2005), "Recent advances towards the discovery of ORL-1 receptor agonists and antagonists," *Expert Opinion on Therapeutic Patents* 15(4):357-388.
Bingham et al. (2001), "Over one hundred solvates of sulfathiazole," *Chem. Comm.*, pp. 603-604.

(Continued)

*Primary Examiner* — San-Ming Hui
*Assistant Examiner* — Andrew Lee
(74) *Attorney, Agent, or Firm* — Dechert LLP

(57) ABSTRACT

The disclosure relates to Phosphorus-Substituted Quinoxaline-Type Piperidine Compounds of Formula (I):

(I)

and pharmaceutically acceptable derivatives thereof wherein the dashed line, A, B, Q, $R_1$, $R_2$, $R_3$, $R_4$, $Y_1$, Z, and a are as defined herein, compositions comprising an effective amount of a Phosphorus-Substituted Quinoxaline-Type Piperidine Compound, and methods to treat or prevent a condition, such as pain, comprising administering to an animal in need thereof an effective amount of a Phosphorus-Substituted Quinoxaline-Type Piperidine Compound.

60 Claims, No Drawings

(56) References Cited

U.S. PATENT DOCUMENTS

| | | | |
|---|---|---|---|
| 7,439,239 B2 | 10/2008 | Coats et al. | |
| 8,110,602 B2 | 2/2012 | Brown et al. | |
| 8,476,271 B2 | 7/2013 | Tsuno et al. | |
| 8,476,277 B2 | 7/2013 | Tafesse | |
| 8,846,929 B2 | 9/2014 | Fuchino et al. | |
| 8,889,690 B2 | 11/2014 | Tafesse | |
| 9,040,533 B2 | 5/2015 | Marra et al. | |
| 9,085,561 B2 | 7/2015 | Tsuno et al. | |
| 9,090,618 B2 | 7/2015 | Yamawaki et al. | |
| 9,145,408 B2 | 9/2015 | Tsuno et al. | |
| 9,278,967 B2 | 3/2016 | Fuchino et al. | |
| 9,290,488 B2 | 3/2016 | Tafesse et al. | |
| 2005/0256000 A1 | 11/2005 | Schaper et al. | |
| 2009/0275574 A1 | 11/2009 | Cheng et al. | |
| 2010/0022519 A1 | 1/2010 | Brown et al. | |
| 2010/0216726 A1 | 8/2010 | Fuchino et al. | |
| 2011/0021426 A1 | 1/2011 | Toll et al. | |
| 2013/0338170 A1 | 12/2013 | Tafesse | |
| 2015/0238485 A1 | 8/2015 | Marra et al. | |
| 2015/0315201 A1 | 11/2015 | Tafesse | |
| 2015/0322066 A1 | 11/2015 | Tanaka et al. | |
| 2016/0002203 A1 | 1/2016 | Tadesse | |
| 2016/0009717 A1 | 1/2016 | Fuchino et al. | |
| 2016/0159785 A1 | 6/2016 | Fuchino et al. | |

FOREIGN PATENT DOCUMENTS

| | | |
|---|---|---|
| WO | WO 00/06545 A1 | 2/2000 |
| WO | WO 01/90102 | 6/2002 |
| WO | WO 03/062234 | 7/2003 |
| WO | WO 2005/028451 | 3/2005 |
| WO | WO 2005/075459 A1 | 8/2005 |
| WO | WO 2009027820 A2 * | 3/2009 |

OTHER PUBLICATIONS

Buchwald et al. (1980), "Long-term, Continuous Intravenous Heparin Administration by an Implantable Infusion Pump in Ambulatory Patients with Recurrent Venous Thrombosis," *Surgery* 88:507-516.
Bundgaard, ed. (1985), *Design of Prodrugs*, Elsevier, Amsterdam.
Bundgaard et al. (1988), "Glycolamide Esters as Biolabile Prodrugs of Carboxylic Acid Agents: Synthesis, Stability, Bioconversion, and Physicochemical Properties," *J. Pharmaceut. Sci.* 77(4):285-298.
Bundgaard (1991), "Design and Application of Prodrugs," *A Textbook of Drug Design and Development*, Krogsgaard-Larsen and Bundgaard, eds., Harwood Academic Publishers, Chapter 5, pp. 113-191.
Bundgaard et al. (1992), "(C) Means to Enhance Penetration (1) Prodrugs as a means to improve the delivery of peptide drugs," *Adv. Drug Delivery Revs.* 8:1-38.
Caira et al. (2004), "Preparation and Crystal Characterization of a Polymorph, a Monohydrate, and an Ethyl Acetate Solvate of the Antifungal Fluconazole," *J. Pharmaceut. Sci.*, 93(3):601-611.
Colowick et al. (1985), "Drug and Enzyme Targeting, Part A," Widder et al., eds., *Methods in Enzymology*, vol. 112, Academic Press.
Cramer et al. (2003), "Enantio selective Desymmetrization of Tropinone Derivatives by Hydroboration," *Synlett.* 14:2175-2177.
D'Amour et al. (1941), "A Method for Determining Loss of Pain Sensation," *J. Pharmacol. Exp. Ther.* 72:74-79.
Dudash et al. (2005), "Synthesis and evaluation of 3-anilinoquinoxalinones as glycogen phosphorylase inhibitors," *Bioorg. Med. Che m. Lett.*, 15(21):4790-4793.
During et al. (1989), "Controlled Release of Dopamine from a Polymeric Brain Implant: In Vivo Characterization," *Ann. Neurol.* 25:351-356.
Filer (1987), "The Preparation and Characterization of Tritiated Neurochemicals," *Isotopes in the Physical and Biomedical Sciences*, vol. 1, *Labeled Compounds (Part A)*, E. Buncel et al, eds., Chapter 6, pp. 155-192.

*Goodman & Gilman's The Pharmacological Basis of Therapeutics* (Goodman et al., Eds., 9$^{th}$ Ed., McGraw-Hill, New York, 1996).
Goodson (1984), "Dental Applications," in *Medical Applications of Controlled Release, vol. 2, Applications and Evaluation*, Langer and Wise, eds., CRC Press, Chapter 6, pp. 115-138.
Grupp et al. (1999), "Protection against Hypoxia-reoxygenation in the Absence of Poly (ADP-ribose) Synthetase in Isolated Working Hearts," *J. Mol. Cell Cardiol.* 31:297-303.
*Handbook of Pharmaceutical Excipients*, (Amer. Pharmaceutical Ass'n, Washington, DC, 1986).
Hanson (1995), "Analgesic, Antipyretic and Anti-Inflammatory Drugs," pp. 1196-1221 in *Remington: The Science and Practice of Pharmacy* vol. II (Gennaro, ed., 19$^{th}$ ed., Mack Publishing, Easton, PA).
Hargreaves et al. (1988), "A New and Sensitive Method for Measuring Thermal Nociception in Cutaneous Hyperalgesia," *Pain* 32(1):77-88.
Henderson et al. (1997), "The orphan opioid receptor and its endogenous ligand—nociceptin/orphanin FQ," *Trends Pharmacol. Sci.* 18(8):293-300.
Howard et al. (1989), "Intracerebral drug delivery in rats with lesion-induced memory deficits," *J. Neurosurg.* 71:105-112.
International Search Report dated Mar. 30, 2012 for International Application No. PCT/IB2011/003132.
IUPAC Compendium of Chemical Terminology, 2$^{nd}$ Ed. (the "Gold Book"), McNaught et al., eds., Blackwell Scientific Publications, Oxford (1997).
Kakeya et al. (1984), "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32:692-698.
Keeton et al. (1981), "Specific and Sensitive Radioimmunoassay for 3-Methoxy-4-hydroxyphenylethyleneglycol (MOPEG)," *Science* 211:586-588.
Kim (1992), "An Experimental Model for Peripheral Neuropathy Produced by Segmental Spinal Nerve Ligation in the Rat," *Pain* 50(3):355-363.
King (1980), "Tablets, Capsules, and Pills," pp. 1553-1593 in *Remington's Pharmaceutical Sciences* (Osol, ed., 16$^{th}$ ed., Mack Publishing, Easton, PA).
Langer et al. (1983), "Chemical and Physical Structure of Polymers as Carriers for Controlled Release of Bioactive Agents: A Review," *J. Macromol. Sci. Rev. Macromol. Chem.* C23(1):61-126.
Langer (1990), "New Methods of Drug Delivery," *Science* 249:1527-1533.
Lazareno (1999), "Measurement of Agonist-stimulated [$^{35}$S ]GTPγS Binding to Cell Membranes," *Methods in Molecular Biology* 106:231-245.
Levy et al. (1985), "Inhibition of Calcification of Bioprosthetic Heart Valves by Local Controlled-Release Diphosphonate," *Science* 228:190-192.
Lewin et al. (1998), "Molecular Features Associated with Polyamine Modulation of NMDA Receptors," *J. Med. Chem.* 41:988-995.
Milligan (2003), "Principles: Extending the Utility of [$^{35}$S]GTPγS Binding Assays," *TIPS* 24(2):87-90.
Narita et al. (1999), "Identification of the G-protein Coupled ORL1 Receptor in the Mouse Spinal Cord by [$^{35}$S]-GTPγS Binding and Immunohistochemistry," *Brit. J. Pharmacol.* 128:1300-1306.
Olofson et al. (1977), "Value of the Vinyloxycarbonyl Unit in Hydroxyl Protection: Application to the Synthesis of Nalorphin," *Tetrahedron Lett.*, 18:1571-1574.
Olofson et al. (1984), "A New Reagent for the Selective, High-Yield N-Dealkylation of Tertiary Amines: Improved Syntheses of Naltrexone and Nalbuphine," *J. Org. Chem.*, 49(11):2081-2082.
Perregaard et al. (1977), "Studies on Organophosphorus Compounds XVIII*. Oxidation of Tertiary Alicyclic Amines with Elemental Sulfur in Hexa-methylphosphoric Triamide (HMPA). Oxidative Rearrangements of Hexahy-Droazepines and Octahydroazocines to bis(3-Pyrrolyl)Polysulfides.," *Bull. Soc. Chim. Belg.* 86:679-691.

(56) References Cited

OTHER PUBLICATIONS

*Pharmaceutical Dosage Forms: Tablets* (Lieberman et al., eds., 2nd ed., Marcel Dekker, Inc., 1989 & 1990).
*Pharmaceutical Dosage Forms: Disperse Systems* (Lieberman et al., eds., 2nd ed., Marcel Dekker, Inc., 1996 & 1998).
Pizey (1974), "Thionyl Chloride," Ch. 4 in *Synthetic Reagents*, John Wiley & Sons, New York, vol. 1, pp. 321-357.
Porter (1973), "The Zinin Reduction of Nitroarenes," *Org. Reactions*, 20:455-481.
Radebough et al. (1995), "Preformulation," pp. 1447-1676 in *Remington's Pharmaceutical Sciences* vol. 2 (Gennaro, ed., 19th ed., Mack Publishing, Easton, PA).
Ross et al. (2001), "Pharmacodynamics: Mechanisms of Drug Action and the Relationship Between Drug Concentration and Effect," in *Goodman & Gilman's The Pharmacological Basis of Therapeutics* pp. 31-43 (Goodman et al., eds., 10th ed., McGraw-Hill, New York).
Rylander (1985), "Hydrogenation of Nitro Compounds," in *Hydrogenation Methods* pp. 104-116 (Academic Press, London).
Saudek et al. (1989), "A Preliminary Trial of the Programmable Implantable Medication System for Insulin Delivery," *New Engl. J. Med.* 321:574-579.
Sefton (1987), "Implantable Pumps," in *CRC Crit. Rev. Biomed. Eng.* 14(3):201-240.
Seltzer et al. (1990), "A Novel Behavioral Model of Neuropathic Pain Disorders Produced in Rats by Partial Sciatic Nerve Injury," *Pain* 43:205-218.
Shimohigashi et al. (1996), "Sensitivity of Opioid Receptor-like Receptor ORL1 for Chemical Modification on Nociceptin, a Naturally Occurring Nociceptive Peptide," *J. Biol. Chem.* 271(39):23642-23645.
Smolen et al.(1984), "Drug Product Design and Performance," *Controlled Drug Bioavailability* vol. 1, John Wiley & Sons, New York.
Stein (1988), "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455.
Sweet et al. (1975), "Synthesis of an Affinity Chromatography Column Designed for Recovery of Labile Proteins," *Biochem. Biophys. Res. Comm.* 63(1):99-105.
Tortolani et al. (1999), "A Convenient Synthesis to N-Aryl-Substituted 4-Piperidones," *Org. Lett.* 1:1261-1262.
Treat et al. (1989), "Liposome Encapsulated Doxorubicin Preliminary Results of Phase I and Phase II Trials," pp. 317-327 and 353-365 in *Liposomes in the Therapy of Infectious Disease and Cancer* (Alan R. Liss, Inc., New York).
Van Tonder et al. (2004), "Preparation and Physicochemical Characterization of 5 Niclosamide Solvates and 1 Hemisolvate," *AAPS Pharm. Sci. Tech.*, 5(1):Article 12 (2004).
Zhang et al., "Screening and Characterization of G-Protein-Coupled Receptor Ligands for Drug Discovery," in *Handbook of Drug Screening*, 2nd Ed., Ramakrishna, ed., Informa Healthcare, New York, NY (2009), pp. 139-188.

\* cited by examiner

PHOSPHORUS-SUBSTITUTED QUINOXALINE-TYPE PIPERIDINE COMPOUNDS AND USES THEREOF

CROSS REFERENCE TO RELATED APPLICATIONS

This application is a national stage entry of International Application No. PCT/IB2011/003132, filed Dec. 21, 2011, which claims the benefit under 35 U.S.C. §119(e) of U.S. Provisional Application No. 61/553,699, filed Oct. 31, 2011, and U.S. Provisional Application No. 61/426,447, filed Dec. 22, 2010, the contents of all of which are incorporated herein by reference.

1. FIELD

The disclosure relates to Phosphorus-Substituted Quinoxaline-Type Piperidine Compounds, compositions comprising an effective amount of a Phosphorus-Substituted Quinoxaline-Type Piperidine Compound and methods to treat or prevent a condition, such as pain, comprising administering to an animal in need thereof an effective amount of a Phosphorus-Substituted Quinoxaline-Type Piperidine Compound.

2. BACKGROUND

Chronic pain is a major contributor to disability and is the cause of much suffering. The successful treatment of severe and chronic pain is a primary goal of the physician, with opioid analgesics being preferred drugs for doing so.

Three major classes of opioid receptors in the central nervous system (CNS) have long been known, with each class having subtype receptors. These receptor classes are known as μ, κ and δ. As opiates have a high affinity for these receptors while not being endogenous to the body, research followed in order to identify and isolate the endogenous ligands to these receptors. These ligands were identified as endorphins, dynorphins and enkephalins, respectively.

Experimentation eventually led to the identification of a cDNA encoding an opioid receptor-like (ORL-1) receptor with a high degree of homology to the known receptor classes. The ORL-1 receptor was classified as an opioid receptor based only on structural grounds, as the receptor did not exhibit pharmacological homology. It was initially demonstrated that non-selective ligands having a high affinity for μ, κ and δ receptors had low affinity for the ORL-1 receptor. This characteristic, along with the fact that an endogenous ligand had not yet been discovered, led to the term "orphan receptor." See, e.g., Henderson et al., "The orphan opioid receptor and its endogenous ligand-nociceptin/orphanin FQ," *Trends Pharmacol. Sci.* 18(8):293-300 (1997).

Subsequent research led to the isolation and structure of the endogenous ligand of the ORL-1 receptor (i.e., nociceptin; also known as orphanin FQ (OFQ)). This ligand is a seventeen amino acid peptide structurally similar to members of the opioid peptide family.

The discovery of the ORL-1 receptor presents an opportunity in drug discovery for novel compounds that can be administered for pain management or other syndromes modulated by this receptor.

International PCT Publication Nos. WO 99/46260, WO 99/50254, WO 01/90102, WO 2005/028451, WO 2003/062234, and U.S. Pat. App. No. 2005/0256000, respectively, describe quinoxalines or derivatives thereof as (i) inhibitors of protein kinase C, (ii) serine protease inhibitors, (iii) herbicides, (iv) M2 acetylcholine receptor agonists, (v) medicaments for diseases involving poly(ADP-ribose) polymerase, and (vi) safeners for plants.

The publication of Baudy et al., "Prodrugs of Perzinfotel with Improved Oral Bioavailability," *J. Med. Chem.* 52:771-778 (2009), describes prodrug derivatives of perzinfotel for increasing low oral bioavailability.

Citation of any reference in Section 2 of this application is not to be construed as an admission that such reference is prior art to the present application.

3. SUMMARY

In one aspect of the disclosure, new compounds that exhibit affinity for the ORL-1 receptor are described.

In some embodiments, such new compounds exhibit agonist activity or partial agonist activity at the ORL-1 receptor. In other embodiments, such new compounds exhibit agonist activity at the ORL-1 receptor. In other embodiments, such new compounds exhibit partial agonist activity at the ORL-1 receptor. In yet other embodiments, such new compounds exhibit antagonist activity at the ORL-1 receptor.

In another embodiment of the disclosure, such new compounds exhibit affinity for the ORL-1 receptor, and also for one or more of the μ, κ or δ receptors. In some embodiments, a new compound of the disclosure exhibits affinity for both the ORL-1 receptor and the μ receptor. In other embodiments, a new compound of the disclosure acts as an ORL-1 receptor agonist or partial agonist and as a μ receptor agonist or partial agonist. In other embodiments, a new compound of the disclosure acts as an ORL-1 receptor agonist and as a μ receptor agonist or partial agonist. In other embodiments, a new compound of the disclosure acts as an ORL-1 receptor partial agonist and as a μ receptor agonist or partial agonist. In other embodiments, a new compound of the disclosure acts as an ORL-1 receptor agonist or partial agonist and as a μ receptor agonist. In other embodiments, a new compound of the disclosure acts as an ORL-1 receptor agonist or partial agonist and as a μ receptor partial agonist. In other embodiments, a new compound of the disclosure acts as an ORL-1 receptor agonist and as a μ receptor agonist. In other embodiments, a new compound of the disclosure acts as an ORL-1 receptor agonist and as a μ receptor partial agonist. In other embodiments, a new compound of the disclosure acts as an ORL-1 receptor partial agonist and as a μ receptor agonist. In other embodiments, a new compound of the disclosure acts as an ORL-1 receptor partial agonist and as a μ receptor partial agonist. In other embodiments, a new compound of the disclosure acts as an ORL-1 receptor agonist or partial agonist and as a μ receptor antagonist. In other embodiments, a new compound of the disclosure acts as an ORL-1 receptor agonist and as a μ receptor antagonist. In other embodiments, a new compound of the disclosure acts as an ORL-1 receptor partial agonist and as a μ receptor antagonist. In other embodiments, a new compound of the disclosure acts as an ORL-1 receptor antagonist and as a μ receptor agonist or partial agonist. In other embodiments, a new compound of the disclosure acts as an ORL-1 receptor antagonist and as a μ receptor agonist. In other embodiments, a new compound of the disclosure acts as an ORL-1 receptor antagonist and as a μ receptor partial agonist.

Certain new compounds of the disclosure can be used to treat an animal suffering from chronic or acute pain.

In another embodiment of the disclosure, methods for treating chronic or acute pain in an animal by administering one or more Phosphorus-Substituted Quinoxaline-Type Piperidine Compounds to an animal in need of such treatment are described. In certain embodiments, such new Phosphorus-Substituted Quinoxaline-Type Piperidine Compounds effectively treat chronic or acute pain in the animal, while producing fewer or reduced side effects compared to previously available compounds.

Compounds of Formula (I) are herein disclosed:

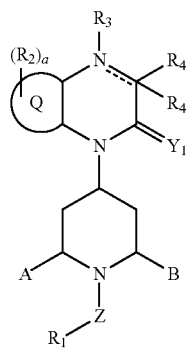

(I)

or pharmaceutically acceptable derivatives thereof where:
$Y_1$ is O or S;
Q is benzo or (5- or 6-membered)heteroaryl;
each $R_2$ is independently selected from:
(a) -halo, —CN, —$NO_2$, —$OT_3$, —C(=O)$T_3$, —C(=O)$OT_3$, —C(=O)N($T_1$)($T_2$), —S(=O)$_2OT_3$, —S(=O)$T_3$, —S(=O)$_2T_3$, —S(=O)$_2$N($T_1$)($T_2$), —N($T_1$)($T_2$), —N($T_3$)C(=O)$T_3$, —N($T_3$)C(=O)N($T_1$)($T_2$), —N($T_3$)S(=O)$_2T_3$, and —N($T_3$)S(=O)$_2$N($T_1$)($T_2$); and
(b) —($C_1$-$C_6$)alkyl, —($C_2$-$C_6$)alkenyl, —($C_2$-$C_6$)alkynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_5$-$C_{10}$)cycloalkenyl, —($C_7$-$C_{14}$)bicycloalkenyl, —($C_8$-$C_{20}$)tricycloalkenyl, -(5- or 6-membered)heterocycle, and -(7- to 10-membered)bicycloheterocycle, each of which is unsubstituted or substituted with 1, 2, or 3 independently selected $R_8$ groups; and
(c) -phenyl, -naphthalenyl, —($C_{14}$)aryl, and -(5- or 6-membered)heteroaryl, each of which is unsubstituted or substituted with 1, 2, or 3 independently selected $R_7$ groups;
a is an integer selected from 0, 1, and 2;
the dashed line in the 6-membered, nitrogen-containing ring that is fused to the Q group denotes the presence or absence of a bond, and when that dashed line is present as a bond to provide one bond of a double bond then one of the two $R_4$ groups is absent and optionally $R_3$ is absent;
$R_3$ is selected from:
(a) —H; and
(b) —($C_1$-$C_4$)alkyl which is unsubstituted or substituted with 1, 2, or 3 groups independently selected from —OH, —($C_1$-$C_4$)alkoxy, —N($R_6$)$_2$, —C(=O)$OR_9$, and —C(=O)N($R_6$)$_2$; and
(c) —($C_3$-$C_7$)cycloalkyl which is unsubstituted or substituted with 1, 2, or 3 groups independently selected from —OH, —($C_1$-$C_4$)alkyl, —($C_1$-$C_4$)alkoxy, —N($R_6$)$_2$, —C(=O)$OR_9$, and —C(=O)N($R_6$)$_2$;
each $R_4$ is independently selected from —H and —$U_1$—$U_2$—$U_3$—$U_4$—$U_5$—$U_6$—$U_7$—U, where at least one $R_4$ is not hydrogen;
U is —P(=O)($OR_9$)([O]$_xR_9$);

$U_1$, $U_3$, $U_5$, and $U_7$ are independently selected from:
(a) a direct bond; and
(b) —($C_1$-$C_6$)alkyl-, —($C_2$-$C_6$)alkenyl-, —($C_6$-$C_{12}$)cycloalkyl-, —($C_6$-$C_{14}$)bicycloalkyl-, —($C_5$-$C_{14}$)cycloalkenyl-, —($C_7$-$C_{14}$)bicycloalkenyl-, -phenyl-, and -(5- or 6-membered)heterocycle-, each of which is unsubstituted or substituted with 1, 2, or 3 independently selected $R_7$ groups; and
(c) absent;
$U_2$, $U_4$, and $U_6$ are independently —Y—, —N($R_9$)—, —C(=Y)—, a single bond, or absent;
each Y is independently O or S;
A and B are independently selected from:
(a) —H, —CN, —C(=O)$OT_3$, and —C(=O)N($T_1$)($T_2$); and
(b) —($C_3$-$C_{12}$)cycloalkyl, —($C_3$-$C_{12}$)cycloalkoxy, —($C_1$-$C_6$)alkyl, —($C_2$-$C_6$)alkenyl, —($C_2$-$C_6$)alkynyl, and —($C_1$-$C_6$)alkoxy, each of which is unsubstituted or substituted with:
(1') 1 or 2 substituents independently selected from —OH, —S(=O)$_2NH_2$, —N($R_6$)$_2$, =N$R_6$, —C(=O)$OT_3$, —C(=O)N($R_6$)$_2$, —N($R_6$)C(=O)$R_9$, and -(5- or 6-membered)heterocycle, or
(2') 1, 2, or 3 independently selected -halo; or
(c) A-B can together form a ($C_2$-$C_6$)bridge, which is unsubstituted or substituted with 1, 2, 3, 4, 5, 6, 7, or 8 substituents independently selected from —OH, —($C_1$-$C_4$)alkyl, -halo, and —C(halo)$_3$, and which bridge optionally contains —HC=CH— or —O— within the ($C_2$-$C_6$)bridge, where the 6-membered, nitrogen-containing ring that is fused to the Q group can be in the endo- or exo-configuration with respect to the A-B bridge; or
(d) A-B can together form a —$CH_2$—N($R_a$)—$CH_2$— bridge, a

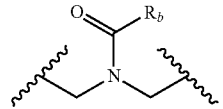

bridge, or a

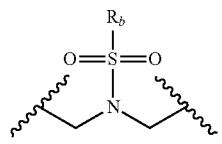

bridge,
where the 6-membered, nitrogen-containing ring that is fused to the Q group can be in the endo- or exo-configuration with respect to the A-B bridge;
$R_a$ is —H, —($C_1$-$C_6$)alkyl, —($C_3$-$C_7$)cycloalkyl, —$CH_2$—C(=O)—$R_c$, —($CH_2$)—C(=O)—$OR_c$, —($CH_2$)—C(=O)—N($R_c$)$_2$, —($CH_2$)$_2$—O—$R_c$, —($CH_2$)$_2$—S(=O)$_2$—N($R_c$)$_2$, $R_c$, or —($CH_2$)$_2$—N($R_c$)S(=O)$_2$—$R_c$;
$R_b$ is selected from:
(a) —H, —($C_1$-$C_6$)alkyl, —($C_3$-$C_7$)cycloalkyl, -(3- to 7-membered)heterocycle, —N($R_c$)$_2$, —N($R_c$)—($C_3$-$C_7$)cycloalkyl, and —N($R_c$)-(3- to 7-membered)heterocycle; and (b) -phenyl, -naphthalenyl, and -(5- or 6-membered)heteroaryl, each of which is unsubstituted or substituted with 1, 2, or 3 independently selected $R_7$ groups; and (c) —N($R_c$)-phenyl, —N($R_c$)-naphthalenyl, —N($R_c$)—($C_{14}$)aryl, and —N($R_c$)-(5- to 10-membered)heteroaryl, each of which is unsubstituted or substituted with 1, 2, or 3 independently selected $R_7$ groups;

each $R_c$ is independently —H or —($C_1$-$C_4$)alkyl;

Z is —[($C_1$-$C_{10}$)alkyl optionally substituted by $R_1$]$_h$—, where h is 0 or 1; —($C_2$-$C_{10}$)alkenyl- optionally substituted by $R_1$; or —($C_1$-$C_{10}$)alkyl-N($R_6$)C(=Y)—;

each $R_1$ is independently selected from:

(a) —H, -halo, —CN, —OH, —CH$_2$OH, —CH$_2$CH$_2$OH, —NO$_2$, —N($R_6$)$_2$, —S(=O)NH$_2$, —S(=O)$_2$NH$_2$, —C(=O)O$V_1$, and —C(=O)CN; and (b) —($C_1$-$C_{10}$)alkyl, —($C_2$-$C_{10}$)alkenyl, —($C_2$-$C_{10}$)alkynyl, —O($C_1$-$C_6$)alkyl, —($C_3$-$C_7$)cycloalkoxy, —($C_6$-$C_{14}$)bicycloalkyl, —($C_8$-$C_{20}$)tricycloalkyl, —($C_8$-$C_{10}$)cycloalkenyl, —($C_7$-$C_{14}$)bicycloalkenyl, —($C_8$-$C_{20}$)tricycloalkenyl, -(3- to 7-membered)heterocycle, and -(7- to 10-membered)bicycloheterocycle, each of which is unsubstituted or substituted with 1, 2, 3, or 4 independently selected $R_8$ groups; and (c)

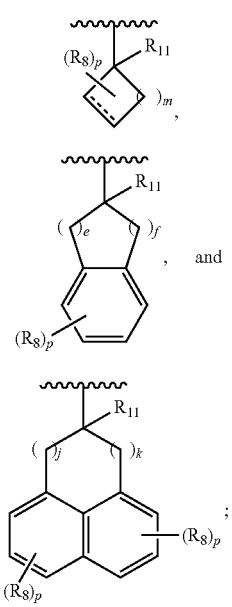

(d) -phenyl, -naphthalenyl, —($C_{14}$)aryl, and -(5- to 10-membered)heteroaryl, each of which is unsubstituted or substituted with a $R_7$ group; or —Z—$R_1$ is 3,3-diphenylpropyl- optionally substituted at the 3 carbon of the propyl with —CN, —C(=O)N($R_6$)$_2$, —C(=O)O$V_1$, or -tetrazolyl; or —Z—$R_1$ is —($C_1$-$C_4$)alkyl substituted with tetrazolyl;

each $R_6$ is independently —H, —($C_1$-$C_6$)alkyl, or —($C_3$-$C_7$)cycloalkyl, or two $R_6$ groups attached to the same nitrogen atom can together form a 5- to 8-membered ring, where the number of atoms in the ring includes the nitrogen atom, and in which one of the 5- to 8-membered ring carbon atoms is optionally replaced by O, S, or N($R_{12}$);

each $R_7$ is independently —($C_1$-$C_4$)alkyl, —($C_2$-$C_6$)alkenyl, —($C_2$-$C_6$)alkynyl, —O$R_9$, —S$R_9$, —C(halo)$_3$, —CH(halo)$_2$, —CH$_2$(halo), —CN, -halo, —N$_3$, —NO$_2$, —CH=N($R_9$), —N($R_9$)$_2$, —N($R_9$)OH, —N($R_9$)S(=O)$R_2$, —N($R_9$)S(=O)$_2$R$_{12}$, —N($R_9$)C(=O)$R_{12}$, —N($R_9$)C(=O)N($T_1$)($T_2$), —N($R_9$)C(=O)O$R_{12}$, —C(=O)$R_9$, —C(=O)N($T_1$)($T_2$), —C(=O)O$R_9$, —OC(=O)$R_9$, —OC(=O)N($T_1$)($T_2$), —OC(=O)O$R_9$, —S(=O)$R_9$, or —S(=O)$_2$R$_9$;

each $R_8$ is independently —($C_1$-$C_6$)alkyl, —($C_2$-$C_6$)alkenyl, —($C_2$-$C_6$)alkynyl, -(5- or 6-membered)heteroaryl, —($C_1$-$C_6$)alkyl-C(=O)O$R_9$, —O$R_9$, —S$R_9$, —C(halo)$_3$, —CH(halo)$_2$, —CH$_2$(halo), —CN, =O, =S, -halo, —N$_3$, —NO$_2$, —CH=N($R_9$), —N($R_9$)($C_1$-$C_6$)alkyl-C(=O)O$R_9$, —N($R_9$)$_2$, —N($R_9$)OH, —N($R_9$)S(=O)$R_{12}$, —N($R_9$)S(=O)$_2$R$_{12}$, —N($R_9$)C(=O)$R_{12}$, —N($R_9$)C(=O)N($R_{12}$)($R_{12}$), —N($R_9$)C(=O)O$R_{12}$, —C(=O)$R_9$, —C(=O)N($R_{12}$)($R_{12}$), —C(=O)O$R_9$, —OC(=O)$R_9$, —OC(=O)N($R_{12}$)($R_{12}$), —OC(=O)O$R_9$, —S(=O)$R_9$, or —S(=O)$_2$R$_9$;

each $R_9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —CH$_2$—O—C(O)-phenyl, —CH$_2$—C(O)—O-phenyl, —CH$_2$—O—C(O)—O-phenyl, —C(halo)$_3$, —CH(halo)$_2$, or —CH$_2$(halo);

if h is 0, then $R_{11}$ can be selected from —H, —CN, —C(=O)O$R_9$, and —C(=O)N($R_6$)$_2$ or $R_{11}$ can be —($C_1$-$C_4$)alkyl which is unsubstituted or substituted with —OH, —($C_1$-$C_4$)alkoxy, —N($R_6$)$_2$, —C(=O)O$R_9$, or —C(=O)N($R_6$)$_2$;

if h is 1, then each $R_{11}$ can be independently selected from —H, —CN, —OH, -halo, —C(=O)O$R_9$, and —C(=O)N($R_6$)$_2$ and each $R_{11}$ can be independently selected from —($C_1$-$C_4$)alkyl which is unsubstituted or substituted with —OH, —($C_1$-$C_4$)alkoxy, —N($R_6$)$_2$, —C(=O)O$R_9$, or —C(=O)N($R_6$)$_2$;

otherwise, where Z is —($C_2$-$C_{10}$)alkenyl- optionally substituted by $R_1$ or —($C_1$-$C_{10}$)alkyl-N($R_6$)C(=Y), then each $R_{11}$ can be independently selected from —H, —CN, —C(=O)O$R_9$, and —C(=O)N($R_6$)$_2$ and each $R_{11}$ can be independently selected from —($C_1$-$C_4$)alkyl which is unsubstituted or substituted with —OH, —($C_1$-$C_4$)alkoxy, —N($R_6$)$_2$, —C(=O)O$R_9$, or —C(=O)N($R_6$)$_2$;

each $R_{12}$ is independently —H or —($C_1$-$C_6$)alkyl;

each m is an integer independently selected from 0, 1, 2, 3, 4, 5, 6, 7, 8, 9, 10, and 11;

each e and f are each an integer independently selected from 0, 1, 2, 3, 4, and 5 provided that 2≤(e+f)≤5;

each j and k are each an integer independently selected from 0, 1, 2, 3, and 4 provided that 1≤(j+k)≤4;

each p is an integer independently selected from 0, 1, 2, 3, and 4;

x is the integer 0 or 1 provided that when the x of [O]$_x$R$_9$ is 0, then the $R_9$ of that [O]$_x$R$_9$ is not —H;

each $T_1$, $T_2$, and $T_3$ is independently —H or —($C_1$-$C_{10}$)alkyl which is unsubstituted or substituted with 1, 2, or 3 independently selected $R_8$ groups and in which 0, 1, 2, or 3 independently selected —($C_1$-$C_{10}$)alkyl carbon atoms except the carbon atom bonded directly to the atom to which $T_1$, $T_2$, or $T_3$ is attached are independently replaced by O, S, or N($R_6$), or $T_1$ and $T_2$ can together form a 5- to 8-membered ring where the number of atoms in the ring includes the nitrogen atom to which $T_1$ and $T_2$ are bonded, said 5- to 8-membered ring is unsubstituted or substituted with 1, 2, or 3 independently selected $R_8$ groups and 0, 1, 2, or 3 independently selected carbon atoms in said 5- to 8-membered ring are independently replaced by O, S, or N($R_6$);

each $V_1$ is independently —H, —($C_1$-$C_6$)alkyl, —($C_3$-$C_7$)cycloalkyl, -phenyl, or -benzyl; and each halo is independently —F, —Cl, —Br, or —I.

A compound of Formula (I) or a pharmaceutically acceptable derivative thereof (a "Phosphorus-Substituted Quinoxaline-Type Piperidine Compound") is useful, e.g., as an analgesic, anti-inflammatory, diuretic, anesthetic agent, neuroprotective agent, anti-hypertensive, an anxiolytic agent, an agent for appetite control, hearing regulator, anti-tussive, anti-asthmatic, modulator of locomotor activity, modulator of learning and memory, regulator of neurotransmitter release, regulator of hormone release, kidney function modulator, anti-depressant, agent to treat memory loss due to Alzheimer's disease and/or other dementias, anti-epileptic, anti-convulsant, agent to treat withdrawal from alcohol, agent to treat withdrawal from drug(s) of addiction, agent to control water balance, agent to control sodium excretion, and/or agent to control arterial blood pressure disorder(s).

A Phosphorus-Substituted Quinoxaline-Type Piperidine Compound is useful for treating and/or preventing pain, anxiety, cough, diarrhea, high blood pressure, epilepsy, anorexia/cachexia, urinary incontinence, drug abuse, memory disorders, obesity, constipation, depression, dementia, or Parkinsonism (each being a "Condition") in an animal.

Compositions comprising an effective amount of a Phosphorus-Substituted Quinoxaline-Type Piperidine Compound and a pharmaceutically acceptable carrier or excipient are disclosed. The compositions are useful for treating or preventing a Condition in an animal.

Methods for treating or preventing a Condition, comprising administering to an animal in need thereof an effective amount of a Phosphorus-Substituted Quinoxaline-Type Piperidine Compound are disclosed. Phosphorus-Substituted Quinoxaline-Type Piperidine Compounds, e.g., of Formula (I), may also be used in the manufacture of a medicament useful for treating a Condition or for preventing a Condition.

Methods for inhibiting ORL-1 receptor function in a cell, comprising contacting a cell capable of expressing the ORL-1 receptor with an ORL-1 receptor function inhibiting amount of a Phosphorus-Substituted Quinoxaline-Type Piperidine Compound are disclosed. In further embodiments of the disclosure, methods for activating ORL-1 receptor function in a cell, comprising contacting a cell capable of expressing the ORL-1 receptor with an ORL-1 receptor function activating amount of a Phosphorus-Substituted Quinoxaline-Type Piperidine Compound are disclosed. In yet another embodiment, methods for preparing a composition, comprising the step of admixing a Phosphorus-Substituted Quinoxaline-Type Piperidine Compound and a pharmaceutically acceptable carrier or excipient, are disclosed.

An embodiment of the disclosure relates to a kit comprising a container containing an effective amount of a Phosphorus-Substituted Quinoxaline-Type Piperidine Compound.

Another embodiment of the disclosure provides novel intermediates for use in making the Phosphorus-Substituted Quinoxaline-Type Piperidine Compounds.

The disclosure can be understood more fully by reference to the following detailed description and illustrative examples, which are intended to exemplify non-limiting embodiments of the disclosure.

4. DETAILED DESCRIPTION

The invention includes the following:

(1) A compound of Formula (I):

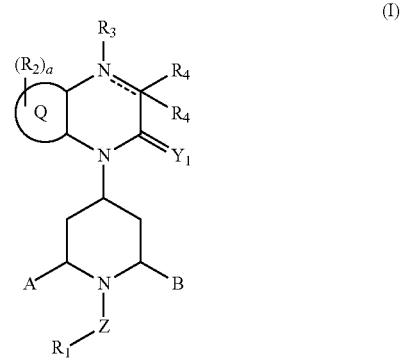

or a pharmaceutically acceptable derivative thereof wherein:

$Y_1$ is O or S;

Q is benzo or (5- or 6-membered)heteroaryl;

each $R_2$ is independently selected from:

(a) -halo, —CN, —$NO_2$, —$OT_3$, —C(=O)$T_3$, —C(=O)$OT_3$, —C(=O)N($T_1$)($T_2$), —S(=O)$_2OT_3$, —S(=O)$T_3$, —S(=O)$_2T_3$, —S(=O)$_2$N($T_1$)($T_2$), —N($T_1$)($T_2$), —N($T_3$)C(=O)$T_3$, —N($T_3$)C(=O)N($T_1$)($T_2$), —N($T_3$)S(=O)$_2T_3$, and —N($T_3$)S(=O)$_2$N(T)($T_2$); and (b) —($C_1$-$C_6$)alkyl, —($C_2$-$C_6$)alkeynyl, —($C_1$-$C_6$)alkoxy, —($C_3$-$C_7$)cycloalkyl, —($C_6$-$C_{14}$)bicycloalkyl, —($C_8$-$C_{20}$)tricycloalkyl, —($C_8$-$C_{10}$)cycloalkenyl, —($C_7$-$C_{14}$)bicycloalkenyl, —($C_8$-$C_{20}$)tricycloalkenyl, -(5- or 6-membered)heterocycle, and -(7- to 10-membered)bicycloheterocycle, each of which is unsubstituted or substituted with 1, 2, or 3 independently selected $R_8$ groups; and (c) -phenyl, -naphthalenyl, —($C_{14}$)aryl, and -(5- or 6-membered)heteroaryl, each of which is unsubstituted or substituted with 1, 2, or 3 independently selected $R_7$ groups;

a is an integer selected from 0, 1, and 2;

the dashed line in the 6-membered, nitrogen-containing ring that is fused to the Q group denotes the presence or absence of a bond, and when that dashed line is present as a bond to provide one bond of a double bond then one of the two $R_4$ groups is absent and optionally $R_3$ is absent;

$R_3$ is selected from:

(a) —H; and (b) —($C_1$-$C_4$)alkyl which is unsubstituted or substituted with 1, 2, or 3 groups independently selected from —OH, —($C_1$-$C_4$)alkoxy, —N($R_6$)$_2$, —C(=O)$OR_9$, and —C(=O)N($R_6$)$_2$; and (c) —($C_3$-$C_7$)cycloalkyl which is unsubstituted or substituted with 1, 2, or 3 groups independently selected from —OH, —($C_1$-$C_4$)alkyl, —($C_1$-$C_4$)alkoxy, —N($R_6$)$_2$, —C(=O)$OR_9$, and —C(=O)N($R_6$)$_2$;

each $R_4$ is independently selected from —H and —$U_1$—$U_2$—$U_3$—$U_4$—$U_5$—$U_6$—$U_7$—U, wherein at least one $R_4$ is not hydrogen;

U is —P(=O)(O$R_9$)([O]$_xR_9$);

$U_1$, $U_3$, $U_5$, and $U_7$ are independently selected from:
(a) a single bond; and
(b) —$(C_1-C_6)$alkyl-, —$(C_2-C_6)$alkenyl-, —$(C_6-C_{12})$cycloalkyl-, —$(C_6-C_{14})$bicycloalkyl-, —$(C_5-C_{14})$cycloalkenyl-, —$(C_7-C_{14})$bicycloalkenyl-, -phenyl-, and -(5- or 6-membered)heterocycle-, each of which is unsubstituted or substituted with 1, 2, or 3 independently selected $R_7$ groups; and
(c) absent;
$U_2$, $U_4$, and $U_6$ are independently —Y—, —$N(R_9)$—, —$C(=Y)$—, a single bond, or absent;
each Y is independently O or S;
A and B are independently selected from:
(a) —H, —CN, —$C(=O)OT_3$, and —$C(=O)N(T_1)(T_2)$; and
(b) —$(C_3-C_{12})$cycloalkyl, —$(C_3-C_{12})$cycloalkoxy, —$(C_1-C_6)$alkyl, —$(C_2-C_6)$alkenyl, —$(C_2-C_6)$alkynyl, and —$(C_1-C_6)$alkoxy, each of which is unsubstituted or substituted with:
(1') 1 or 2 substituents independently selected from —OH, —$S(=O)_2NH_2$, —$N(R_6)_2$, =$NR_6$, —$C(=O)OT_3$, —$C(=O)N(R_6)_2$, —$N(R_6)C(=O)R_9$, and -(5- or 6-membered)heterocycle, or
(2') 1, 2, or 3 independently selected -halo; or
(c) A-B can together form a $(C_2-C_6)$bridge, which is unsubstituted or substituted with 1, 2, 3, 4, 5, 6, 7, or 8 substituents independently selected from —OH, —$(C_1-C_4)$alkyl, -halo, and —$C(halo)_3$, and which bridge optionally contains —HC=CH— or —O— within the $(C_2-C_6)$bridge, wherein the 6-membered, nitrogen-containing ring that is fused to the Q group can be in the endo- or exo-configuration with respect to the A-B bridge; or
(d) A-B can together form a —$CH_2$—$N(R_a)$—$CH_2$— bridge, a

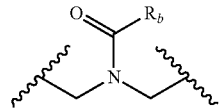

bridge, or a

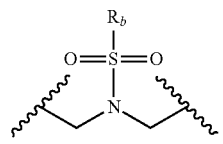

bridge,
wherein the 6-membered, nitrogen-containing ring that is fused to the Q group can be in the endo- or exo-configuration with respect to the A-B bridge;
$R_a$ is —H, —$(C_1-C_6)$alkyl, —$(C_3-C_7)$cycloalkyl, —$CH_2$—$C(=O)$—$R_c$, —$(CH_2)$—$C(=O)$—$OR_c$, —$(CH_2)$—$C(=O)$—$N(R_c)_2$, —$(CH_2)_2$—O—$R_c$, —$(CH_2)_2$—$S(=O)_2$—$N(R_c)_2$, $R_c$, or —$(CH_2)_2$—$N(R_c)S(=O)_2$—$R_c$;
$R_b$ is selected from:
(a) —H, —$(C_1-C_6)$alkyl, —$(C_3-C_7)$cycloalkyl, -(3- to 7-membered)heterocycle, —$N(R_c)_2$, —$N(R_c)$—$(C_3-C_7)$cycloalkyl, and —$N(R_c)$-(3- to 7-membered)heterocycle; and (b) -phenyl, -naphthalenyl, and -(5- or 6-membered)heteroaryl, each of which is unsubstituted or substituted with 1, 2, or 3 independently selected $R_7$ groups; and
(c) —$N(R_c)$-phenyl, —$N(R_c)$-naphthalenyl, —$N(R_c)$—$(C_{14})$aryl, and —$N(R_c)$-(5- to 10-membered)heteroaryl, each of which is unsubstituted or substituted with 1, 2, or 3 independently selected $R_7$ groups;
each $R_c$ is independently —H or —$(C_1-C_4)$alkyl;
Z is —$[(C_1-C_{10})$alkyl optionally substituted by $R_1]_h$—, wherein h is 0 or 1; —$(C_2-C_{10})$alkenyl- optionally substituted by $R_1$; or —$(C_1-C_{10})$alkyl-$N(R_6)C(=Y)$—;
each $R_1$ is independently selected from:
(a) —H, -halo, —CN, —OH, —$CH_2OH$, —$CH_2CH_2OH$, —$NO_2$, —$N(R_6)_2$, —$S(=O)NH_2$, —$S(=O)_2NH_2$, —$C(=O)OV_1$, and —$C(=O)CN$; and
(b) —$(C_1-C_{10})$alkyl, —$(C_2-C_{10})$alkenyl, —$(C_2-C_{10})$alkynyl, —$O(C_1-C_6)$alkyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, and -(7- to 10-membered)bicycloheterocycle, each of which is unsubstituted or substituted with 1, 2, 3, or 4 independently selected $R_8$ groups; and
(c)

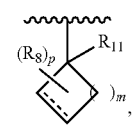

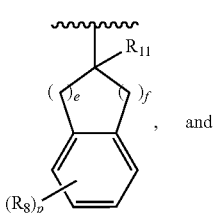

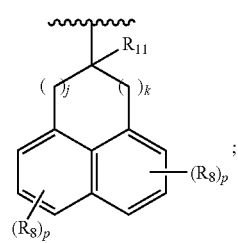

(d) -phenyl, -naphthalenyl, —$(C_{14})$aryl, and -(5- to 10-membered)heteroaryl, each of which is unsubstituted or substituted with a $R_7$ group; or
—Z—$R_1$ is 3,3-diphenylpropyl- optionally substituted at the 3 carbon of the propyl with —CN, —$C(=O)N(R_6)_2$, —$C(=O)OV_1$, or -tetrazolyl; or
—Z—$R_1$ is —$(C_1-C_4)$alkyl substituted with tetrazolyl;
each $R_6$ is independently —H, —$(C_1-C_6)$alkyl, or —$(C_3-C_7)$cycloalkyl, or two $R_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or $N(R_{12})$;
each $R_7$ is independently —$(C_1-C_4)$alkyl, —$(C_2-C_6)$alkenyl, —$(C_2-C_6)$alkynyl, —$OR_9$, —$SR_9$, —$C(halo)_3$, —CH$(halo)_2$, —$CH_2(halo)$, —CN, -halo, —$N_3$, —$NO_2$, —CH═N(R$_9$), —N(R$_9$)$_2$, —N(R$_9$)OH, —N(R$_9$)S(═O)R$_{12}$, —N(R$_9$)S(═O)$_2$R$_{12}$, —N(R$_9$)C(═O)R$_{12}$, —N(R$_9$)C(═O)N(T$_1$)(T$_2$), —N(R$_9$)C(═O)OR$_{12}$, —C(═O)R$_9$, —C(═O)N(T$_1$)(T$_2$), —C(═O)OR$_9$, —OC(═O)R$_9$, —OC(═O)N(T$_1$)(T$_2$), —OC(═O)OR$_9$, —S(═O)R$_9$, or —S(═O)$_2$R$_9$;

each R$_8$ is independently —(C$_1$-C$_6$)alkyl, —(C$_2$-C$_6$)alkenyl, —(C$_2$-C$_6$)alkynyl, -(5- or 6-membered)heteroaryl, —(C$_1$-C$_6$)alkyl-C(═O)OR$_9$, —OR$_9$, —SR$_9$, —C(halo)$_3$, —CH(halo)$_2$, —CH$_2$(halo), —CN, ═O, ═S, -halo, —N$_3$, —NO$_2$, —CH═N(R$_9$), —N(R$_9$)(C$_1$-C$_6$)alkyl-C(═O)OR$_9$, —N(R$_9$)$_2$, —N(R$_9$)OH, —N(R$_9$)S(═O)R$_2$, —N(R$_9$)S(═O)$_2$R$_{12}$, —N(R$_9$)C(═O)R$_{12}$, —N(R$_9$)C(═O)N(R$_{12}$)(R$_{12}$), —N(R$_9$)C(═O)OR$_{12}$, —C(═O)R$_9$, —C(═O)N(R$_{12}$)(R$_{12}$), —C(═O)OR$_9$, —OC(═O)R$_9$, —OC(═O)N(R$_{12}$)(R$_{12}$), —OC(═O)OR$_9$, —S(═O)R$_9$, or —S(═O)$_2$R$_9$;

each R$_9$ is independently —H, —(C$_1$-C$_6$)alkyl, —(C$_2$-C$_6$)alkenyl, —(C$_2$-C$_6$)alkynyl, —(C$_3$-C$_8$)cycloalkyl, —(C$_5$-C$_8$)cycloalkenyl, -phenyl, -benzyl, —CH$_2$—O—C(O)-phenyl, —CH$_2$—C(O)—O-phenyl, —CH$_2$—O—C(O)—O-phenyl, —C(halo)$_3$, —CH(halo)$_2$, or —CH$_2$(halo);

if h is 0, then R$_{11}$ can be selected from —H, —CN, —C(═O)OR$_9$, and —C(═O)N(R$_6$)$_2$ or R$_{11}$ can be —(C$_1$-C$_4$)alkyl which is unsubstituted or substituted with —OH, —(C$_1$-C$_4$)alkoxy, —N(R$_6$)$_2$, —C(═O)OR$_9$, or —C(═O)N(R$_6$)$_2$;

if h is 1, then each R$_{11}$ can be independently selected from —H, —CN, —OH, -halo, —C(═O)OR$_9$, and —C(═O)N(R$_6$)$_2$ and each R$_{11}$ can be independently selected from —(C$_1$-C$_4$)alkyl which is unsubstituted or substituted with —OH, —(C$_1$-C$_4$)alkoxy, —N(R$_6$)$_2$, —C(═O)OR$_9$, or —C(═O)N(R$_6$)$_2$;

otherwise, where Z is —(C$_2$-C$_{10}$)alkenyl- optionally substituted by R$_1$ or —(C$_1$-C$_{10}$)alkyl-N(R$_6$)C(═Y)—, then each R$_{11}$ can be independently selected from —H, —CN, —C(═O)OR$_9$, and —C(═O)N(R$_6$)$_2$ and each R$_{11}$ can be independently selected from —(C$_1$-C$_4$)alkyl which is unsubstituted or substituted with —OH, —(C$_1$-C$_4$)alkoxy, —N(R$_6$)$_2$, —C(═O)OR$_9$, or —C(═O)N(R$_6$)$_2$;

each R$_{12}$ is independently —H or —(C$_1$-C$_6$)alkyl;

each m is an integer independently selected from 0, 1, 2, 3, 4, 5, 6, 7, 8, 9, 10, and 11;

each e and f are each an integer independently selected from 0, 1, 2, 3, 4, and 5 provided that 2≤(e+f)≤5;

each j and k are each an integer independently selected from 0, 1, 2, 3, and 4 provided that 1≤(j+k)≤4;

each p is an integer independently selected from 0, 1, 2, 3, and 4;

x is the integer 0 or 1 provided that when the x of [O]$_x$R$_9$ is 0, then the R$_9$ of that [O]$_x$R$_9$ is not —H;

each T$_1$, T$_2$, and T$_3$ is independently —H or —(C$_1$-C$_{10}$)alkyl which is unsubstituted or substituted with 1, 2, or 3 independently selected R$_8$ groups and in which 0, 1, 2, or 3 independently selected —(C$_1$-C$_{10}$)alkyl carbon atoms except the carbon atom bonded directly to the atom to which T$_1$, T$_2$, or T$_3$ is attached are independently replaced by O, S, or N(R$_6$), or T$_1$ and T$_2$ can together form a 5- to 8-membered ring where the number of atoms in the ring includes the nitrogen atom to which T$_1$ and T$_2$ are bonded, said 5- to 8-membered ring is unsubstituted or substituted with 1, 2, or 3 independently selected R$_8$ groups and 0, 1, 2, or 3 independently selected carbon atoms in said 5- to 8-membered ring are independently replaced by O, S, or N(R$_6$);

each V$_1$ is independently —H, —(C$_1$-C$_6$)alkyl, —(C$_3$-C$_7$)cycloalkyl, -phenyl, or -benzyl; and each halo is independently —F, —Cl, —Br, or —I.

(2) The compound of the above (1), wherein Y$_1$ is O.

(3) The compound of any one of the above (1) or (2), wherein the dashed line is present as a direct bond to provide one bond of a double bond, one R$_4$ is present, and preferably R$_3$ is absent.

(4) The compound of any one of the above (1) to (3), wherein Q is benzo, pyridino, pyrimidino, pyrazino, or pyridazino, and preferably Q is benzo or pyridino, wherein preferably the 2- and 3-positions of the pyridino are fused to the 6-membered, nitrogen-containing ring.

(5) The compound of any one of the above (1) to (4), wherein Q is benzo.

(6) The compound of any one of the above (1) to (5), wherein a is 0.

(7) The compound of any one of the above (1) to (6), which is:

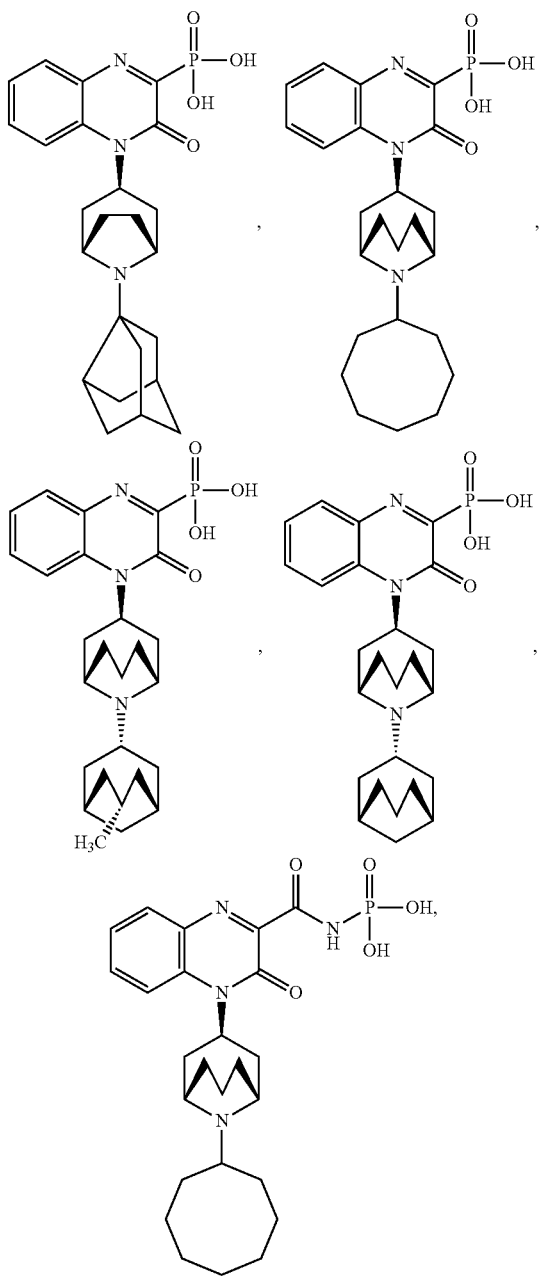

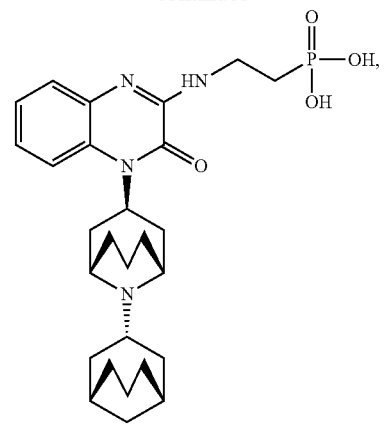
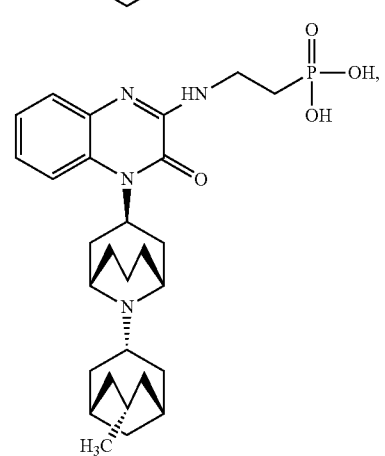
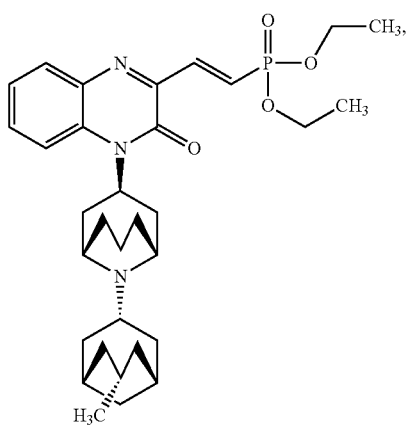
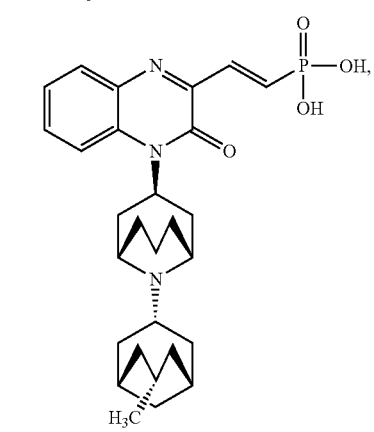
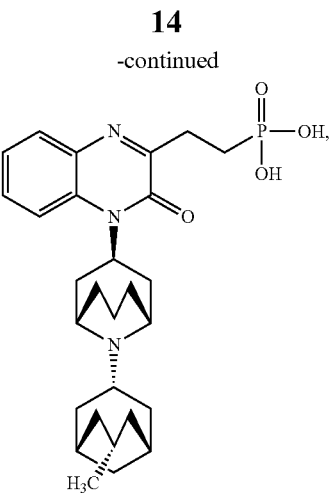
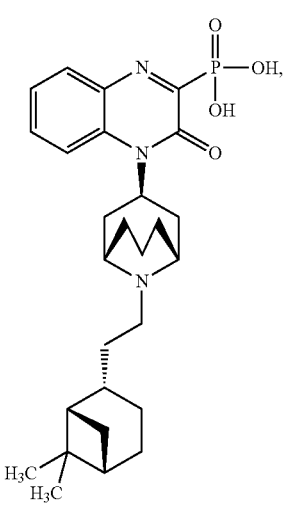
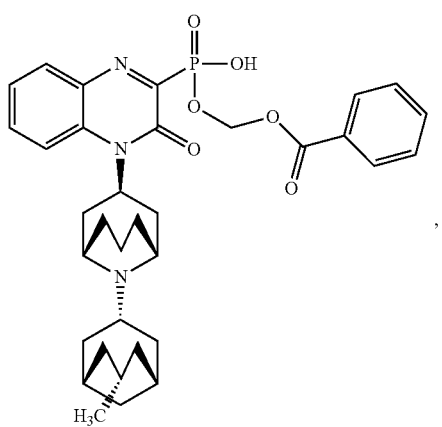

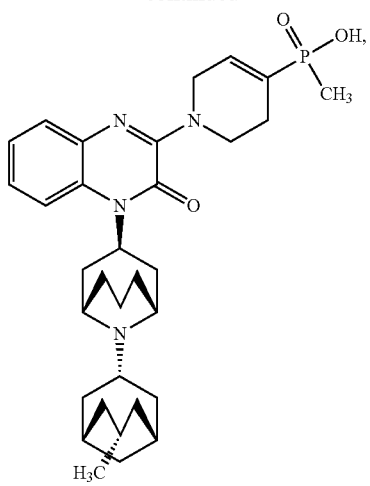
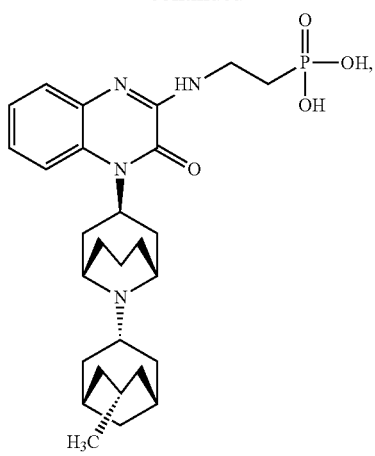
or a pharmaceutically acceptable derivative thereof.
(8) The compound of any one of the above (1) to (7), which is:
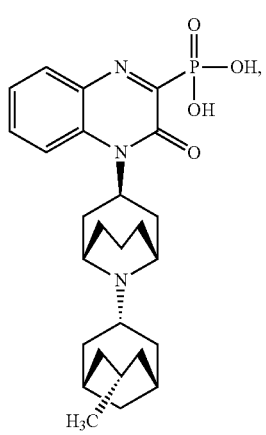
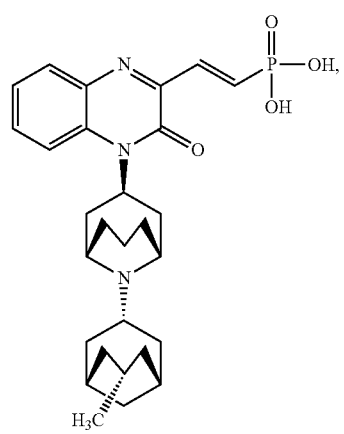
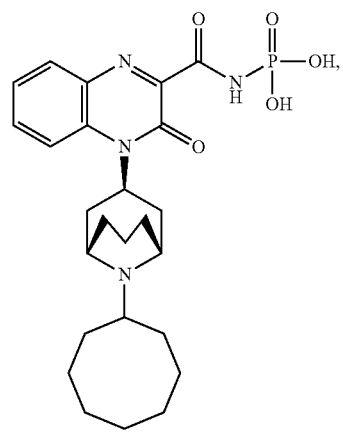
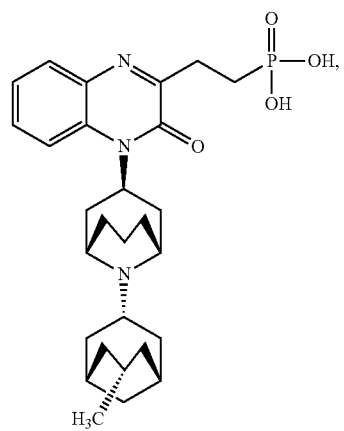

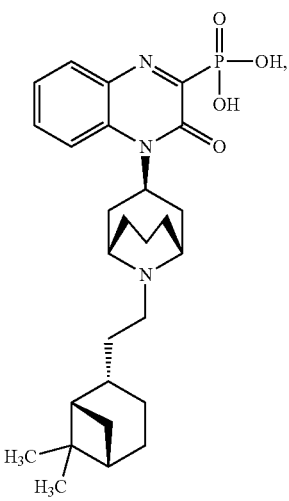

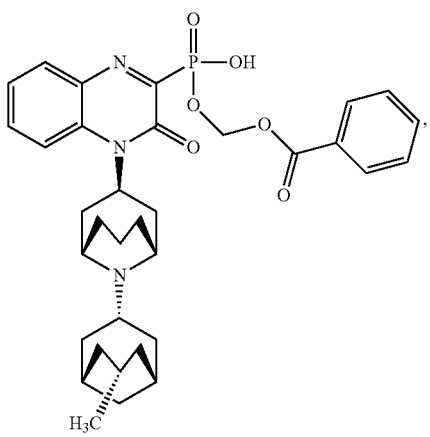

or a pharmaceutically acceptable derivative thereof.

(9) The compound of any one of the above (1) to (8), which is:

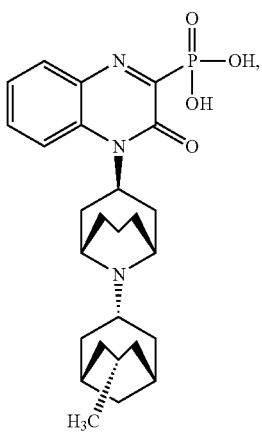

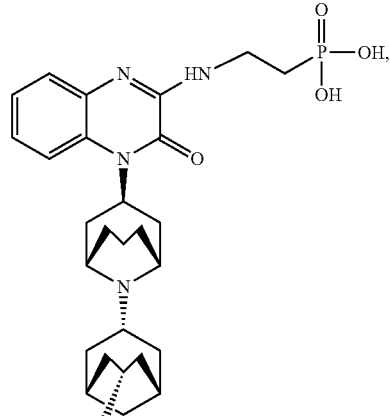

or a pharmaceutically acceptable derivative thereof.

(10) The compound of any one of the above (1) to (6), wherein $U_5$, $U_6$, and $U_7$ are absent;

each $R_4$ is independently selected from —H and —$U_1$—$U_2$—$U_3$—$U_4$—U, wherein at least one $R_4$ is not hydrogen.

(11) The compound of any one of the above (1) to (6) or (10), wherein U is

—P(=O)(OR$_9$)$_2$.

(12) The compound of any one of the above (1) to (6), (10) or (11), wherein $U_1$ and $U_3$ are independently —(C$_1$-C$_6$)alkyl- or —(C$_2$-C$_6$)alkenyl-, which is unsubstituted or substituted with 1 or 2 independently selected $R_7$ groups, a single bond, or absent.

(13) The compound of any one of the above (1) to (6) or (10) to (12), wherein $U_2$ and $U_4$ are independently —Y—, —N($R_9$)—, —C(=Y)—, a single bond, or absent.

(14) The compound of any one of the above (1) hydrogen to (6) or (10) to (13) wherein each Y is O.

(15) The compound of any one of the above (1) to (6) or (10) to (14), wherein U is —P(=O)(OH)$_2$, —P(=O)(OCH$_2$CH$_3$)$_2$ or —P(=O)(OH)(O—CH$_2$—O—C(O)-phenyl).

(16) The compound of any one of the above (1) to (6) or (10) to (15), wherein $U_1$ is a bond and $U_2$, $U_3$, and $U_4$ are each absent.

(17) The compound of any one of the above (1) to (6), (10), (11), (13) or (14), wherein $U_1$ and $U_3$ are each a single bond, $U_2$ is —C(O)—, and $U_4$ is —NH—.

(18) The compound of any one of the above (1) to (6), (10), (11), (13) or (14), wherein $U_1$ and $U_4$ are each a single bond, $U_2$ is —NH—, and $U_3$ is —($C_1$-$C_6$)alkyl- which is unsubstituted, preferably —($C_1$-$C_2$)alkyl-.

(19) The compound of any one of the above (1) to (6), (10), (11), (13) or (14), wherein $U_2$ is single bond, $U_3$, and $U_4$ are each absent, and $U_1$ is —($C_1$-$C_6$)alkyl- which is unsubstituted, preferably —($C_1$-$C_2$)alkyl-.

(20) The compound of any one of the above (1) to (6), (10), (11), (13) or (14), wherein $U_2$ is single bond, $U_3$, and $U_4$ are each absent, and $U_1$ is —($C_2$-$C_6$)alkenyl- which is unsubstituted, preferably —($C_2$-$C_3$)alkenyl-.

(21) The compound of any one of the above (1) to (6) or (10) to (20), wherein U is —P(=O)(OH)$_2$.

(22) The compound of any one of the above (1) to (6) or (10) to (20), wherein U is —P(=O)(OH)(O—CH$_2$—O—C(O)-phenyl).

(23) The compound of any one of the above (1) to (6) or (10) to (20), wherein U is —P(=O)(OCH$_2$CH$_3$)$_2$.

(24) The compound of any one of the above (1) to (6), (10) to (12), (14), (15) or (19) to (23), wherein $U_1$ is a -(5- or 6-membered heterocycle).

(25) The compound of the above (24), wherein $U_1$ is tetrahydropyridinyl.

(26) The compound of any one of the above (1) to (6), (10), (16), or (21) to (24), wherein
$U_3$, $U_4$, $U_5$, $U_6$, and $U_7$ are absent;
each $R_4$ is independently selected from —H and —$U_1$—$U_2$—U, wherein at least one $R_4$ is not hydrogen;
$U_1$ is -phenyl- or -(5- or 6-membered)heterocycle-, which is unsubstituted or substituted with 1 or 2 independently selected $R_7$ groups;
$U_2$ is —Y—, —N($R_9$)—, —C(=Y)—, a single bond, or absent; and
each Y is O.

(27) The compound of any one of the above (1) to (6), (10) to (14) or (16) to (26), wherein U is —P(=O)(OH)(CH$_3$), —P(=O)(OCH$_2$CH$_3$)(CH$_3$), —P(=O)(O—CH$_2$—O—C(O)-phenyl)(CH$_3$), —P(=O)(OH)(CH$_2$CH$_3$), —P(=O)(OCH$_2$CH$_3$)(CH$_2$CH$_3$), or —P(=O)(O—CH$_2$—O—C(O)-phenyl)(CH$_2$CH$_3$).

(28) The compound of any one of the above (1) to (6), (26), or (27), wherein $U_1$ is -(5- or 6-membered)heterocycle-, preferably -(6-membered)heterocycle-, which is unsubstituted or substituted with 1 or 2 independently selected $R_7$ groups and $U_2$ is absent.

(29) The compound of any one of the above (1) to (6) or (26) to (28), wherein $U_1$ is 1,4-piperidinyl, 1,4-[1,2,3,6-tetrahydropyridinyl], or 1,4-piperazinyl which is unsubstituted or substituted with 1 or 2 independently selected $R_7$ groups and $U_2$ is absent.

(30) The compound of any one of the above (1) to (6) or (26) to (29), wherein $U_1$ is 1,4-piperidinyl, 1,4-[1,2,3,6-tetrahydropyridinyl], or 1,4-piperazinyl which is unsubstituted and $U_2$ is absent.

(31) The compound of any one of the above (1) to (6), (26), or (27), wherein $U_1$ is -(5- or 6-membered)heterocycle-, preferably -(6-membered)heterocycle-, which is unsubstituted or substituted with 1 or 2 independently selected $R_7$ groups and $U_2$ is —O—.

(32) The compound of any one of the above (1) to (6), (26), (27), or (31), wherein $U_1$ is 1,4-piperidinyl, 1,4-[1,2,3,6-tetrahydropyridinyl], or 1,4-piperazinyl which is unsubstituted or substituted with 1 or 2 independently selected $R_7$ groups and $U_2$ is —O—.

(33) The compound of any one of the above (1) to (6), (26), (27), (31), or (32), wherein $U_1$ is 1,4-piperidinyl, 1,4-[1,2,3,6-tetrahydropyridinyl], or 1,4-piperazinyl which is unsubstituted and $U_2$ is —O—.

(34) The compound of any one of the above (1) to (6) or (26) to (33), wherein U is —P(=O)(OH)(CH$_3$).

(35) The compound of any one of the above (1) to (6) or (26) to (33), wherein U is —P(=O)(OCH$_2$CH$_3$)(CH$_3$).

(36) The compound of any one of the above (1) to (6) or (10) to (35), wherein A and B are independently —H or —($C_1$-$C_6$)alkyl and preferably A and B are each —H or A is —H and B is —CH$_3$.

(37) The compound of any one of the above (1) to (6) or (10) to (35), wherein A and B together form a bridge such that the bridged-piperidine is:

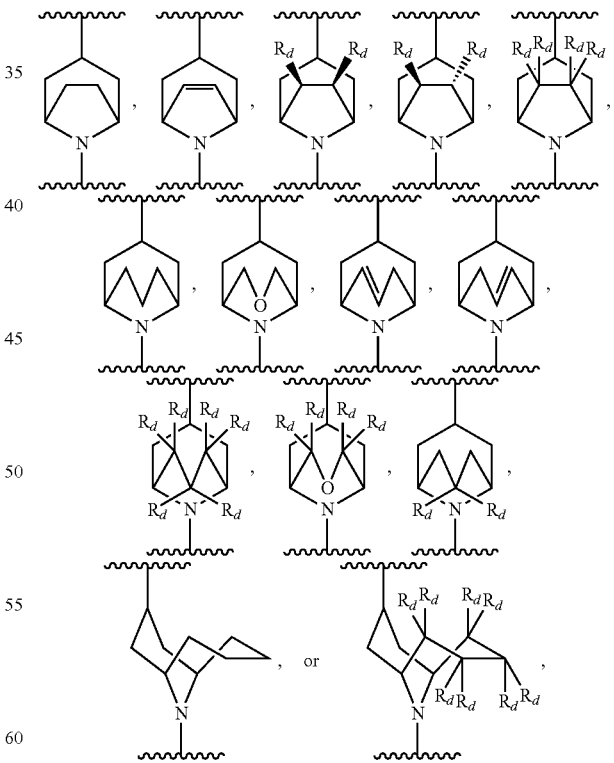

wherein each $R_d$ is independently —H, —($C_1$-$C_4$)alkyl, -halo, or —C(halo)$_3$.

(38) The compound of any one of the above (1) to (6), (10) to (35), or (37), wherein A and B together form a bridge such that the bridged-piperidine is:

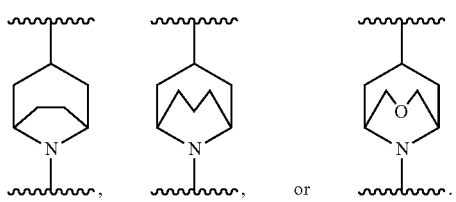 [SMILES: *C1CC2CCC(C1)N2* ; *C1CC2CCCC(C1)N2* ; *C1CC2COCC(C1)N2*]

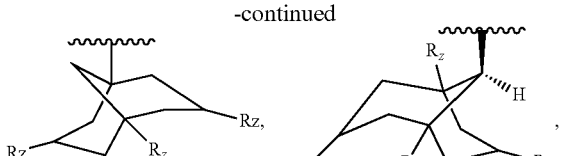

(39) The compound of any one of the above (1) to (6), (10) to (35), (37), or (38), wherein A and B together form a bridge such that the bridged-piperidine is:

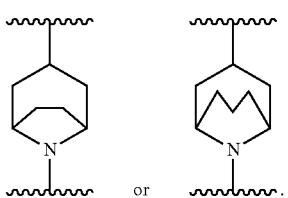 [SMILES: *C1CC2CCC(C1)N2* ; *C1CC2CCCC(C1)N2*]

(40) The compound of any one of the above (1) to (35) or (37) to (39), wherein the 6-membered, nitrogen-containing ring that is fused to the Q group is in the endo configuration with respect to the A-B bridge of the bridged-piperidine.

(41) The compound of any one of the above (1) to (6) or (10) to (40), wherein h is 0 and $R_1$ is —($C_1$-$C_{10}$)alkyl, —($C_2$-$C_{10}$)alkenyl, —($C_2$-$C_{10}$)alkynyl, —($C_3$-$C_{14}$)cycloalkyl, —($C_3$-$C_{14}$)cycloalkenyl, —($C_5$-$C_{10}$)cycloalkenyl, —($C_6$-$C_{14}$)bicycloalkyl, —($C_7$-$C_{14}$)bicycloalkenyl, or —($C_8$-$C_{20}$)tricycloalkyl, each of which is unsubstituted or substituted with 1, 2, 3, or 4 independently selected $R_8$ groups and preferably $R_1$ is —($C_3$-$C_{14}$)cycloalkyl, —($C_3$-$C_{14}$)cycloalkenyl, —($C_5$-$C_{10}$)cycloalkenyl, —($C_6$-$C_{14}$)bicycloalkyl, —($C_7$-$C_{14}$)bicycloalkenyl, or —($C_8$-$C_{20}$)tricycloalkyl, each of which is unsubstituted or substituted with 1, 2, 3, or 4 independently selected $R_8$ groups.

(42) The compound of any one of the above (1) to (6) or (10) to (41), wherein h is 0 and $R_1$ is:

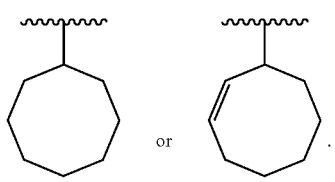 [SMILES: *C1CCCCCCC1 ; *C1/C=C\CCCCC1]

(43) The compound of any one of the above (1) to (6) or (10) to (41), wherein —Z—$R_1$ is:

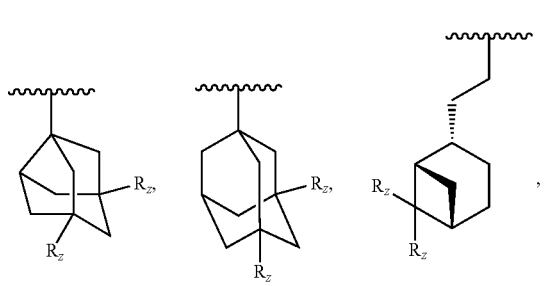

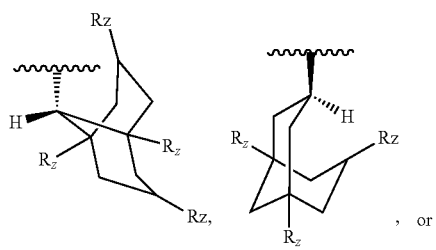

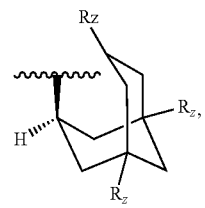

wherein each $R_z$ is independently —H, —($C_1$-$C_4$)alkyl, —OH, or —CN and preferably each $R_z$ is independently —H or —$CH_3$.

(44) The compound of any one of the above (1) to (6), (10) to (41), or (43), wherein h is 0 and $R_1$ is:

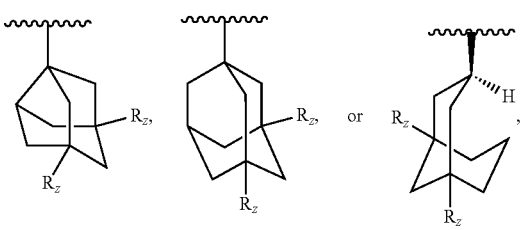

wherein each $R_z$ is independently —H, —($C_1$-$C_4$)alkyl, —OH, or —CN and preferably each $R_z$ is independently —H or —$CH_3$.

(45) The compound of any one of the above (1) to (6), (10) to (41), (43), or (44), wherein h is 0 and $R_1$ is:

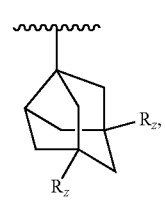

wherein each $R_z$ is —H.

(46) The compound of any one of the above (1) to (6), (10) to (41), or (43), wherein h is 0 and $R_1$ is:

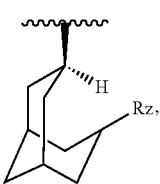

wherein $R_z$ is —H or —CH$_3$.

(47) The compound of any one of the above (1) to (5) or (10) to (46), wherein a is 1 and $R_2$ is -halo, preferably $R_2$ is —F.

(48) The compound of any one of the above (1) to (6), (9) to (35), (37) to (41), or (43) to (47), wherein the $R_1$ group is in the exo-configuration with respect to the A-B bridge of the bridged piperidine.

(49) The compound of any one of the above (1) to (6) or (10) to (41), wherein —$R_1$ is selected from:
  (a) ($C_6$-$C_{12}$)cycloalkyl, wherein preferably —$R_1$ is cyclooctyl, cyclononyl, cyclodecyl, cycloundecyl, or cyclododecyl; and
  (b) ($C_5$-$C_{12}$)cycloalkenyl or —($C_5$-$C_{10}$)cycloalkenyl, wherein preferably —$R_1$ is cyclohexenyl, cycloheptenyl, or cyclooctenyl; and
  (c)

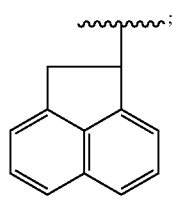 [SMILES: *C1Cc2cccc3cccc1c23]

and
  (d) ($C_6$-$C_{12}$)cycloalkyl optionally substituted by one —($C_1$-$C_4$)alkyl.

(50) The compound of any one of the above (1) to (6), (37), (38), or (40), wherein the compound is:

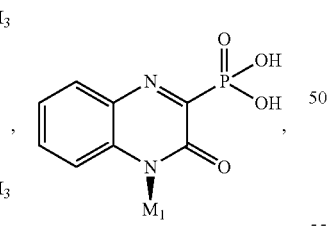

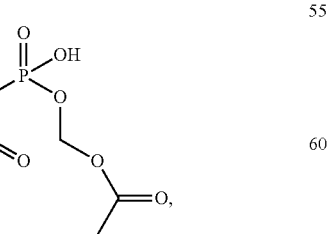

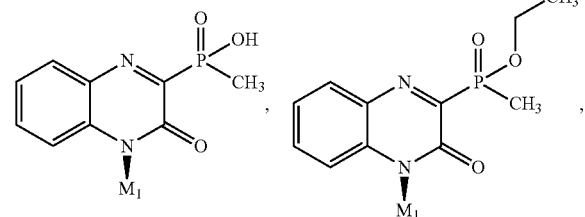

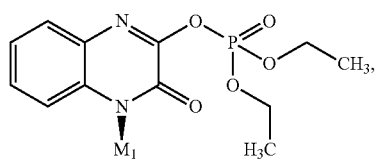

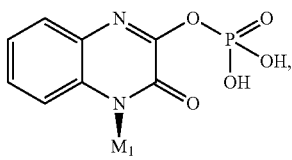

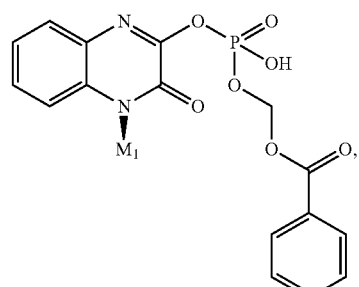

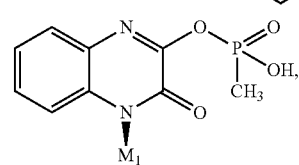

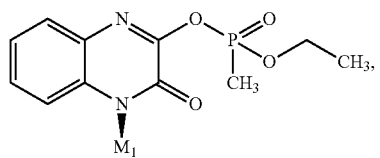

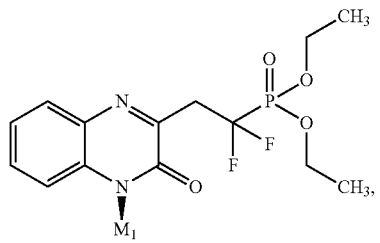

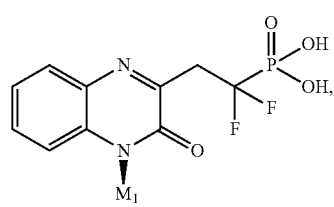

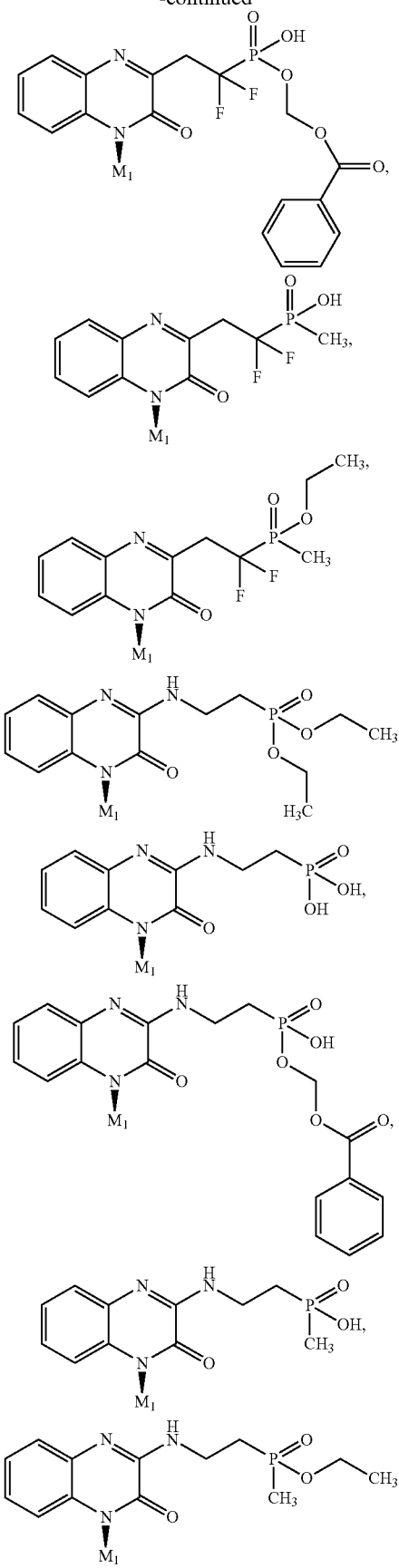
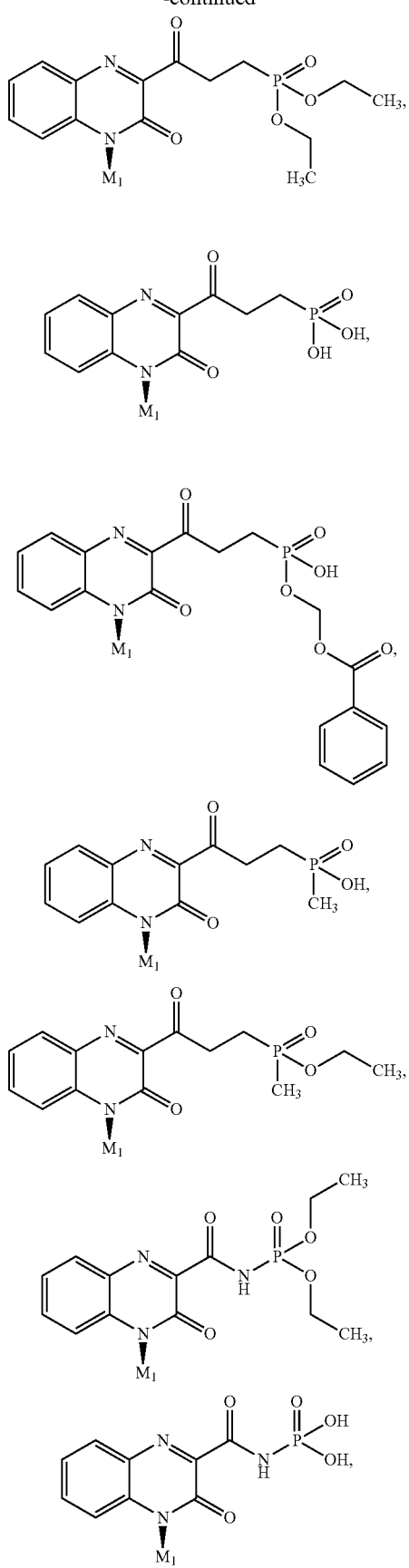

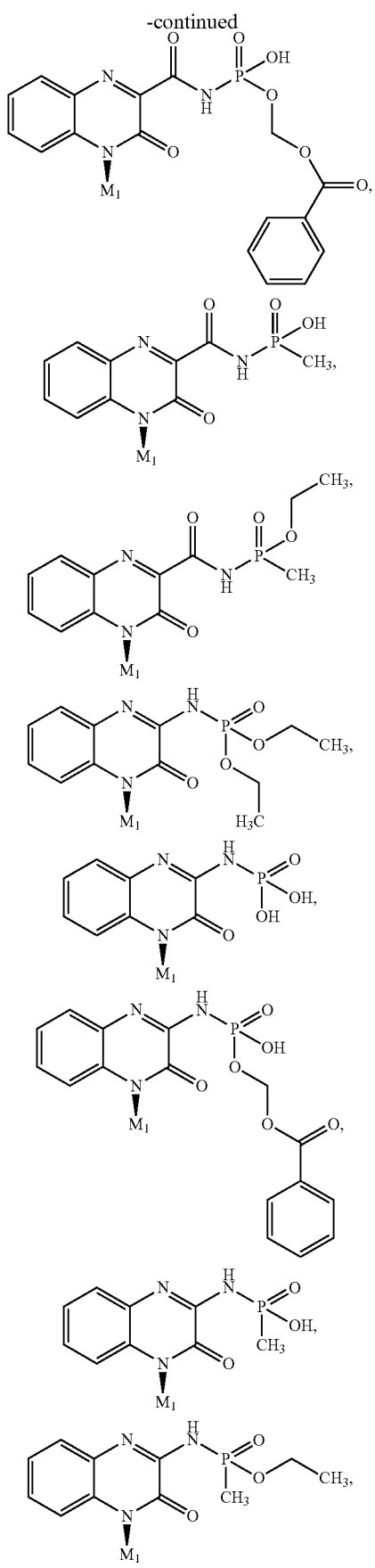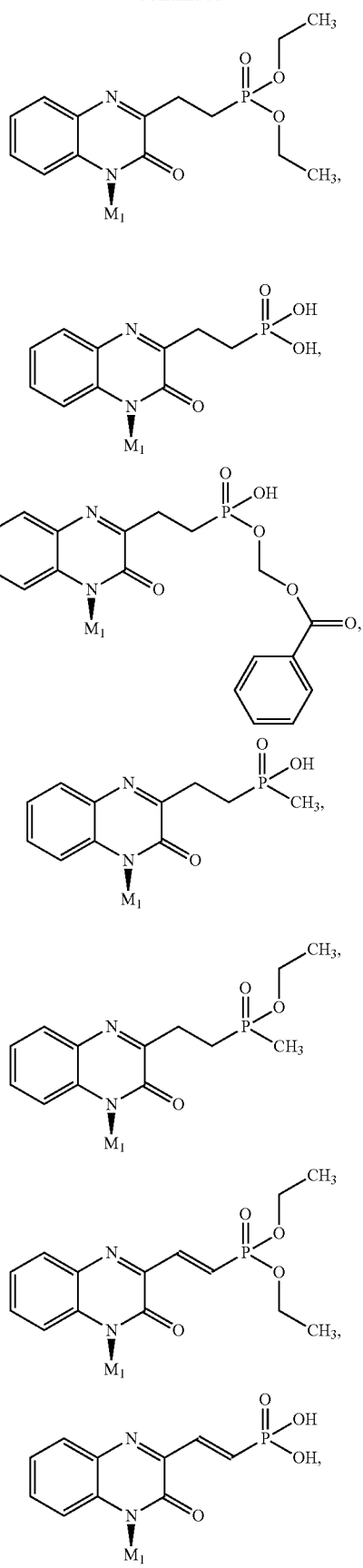

-continued
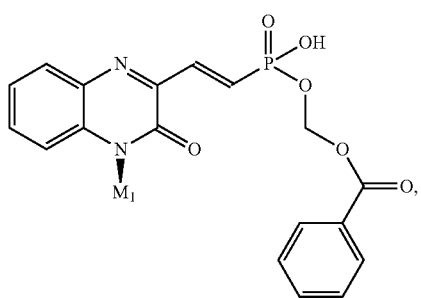
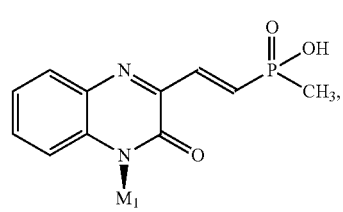
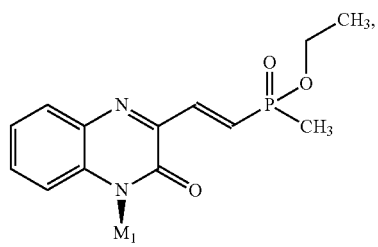
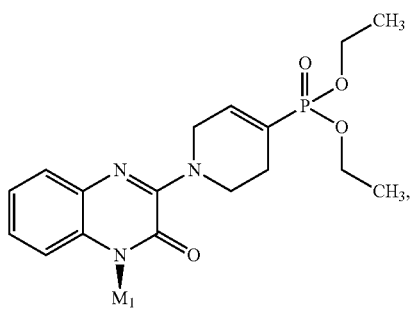
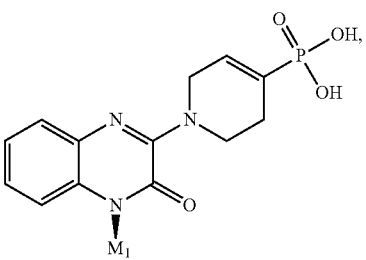
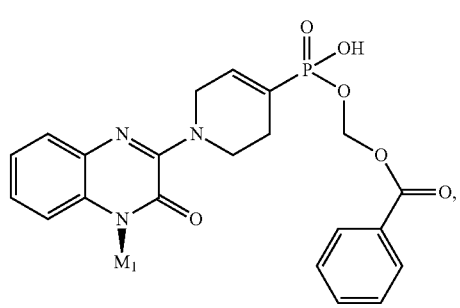
-continued
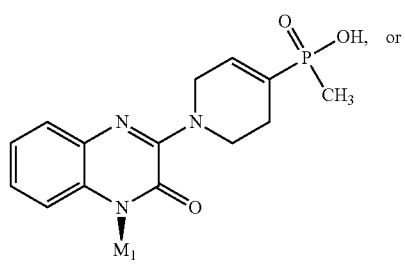
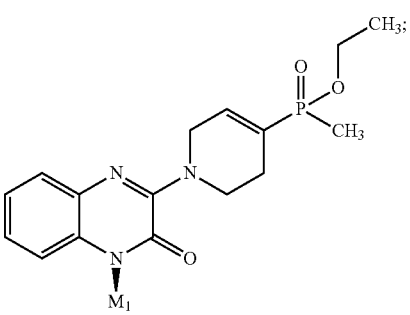
wherein $M_1$ is:
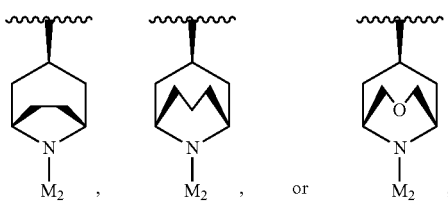
$M_2$ is:
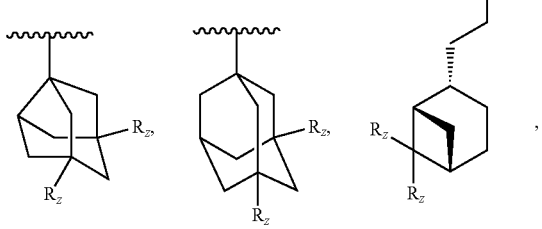
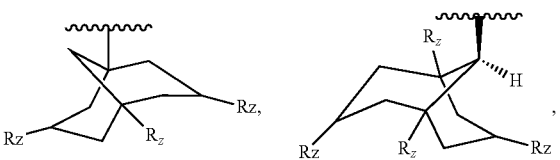

-continued

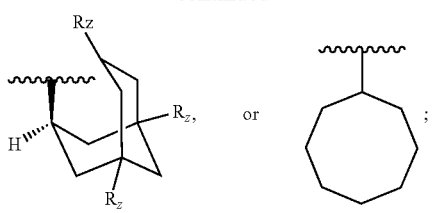

and each $R_z$ is independently —H or —CH$_3$ or a pharmaceutically acceptable derivative thereof.

(51) The compound of any one of the above (1) to (6), (37), (38), (40), or (41), wherein the compound is:

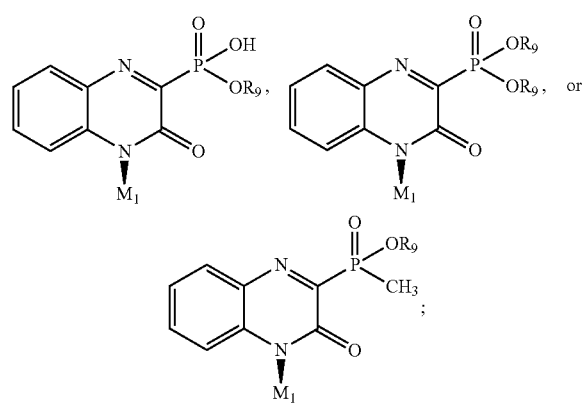

wherein each $R_9$ is independently —H, —(C$_1$-C$_6$)alkyl, —(C$_2$-C$_6$)alkenyl, -phenyl, -benzyl, or —CH$_2$—O—C(O)-phenyl;

$M_1$ is:

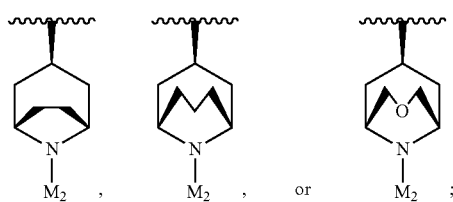

and $M_2$ is:

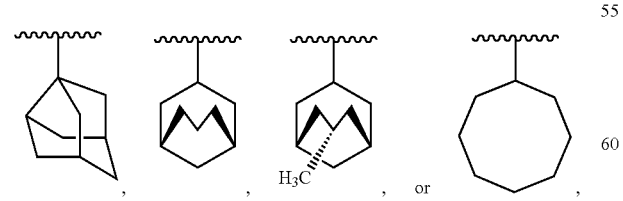

or a pharmaceutically acceptable derivative thereof.

(52) The compound of the above (51), wherein the compound is:

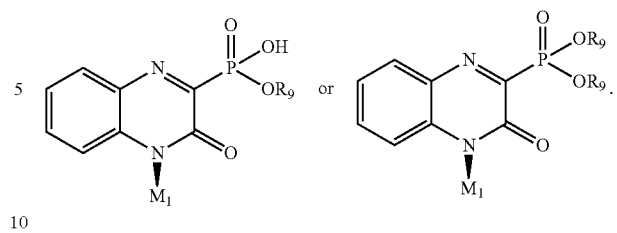

(53) A compound which is:

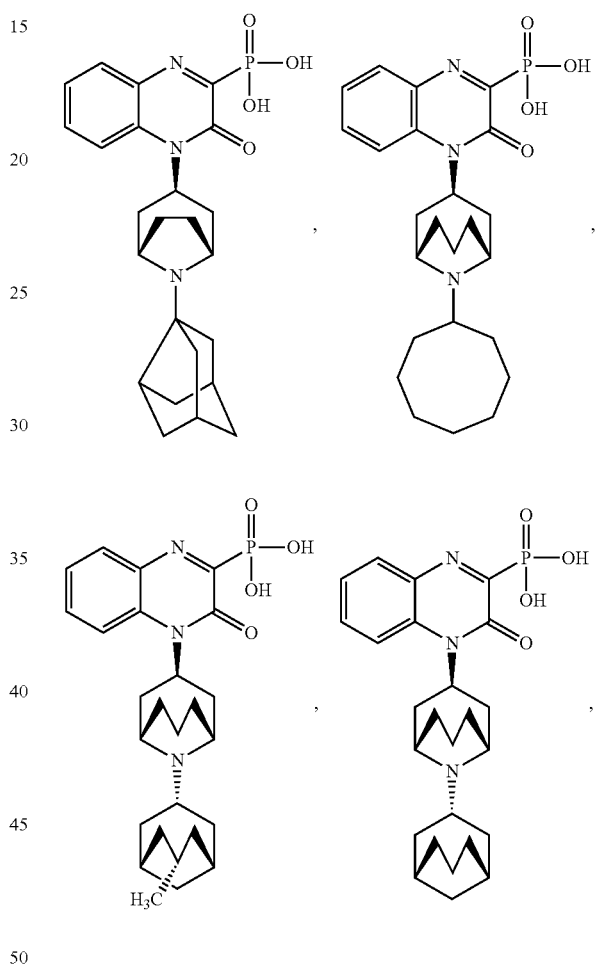

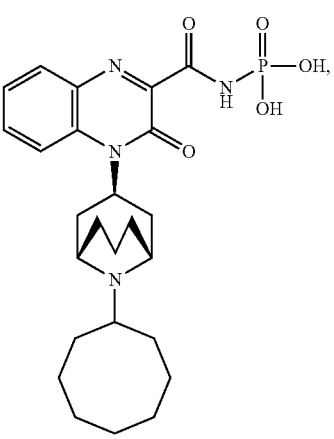

33
-continued
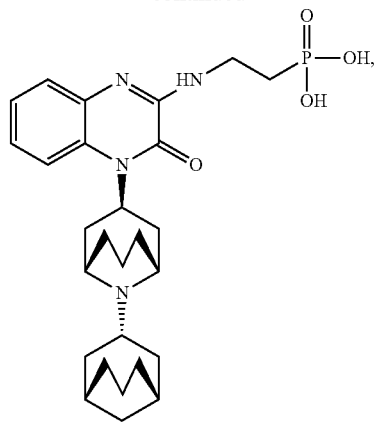
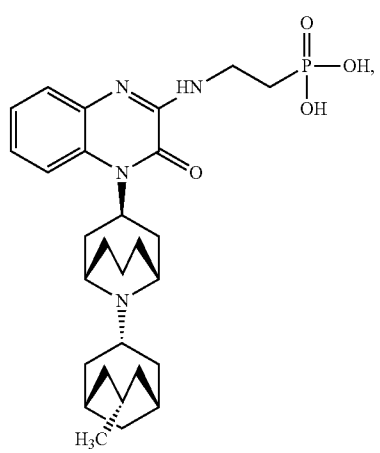
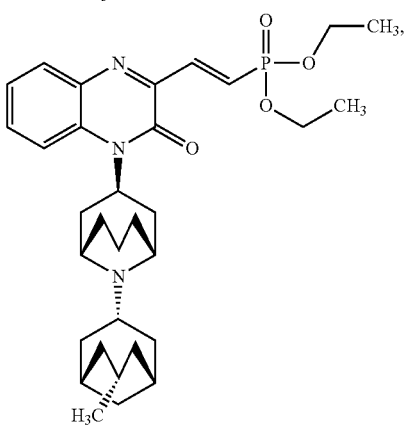
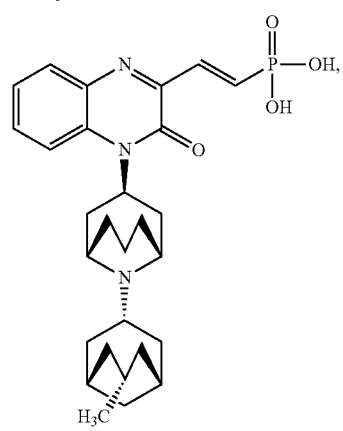
34
-continued
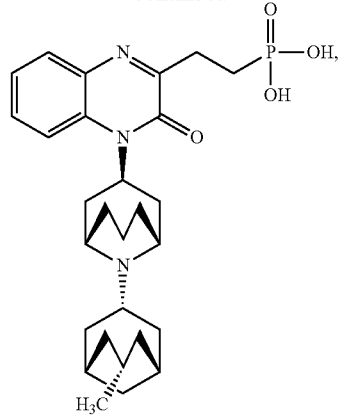
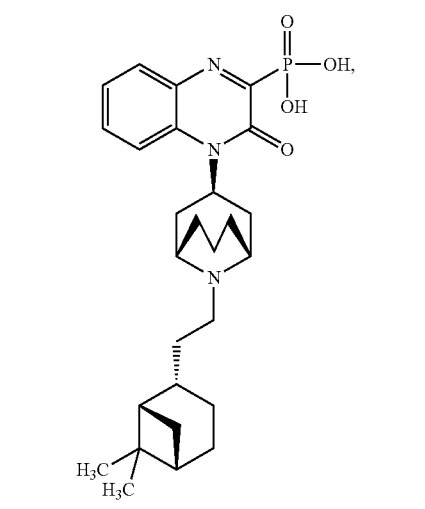
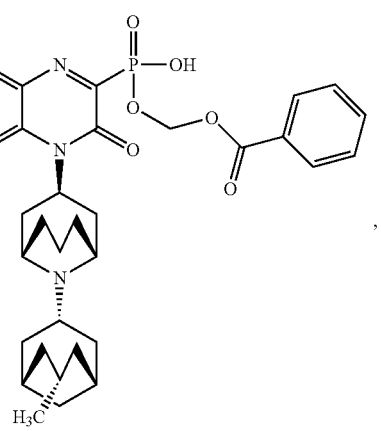

-continued

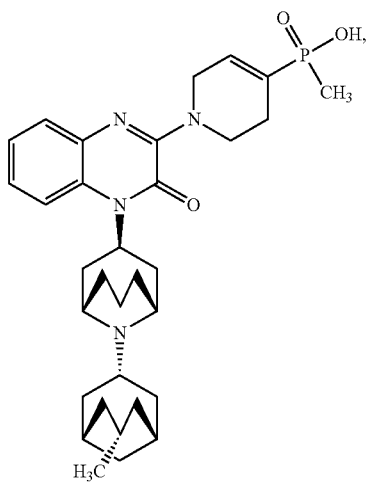

or a pharmaceutically acceptable derivative thereof.

(54) The compound of the above (53) which is:

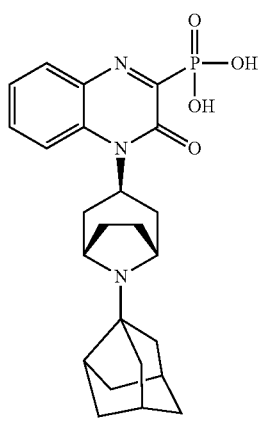 [SMILES: O=c1c(P(=O)(O)O)nc2ccccc2n1[C@H]1C[C@H]2CC[C@@H](C1)N2C12CC3CC(CC1C3)C2]

or a pharmaceutically acceptable derivative thereof.

(55) The compound of the above (53) which is:

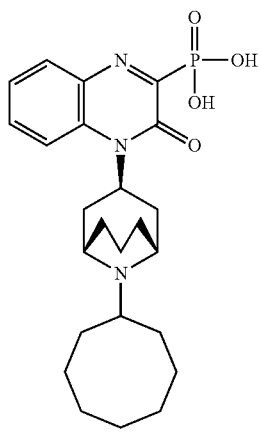 [SMILES: O=c1c(P(=O)(O)O)nc2ccccc2n1[C@H]1C[C@H]2CCC[C@@H](C1)N2C1CCCCCCC1]

or a pharmaceutically acceptable derivative thereof.

(56) The compound of the above (53) which is:

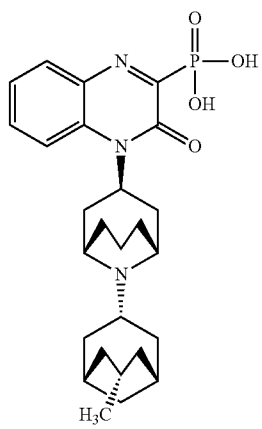 [SMILES: C[C@@H]1C[C@@H]2C[C@H](C1)C[C@@H](N1[C@@H]3CCC[C@H]1C[C@@H](n1c(=O)c(P(=O)(O)O)nc4ccccc41)C3)C2]

or a pharmaceutically acceptable derivative thereof.

(57) The compound of the above (53) which is:

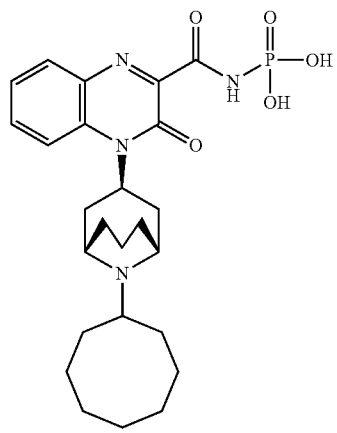 [SMILES: O=C(NP(=O)(O)O)c1nc2ccccc2n([C@H]2C[C@H]3CCC[C@@H](C2)N3C2CCCCCCC2)c1=O]

or a pharmaceutically acceptable derivative thereof.

(58) The compound of the above (53) which is:

or a pharmaceutically acceptable derivative thereof.

(59) The compound of the above (53) which is:

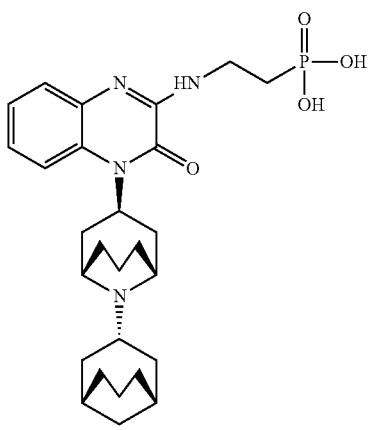 [SMILES: O=c1c(NCCP(=O)(O)O)nc2ccccc2n1[C@H]1C[C@H]2CCC[C@@H](C1)N2[C@H]1C[C@@H]2CCC[C@@H](C2)C1]

or a pharmaceutically acceptable derivative thereof.

(60) The compound of the above (53) which is:

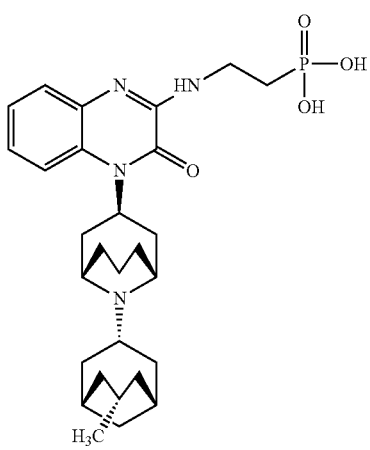 [SMILES: C[C@@H]1C[C@@H]2C[C@H](C1)C[C@@H](N1[C@@H]3CCC[C@H]1C[C@@H](n1c(=O)c(NCCP(=O)(O)O)nc4ccccc41)C3)C2]

or a pharmaceutically acceptable derivative thereof.

(61) The compound of the above (53) which is:

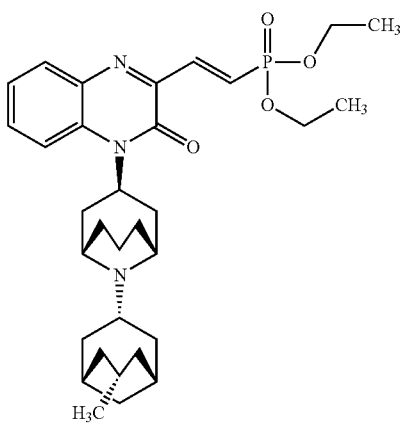 [SMILES: CCOP(=O)(/C=C/c1nc2ccccc2n([C@H]2C[C@H]3CCC[C@@H](C2)N3[C@H]2C[C@@H]3C[C@@H](C)C[C@@H](C3)C2)c1=O)OCC]

or a pharmaceutically acceptable derivative thereof.

(62) The compound of the above (53) which is:

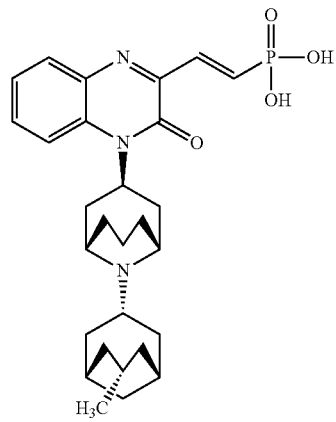 [SMILES: C[C@@H]1C[C@@H]2C[C@H](C1)C[C@@H](N1[C@@H]3CCC[C@H]1C[C@@H](n1c(=O)c(/C=C/P(=O)(O)O)nc4ccccc41)C3)C2]

or a pharmaceutically acceptable derivative thereof.

(63) The compound of the above (53) which is:

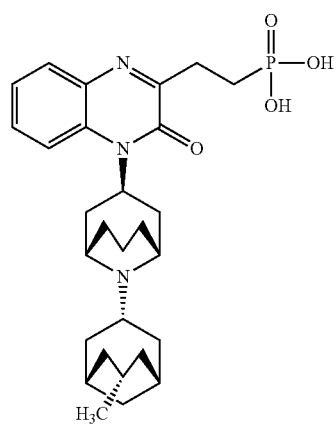 [SMILES: C[C@@H]1C[C@@H]2C[C@H](C1)C[C@@H](N1[C@@H]3CCC[C@H]1C[C@@H](n1c(=O)c(CCP(=O)(O)O)nc4ccccc41)C3)C2]

or a pharmaceutically acceptable derivative thereof.

(64) The compound of the above (53) which is:

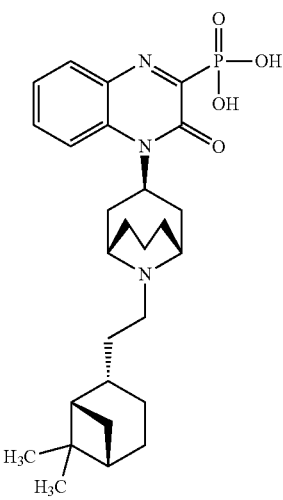 [SMILES: CC1(C)[C@H]2CC[C@@H](CCN3[C@@H]4CCC[C@H]3C[C@@H](n3c(=O)c(P(=O)(O)O)nc5ccccc53)C4)[C@@H]1C2]

or a pharmaceutically acceptable derivative thereof.

(65) The compound of the above (53) which is:

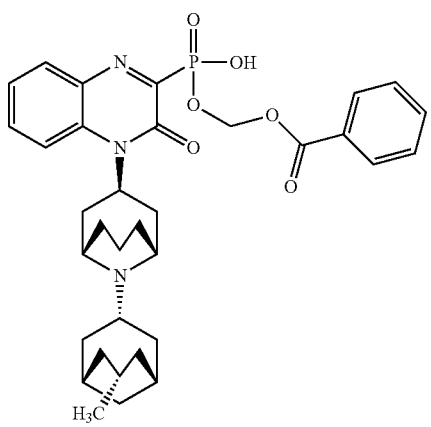 [SMILES: C[C@@H]1C[C@@H]2C[C@H](C1)C[C@@H](N1[C@@H]3CCC[C@H]1C[C@@H](n1c(=O)c(P(=O)(O)OCOC(=O)c4ccccc4)nc4ccccc41)C3)C2]

or a pharmaceutically acceptable derivative thereof.

(66) The compound of the above (53) which is:

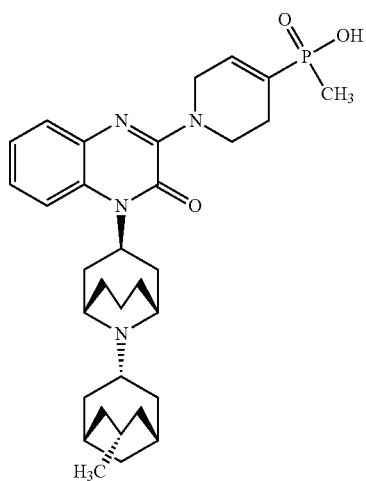 [SMILES: C[C@@H]1C[C@@H]2C[C@H](C1)C[C@@H](N1[C@@H]3CCC[C@H]1C[C@@H](n1c(=O)c(N4CC=C(P(C)(=O)O)CC4)nc4ccccc41)C3)C2]

or a pharmaceutically acceptable derivative thereof.

(67) The compound of any one of the above (1) to (66), wherein the pharmaceutically acceptable derivative is a pharmaceutically acceptable salt.

(68) The compound of any one of the above (1) to (67) or a pharmaceutically acceptable salt thereof, which is radiolabeled.

(69) The compound of any one of the above (1) to (68), wherein the pharmaceutically acceptable salt is a hydrochloride-salt, a sodium-salt, a potassium-salt, or a para-toluenesulfonic acid-salt.

(70) A composition comprising an effective amount of the compound or a pharmaceutically acceptable salt of the compound of any one of the above (1) to (69) and a pharmaceutically acceptable carrier or excipient.

(71) A method for preparing a composition, comprising the step of admixing a compound or a pharmaceutically acceptable salt of the compound of any one of the above (1) to (69) and a pharmaceutically acceptable carrier or excipient.

(72) A method for modulating ORL-1 receptor function in a cell, comprising contacting a cell capable of expressing the ORL-1 receptor with an effective amount of the composition or the compound or a pharmaceutically acceptable salt of the compound of any one of the above (1) to (69).

(73) The method of the above (72), wherein the composition or the compound or the pharmaceutically acceptable salt of the compound acts as an agonist at the ORL-1 receptor.

(74) The method of the above (72), wherein the composition or the compound or the pharmaceutically acceptable salt of the compound acts as a partial agonist at the ORL-1 receptor.

(75) The method of the above (72), wherein the composition or the compound or the pharmaceutically acceptable salt of the compound acts as an antagonist at the ORL-1 receptor.

(76) A method for treating pain in an animal, comprising administering to an animal in need thereof an effective amount of the composition or the compound or a pharmaceutically acceptable salt of the compound of any one of the above (1) to (70).

(77) A method for treating a memory disorder, obesity, constipation, depression, dementia, Parkinsonism, anxiety, cough, diarrhea, high blood pressure, epilepsy, anorexia/cachexia, urinary incontinence, or drug abuse in an animal, comprising administering to an animal in need thereof an effective amount of the composition or the compound or a pharmaceutically acceptable salt of the compound of any one of the above (1) to (70).

(78) Use of a compound or the pharmaceutically acceptable salt of the compound of any one of the above (1) to (69) for the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, or drug abuse.

(79) The compound or the pharmaceutically acceptable salt of the compound of any one of the above (1) to (69) for use in the treatment of pain, a memory disorder, obesity, constipation, depression, dementia, Parkinsonism, anxiety, cough, diarrhea, high blood pressure, epilepsy, anorexia/cachexia, urinary incontinence, or drug abuse.

(80) A kit, comprising a container containing an effective amount of the composition or the compound or a pharmaceutically acceptable salt of the compound of any one of the above (1) to (70).

(101) A compound of Formula (I):

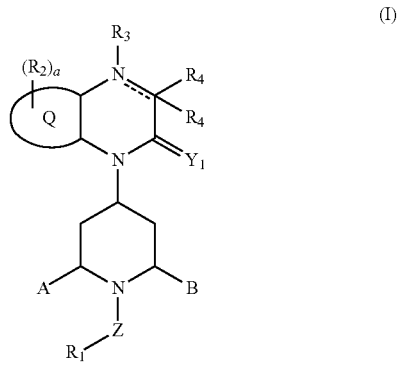

including the pharmaceutically acceptable derivatives thereof wherein:

$Y_1$ is O or S;

Q is fused benzo or (5- or 6-membered)heteroaryl;

each $R_2$ is independently:
(a) -halo, —CN, —NO$_2$, —OT$_3$, —C(=O)OT$_3$, —C(=O)N(T$_1$)(T$_2$), —S(=O)$_2$OH, —S(=O)T$_3$, —S(=O)$_2$T$_3$, —S(=OO)$_2$N(T$_1$)(T$_2$), —N(T$_1$)(T$_2$), —N(T$_3$)C(=O)T$_3$, —N(T$_3$)C(=O)N(T$_1$)(T$_2$), —N(T$_3$)S(=O)$_2$T$_3$, or —N(T$_3$)S(=O)$_2$N(T$_1$)(T$_2$); or
(b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered)heterocycle, or -(7- to 10-membered)bicycloheterocycle, each of which is unsubstituted or substituted with 1, 2, or 3 independently selected $R_8$ groups; or
(c) -phenyl, -naphthalenyl, —(C$_{14}$)aryl, or -(5- or 6-membered)heteroaryl, each of which is unsubstituted or substituted with 1, 2, or 3 independently selected $R_7$ groups;
a is an integer selected from 0, 1, and 2;
the dashed line in the 6-membered, nitrogen-containing ring that is fused to the Q group denotes the presence or absence of a bond, and when that dashed line is present as a bond to provide one bond of a double bond then one of the two $R_4$ groups is absent and optionally $R_3$ is absent;
$R_3$ is:
(a) —H; or
(b) —(C$_1$-C$_4$)alkyl which is unsubstituted or substituted with 1, 2, or 3 groups independently selected from —OH, —(C$_1$-C$_4$)alkoxy, —N(R$_6$)$_2$, —C(=OO)OR$_9$, and —C(=O)N(R$_6$)$_2$; or
(c) —(C$_3$-C$_7$)cycloalkyl which is unsubstituted or substituted with 1, 2, or 3 groups independently selected from —OH, —(C$_1$-C$_4$)alkyl, —(C$_1$-C$_4$)alkoxy, —N(R$_6$)$_2$, —C(=O)OR$_9$, and —C(=O)N(R$_6$)$_2$;
each $R_4$ is independently:
(a) —H; or
(b) —U$_1$—U$_2$—U$_3$—U$_4$—U$_5$—U$_6$—U$_7$—U;
wherein at least one $R_4$ is not hydrogen;
U is —P(=O)(OR$_9$)$_2$;
$U_1$, $U_3$, $U_5$, and $U_7$ are independently:
(a) a single bond; or
(b) —(C$_1$-C$_6$)alkyl-, —(C$_2$-C$_6$)alkenyl-, —(C$_6$-C$_{12}$)cycloalkyl-, —(C$_6$-C$_{14}$)bicycloalkyl-, —(C$_5$-C$_{14}$)cycloalkenyl-, —(C$_7$-C$_{14}$)bicycloalkenyl-, -phenyl-, or -(5- or 6-membered)heterocycle-, each of which is unsubstituted or substituted with 1, 2, or 3 independently selected $R_7$ groups; or
(c) absent;
$U_2$, $U_4$, and $U_6$ are independently —Y—, —N(R$_9$)—, —C(=Y)—, a single bond, or absent;
each Y is independently O or S;
A and B are independently:
(a) —H, —CN, —C(=O)OT$_3$, or —C(=O)N(T$_1$)(T$_2$); or
(b) —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl, or —(C$_1$-C$_6$)alkoxy, each of which is unsubstituted or substituted with:
(1') 1 or 2 substituents independently selected from —OH, —S(=O)$_2$NH$_2$, —N(R$_6$)$_2$, =NR$_6$, —C(=O)OT$_3$, —C(=O)N(R$_6$)$_2$, —N(R$_6$)C(=O)R$_9$, and -(5- or 6-membered)heterocycle, or
(2') 1, 2, or 3 independently selected -halo; or
(c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge, wherein the 6-membered, nitrogen-containing ring that is fused to the Q group can be in the endo- or exo-configuration with respect to the A-B bridge; or
(d) A-B can together form a —CH$_2$—N(R$_a$)—CH$_2$— bridge, a

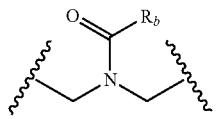

bridge, or a

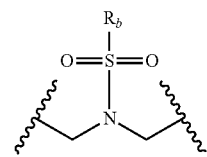

bridge,
wherein the 6-membered, nitrogen-containing ring that is fused to the Q group can be in the endo-or exo-configuration with respect to the A-B bridge;
$R_a$ is —H, —(C$_1$-C$_6$)alkyl, —(C$_3$-C$_7$)cycloalkyl, —CH$_2$—C(=O)—R$_c$, —(CH$_2$)—C(=O)—OR$_c$, —(CH$_2$)—C(=O)—N(R$_c$)$_2$, —(CH$_2$)$_2$—O—R$_c$, —(CH$_2$)$_2$—S(=O)$_2$—N(R$_c$)$_2$, R$_c$, or —(CH$_2$)$_2$—N(R$_c$)S(=O)$_2$—R$_c$;
$R_b$ is:
(a) —H, —(C$_1$-C$_6$)alkyl, —(C$_3$-C$_7$)cycloalkyl, -(3- to 7-membered)heterocycle, —N(R$_c$)$_2$, —N(R$_c$)—(C$_3$-C$_7$)cycloalkyl, or —N(R$_c$)-(3- to 7-membered)heterocycle; or
(b) -phenyl, -naphthalenyl, or -(5- or 6-membered)heteroaryl, each of which is unsubstituted or substituted with 1, 2, or 3 independently selected $R_7$ groups; or
(c) —N(R$_c$)-phenyl, —N(R$_c$)-naphthalenyl, —N(R$_c$)—(C$_{14}$)aryl, or —N(R$_c$)-(5- to 10-membered)heteroaryl, each of which is unsubstituted or substituted with 1, 2, or 3 independently selected $R_7$ groups;
each $R_c$ is independently —H or —(C$_1$-C$_4$)alkyl;
Z is —[(C$_1$-C$_{10}$)alkyl optionally substituted by R$_1$]$_h$—, wherein h is 0 or 1; —(C$_2$-C$_{10}$)alkenyl- optionally substituted by R$_1$; or —(C$_1$-C$_{10}$)alkyl-N(R$_6$)C(=Y)—;
each $R_1$ is independently:
(a) —H, -halo, —CN, —OH, —CH$_2$OH, —CH$_2$CH$_2$OH, —NO$_2$, —N(R$_6$)$_2$, —S(=O)NH$_2$, —S(=O)$_2$NH$_2$, —C(=O)OV$_1$, or —C(=O)CN; or
(b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, or -(7- to 10-membered)bicycloheterocycle, each of which is unsubstituted or substituted with 1, 2, 3, or 4 independently selected $R_8$ groups; or (c)

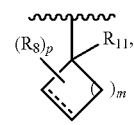
(i)

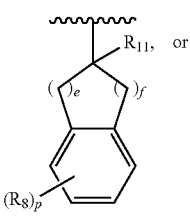
(ii)

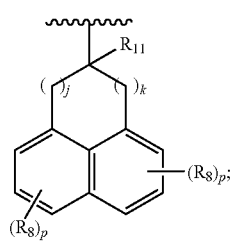
(iii)

(d) -phenyl, -naphthalenyl, —$(C_{14})$aryl, or -(5- to 10-membered)heteroaryl, each of which is unsubstituted or substituted with a $R_7$ group; or —Z—$R_1$ is 3,3-diphenylpropyl- optionally substituted at the 3 carbon of the propyl with —CN, —C(=O)N($R_6$)$_2$, —C(=O)O$V_1$, or -tetrazolyl; or —Z—$R_1$ is —$(C_1$-$C_4)$alkyl substituted with tetrazolyl;

each $R_6$ is independently —H, —$(C_1$-$C_6)$alkyl, or —$(C_3$-$C_7)$cycloalkyl, or two $R_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N($R_{12}$);

each $R_7$ is independently —$(C_1$-$C_4)$alkyl, —$(C_2$-$C_6)$alkenyl, —$(C_2$-$C_6)$alkynyl, —O$R_9$, —S$R_9$, —C(halo)$_3$, —CH(halo)$_2$, —CH$_2$(halo), —CN, -halo, —N$_3$, —NO$_2$, —CH=N($R_9$), —N($R_9$)$_2$, —N($R_9$)OH, —N($R_9$)S(=O)$R_{12}$, —N($R_9$)S(=O)$_2R_{12}$, —N($R_9$)C(=O)$R_{12}$, —N($R_9$)C(=O)N($T_1$)($T_2$), —N($R_9$)C(=O)O$R_{12}$, —C(=O)$R_9$, —C(=O)N($T_1$)($T_2$), —C(=O)O$R_9$, —OC(=O)$R_9$, —OC(=O)N($T_1$)($T_2$), —OC(=O)O$R_9$, —S(=O)$R_9$, or —S(=O)$_2R_9$;

each $R_8$ is independently —$(C_1$-$C_6)$alkyl, —$(C_2$-$C_6)$alkenyl, —$(C_2$-$C_6)$alkynyl, -(5- or 6-membered)heteroaryl, —$(C_1$-$C_6)$alkyl-C(=O)O$R_9$, —O$R_9$, —S$R_9$, —C(halo)$_3$, —CH(halo)$_2$, —CH$_2$(halo), —CN, =O, =S, -halo, —N$_3$, —NO$_2$, —CH=N($R_9$), —N($R_9$)($C_1$-$C_6$)alkyl-C(=O)O$R_9$, —N($R_9$)$_2$, —N($R_9$)OH, —N($R_9$)S(=O)$R_{12}$, —N($R_9$)S(=O)$_2R_{12}$, —N($R_9$)C(=O)$R_{12}$, —N($R_9$)C(=O)N($R_{12}$)($R_{12}$), —N($R_9$)C(=O)O$R_{12}$, —C(=O)$R_9$, —C(=O)N($R_{12}$)($R_{12}$), —C(=O)O$R_9$, —OC(=O)$R_9$, —OC(=O)N($R_{12}$)($R_{12}$), —OC(=O)O$R_9$, —S(=O)$R_9$, or —S(=O)$_2R_9$;

each $R_9$ is independently —H, —$(C_1$-$C_6)$alkyl, —$(C_2$-$C_6)$alkenyl, —$(C_2$-$C_6)$alkynyl, —$(C_3$-$C_8)$cycloalkyl, —$(C_5$-$C_8)$ cycloalkenyl, -phenyl, -benzyl, —CH$_2$—O—C(O)-phenyl, —CH$_2$—C(O)—O-phenyl, —C(halo)$_3$, —CH(halo)$_2$, or —CH$_2$(halo);

if h is 0, then $R_{11}$ can be selected from —H, —CN, —C(=O)O$R_9$, and —C(=O)N($R_6$)$_2$ or $R_{11}$ can be —$(C_1$-$C_4)$alkyl which is unsubstituted or substituted with —OH, —$(C_1$-$C_4)$alkoxy, —N($R_6$)$_2$, —C(=O)O$R_9$, or —C(=O)N($R_6$)$_2$;

if h is 1, then $R_{11}$ can be selected from —H, —CN, —OH, -halo, —C(=O)O$R_9$, and —C(=O)N($R_6$)$_2$ or $R_{11}$ can be —$(C_1$-$C_4)$alkyl which is unsubstituted or substituted with —OH, —$(C_1$-$C_4)$alkoxy, —N($R_6$)$_2$, —C(=O)O$R_9$, or —C(=O)N($R_6$)$_2$;

otherwise, where Z is —$(C_1$-$C_{10})$alkyl-N($R_6$)C(=Y)—, then $R_{11}$ can be selected from —H, —CN, —C(=O)O$R_9$, and —C(=O)N($R_6$)$_2$ or $R_{11}$ can be —$(C_1$-$C_4)$alkyl which is unsubstituted or substituted with —OH, —$(C_1$-$C_4)$alkoxy, —N($R_6$)$_2$, —C(=O)O$R_9$, or —C(=O)N($R_6$)$_2$;

each $R_{12}$ is independently —H or —$(C_1$-$C_6)$alkyl;

m is an integer selected from 0, 1, 2, 3, 4, 5, 6, 7, 8, 9, 10, and 11;

e and f are each an integer independently selected from 0, 1, 2, 3, 4, and 5 provided that 2≤(e+f)≤5;

j and k are each an integer independently selected from 0, 1, 2, 3, and 4 provided that 1≤(j+k)≤4;

each p is an integer independently selected from 0, 1, 2, 3, and 4;

each $T_1$, $T_2$, and $T_3$ is independently —H or —$(C_1$-$C_{10})$alkyl which is unsubstituted or substituted with 1, 2, or 3 independently selected $R_8$ groups and in which 0, 1, 2, or 3 independently selected —$(C_1$-$C_{10})$alkyl carbon atoms except the carbon atom bonded directly to the atom to which $T_1$, $T_2$, or $T_3$ is attached are independently replaced by O, S, or N($R_6$), or $T_1$ and $T_2$ can together form a 5- to 8-membered ring where the number of atoms in the ring includes the nitrogen atom to which $T_1$ and $T_2$ are bonded, said 5- to 8-membered ring is unsubstituted or substituted with 1, 2, or 3 independently selected $R_8$ groups and 0, 1, 2, or 3 independently selected carbon atoms in said 5- to 8-membered ring are independently replaced by O, S, or N($R_6$);

each $V_1$ is independently —H, —$(C_1$-$C_6)$alkyl, —$(C_3$-$C_7)$cycloalkyl, -phenyl, or -benzyl; and each halo is independently —F, —Cl, —Br, or —I.

(102) The compound of the above (101), wherein $Y_1$ is O.

(103) The compound of any one of the above (101) or (102), wherein the dashed line is present as a bond to provide one bond of a double bond, one $R_4$ is present, and preferably $R_3$ is absent.

(104) The compound of any one of the above (101) to (103), wherein Q is benzo, pyridino, pyrimidino, pyrazino, or pyridazino, and preferably Q is benzo or pyridino, and preferably the 2- and 3-positions of the pyridino are fused to the 6-membered, nitrogen-containing ring.

(105) The compound of any one of the above (101) to (104), wherein Q is benzo.

(106) The compound of any one of the above (101) to (105), wherein a is 0.

(107) The compound of any one of the above (101) to (106), which is:

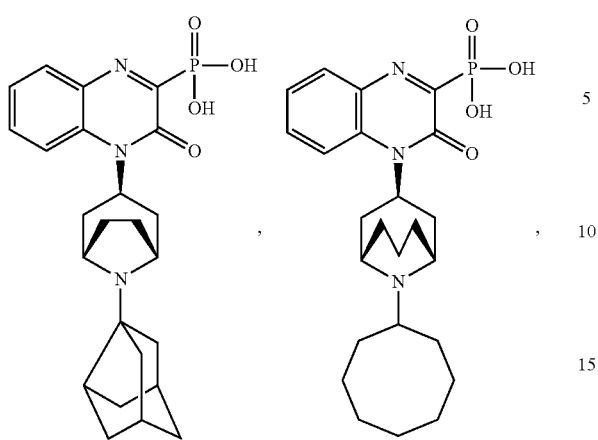
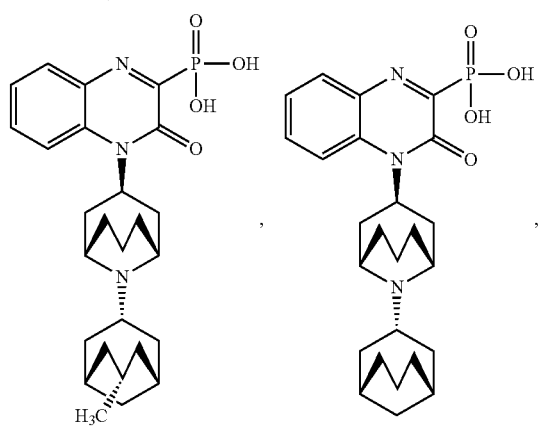
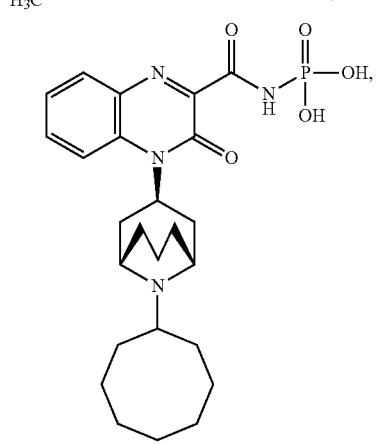
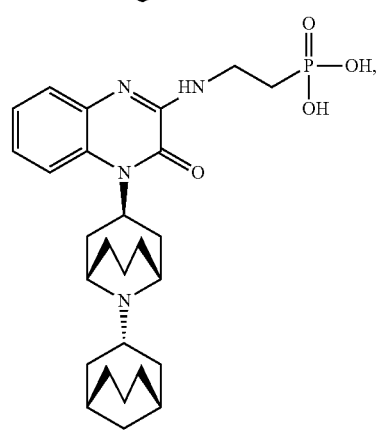
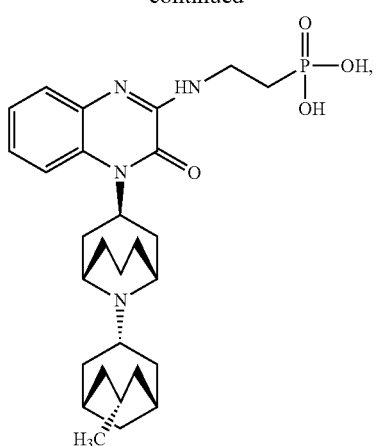
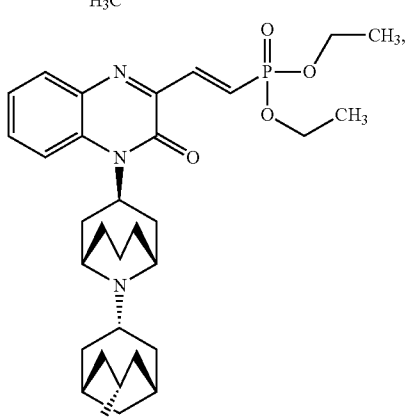
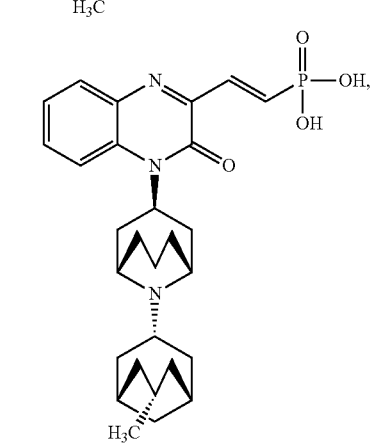
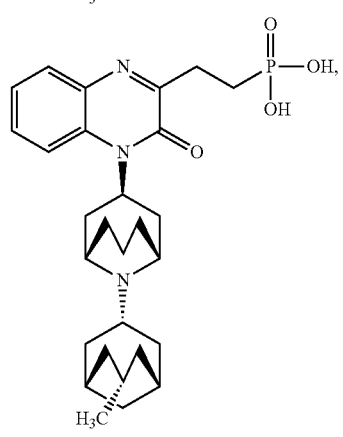

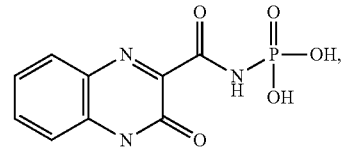
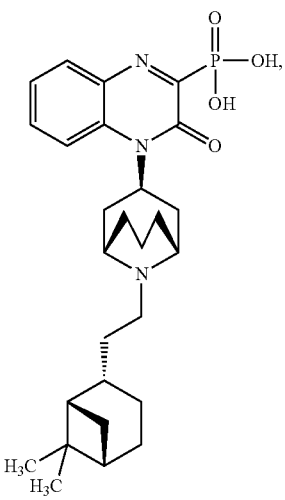
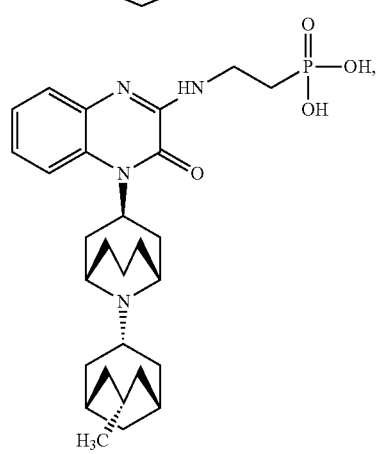
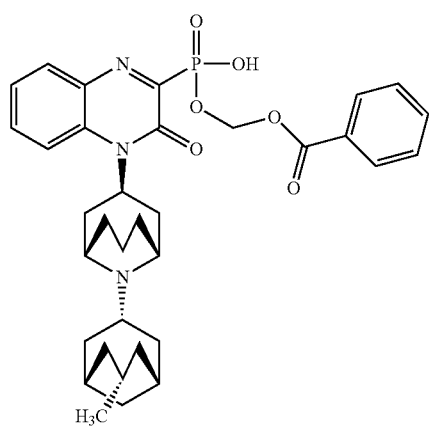
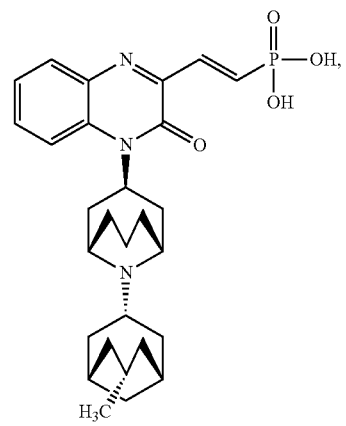
or a pharmaceutically acceptable salt thereof.
(108) The compound of any one of the above (101) to (107), which is:
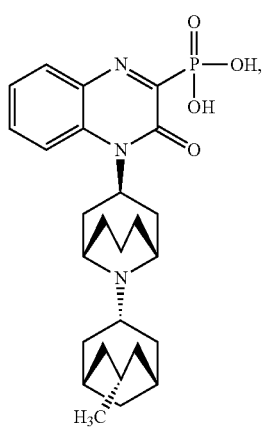
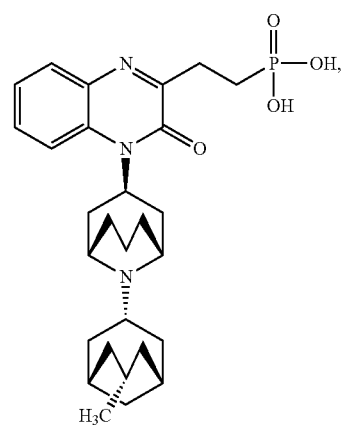

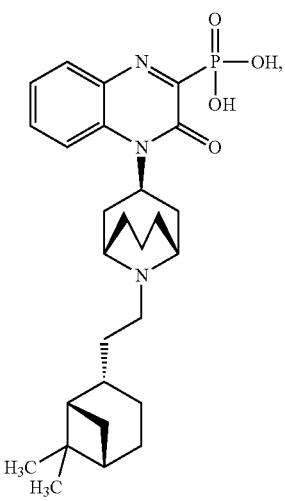

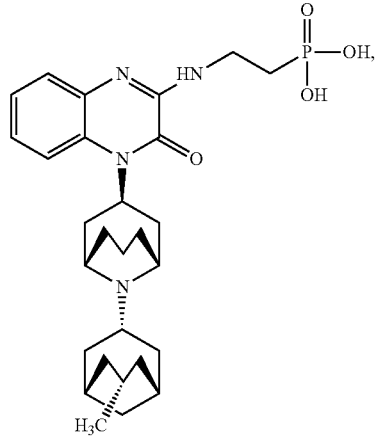

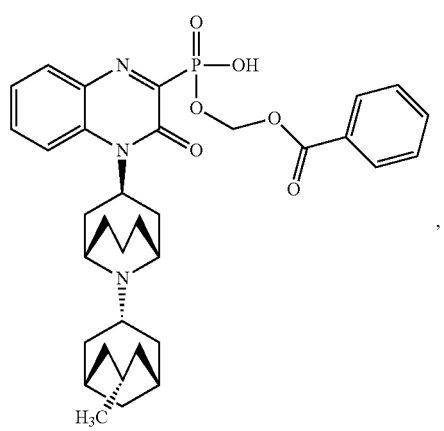

or a pharmaceutically acceptable salt thereof.

(109) The compound of any one of the above (101) to (108), which is:

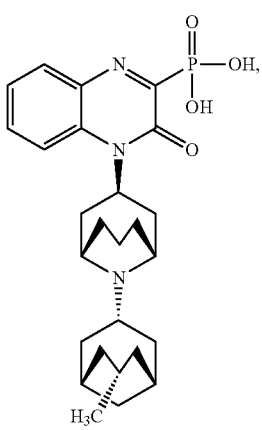

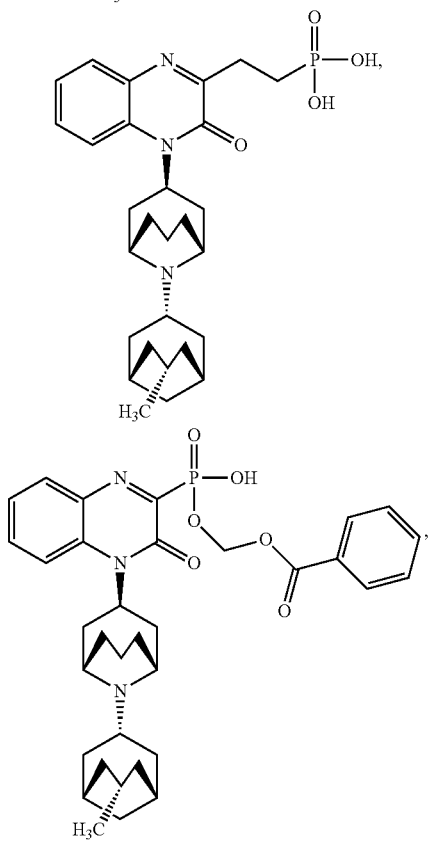

or a pharmaceutically acceptable salt thereof.

(110) The compound of any one of the above (101) to (106), wherein $U_5$, $U_6$, and $U_7$ are absent;

each $R_4$ is independently:

(a) —H; or (b) —$U_1$—$U_2$—$U_3$—$U_4$—U wherein at least one $R_4$ is not hydrogen;

U is —P(=O)(OR$_9$)$_2$;

$U_1$ and $U_3$ are independently —($C_1$-$C_6$)alkyl- or —($C_2$-$C_6$)alkenyl-, which is unsubstituted or substituted with 1 or 2 independently selected $R_7$ groups, a single bond, or absent;

$U_2$ and $U_4$ are independently —Y—, —N(R$_9$)—, —C(=Y)—, a single bond, or absent; and each Y is O.

(111) The compound of any one of the above (101) to (106) or (110), wherein U is —P(=O)(OH)$_2$, —P(=O)(OCH$_2$CH$_3$)$_2$ or —P(=O)(OH)(O—CH$_2$—O—C(O)-phenyl).

(112) The compound of any one of the above (101) to (106), (110), or (111), wherein U$_1$ is a bond and U$_2$, U$_3$, and U$_4$ are each absent.

(113) The compound of any one of the above (101) to (106), (110), or (111), wherein U$_1$ and U$_3$ are each a single bond, U$_2$ is —C(O)—, and U$_4$ is —NH—.

(114) The compound of any one of the above (101) to (106), (110), or (111), wherein U$_1$ and U$_4$ are each a single bond, U$_2$ is —NH—, and U$_3$ is —(C$_1$-C$_6$)alkyl- which is unsubstituted, preferably —(C$_1$-C$_2$)alkyl-.

(115) The compound of any one of the above (101) to (106), (110), or (111), wherein U$_2$ is single bond, U$_3$, and U$_4$ are each absent, and U$_1$ is —(C$_1$-C$_6$)alkyl- which is unsubstituted, preferably —(C$_1$-C$_2$)alkyl-.

(116) The compound of any one of the above (101) to (106), (110), or (111), wherein U$_2$ is single bond, U$_3$, and U$_4$ are each absent, and U$_1$ is —(C$_2$-C$_6$)alkenyl- which is unsubstituted, preferably —(C$_2$-C$_3$)alkenyl-.

(117) The compound of any one of the above (101) to (106) or (110) to (116), wherein U is —P(=O)(OH)$_2$.

(118) The compound of any one of the above (101) to (106) or (110) to (116), wherein U is —P(=O)(OH)(O—CH$_2$—O—C(O)-phenyl).

(119) The compound of any one of the above (101) to (106) or (110) to (118), wherein A and B are independently —H or —(C$_1$-C$_6$)alkyl and preferably A and B are each —H or A is —H and B is —CH$_3$.

(120) The compound of any one of the above (101) to (106) or (110) to (118), wherein A and B together form a bridge such that the bridged-piperidine is:

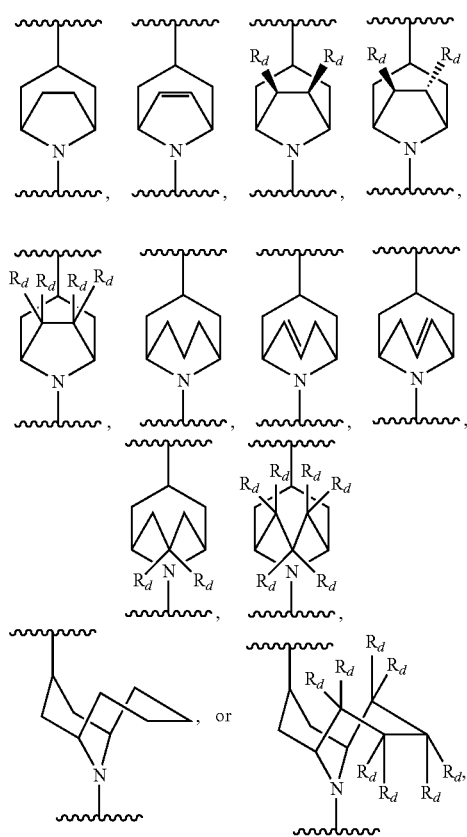

wherein each R$_d$ is independently —H, —(C$_1$-C$_4$)alkyl, -halo, or —C(halo)$_3$.

(121) The compound of any one of the above (101) to (106), (110) to (118), or (120), wherein A and B together form a bridge such that the bridged-piperidine is:

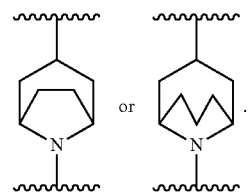

(122) The compound of any one of the above (101) to (118), (120), or (121), wherein the 6-membered, nitrogen-containing ring that is fused to the Q group is in the endo configuration with respect to the A-B bridge of the bridged-piperidine.

(123) The compound of any one of the above (101) to (106) or (110) to (122), wherein h is 0 and R$_1$ is —(C$_1$-C$_{10}$)alkyl, —(C$_2$-C$_{10}$)alkenyl, —(C$_2$-C$_{10}$)alkynyl, —(C$_3$-C$_{14}$)cycloalkyl, —(C$_3$-C$_{14}$)cycloalkenyl, —(C$_6$-C$_{14}$)bicycloalkyl, —(C$_7$-C$_{14}$)bicycloalkenyl, or —(C$_8$-C$_{20}$)tricycloalkyl, each of which is unsubstituted or substituted with 1, 2, 3, or 4 independently selected R$_8$ groups and preferably R$_1$ is —(C$_3$-C$_{14}$)cycloalkyl, —(C$_3$-C$_{14}$)cycloalkenyl, —(C$_6$-C$_{14}$)bicycloalkyl, —(C$_7$-C$_{14}$)bicycloalkenyl, or —(C$_8$-C$_{20}$)tricycloalkyl, each of which is unsubstituted or substituted with 1, 2, 3, or 4 independently selected R$_8$ groups.

(124) The compound of any one of the above (101) to (106) or (110) to (123), wherein h is 0 and R$_1$ is:

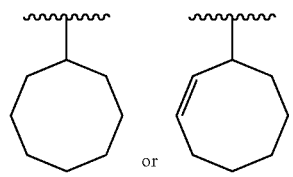

(125) The compound of any one of the above (101) to (106) or (110) to (123), wherein —Z—R$_1$ is:

-continued

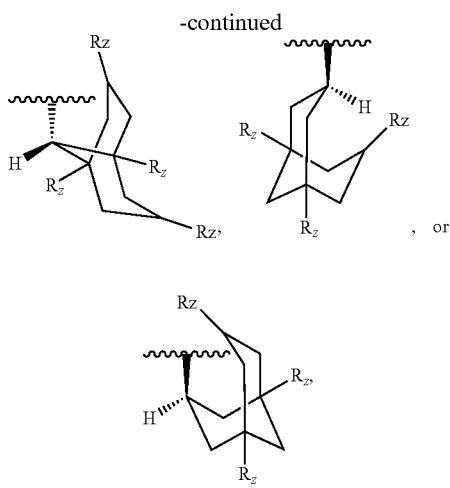

wherein each $R_z$ is independently —H, —$(C_1-C_4)$alkyl, —OH, or —CN and preferably each $R_z$ is independently —H or —$CH_3$.

(126) The compound of any one of the above (101) to (106), (110) to (123), or (125), wherein h is 0 and $R_1$ is:

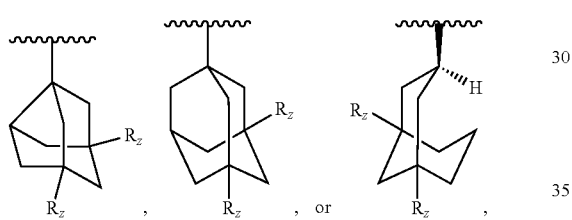

wherein each $R_z$ is independently —H, —$(C_1-C_4)$alkyl, —OH, or —CN and preferably each $R_z$ is independently —H or —$CH_3$.

(127) The compound of any one of the above (101) to (106), (110) to (123), (125), or (126), wherein h is 0 and $R_1$ is:

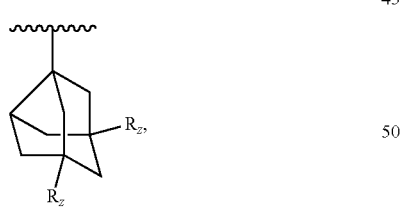

wherein each $R_z$ is —H.

(128) The compound of any one of the above (101) to (105) or (110) to (127), wherein a is 1 and $R_2$ is -halo, preferably $R_2$ is —F.

(129) The compound of any one of the above (101) to (106), (109) to (118), (120) to (123), or (126) to (128), wherein the $R_1$ group is in the exo-configuration with respect to the A-B bridge of the bridged piperidine.

(130) The compound of any one of the above (101) to (106) or (110) to (123), wherein —$R_1$ is:
  (a) $(C_6-C_{12})$cycloalkyl, and preferably —$R_1$ is cyclooctyl, cyclononyl, cyclodecyl, cycloundecyl, or cyclododecyl; or
  (b) $(C_5-C_{12})$cycloalkenyl, and preferably —$R_1$ is cyclohexenyl, cycloheptenyl, or cyclooctenyl; or
  (c)

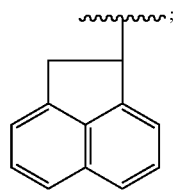 [SMILES: *C1Cc2cccc3cccc1c23]

(d) $(C_6-C_{12})$cycloalkyl optionally substituted by one —$(C_1-C_4)$alkyl.

(131) The compound of any one of the above (101) to (106), (110), or (120) to (123), wherein the compound is:

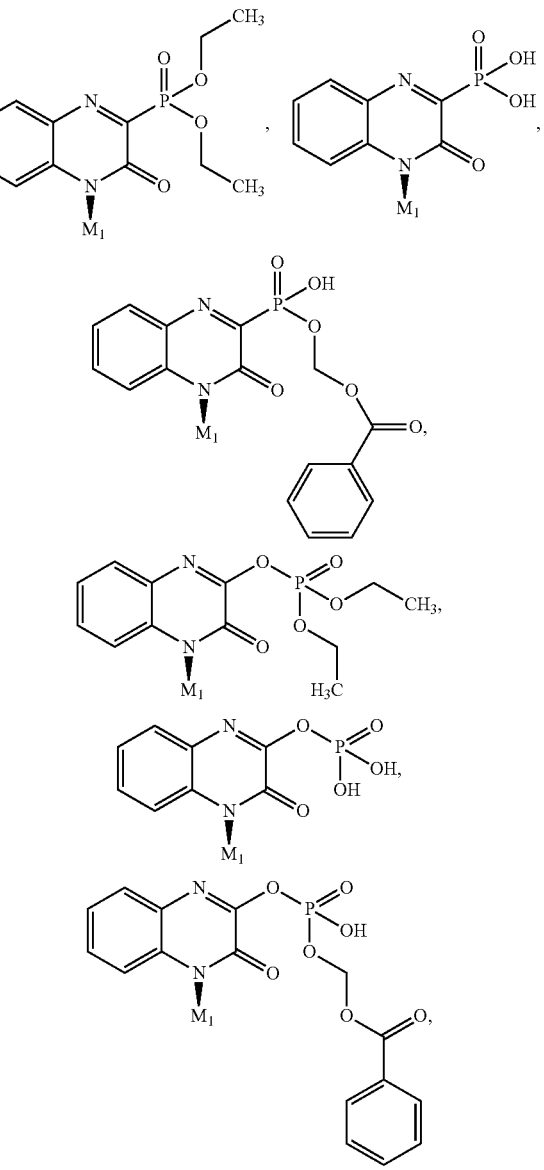

-continued
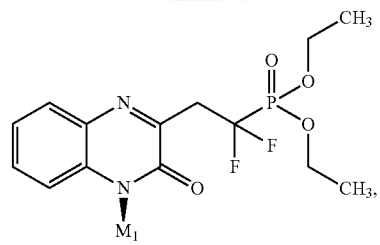
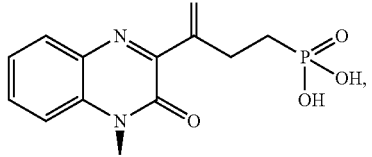
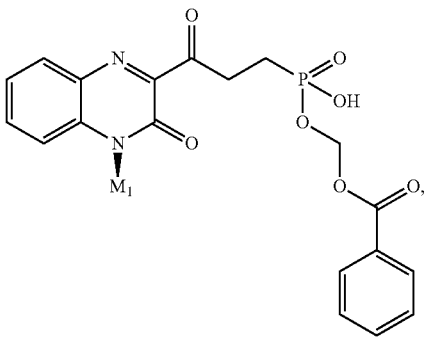
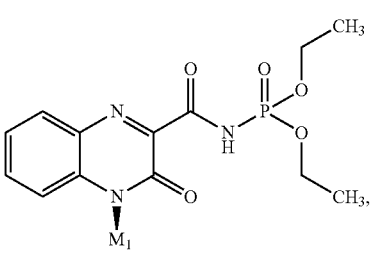
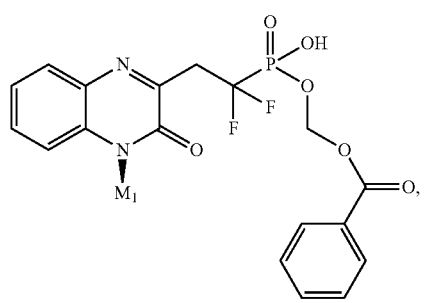
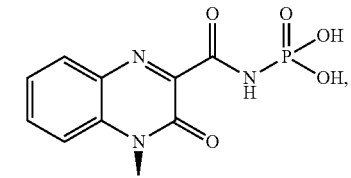
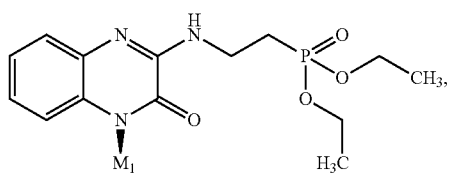
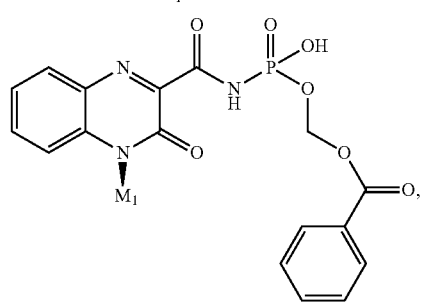
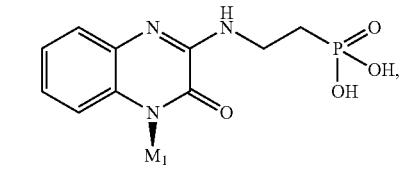
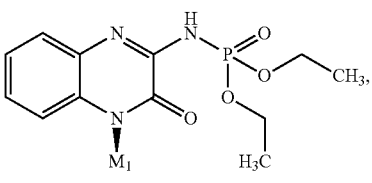
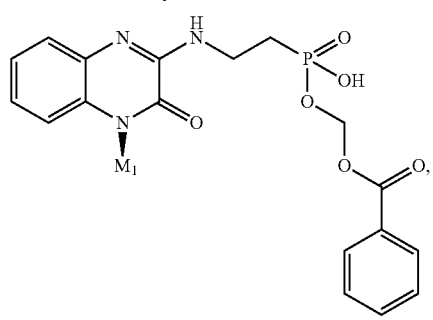
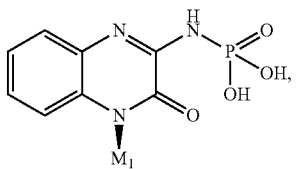
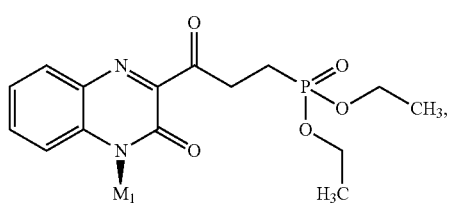

57
-continued
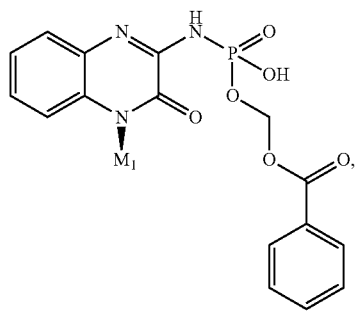
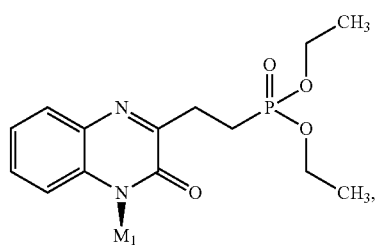
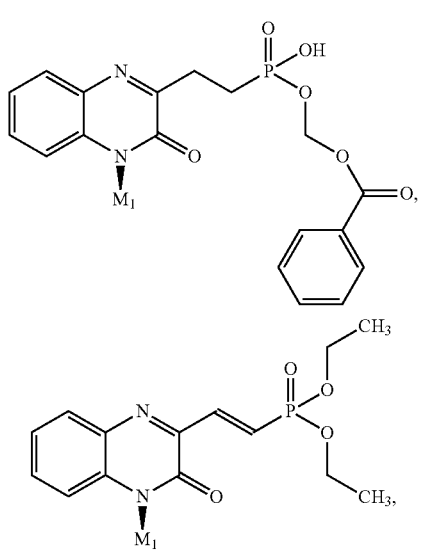
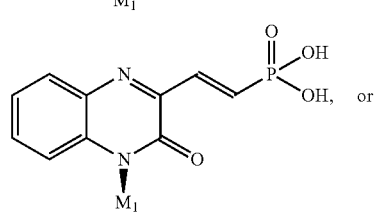
58
-continued
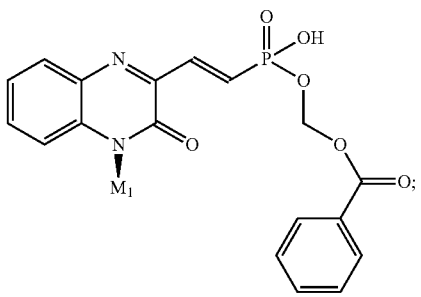
wherein M₁ is:
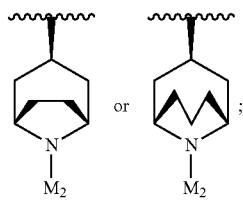
M₂ is:
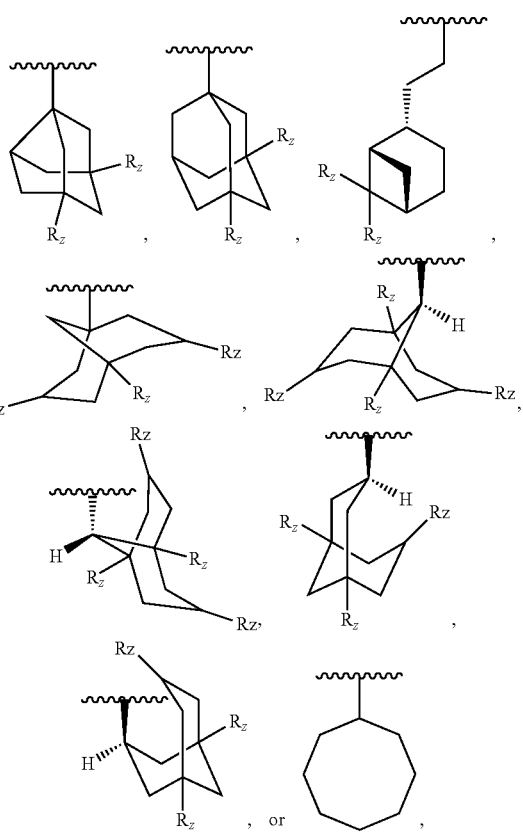
each $R_z$ is independently —H or —CH₃.
(132) The compound of any one of the above (101) to (106), (110), or (120) to (123), wherein the compound is:

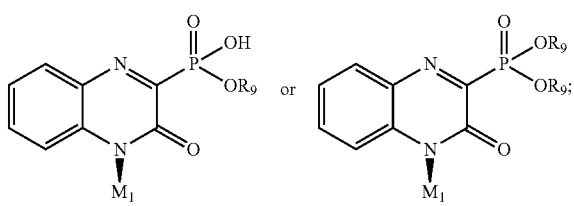

wherein each $R_9$ is independently —H, —$(C_1$-$C_6)$alkyl, —$(C_2$-$C_6)$alkenyl, -phenyl, -benzyl, or —$CH_2$—O—C(O)-phenyl;

$M_1$ is:

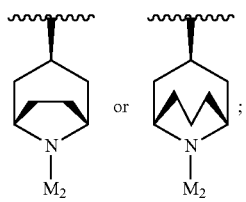

and $M_2$ is:

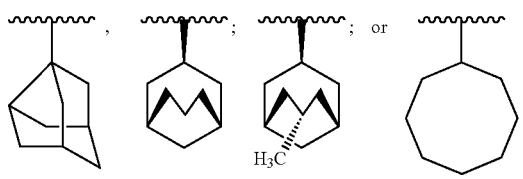

(133) The compound of any one of the above (101) to (106) or (110) to (132), wherein the pharmaceutically acceptable derivative is a pharmaceutically acceptable salt, radiolabeled form, stereoisomer, geometric isomer, or tautomer.

(134) The compound of any one of the above (101) to (106) or (110) to (133), wherein the pharmaceutically acceptable derivative is a pharmaceutically acceptable salt.

(135) The compound of any one of the above (101) to (134), wherein the pharmaceutically acceptable derivative is a hydrochloride-salt, a sodium-salt, a potassium-salt, or a para-toluenesulfonic acid-salt.

(136) A composition comprising an effective amount of the compound or a pharmaceutically acceptable derivative of the compound of any one of the above (101) to (135) and a pharmaceutically acceptable carrier or excipient.

(137) A method for preparing a composition, comprising the step of admixing a compound or a pharmaceutically acceptable derivative of the compound of any one of the above (101) to (135) and a pharmaceutically acceptable carrier or excipient.

(138) A method for modulating ORL-1 receptor function in a cell, comprising contacting a cell capable of expressing the ORL-1 receptor with an effective amount of the composition or the compound or a pharmaceutically acceptable derivative of the compound of any one of the above (101) to (136).

(139) The method of the above (138), wherein the composition or the compound or the pharmaceutically acceptable derivative of the compound acts as an agonist at the ORL-1 receptor.

(140) The method of the above (138), wherein the composition or the compound or the pharmaceutically acceptable derivative of the compound acts as a partial agonist at the ORL-1 receptor.

(141) The method of the above (138), wherein the composition or the compound or the pharmaceutically acceptable derivative of the compound acts as an antagonist at the ORL-1 receptor.

(142) A method for treating pain in an animal, comprising administering to an animal in need thereof an effective amount of the composition or the compound or a pharmaceutically acceptable derivative of the compound of any one of the above (101) to (136).

(143) A method for treating a memory disorder, obesity, constipation, depression, dementia, Parkinsonism, anxiety, cough, diarrhea, high blood pressure, epilepsy, anorexia/cachexia, urinary incontinence, or drug abuse in an animal, comprising administering to an animal in need thereof an effective amount of the composition or the compound or a pharmaceutically acceptable derivative of the compound of any one of the above (101) to (136).

(144) Use of a compound or the pharmaceutically acceptable derivative of the compound of any one of the above (101) to (135) for the manufacture of a medicament useful for treating pain, a memory disorder, obesity, constipation, depression, dementia, Parkinsonism, anxiety, cough, diarrhea, high blood pressure, epilepsy, anorexia/cachexia, urinary incontinence, or drug abuse.

(145) The compound or the pharmaceutically acceptable derivative of the compound of any one of the above (101) to (135) for use in the treatment of pain, a memory disorder, obesity, constipation, depression, dementia, Parkinsonism, anxiety, cough, diarrhea, high blood pressure, epilepsy, anorexia/cachexia, urinary incontinence, or drug abuse.

(146) A kit, comprising a container containing an effective amount of the composition or the compound or a pharmaceutically acceptable derivative of the compound of any one of the above (101) to (136).

4.1 Phosphorus-Substituted Quinoxaline-Type Piperidine Compounds of Formula (I)

As stated above, the disclosure encompasses Phosphorus-Substituted Quinoxaline-Type Piperidine Compounds of Formula (I):

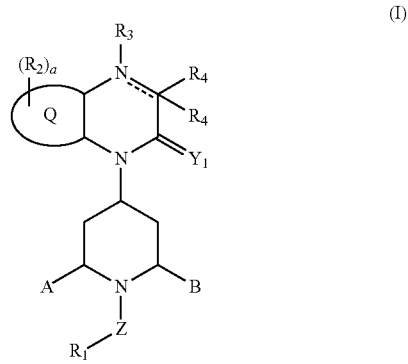

or a pharmaceutically acceptable derivative thereof where $R_1$, $R_2$, $R_3$, $R_4$, Q, $Y_1$, Z, A, B, a, and the dashed line are defined above for the Phosphorus-Substituted Quinoxaline-Type Piperidine Compounds.

In one embodiment, the dashed line in the 6-membered, nitrogen-containing ring that is fused to the Q group is present as a bond to provide one bond of a double bond and $R_3$ and one of the two $R_4$ groups are absent, i.e.:

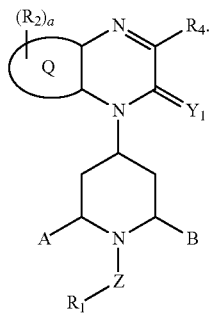

In another embodiment, the dashed line in the 6-membered, nitrogen-containing ring that is fused to the Q group is present as a bond to provide one bond of a double bond, $R_3$ is present, and one of the two $R_4$ groups is absent, i.e.:

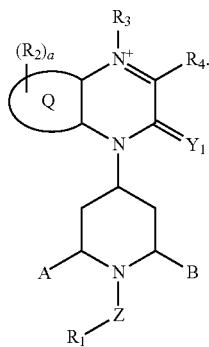

For example, $R_3$ can be an alkyl, e.g., methyl, of the quaternized nitrogen or the hydrogen of a hydrochloride salt.

In another embodiment, the dashed line in the 6-membered, nitrogen-containing ring that is fused to the Q group is absent so there is a single bond between the ring-carbon to which the $R_4$ groups are attached and the adjacent ring-nitrogen and $R_3$ is present, i.e.:

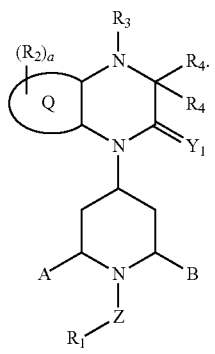

In another embodiment, $Y_1$ is O. In another embodiment, $Y_1$ is S.

In another embodiment, A and B are independently selected from:

(a) —H, —CN, —C(=O)OT$_3$, and —C(=O)N(T$_1$)(T$_2$); and (b) —(C$_3$-C$_{12}$)cycloalkyl, —(C$_3$-C$_{12}$)cycloalkoxy, —(C$_1$-C$_6$)alkyl, —(C$_2$-C$_6$)alkenyl, —(C$_2$-C$_6$)alkynyl, and —(C$_1$-C$_6$)alkoxy, each of which is unsubstituted or substituted with:

(1') 1 or 2 substituents independently selected from —OH, —S(=O)$_2$NH$_2$, —N(R$_6$)$_2$, =NR$_6$, —C(=O)OT$_3$, —C(=O)N(R$_6$)$_2$, —N(R$_6$)C(=O)R$_9$, and -(5- or 6-membered)heterocycle, or (2') 1, 2, or 3 independently selected -halo; or (c) A-B can together form a (C$_2$-C$_6$)bridge, which is unsubstituted or substituted with 1, 2, 3, 4, 5, 6, 7, or 8 substituents independently selected from —OH, —(C$_1$-C$_4$)alkyl, -halo, and —C(halo)$_3$, and which bridge optionally contains —HC=CH— or —O— within the (C$_2$-C$_6$)bridge, wherein the 6-membered, nitrogen-containing ring that is fused to the Q group can be in the endo- or exo-configuration with respect to the A-B bridge.

In another embodiment, A is H. In another embodiment, B is H. In another embodiment, A is H and B is H.

In another embodiment, a is 0 or 1. In another embodiment, a is 0. In another embodiment, a is 1. In another embodiment, a is 2.

In another embodiment, h is 0. In another embodiment, h is 1.

In another embodiment, h is 1 and Z is a —(C$_1$-C$_3$)alkyl-. In another embodiment, h is 1 and Z is —CH$_2$—. In another embodiment, h is 1 and Z is —CH$_2$—CH$_2$—. In another embodiment, h is 1 and Z is —CH$_2$—CH$_2$—CH$_2$—. In another embodiment, h is 1, Z is a —(C$_1$-C$_3$)alkyl-, R$_1$ is phenyl, and the Z group (i.e., —(C$_1$-C$_3$)alkyl-) is substituted by a second independently selected R$_1$ group. In another embodiment, h is 1, Z is a —(C$_1$-C$_3$)alkyl-, R$_1$ is optionally-substituted phenyl, and the Z group (i.e., —(C$_1$-C$_3$)alkyl-) is substituted by a second independently selected R$_1$ group which is optionally-substituted phenyl. In another embodiment, h is 1, Z is a —(C$_1$-C$_3$)alkyl-, R$_1$ is phenyl, and the Z group (i.e., —(C$_1$-C$_3$)alkyl-) is substituted by a second independently selected R$_1$ group which is phenyl. In another embodiment, h is 1, Z is a —(C$_1$-C$_3$)alkyl-, and the Z group is substituted by a second independently selected R$_1$ group which is —CF$_3$. In another embodiment, h is 1 and Z-(second independently selected R$_1$ group) is —CH$_2$—CH(CF$_3$)—CH$_2$—.

In another embodiment, R$_1$ is —(C$_1$-C$_6$)alkyl, —(C$_2$-C$_6$)alkenyl, —(C$_2$-C$_6$)alkynyl, —O(C$_1$-C$_6$)alkyl, —(C$_3$-C$_7$)cycloalkoxy, —(C$_6$-C$_{14}$)bicycloalkyl, —(C$_9$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, or -(7- to 10-membered)bicycloheterocycle, each of which is unsubstituted or substituted with 1, 2, 3, or 4 independently selected R$_8$ groups.

In another embodiment, Z is a —(C$_2$-C$_{10}$)alkenyl-. In another embodiment, Z is a —(C$_2$-C$_6$)alkenyl-. In another embodiment, Z is —CH$_2$—CH=CH—. In another embodiment, Z is —CH$_2$—CH=CH—CH$_2$—. In another embodiment, Z is a —(C$_3$)alkenyl-. In another embodiment, Z is n-prop-1,3-diyl and R$_1$ is optionally substituted —(C$_6$-C$_{14}$)bicycloalkyl or optionally substituted —(C$_8$-C$_{20}$)tricycloalkyl. In another embodiment, Z—R$_1$ is —CH$_2$—CH=CH—R$_1$. In another embodiment, Z—R$_1$ is 3-R$_1$ idenepropyl- where R$_1$ is —(C$_6$-C$_{14}$)bicycloalkyl or —(C$_8$-C$_{20}$)tricycloalkyl, each of which is optionally substituted. In another embodiment, h is 1, and Z—R$_1$ is

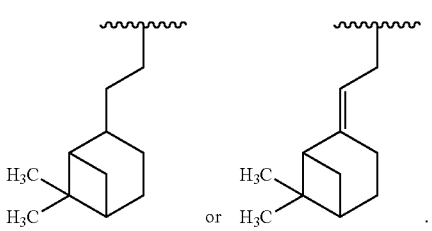 [SMILES: *CCC1CCC2CC1C2(C)C ; *C/C=C1\CCC2CC1C2(C)C]

In another embodiment, Z is —CH$_2$—NH—C(=O)—. Z is —CH$_2$—CH$_2$—NH—C(=O)—. In another embodiment, Z is —CH$_2$—NH—C(=S)—. Z is —CH$_2$—CH$_2$—NH—C(=S)—. In another embodiment, Z is —CH$_2$—N(CH$_3$)—C(=O)—. Z is —CH$_2$—CH$_2$—N(CH$_3$)—C(=O)—. In another embodiment, Z is —CH$_2$—N(CH$_3$)—C(=S)—. Z is —CH$_2$—CH$_2$—N(CH$_3$)—C(=S)—.

In another embodiment, each R$_1$ is independently selected from:

(a) -halo, —CN, —OH, —CH$_2$OH, —CH$_2$CH$_2$OH, —NO$_2$, —N(R$_6$)$_2$, —S(=O)NH$_2$, —S(=O)$_2$NH$_2$, —C(=O)OV$_1$, and —C(=O)CN; and (b) —(C$_1$-C$_{10}$)alkyl, —(C$_2$-C$_{10}$)alkenyl, —(C$_2$-C$_{10}$)alkynyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, and -(7- to 10-membered)bicycloheterocycle, each of which is unsubstituted or substituted with 1, 2, 3, or 4 independently selected R$_8$ groups; and (c)

and (d) -phenyl, -naphthalenyl, —(C$_{14}$)aryl, and -(5- to 10-membered)heteroaryl, each of which is unsubstituted or substituted with a R$_7$ group.

In another embodiment, each R$_1$ is independently selected from:

(a) -halo, —CN, —OH, —CH$_2$OH, —CH$_2$CH$_2$OH, —NO$_2$, —N(R$_6$)$_2$, —S(=O)NH$_2$, —S(=O)$_2$NH$_2$, —C(=O)OV$_1$, and —C(=O)CN; and (b) —(C$_1$-C$_{10}$)alkyl, —O(C$_1$-C$_6$)alkyl, —(C$_3$-C$_7$)cycloalkoxy, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(3- to 7-membered)heterocycle, and -(7- to 10-membered)bicycloheterocycle, each of which is unsubstituted or substituted with 1, 2, or 3 independently selected R$_8$ groups; and (c)

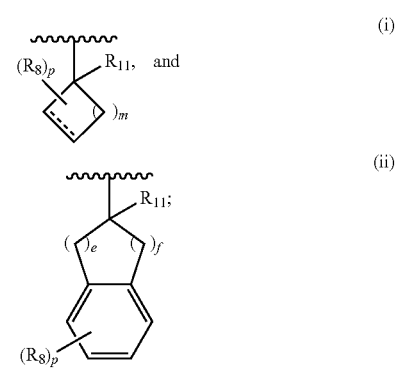

and (d) -phenyl, -naphthalenyl, —(C$_{14}$)aryl, and -(5- to 10-membered)heteroaryl, each of which is unsubstituted or substituted with a R$_7$ group.

In another embodiment, each m is independently 1, 2, 3, 4, 5, 6, 7, 8, or 9. In another embodiment, each m is independently 2, 3, 4, 5, 6, or 7. In another embodiment, each m is independently 2, 3, 4, 5, 6, or 7. In another embodiment, each m is independently 2, 3, 4, 5, or 6. In another embodiment, each m is independently 2, 3, 4, or 5. In another embodiment, each m is 2. In another embodiment, each m is 3. In another embodiment, each m is 4. In another embodiment, each m is 5.

In another embodiment, e is 1 and f is 1. In another embodiment, e is 1 and f is 2. In another embodiment, e is 2 and f is 1. In another embodiment, e is 2 and f is 2. In another embodiment, each e is 0 and each f is 0. In another embodiment, each e is 0 and each f is 1. In another embodiment, each e is 1 and each f is 0. In another embodiment, each e is 1 and each f is 1. In another embodiment, each e is 1 and each f is 2. In another embodiment, each e is 2 and each f is 1. In another embodiment, each e is 2 and each f is 2.

In another embodiment, j is 0 and k is 1. In another embodiment, j is 1 and k is 0. In another embodiment, j is 1 and k is 1. In another embodiment, j is 1 and k is 2. In another embodiment, j is 2 and k is 1. In another embodiment, j is 2 and k is 2. In another embodiment, each j is 0 and each k is 0. In another embodiment, each j is 0 and each k is 1. In another embodiment, each j is 1 and each k is 0. In another embodiment, each j is 1 and each k is 1. In another embodiment, each j is 1 and each k is 2. In another embodiment, each j is 2 and each k is 1. In another embodiment, each j is 2 and each k is 2.

In another embodiment, R$_1$ is optionally substituted cyclooctyl. In another embodiment, R$_1$ is optionally substituted cyclooctenyl. In another embodiment, R$_1$ is optionally substituted anthryl.

In another embodiment, h is 0 and R$_1$ is optionally substituted cyclooctyl. In another embodiment, h is 0 and R$_1$ is optionally substituted cycloundecyl. In another embodiment, h is 0 and $R_1$ is optionally substituted cyclooctenyl. In another embodiment, h is 0 and $R_1$ is optionally substituted anthryl. In another embodiment, h is 0 and $R_1$ is optionally substituted —$(C_6$-$C_{14})$bicycloalkyl. In another embodiment, h is 0 and $R_1$ is optionally substituted bicyclo[3.3.1]nonyl. In another embodiment, h is 0 and $R_1$ is optionally substituted bicyclo[2.2.1.]hepyl. In another embodiment, h is 0 and $R_1$ is optionally substituted —$(C_8$-$C_{20})$tricycloalkyl. In another embodiment, h is 0 and $R_1$ is optionally substituted adamantyl. In another embodiment, h is 0 and $R_1$ is optionally substituted noradamantyl.

In another embodiment, $Y_1$ is O, A and B are each H, and a is 0 or 1. In another embodiment, $Y_1$ is S, A and B are each H, and a is 0 or 1. In another embodiment, $Y_1$ is O, A and B are each H, and a is 0. In another embodiment, $Y_1$ is S, A and B are each H, and a is 0. In another embodiment, $Y_1$ is O, A and B are each H, and a is 1. In another embodiment, $Y_1$ is S, A and B are each H, and a is 1.

In another embodiment, the dashed line in the 6-membered, nitrogen-containing ring that is fused to the Q group is present as a bond to provide one bond of a double bond and $R_3$ is absent.

In another embodiment, $R_3$ is —H, —$(C_1$-$C_4)$alkyl, or —$(C_3$-$C_7)$cycloalkyl. In another embodiment, $R_3$ is —H. In another embodiment, $R_3$ is —$(C_1$-$C_4)$alkyl. In another embodiment, $R_3$ is methyl, ethyl, n-propyl or iso-propyl, each optionally substituted with one —OH, —$(C_1$-$C_4)$alkoxy, —$N(R_6)_2$, —$C(=O)OR_9$, or —$C(=O)N(R_6)_2$ group. In another embodiment, $R_3$ is —$(C_3$-$C_7)$cycloalkyl. In another embodiment, $R_3$ is cyclopropyl, cyclobutyl, cyclopentyl, cyclohexyl, or cycloheptyl, each optionally substituted with 1 or 2-$CH_3$ groups. In another embodiment, $R_3$ is cyclopentyl, cyclohexyl, or cycloheptyl, each optionally substituted with one —OH, —$(C_1$-$C_4)$alkyl, —$(C_1$-$C_4)$alkoxy, —$N(R_6)_2$, —$C(=O)OR_9$, or —$C(=O)N(R_6)_2$ group.

In another embodiment, each $R_{11}$ is —H. In another embodiment, each $R_{11}$ is not —$C(=O)OH$.

In another embodiment, $Y_1$ is O, A and B are each H, the dashed line in the 6-membered, nitrogen-containing ring that is fused to the Q group is present as a bond to provide one bond of a double bond, $R_3$ is absent, and a is 0 or 1. In another embodiment, $Y_1$ is S, A and B are each H, the dashed line in the 6-membered, nitrogen-containing ring that is fused to the Q group is present as a bond to provide one bond of a double bond, $R_3$ is absent, and a is 0 or 1. In another embodiment, $Y_1$ is O, A and B are each H, the dashed line in the 6-membered, nitrogen-containing ring that is fused to the Q group is present as a bond to provide one bond of a double bond, $R_3$ is absent, and a is 0. In another embodiment, $Y_1$ is S, A and B are each H, the dashed line in the 6-membered, nitrogen-containing ring that is fused to the Q group is present as a bond to provide one bond of a double bond, $R_3$ is absent, and a is 0. In another embodiment, $Y_1$ is O, A and B are each H, the dashed line in the 6-membered, nitrogen-containing ring that is fused to the Q group is present as a bond to provide one bond of a double bond, $R_3$ is absent, and a is 1. In another embodiment, $Y_1$ is S, A and B are each H, the dashed line in the 6-membered, nitrogen-containing ring that is fused to the Q group is present as a bond to provide one bond of a double bond, $R_3$ is absent, and a is 1.

In another embodiment, $Y_1$ is O, A and B are each H, $R_3$ is —H, —$(C_1$-$C_4)$alkyl, or —$(C_3$-$C_7)$cycloalkyl, and a is 0 or 1. In another embodiment, $Y_1$ is S, A and B are each H, $R_3$ is —H, —$(C_1$-$C_4)$alkyl, or —$(C_3$-$C_7)$cycloalkyl, and a is 0 or 1. In another embodiment, $Y_1$ is O, A and B are each H, $R_3$ is —H, —$(C_1$-$C_4)$alkyl, or —$(C_3$-$C_7)$cycloalkyl, and a is 0. In another embodiment, $Y_1$ is S, A and B are each H, $R_3$ is —H, —$(C_1$-$C_4)$alkyl, or —$(C_3$-$C_7)$cycloalkyl, and a is 0. In another embodiment, $Y_1$ is O, A and B are each H, $R_3$ is —H, —$(C_1$-$C_4)$alkyl, or —$(C_3$-$C_7)$cycloalkyl, and a is 1. In another embodiment, $Y_1$ is S, A and B are each H, $R_3$ is —H, —$(C_1$-$C_4)$alkyl, or —$(C_3$-$C_7)$cycloalkyl, and a is 1.

In another embodiment, each $R_2$ is independently -halo, —OH, —$NH_2$, —CN, —$(C_1$-$C_6)$alkyl, —$(C_3$-$C_7)$cycloalkyl, -(5- or 6-membered)heterocycle, -phenyl, -naphthalenyl, or -(5- or 6-membered)heteroaryl.

In another embodiment, a is 1 and $R_2$ is -halo, —OH, —$NH_2$, —CN, —$(C_1$-$C_6)$alkyl, —$(C_3$-$C_7)$cycloalkyl, -(5- or 6-membered)heterocycle, -phenyl, -naphthalenyl, or -(5- or 6-membered)heteroaryl. In another embodiment, a is 1 and $R_2$ is -halo, —OH, —$NH_2$, —CN, methyl, ethyl, n-propyl, iso-propyl, cyclopentyl, cyclohexyl, cycloheptyl, or phenyl. In another embodiment, a is 1 and $R_2$ is -halo. In another embodiment, a is 1 and $R_2$ is —F or —Cl. In another embodiment, a is 1 and $R_2$ is —F. In another embodiment, a is 1 and $R_2$ is —Cl.

In another embodiment, a is 2 and each $R_2$ is independently -halo, —OH, —$NH_2$, —CN, —$(C_1$-$C_6)$alkyl, —$(C_3$-$C_7)$cycloalkyl, -(5- or 6-membered)heterocycle, -phenyl, -naphthalenyl, or -(5- or 6-membered)heteroaryl. In another embodiment, a is 2 and each $R_2$ is independently -halo, —OH, —$NH_2$, —CN, methyl, ethyl, n-propyl, iso-propyl, cyclopentyl, cyclohexyl, cycloheptyl, or phenyl.

In another embodiment, Q is benzo, pyridino, pyrimidino, pyrazino, pyridazino, pyrrolino, imidazolino, pyrazolino, triazolino, furano, oxazolino, isoxazolino, oxadiazolino, thiopheno, thiazolino, isothiazolino, or thiadiazolino. In another embodiment, Q is benzo or pyridino.

In another embodiment, a is 1, Q is benzo or pyridino, and $R_2$ is attached at the position shown below, denoted for purposes of the $R_2$-attachment-position herein as the "6-position", of the benzo or pyridino, e.g., as illustrated below:

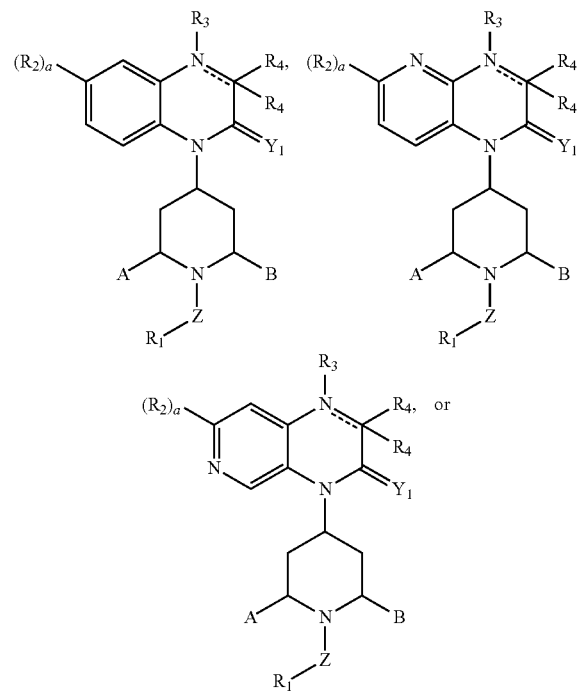

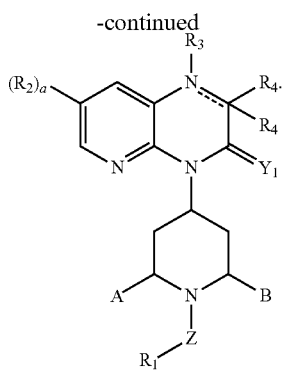

In another embodiment, a is 1, Q is benzo or pyridino, $R_2$ is -halo, and $R_2$ is attached at the 6-position of the benzo or pyridino as illustrated immediately above. In another embodiment, a is 1, Q is benzo or pyridino, $R_2$ is —F, and $R_2$ is attached at the 6-position of the benzo or pyridino as illustrated immediately above.

In another embodiment, Q is benzo. In another embodiment, Q is pyridino. In another embodiment, Q is pyridino and the 2- and 3-positions of the pyridino are fused to the 6-membered, nitrogen-containing ring as illustrated, inter alia, for compounds according to Formula (IB) in Table 1, and the like. In another embodiment, Q is pyridino and the 2- and 3-positions of the pyridino are fused to the 6-membered, nitrogen-containing ring as illustrated, inter alia, for compounds according to Formula (IC) in Table 1, and the like.

In another embodiment, each Y is O. In another embodiment, each Y is S.

In another embodiment, A-B together form a ($C_2$)bridge which bridge is substituted or unsubstituted. In another embodiment, A-B together form a ($C_2$)bridge which bridge is unsubstituted. In another embodiment, A-B together form a ($C_2$)bridge which bridge is substituted by one or two methyl groups. In another embodiment, A-B together form a ($C_3$)bridge which bridge is substituted or unsubstituted. In another embodiment, A-B together form a ($C_3$)bridge which bridge is unsubstituted. In another embodiment, A-B together form a ($C_3$)bridge which bridge is substituted by one or two methyl groups. In another embodiment, A-B together form a ($C_4$)bridge which bridge is substituted or unsubstituted. In another embodiment, A-B together form a ($C_4$)bridge which bridge is unsubstituted. In another embodiment, A-B together form a ($C_4$)bridge which bridge is substituted by one or two methyl groups. In another embodiment, A-B together form a ($C_5$)bridge which bridge is substituted or unsubstituted. In another embodiment, A-B together form a ($C_5$)bridge which bridge is unsubstituted. In another embodiment, A-B together form a ($C_5$)bridge which bridge is substituted by one or two methyl groups. In another embodiment, A-B together form a ($C_6$)bridge which bridge is substituted or unsubstituted. In another embodiment, A-B together form a ($C_6$)bridge which bridge is unsubstituted. In another embodiment, A-B together form a ($C_6$)bridge which bridge is substituted by one or two methyl groups.

In another embodiment, A-B together form a ($C_2$)bridge which bridge is —HC=CH— and is substituted or unsubstituted. In another embodiment, A-B together form a ($C_2$)bridge which bridge is —HC=CH— and is unsubstituted. In another embodiment, A-B together form a ($C_2$)bridge which is —HC=CH— and is substituted by one or two methyl groups. In another embodiment, A-B together form a ($C_3$)bridge which is —CH$_2$—HC=CH— or —HC=CH—CH$_2$— and is substituted or unsubstituted. In another embodiment, A-B together form a ($C_3$)bridge which is —CH$_2$—HC=CH— or —HC=CH—CH$_2$— and is unsubstituted. In another embodiment, A-B together form a ($C_3$)bridge which is —CH$_2$—HC=CH— or —HC=CH—CH$_2$— and is substituted by one or two methyl groups. In another embodiment, A-B together form a ($C_4$)bridge which is —CH$_2$—CH$_2$—HC=CH—, —CH$_2$—HC=CH—CH$_2$—, or —HC=CH—CH$_2$—CH$_2$— and is substituted or unsubstituted. In another embodiment, A-B together form a ($C_4$)bridge which is —CH$_2$—CH$_2$—HC=CH—, —CH$_2$—HC=CH—CH$_2$—, or —HC=CH—CH$_2$—CH$_2$— and is unsubstituted. In another embodiment, A-B together form a ($C_4$)bridge which is —CH$_2$—CH$_2$—HC=CH—, —CH$_2$—HC=CH—CH$_2$—, or —HC=CH—CH$_2$—CH$_2$— and is substituted by one or two methyl groups.

In another embodiment, A-B together form a ($C_2$)bridge which is —CH$_2$—O—CH$_2$— and is substituted or unsubstituted. In another embodiment, A-B together form a ($C_2$)bridge which is —CH$_2$—O—CH$_2$— and is unsubstituted. In another embodiment, A-B together form a ($C_2$)bridge which is —CH$_2$—O—CH$_2$— and is substituted by one or two methyl groups. In another embodiment, A-B together form a ($C_3$)bridge which is —CH$_2$—O—CH$_2$—CH$_2$— or —CH$_2$—CH$_2$—O—CH$_2$— and is substituted or unsubstituted. In another embodiment, A-B together form a ($C_3$)bridge which is —CH$_2$—O—CH$_2$—CH$_2$— or —CH$_2$—CH$_2$—O—CH$_2$— and is unsubstituted. In another embodiment, A-B together form a ($C_3$)bridge which is —CH$_2$—O—CH$_2$—CH$_2$— or —CH$_2$—CH$_2$—O—CH$_2$— and is substituted by one or two methyl groups. In another embodiment, A-B together form a ($C_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is substituted or unsubstituted. In another embodiment, A-B together form a ($C_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is unsubstituted. In another embodiment, A-B together form a ($C_4$)bridge which is —CH$_2$—O—CH$_2$—CH$_2$—CH$_2$—, —CH$_2$—CH$_2$—O—CH$_2$—CH$_2$—, or —CH$_2$—CH$_2$—CH$_2$—O—CH$_2$— and is substituted by one or two methyl groups.

In another embodiment, A-B together form a —CH$_2$—NH—CH$_2$— bridge. In another embodiment, A-B together form a —CH$_2$—N(CH$_3$)—CH$_2$— bridge. In another embodiment, A-B together form a —CH$_2$—N(cyclohexyl)-CH$_2$— bridge. In another embodiment, A-B together form a —CH$_2$—N(CH$_2$—CH$_2$—OH)—CH$_2$-bridge.

In another embodiment, A-B together form a

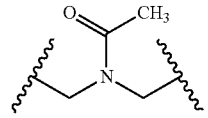 [SMILES: *CN(C*)C(C)=O]

bridge. In another embodiment, A-B together form a

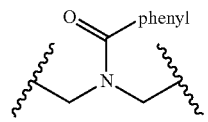

bridge. In another embodiment, A-B together form a

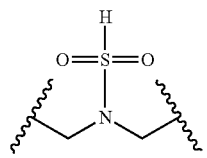 [SMILES: *CN(C*)[SH](=O)=O]

bridge. In another embodiment, A-B together form a

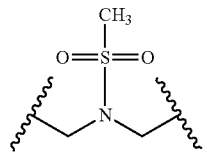

bridge.

In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(OH)(CH$_2$CH$_3$). In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(OCH$_2$CH$_3$)(CH$_2$CH$_3$). In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(O—CH$_2$—O—C(O)-phenyl)(CH$_2$CH$_3$). In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(OH)(CH$_3$). In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(OCH$_2$CH$_3$)(CH$_3$). In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(O—CH$_2$—O—C(O)-phenyl)(CH$_3$). In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(OH)(phenyl). In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(OCH$_2$CH$_3$)(phenyl). In another embodiment, U is —P(=O)(OH)$_2$, —P(=O)(OCH$_2$CH$_3$)$_2$, —P(=O)(OH)(O—CH$_2$—O—C(O)-phenyl), —P(=O)(OH)(O—CH$_2$—O—C(O)—O-phenyl), or —P(=O)(O—CH$_2$—O—C(O)-phenyl)(phenyl).

In another embodiment, U is —P(=O)(OH)$_2$, —P(=O)(OCH$_2$CH$_3$)$_2$, or —P(=O)(OH)(CH$_2$CH$_3$). In another embodiment, U is —P(=O)(OH)$_2$, —P(=O)(OCH$_2$CH$_3$)$_2$, or —P(=O)(OCH$_2$CH$_3$)(CH$_2$CH$_3$). In another embodiment, U is —P(=O)(OH)$_2$, —P(=O)(OCH$_2$CH$_3$)$_2$, or —P(=O)(O—CH$_2$—O—C(O)-phenyl)(CH$_2$CH$_3$). In another embodiment, U is —P(=O)(OH)$_2$, —P(=O)(OCH$_2$CH$_3$)$_2$, or —P(=O)(OH)(CH$_3$). In another embodiment, U is —P(=O)(OH)$_2$, —P(=O)(OCH$_2$CH$_3$)$_2$, or —P(=O)(OCH$_2$CH$_3$)(CH$_3$). In another embodiment, U is —P(=O)(OH)$_2$, —P(=O)(OCH$_2$CH$_3$)$_2$, or —P(=O)(O—CH$_2$—O—C(O)-phenyl)(CH$_3$). In another embodiment, U is —P(=O)(OH)$_2$, —P(=O)(OCH$_2$CH$_3$)$_2$, or —P(=O)(OH)(phenyl). In another embodiment, U is —P(=O)(OH)$_2$, —P(=O)(OCH$_2$CH$_3$)$_2$, or —P(=O)(OCH$_2$CH$_3$)(phenyl). In another embodiment, U is —P(=O)(OH)$_2$, —P(=O)(OCH$_2$CH$_3$)$_2$, or —P(=O)(O—CH$_2$—O—C(O)-phenyl)(phenyl). In another embodiment, U is —P(=O)(OH)$_2$ or —P(=O)(OH)(CH$_2$CH$_3$). In another embodiment, U is —P(=O)(OH)$_2$ or —P(=O)(OCH$_2$CH$_3$)(CH$_2$CH$_3$). In another embodiment, U is —P(=O)(OH)$_2$ or —P(=O)(O—CH$_2$—O—C(O)-phenyl)(CH$_2$CH$_3$). In another embodiment, U is —P(=O)(OH)$_2$ or —P(=O)(OH)(CH$_3$). In another embodiment, U is —P(=O)(OH)$_2$ or —P(=O)(OCH$_2$CH$_3$)(CH$_3$). In another embodiment, U is —P(=O)(OH)$_2$ or —P(=O)(O—CH$_2$—O—C(O)-phenyl)(CH$_3$). In another embodiment, U is —P(=O)(OCH$_2$CH$_3$)$_2$ or —P(=O)(OH)(CH$_2$CH$_3$). In another embodiment, U is —P(=O)(OCH$_2$CH$_3$)$_2$ or —P(=O)(OCH$_2$CH$_3$)(CH$_2$CH$_3$). In another embodiment, U is —P(=O)(OCH$_2$CH$_3$)$_2$ or —P(=O)(O—CH$_2$—O—C(O)-phenyl)(CH$_2$CH$_3$). In another embodiment, U is —P(=O)(OCH$_2$CH$_3$)$_2$ or —P(=O)(OH)(CH$_3$). In another embodiment, U is —P(=O)(OCH$_2$CH$_3$)$_2$ or —P(=O)(OCH$_2$CH$_3$)(CH$_3$). In another embodiment, U is —P(=O)(OCH$_2$CH$_3$)$_2$ or —P(=O)(O—CH$_2$—O—C(O)-phenyl)(CH$_3$).

In another embodiment, U is —P(=O)(OR)(R$_9$). In another embodiment, U is —P(=O)(OH)(R$_9$). In another embodiment, U is —P(=O)(OCH$_2$CH$_3$)(R$_9$). In another embodiment, U is —P(=O)(O—CH$_2$—O—C(O)-phenyl)(R$_9$). In another embodiment, U is —P(=O)(O—CH$_2$—O—C(O)—O-phenyl)(R$_9$). In another embodiment, U is —P(=O)(OR$_9$)(R$_9$). In another embodiment, U is —P(=O)(OR$_9$)((C$_1$-C$_6$)alkyl). In another embodiment, U is —P(=O)(OR$_9$)((C$_1$-C$_4$)alkyl). In another embodiment, U is —P(=O)(OR$_9$)((C$_1$-C$_3$)alkyl). In another embodiment, U is —P(=O)(OR$_9$)(CH$_2$CH$_3$). In another embodiment, U is —P(=O)(OR$_9$)(CH$_3$). In another embodiment, U is —P(=O)(OR$_9$)(phenyl). In another embodiment, U is —P(=O)(OR$_9$)(benzyl). In another embodiment, U is —P(=O)(OH)((C$_1$-C$_6$)alkyl). In another embodiment, U is —P(=O)(OCH$_2$CH$_3$)((C$_1$-C$_6$)alkyl). In another embodiment, U is —P(=O)(O—CH$_2$—O—C(O)-phenyl)((C$_1$-C$_6$)alkyl). In another embodiment, U is —P(=O)(OH)((C$_1$-C$_4$)alkyl). In another embodiment, U is —P(=O)(OCH$_2$CH$_3$)((C$_1$-C$_4$)alkyl). In another embodiment, U is —P(=O)(O—CH$_2$—O—C(O)-phenyl)((C$_1$-C$_4$)alkyl). In another embodiment, U is —P(=O)(OH)((C$_1$-C$_3$)alkyl). In another embodiment, U is —P(=O)(OCH$_2$CH$_3$)((C$_1$-C$_3$)alkyl). In another embodiment, U is —P(=O)(O—CH$_2$—O—C(O)-phenyl)((C$_1$-C$_3$)alkyl). In another embodiment, U is —P(=O)(OH)(CH$_2$CH$_3$). In another embodiment, U is —P(=O)(OCH$_2$CH$_3$)(CH$_2$CH$_3$). In another embodiment, U is —P(=O)(O—CH$_2$—O—C(O)-phenyl)(CH$_2$CH$_3$). In another embodiment, U is —P(=O)(OH)(CH$_3$). In another embodiment, U is —P(=O)(OCH$_2$CH$_3$)(CH$_3$). In another embodiment, U is —P(=O)(O—CH$_2$—O—C(O)-phenyl)(CH$_3$). In another embodiment, U is —P(=O)(OH)(phenyl). In another embodiment, U is —P(=O)(OCH$_2$CH$_3$)(phenyl). In another embodiment, U is —P(=O)(O—CH$_2$—O—C(O)-phenyl)(phenyl). In another embodiment, U is —P(=O)(OH)(benzyl). In another embodiment, U is —P(=O)(OCH$_2$CH$_3$)(benzyl). In another embodiment, U is —P(=O)(O—CH$_2$—O—C(O)-phenyl)(benzyl).

In another embodiment, U is —P(=O)(OR$_9$)$_2$. In another embodiment, U is —P(=O)(OH)$_2$, —P(=O)(OCH$_2$CH$_3$)$_2$, —P(=O)(OH)(O—CH$_2$—O—C(O)-phenyl), or —P(=O)(OH)(O—CH$_2$—O—C(O)—O-phenyl). In another embodiment, U is —P(=O)(OH)$_2$, —P(=O)(OCH$_2$CH$_3$)$_2$, or —P(=O)(OH)(O—CH$_2$—O—C(O)—O-phenyl). In another embodiment, U is —P(=O)(OH)$_2$, —P(=O)(OH)(O—CH$_2$—O—C(O)-phenyl), or —P(=O)(OH)(O—CH$_2$—O—C(O)—O-phenyl). In another embodiment, U is —P(=O)(OCH$_2$CH$_3$)$_2$, —P(=O)(OH)(O—CH$_2$—O—C(O)-phenyl), or —P(=O)(OH)(O—CH$_2$—O—C(O)—O-phenyl). In another embodiment, U is —P(=O)(OH)(O—CH$_2$—O—C(O)-phenyl) or —P(=O)(OH)(O—CH$_2$—O—C(O)—O-phenyl). In another embodiment, U is —P(=O)(OCH$_2$CH$_3$)$_2$ or —P(=O)(OH)(O—CH$_2$—O—C(O)—O-phenyl). In another embodiment, U is —P(=O)(OH)$_2$ or —P(=O)(OH)(O—CH$_2$—O—C(O)-phenyl). In another embodiment, U is —P(=O)(OH)(O—CH$_2$—O—C(O)—O-phenyl). In another embodiment, U is —P(=O)(OH)$_2$, —P(=O)(OCH$_2$CH$_3$)$_2$, or —P(=O)(OH)(O—CH$_2$—O—C(O)-phenyl). In another embodiment, U is —P(=O)(OCH$_2$CH$_3$)$_2$ or —P(=O)(OH)(O—CH$_2$—O—C(O)-phenyl). In another embodiment, U is —P(=O)(OH)$_2$ or —P(=O)(OH)(O—CH$_2$—O—C(O)-phenyl). In another embodiment, U is —P(=O)(OH)$_2$ or —P(=O)(OCH$_2$CH$_3$)$_2$. In another embodiment, U is —P(=O)(OH)$_2$. In another embodiment, U is —P(=O)(OCH$_2$CH$_3$)$_2$. In another embodiment, U is —P(=O)(OH)(O—CH$_2$—O—C(O)-phenyl).

In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is —(C$_1$-C$_6$)alkyl-. In another embodiment, $U_1$ is —(C$_2$-C$_6$)alkenyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is —(C$_2$-C$_6$)alkenyl-, $U_4$ is —Y—, $U_5$ is —(C$_1$-C$_6$)alkyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_2$-C$_6$)alkenyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is —(C$_2$-C$_6$)alkenyl-. In another embodiment, $U_1$ is -cyclohexyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is -cyclohexyl-, $U_4$ is —Y—, $U_5$ is —(C$_1$-C$_6$)alkyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is -cyclohexyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is -cyclohexyl-. In another embodiment, $U_1$ is -phenyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is -phenyl-, $U_4$ is —Y—, $U_5$ is —(C$_1$-C$_6$)alkyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is -phenyl-, $U_6$ is —Y—, and $U_7$ is —(C$_1$-C$_6$)alkyl-. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is -phenyl-.

In another embodiment, $U_1$ is -ethyl-, $U_2$ is —O—, $U_3$ is -ethyl-, $U_4$ is —O—, $U_5$ is -ethyl-, $U_6$ is —O—, and $U_7$ is -ethyl-. In another embodiment, $U_1$ is -vinyl-, $U_2$ is —O—, $U_3$ is -ethyl-, $U_4$ is —O—, $U_5$ is -ethyl-, $U_6$ is —O—, and $U_7$ is -ethyl-. In another embodiment, $U_1$ is -ethyl-, $U_2$ is —O—, $U_3$ is -vinyl-, $U_4$ is —O—, $U_5$ is -ethyl-, $U_6$ is —O—, and $U_7$ is -ethyl-. In another embodiment, $U_1$ is -ethyl-, $U_2$ is —O—, $U_3$ is -ethyl-, $U_4$ is —O—, $U_5$ is -vinyl-, $U_6$ is —O—, and $U_7$ is -ethyl-. In another embodiment, $U_1$ is -ethyl-, $U_2$ is —O—, $U_3$ is -ethyl-, $U_4$ is —O—, $U_5$ is -ethyl-, $U_6$ is —O—, and $U_7$ is -vinyl-. In another embodiment, $U_1$ is -cyclohexyl-, $U_2$ is —O—, $U_3$ is -ethyl-, $U_4$ is —O—, $U_5$ is -ethyl-, $U_6$ is —O—, and $U_7$ is -ethyl-. In another embodiment, $U_1$ is -ethyl-, $U_2$ is —O—, $U_3$ is -cyclohexyl-, $U_4$ is —O—, $U_5$ is -ethyl-, $U_6$ is —O—, and $U_7$ is -ethyl-. In another embodiment, $U_1$ is -ethyl-, $U_2$ is —O—, $U_3$ is -ethyl-, $U_4$ is —O—, $U_5$ is -cyclohexyl-, $U_6$ is —O—, and $U_7$ is -ethyl-. In another embodiment, $U_1$ is -ethyl-, $U_2$ is —O—, $U_3$ is -ethyl-, $U_4$ is —O—, $U_5$ is -ethyl-, $U_6$ is —O—, and $U_7$ is -cyclohexyl-. In another embodiment, $U_1$ is -phenyl-, $U_2$ is —O—, $U_3$ is -ethyl-, $U_4$ is —O—, $U_5$ is -ethyl-, $U_6$ is —O—, and $U_7$ is -ethyl-. In another embodiment, $U_1$ is -ethyl-, $U_2$ is —O—, $U_3$ is -phenyl-, $U_4$ is —O—, $U_5$ is -ethyl-, $U_6$ is —O—, and $U_7$ is -ethyl-. In another embodiment, $U_1$ is -ethyl-, $U_2$ is —O—, $U_3$ is -ethyl-, $U_4$ is —O—, $U_5$ is -phenyl-, $U_6$ is —O—, and $U_7$ is -ethyl-. In another embodiment, $U_1$ is -ethyl-, $U_2$ is —O—, $U_3$ is -ethyl-, $U_4$ is —O—, $U_5$ is -ethyl-, $U_6$ is —O—, and $U_7$ is -phenyl-.

In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is a bond. In another embodiment, $U_1$ is —(C$_2$-C$_6$)alkenyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is a bond. In another embodiment, $U_1$ is —(C$_1$-C$_6$)alkyl-, $U_2$ is —Y—, $U_3$ is —(C$_2$-C$_6$)alkenyl-, $U_4$ is —Y—, $U_5$ is —(C$_1$-C$_6$)alkyl-, $U_6$ is —Y—, and $U_7$ is a bond. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_2$-C$_6$)alkenyl-, $U_6$ is —Y—, and $U_7$ is a bond. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is a bond. In another embodiment, $U_1$ is -cyclohexyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is a bond. In another embodiment, $U_1$ is —(C$_1$-C$_6$)alkyl-, $U_2$ is —Y—, $U_3$ is -cyclohexyl-, $U_4$ is —Y—, $U_5$ is —(C$_1$-C$_6$)alkyl-, $U_6$ is —Y—, and $U_7$ is a bond. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is -cyclohexyl-, $U_6$ is —Y—, and $U_7$ is a bond. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is a bond. In another embodiment, $U_1$ is -phenyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is a bond. In another embodiment, $U_1$ is —(C$_1$-C$_6$)alkyl-, $U_2$ is —Y—, $U_3$ is -phenyl-, $U_4$ is —Y—, $U_5$ is —(C$_1$-C$_6$)alkyl-, $U_6$ is —Y—, and $U_7$ is a bond. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is -phenyl-, $U_6$ is —Y—, and $U_7$ is a bond. In another embodiment, $U_1$ is —(C$_1$-C$_6$)alkyl-, $U_2$ is —Y—, $U_3$ is —(C$_1$-C$_6$)alkyl-, $U_4$ is —Y—, $U_5$ is —(C$_1$-C$_6$)alkyl-, $U_6$ is —Y—, and $U_7$ is a bond.

In another embodiment, $U_1$ is -ethyl-, $U_2$ is —O—, $U_3$ is -ethyl-, $U_4$ is —O—, $U_5$ is -ethyl-, $U_6$ is —O—, and $U_7$ is a bond. In another embodiment, $U_1$ is -vinyl-, $U_2$ is —O—, $U_3$ is -ethyl-, $U_4$ is —O—, $U_5$ is -ethyl-, $U_6$ is —O—, and $U_7$ is a bond. In another embodiment, $U_1$ is -ethyl-, $U_2$ is —O—, $U_3$ is -vinyl-, $U_4$ is —O—, $U_5$ is -ethyl-, $U_6$ is —O—, and $U_7$ is a bond. In another embodiment, $U_1$ is -ethyl-, $U_2$ is —O—, $U_3$ is -ethyl-, $U_4$ is —O—, $U_5$ is -vinyl-, $U_6$ is —O—, and $U_7$ is a bond. In another embodiment, $U_1$ is -ethyl-, $U_2$ is —O—, $U_3$ is -ethyl-, $U_4$ is —O—, $U_5$ is -ethyl-, $U_6$ is —O—, and $U_7$ is a bond. In another embodiment, $U_1$ is -cyclohexyl-, $U_2$ is —O—, $U_3$ is -ethyl-, $U_4$ is —O—, $U_5$ is -ethyl-, $U_6$ is —O—, and $U_7$ is a bond. In another embodiment, $U_1$ is -ethyl-, $U_2$ is —O—, $U_3$ is -cyclohexyl-, $U_4$ is —O—, $U_5$ is -ethyl-, $U_6$ is —O—, and $U_7$ is a bond. In another embodiment, $U_1$ is -ethyl-, $U_2$ is —O—, $U_3$ is -ethyl-, $U_4$ is —O—, $U_5$ is -cyclohexyl-, $U_6$ is —O—, and $U_7$ is a bond. In another embodiment, $U_1$ is -ethyl-, $U_2$ is —O—, $U_3$ is -ethyl-, $U_4$ is —O—, $U_5$ is -ethyl-, $U_6$ is —O—, and $U_7$ is a bond. In another embodiment, $U_1$ is -phenyl-, $U_2$ is —O—, $U_3$ is -ethyl-, $U_4$ is —O—, $U_5$ is -ethyl-, $U_6$ is —O—, and $U_7$ is a bond. In another embodiment, $U_1$ is -ethyl-, $U_2$ is —O—, $U_3$ is -phenyl-, $U_4$ is —O—, $U_5$ is -ethyl-, $U_6$ is —O—, and $U_7$ is a bond. In another embodiment, $U_1$ is -ethyl-, $U_2$ is —O—, $U_3$ is -ethyl-, $U_4$ is —O—, $U_5$ is -phenyl-, $U_6$ is —O—, and $U_7$ is a bond. In another embodiment, $U_1$ is -ethyl-, $U_2$ is —O—, $U_3$ is -ethyl-, $U_4$ is —O—, $U_5$ is -ethyl-, $U_6$ is —O—, and $U_7$ is a bond.

In another embodiment, $U_1$ is —($C_1$-$C_6$)alkyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is —($C_1$-$C_6$)alkyl-. In another embodiment, $U_1$ is —($C_1$-$C_6$)alkyl-, $U_2$ is —C(=Y)—, $U_3$ is a bond, $U_4$ is —N($R_9$)—, $U_5$ is —($C_1$-$C_6$)alkyl-, $U_6$ is —Y—, and $U_7$ is —($C_1$-$C_6$)alkyl-. In another embodiment, $U_1$ is —($C_1$-$C_6$)alkyl-, $U_2$ is —Y—, $U_3$ is —($C_1$-$C_6$)alkyl-, $U_4$ is —N($R_9$)—, $U_5$ is a bond, $U_6$ is —C(=Y)—, and $U_7$ is —($C_1$-$C_6$)alkyl-. In another embodiment, $U_1$ is —($C_1$-$C_6$)alkyl-, $U_2$ is —Y—, $U_3$ is —($C_1$-$C_6$)alkyl-, $U_4$ is —C(=Y)—, $U_5$ is a bond, $U_6$ is —N($R_9$)—, and $U_7$ is —($C_1$-$C_6$)alkyl-. In another embodiment, $U_1$ is —($C_2$-$C_6$)alkenyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is —($C_1$-$C_6$)alkyl-. In another embodiment, $U_1$ is —($C_1$-$C_6$)alkyl-, $U_2$ is —N($R_9$)—, $U_3$ is a bond, $U_4$ is —C(=Y)—, $U_5$ is —($C_2$-$C_6$)alkenyl-, $U_6$ is —Y—, and $U_7$ is —($C_1$-$C_6$)alkyl-. In another embodiment, $U_1$ is —($C_1$-$C_6$)alkyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is —($C_2$-$C_6$)alkenyl-. In another embodiment, $U_1$ is -cyclohexyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is —($C_1$-$C_6$)alkyl-. In another embodiment, $U_1$ is —($C_1$-$C_6$)alkyl-, $U_2$ is —N($R_9$)—, $U_3$ is a bond, $U_4$ is —C(=Y)—, $U_5$ is -cyclohexyl-, $U_6$ is —Y—, and $U_7$ is —($C_1$-$C_6$)alkyl-. In another embodiment, $U_1$ is —($C_1$-$C_6$)alkyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is -cyclohexyl-. In another embodiment, $U_1$ is -phenyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is —($C_1$-$C_6$)alkyl-. In another embodiment, $U_1$ is —($C_1$-$C_6$)alkyl-, $U_2$ is —N($R_9$)—, $U_3$ is a bond, $U_4$ is —C(=Y)—, $U_5$ is -phenyl-, $U_6$ is —Y—, and $U_7$ is —($C_1$-$C_6$)alkyl-. In another embodiment, $U_1$ is —($C_1$-$C_6$)alkyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is -phenyl-. In another embodiment, $U_1$ is —($C_1$-$C_6$)alkyl-, $U_2$ is —C(=Y)—, $U_3$ is a bond, $U_4$ is —N($R_9$)—, $U_5$ is —($C_1$-$C_6$)alkyl-, $U_6$ is —Y—, and $U_7$ is —($C_1$-$C_6$)alkyl-. In another embodiment, $U_1$ is —($C_1$-$C_6$)alkyl-, $U_2$ is —Y—, $U_3$ is —($C_1$-$C_6$)alkyl-, $U_4$ is —N($R_9$)—, $U_5$ is a bond, $U_6$ is —C(=Y)—, and $U_7$ is —($C_1$-$C_6$)alkyl-. In another embodiment, $U_1$ is —($C_1$-$C_6$)alkyl-, $U_2$ is —Y—, $U_3$ is —($C_1$-$C_6$)alkyl-, $U_4$ is —C(=Y)—, $U_5$ is a bond, $U_6$ is —N($R_9$)—, and $U_7$ is —($C_1$-$C_6$)alkyl-.

In another embodiment, $U_1$ is -ethyl-, $U_2$ is —NH—, $U_3$ is a bond, $U_4$ is —C(=O)—, $U_5$ is -ethyl-, $U_6$ is —O—, and $U_7$ is -ethyl-. In another embodiment, $U_1$ is -ethyl-, $U_2$ is —C(=O)—, $U_3$ is a bond, $U_4$ is —NH—, $U_5$ is -ethyl-, $U_6$ is —O—, and $U_7$ is -ethyl-. In another embodiment, $U_1$ is -ethyl-, $U_2$ is —O—, $U_3$ is -ethyl-, $U_4$ is —NH—, $U_5$ is a bond, $U_6$ is —C(=O)—, and $U_7$ is -ethyl-. In another embodiment, $U_1$ is -ethyl-, $U_2$ is —O—, $U_3$ is -ethyl-, $U_4$ is —C(=O)—, $U_5$ is a bond, $U_6$ is —NH—, and $U_7$ is -ethyl-. In another embodiment, $U_1$ is -vinyl-, $U_2$ is —NH—, $U_3$ is a bond, $U_4$ is —C(=O)—, $U_5$ is -ethyl-, $U_6$ is —O—, and $U_7$ is -ethyl-. In another embodiment, $U_1$ is -ethyl-, $U_2$ is —NH—, $U_3$ is a bond, $U_4$ is —C(=O)—, $U_5$ is -vinyl-, $U_6$ is —O—, and $U_7$ is -ethyl-. In another embodiment, $U_1$ is -ethyl-, $U_2$ is —NH—, $U_3$ is a bond, $U_4$ is —C(=O)—, $U_5$ is -ethyl-, $U_6$ is —O—, and $U_7$ is -vinyl-. In another embodiment, $U_1$ is -cyclohexyl-, $U_2$ is —NH—, $U_3$ is a bond, $U_4$ is —C(=O)—, $U_5$ is -ethyl-, $U_6$ is —O—, and $U_7$ is -ethyl-. In another embodiment, $U_1$ is -ethyl-, $U_2$ is —NH—, $U_3$ is a bond, $U_4$ is —C(=O)—, $U_5$ is -cyclohexyl-, $U_6$ is —O—, and $U_7$ is -ethyl-. In another embodiment, $U_1$ is -ethyl-, $U_2$ is —NH—, $U_3$ is a bond, $U_4$ is —C(=O)—, $U_5$ is -ethyl-, $U_6$ is —O—, and $U_7$ is -cyclohexyl-. In another embodiment, $U_1$ is -phenyl-, $U_2$ is —NH—, $U_3$ is a bond, $U_4$ is —C(=O)—, $U_5$ is -ethyl-, $U_6$ is —O—, and $U_7$ is -ethyl-. In another embodiment, $U_1$ is -ethyl-, $U_2$ is —NH—, $U_3$ is a bond, $U_4$ is —C(=O)—, $U_5$ is -phenyl-, $U_6$ is —O—, and $U_7$ is -ethyl-. In another embodiment, $U_1$ is -ethyl-, $U_2$ is —NH—, $U_3$ is a bond, $U_4$ is —C(=O)—, $U_5$ is -ethyl-, $U_6$ is —O—, and $U_7$ is -phenyl-. In another embodiment, $U_1$ is -ethyl-, $U_2$ is —C(=O)—, $U_3$ is a bond, $U_4$ is —NH—, $U_5$ is -ethyl-, $U_6$ is —O—, and $U_7$ is -ethyl-. In another embodiment, $U_1$ is -ethyl-, $U_2$ is —O—, $U_3$ is -ethyl-, $U_4$ is —NH—, $U_5$ is a bond, $U_6$ is —C(=O)—, and $U_7$ is -ethyl-. In another embodiment, $U_1$ is -ethyl-, $U_2$ is —O—, $U_3$ is -ethyl-, $U_4$ is —C(=O)—, $U_5$ is a bond, $U_6$ is —NH—, and $U_7$ is -ethyl-.

In another embodiment, $U_1$ is —($C_1$-$C_6$)alkyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is a bond. In another embodiment, $U_1$ is —($C_1$-$C_6$)alkyl-, $U_2$ is —C(=Y)—, $U_3$ is a bond, $U_4$ is —N($R_9$)—, $U_5$ is —($C_1$-$C_6$)alkyl-, $U_6$ is —Y—, and $U_7$ is a bond. In another embodiment, $U_1$ is —($C_1$-$C_6$)alkyl-, $U_2$ is —Y—, $U_3$ is —($C_1$-$C_6$)alkyl-, $U_4$ is —N($R_9$)—, $U_5$ is a bond, $U_6$ is —C(=Y)—, and $U_7$ is a bond. In another embodiment, $U_1$ is —($C_1$-$C_6$)alkyl-, $U_2$ is —Y—, $U_3$ is —($C_1$-$C_6$)alkyl-, $U_4$ is —C(=Y)—, $U_5$ is a bond, $U_6$ is —N($R_9$)—, and $U_7$ is a bond. In another embodiment, $U_1$ is —($C_2$-$C_6$)alkenyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is a bond. In another embodiment, $U_1$ is —($C_1$-$C_6$)alkyl-, $U_2$ is —N($R_9$)—, $U_3$ is a bond, $U_4$ is —C(=Y)—, $U_5$ is —($C_2$-$C_6$)alkenyl-, $U_6$ is —Y—, and $U_7$ is a bond. In another embodiment, $U_1$ is —($C_1$-$C_6$)alkyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is a bond. In another embodiment, $U_1$ is -cyclohexyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is a bond. In another embodiment, $U_1$ is —($C_1$-$C_6$)alkyl-, $U_2$ is —N($R_9$)—, $U_3$ is a bond, $U_4$ is —C(=Y)—, $U_5$ is -cyclohexyl-, $U_6$ is —Y—, and $U_7$ is a bond. In another embodiment, $U_1$ is —($C_1$-$C_6$)alkyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is a bond. In another embodiment, $U_1$ is -phenyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is a bond. In another embodiment, $U_1$ is —($C_1$-$C_6$)alkyl-, $U_2$ is —N($R_9$)—, $U_3$ is a bond, $U_4$ is —C(=Y)—, $U_5$ is -phenyl-, $U_6$ is —Y—, and $U_7$ is a bond. In another embodiment, $U_1$ is —($C_1$-$C_6$)alkyl-, $U_2$ is —N($R_9$)—, $U_3$ is a bond, $U_4$ is —C(=Y)—, $U_5$ is —($C_1$-$C_6$)alkyl-, $U_6$ is —Y—, and $U_7$ is a bond. In another embodiment, $U_1$ is —($C_1$-$C_6$)alkyl-, $U_2$ is —C(=Y)—, $U_3$ is a bond, $U_4$ is —N($R_9$)—, $U_5$ is —($C_1$-$C_6$)alkyl-, $U_6$ is —Y—, and $U_7$ is a bond. In another embodiment, $U_1$ is —($C_1$-$C_6$)alkyl-, $U_2$ is —Y—, $U_3$ is —($C_1$-$C_6$)alkyl-, $U_4$ is —N($R_9$)—, $U_5$ is a bond, $U_6$ is —C(=Y)—, and $U_7$ is a bond. In another embodiment, $U_1$ is —($C_1$-$C_6$)alkyl-, $U_2$ is —Y—, $U_3$ is —($C_1$-$C_6$)alkyl-, $U_4$ is —C(=Y)—, $U_5$ is a bond, $U_6$ is —N($R_9$)—, and $U_7$ is a bond.

In another embodiment, $U_1$ is -ethyl-, $U_2$ is —NH—, $U_3$ is a bond, $U_4$ is —C(=O)—, $U_5$ is -ethyl-, $U_6$ is —O—, and $U_7$ is a bond. In another embodiment, $U_1$ is -ethyl-, $U_2$ is —C(=O)—, $U_3$ is a bond, $U_4$ is —NH—, $U_5$ is -ethyl-, $U_6$ is —O—, and $U_7$ is a bond. In another embodiment, $U_1$ is -ethyl-, $U_2$ is —O—, $U_3$ is -ethyl-, $U_4$ is —NH—, $U_5$ is a bond, $U_6$ is —C(=O)—, and $U_7$ is a bond. In another embodiment, $U_1$ is -ethyl-, $U_2$ is —O—, $U_3$ is -ethyl-, $U_4$ is —C(=O)—, $U_5$ is a bond, $U_6$ is —NH—, and $U_7$ is a bond. In another embodiment, $U_1$ is -vinyl-, $U_2$ is —NH—, $U_3$ is a bond, $U_4$ is —C(=O)—, $U_5$ is -ethyl-, $U_6$ is —O—, and $U_7$ is a bond. In another embodiment, $U_1$ is -ethyl-, $U_2$ is —NH—, $U_3$ is a bond, $U_4$ is —C(=O)—, $U_5$ is -vinyl-, $U_6$ is —O—, and $U_7$ is a bond. In another embodiment, $U_1$ is -ethyl-, $U_2$ is —NH—, $U_3$ is a bond, $U_4$ is —C(=O)—, $U_5$ is -ethyl-, $U_6$ is —O—, and $U_7$ is a bond. In another embodiment, $U_1$ is -cyclohexyl-, $U_2$ is —NH—, $U_3$ is a bond, $U_4$ is —C(=O)—, $U_5$ is -ethyl-, $U_6$ is —O—, and $U_7$ is a bond. In another embodiment, $U_1$ is -ethyl-, $U_2$ is —NH—, $U_3$ is a bond, $U_4$ is —C(=O)—, $U_5$ is -cyclohexyl-, $U_6$ is —O—, and $U_7$ is a bond. In another embodiment, $U_1$ is -ethyl-, $U_2$ is —NH—, $U_3$ is a bond, $U_4$ is —C(=O)—, $U_5$ is -ethyl-, $U_6$ is —O—, and $U_7$ is a bond. In another embodiment, $U_1$ is -phenyl-, $U_2$ is —NH—, $U_3$ is a bond, $U_4$ is —C(=O)—, $U_5$ is -ethyl-, $U_6$ is —O—, and $U_7$ is a bond. In another embodiment, $U_1$ is -ethyl-, $U_2$ is —NH—, $U_3$ is a bond, $U_4$ is —C(=O)—, $U_5$ is -phenyl-, $U_6$ is —O—, and $U_7$ is a bond. In another embodiment, $U_1$ is -ethyl-, $U_2$ is —NH—, $U_3$ is a bond, $U_4$ is —C(=O)—, $U_5$ is -ethyl-, $U_6$ is —O—, and $U_7$ is a bond. In another embodiment, $U_1$ is -ethyl-, $U_2$ is —C(=O)—, $U_3$ is a bond, $U_4$ is —NH—, $U_5$ is -ethyl-, $U_6$ is —O—, and $U_7$ is a bond. In another embodiment, $U_1$ is -ethyl-, $U_2$ is —O—, $U_3$ is -ethyl-, $U_4$ is —NH—, $U_5$ is a bond, $U_6$ is —C(=O)—, and $U_7$ is a bond. In another embodiment, $U_1$ is -ethyl-, $U_2$ is —O—, $U_3$ is -ethyl-, $U_4$ is —C(=O)—, $U_5$ is a bond, $U_6$ is —NH—, and $U_7$ is a bond.

In another embodiment, each $R_9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_3$-$C_8$)cycloalkenyl, -phenyl, -benzyl, —$CH_2$—O—C(O)-phenyl, —$CH_2$—C(O)—O-phenyl, —C(halo)$_3$, —CH(halo)$_2$, or —$CH_2$(halo) provided that when the x of [O]$_x$$R_9$ is 0, then the $R_9$ of that [O]$_x$$R_9$ is not —H. In another embodiment, each $R_9$ is independently —H, —($C_1$-$C_6$)alkyl, —($C_2$-$C_6$)alkenyl, -phenyl, -benzyl, or —$CH_2$—O—C(O)-phenyl provided that when the x of [O]$_x$$R_9$ is 0, then the $R_9$ of that [O]$_x$$R_9$ is not —H. In another embodiment, each $R_9$ is independently —H, —($C_1$-$C_4$)alkyl, -phenyl, -benzyl, or —$CH_2$—O—C(O)-phenyl provided that when the x of [O]$_x$$R_9$ is 0, then the $R_9$ of that [O]$_x$$R_9$ is not —H. In another embodiment, each $R_9$ is independently —H, —($C_1$-$C_3$)alkyl, -phenyl, -benzyl, or —$CH_2$—O—C(O)-phenyl provided that when the x of [O]$_x$$R_9$ is 0, then the $R_9$ of that [O]$_x$$R_9$ is not —H.

In another embodiment, x is 0.

In another embodiment, x is 1.

In another embodiment, x is 0 and the $R_9$ of the phosphorus substituent comprising that x, i.e., the $R_9$ of ([O]$_x$$R_9$), is —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —$CH_2$—O—C(O)-phenyl, or —$CH_2$—C(O)—O-phenyl. In another embodiment, x is 0 and the $R_9$ of ([O]$_x$$R_9$) is —($C_1$-$C_6$)alkyl, —($C_2$-$C_6$)alkenyl, or —($C_2$-$C_6$)alkynyl. In another embodiment, x is 0 and the $R_9$ of ([O]$_x$$R_9$) is —($C_1$-$C_4$)alkyl. In another embodiment, x is 0 and the $R_9$ of ([O]$_x$$R_9$) is —($C_1$-$C_3$)alkyl. In another embodiment, x is 0 and the $R_9$ of ([O]$_x$$R_9$) is —$CH_3$.

In another embodiment, x is 1 and each $R_9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —$CH_2$—O—C(O)-phenyl, —$CH_2$—C(O)—O-phenyl, —C(halo)$_3$, —CH(halo)$_2$, or —$CH_2$(halo). In another embodiment, x is 1 and each $R_9$ is independently —H, —($C_1$-$C_6$)alkyl, —($C_2$-$C_6$)alkenyl, -phenyl, -benzyl, or —$CH_2$—O—C(O)-phenyl. In another embodiment, x is 1 and each $R_9$ is independently —H, —($C_1$-$C_4$)alkyl, -phenyl, -benzyl, or —$CH_2$—O—C(O)-phenyl. In another embodiment, x is 1 and each $R_9$ is independently —H, —($C_1$-$C_3$)alkyl, -phenyl, -benzyl, or —$CH_2$—O—C(O)-phenyl.

In another embodiment, the pharmaceutically acceptable derivative of a compounds of Formula (I) is a pharmaceutically acceptable salt. In another embodiment, the pharmaceutically acceptable salt is a hydrochloride salt. In another embodiment, the pharmaceutically acceptable salt is a sodium salt. In another embodiment, the pharmaceutically acceptable salt is a potassium salt. In another embodiment, the pharmaceutically acceptable salt is a para-toluenesulfonic acid salt.

In other embodiments, the Phosphorus-Substituted Quinoxaline-Type Piperidine Compound of Formula (I) has one of the formulae of Table 1.

TABLE 1

| Formula | Compound |
|---------|----------|
| IA | ($R_2$)$_a$ quinoxalinone-piperidine structure with $R_4$, Z, $R_1$ |
| IB | ($R_2$)$_a$ pyrido-pyrazinone-piperidine structure with $R_4$, Z, $R_1$ |

TABLE 1-continued

| Formula | Compound |
|---|---|
| IC | |
| ID | |
| ID$_1$† | |
| ID$_2$‡ | |
| IE | |
| IE$_1$† | |
| IE$_2$‡ | |
| IF | |
| IF$_1$† | |
| IF$_2$‡ | |

| Formula | Compound |
|---|---|
| IG | 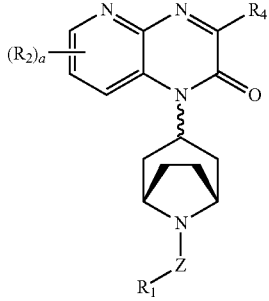 |
| IG₁† | 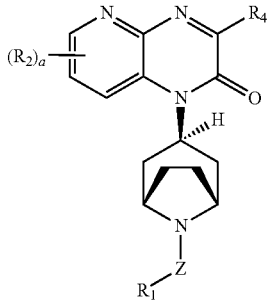 |
| IG₂‡ | 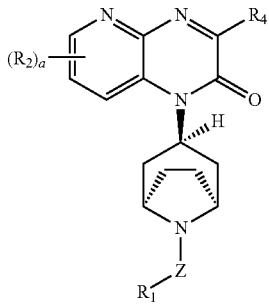 |
| IH | 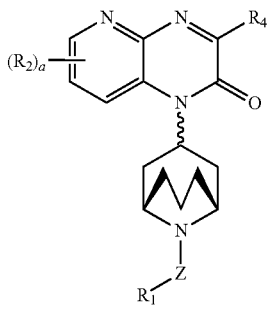 |
| IH₁† | 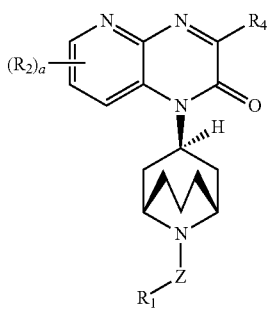 |
| IH₂‡ | 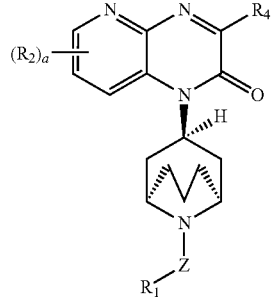 |
| IJ | 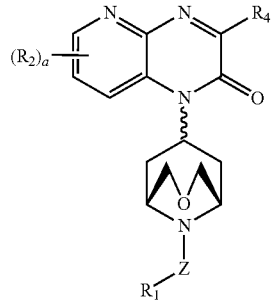 |
| IJ₁† | 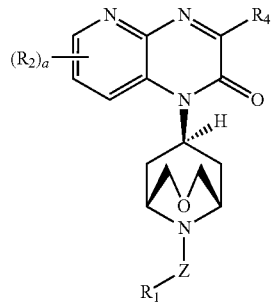 |
| IJ₂‡ | 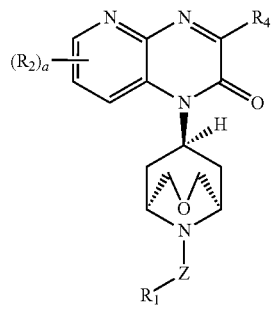 |
| IK | 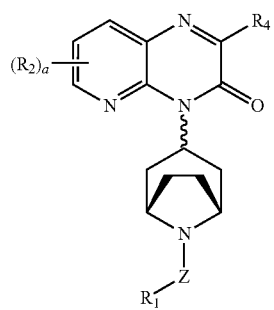 |

TABLE 1-continued

| Formula | Compound |
|---|---|
| IK₁† | (structure) |
| IK₂‡ | (structure) |
| IL | (structure) |
| IL₁† | (structure) |
| IL₂‡ | (structure) |
| IM | (structure) |
| IM₁† | (structure) |
| IM₂‡ | (structure) |
| IN | (structure) |
| IO | (structure) |

TABLE 1-continued

| Formula | Compound |
|---|---|
| IP | |
| IQ | |
| IQ₁† | |
| IQ₂‡ | |
| IR | |
| IR₁† | |
| IR₂‡ | |
| IS | |

TABLE 1-continued
| Formula | Compound |
|---|---|
| IS₁† | 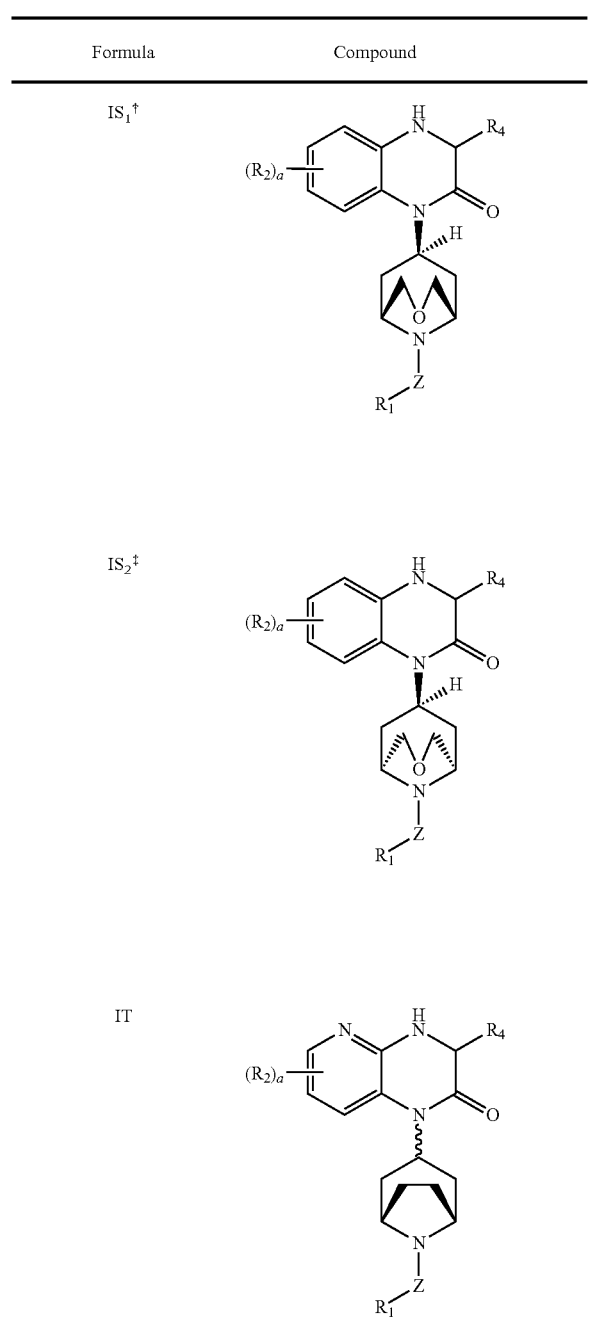 |
| IS₂‡ | |
| IT | |
| IT₁† | |
| IT₂‡ | 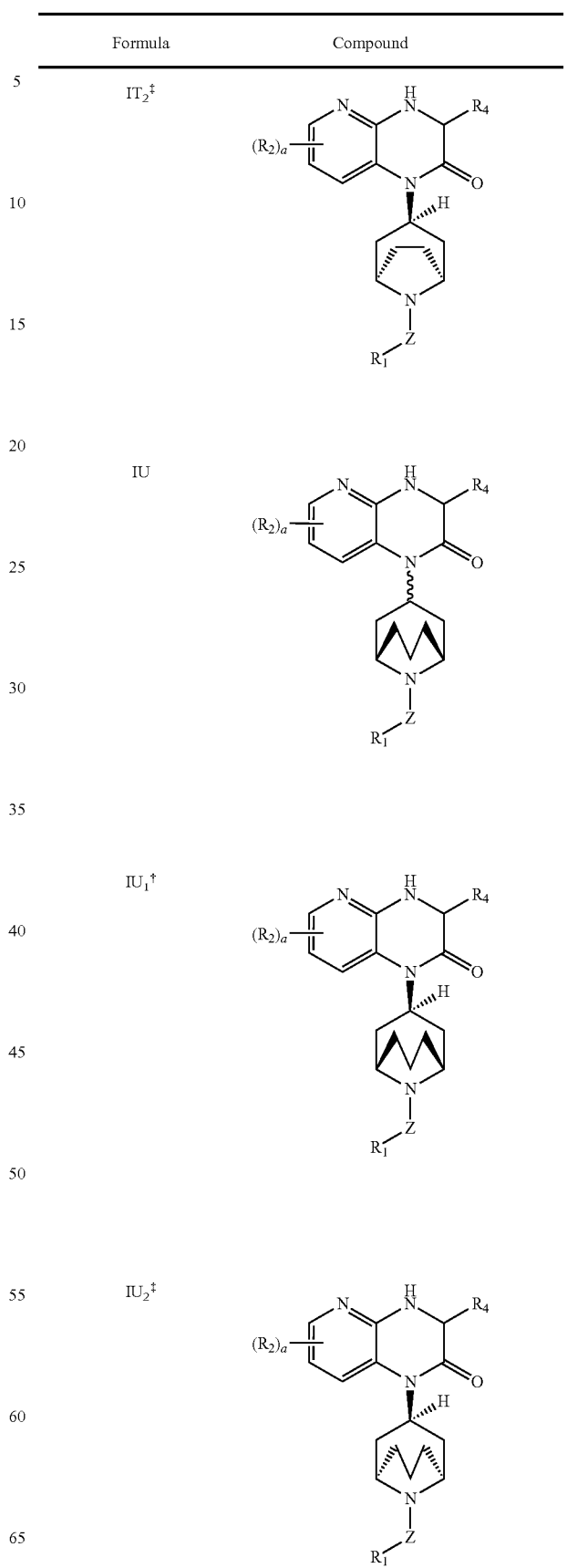 |
| IU | |
| IU₁† | |
| IU₂‡ | |

TABLE 1-continued

| Formula | Compound |
|---|---|
| IV | *(structure)* |
| IV$_1$† | *(structure)* |
| IV$_2$‡ | *(structure)* |
| IW | *(structure)* |
| IW$_1$† | *(structure)* |
| IW$_2$‡ | *(structure)* |
| IX | *(structure)* |
| IX$_1$† | *(structure)* |

TABLE 1-continued

| Formula | Compound |
|---|---|
| IX₂‡ | (structure: pyrido-fused dihydropyrazinone with R₄, (R₂)ₐ, and azabicyclic substituent with N–Z–R₁, exo) |
| IY | (structure: pyrido-fused dihydropyrazinone with R₄, (R₂)ₐ, and oxa-azabicyclic substituent with N–Z–R₁, wavy bond) |
| IY₁† | (structure: pyrido-fused dihydropyrazinone with R₄, (R₂)ₐ, and oxa-azabicyclic substituent with N–Z–R₁, endo) |
| IY₂‡ | (structure: pyrido-fused dihydropyrazinone with R₄, (R₂)ₐ, and oxa-azabicyclic substituent with N–Z–R₁, exo) |

† indicates the 6-membered, nitrogen-containing ring that is fused to the benzo or pyridino is in the endo-configuration with respect to the alkyl or —CH₂—O—CH₂— bridge.

‡ indicates the 6-membered, nitrogen-containing ring that is fused to the benzo or pyridino is in the exo-configuration with respect to the alkyl or —CH₂—O—CH₂— bridge.

where $R_1$, $R_2$, $R_4$, Z, and a are as defined above for the Phosphorus-Substituted Quinoxaline-Type Piperidine Compounds of Formula (I).

In other embodiments, the Phosphorus-Substituted Quinoxaline-Type Piperidine Compound of Formula (I) has one of the structures of Table 2.

TABLE 2

| Compound | Structure |
|---|---|
| AA | (quinoxalinone with diethyl phosphonate, N-linked azabicyclic with N-adamantyl) |
| BB | (quinoxalinone with phosphonic acid P(O)(OH)₂, N-linked azabicyclic with N-adamantyl) |
| CC | (quinoxalinone with diethyl phosphonate, N-linked azabicyclic with N-cyclooctyl) |

TABLE 2-continued
| Compound | Structure |
|---|---|
| DD | 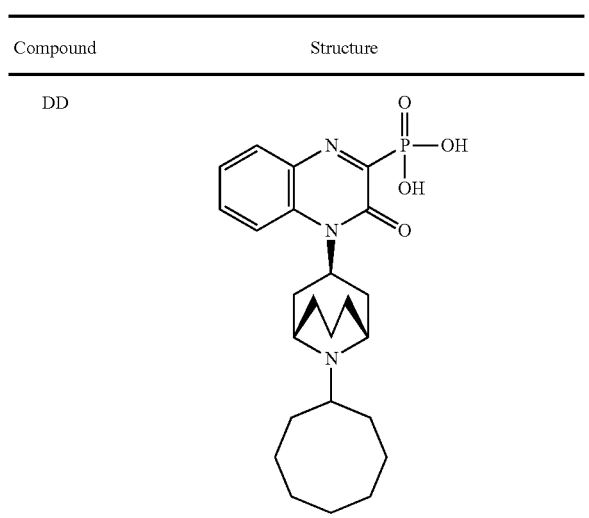 |
| EE | 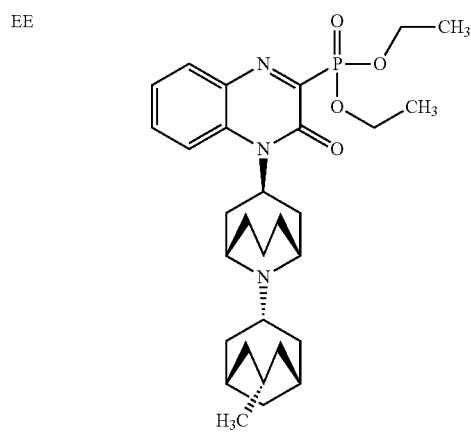 |
| FF | 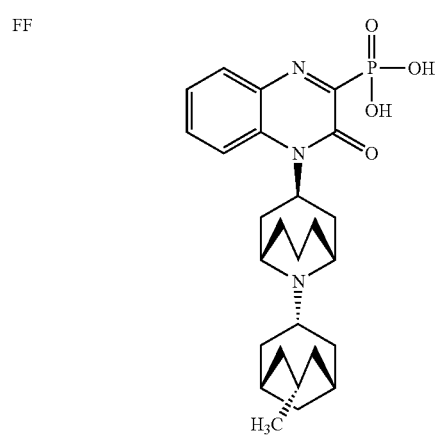 |
| GG | 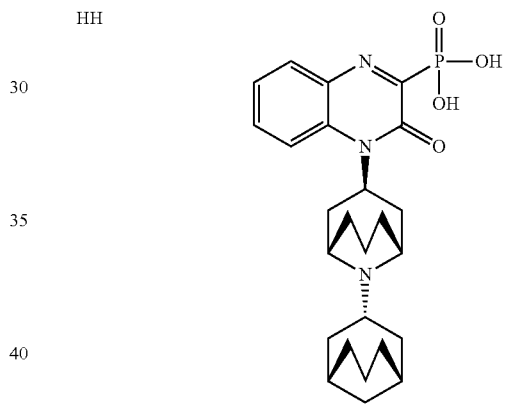 |
| HH | (structure) |
| JJ | 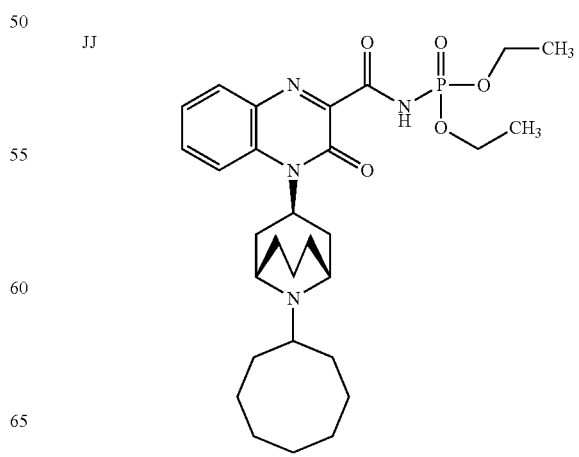 |

TABLE 2-continued
| Compound | Structure |
|---|---|
| KK | 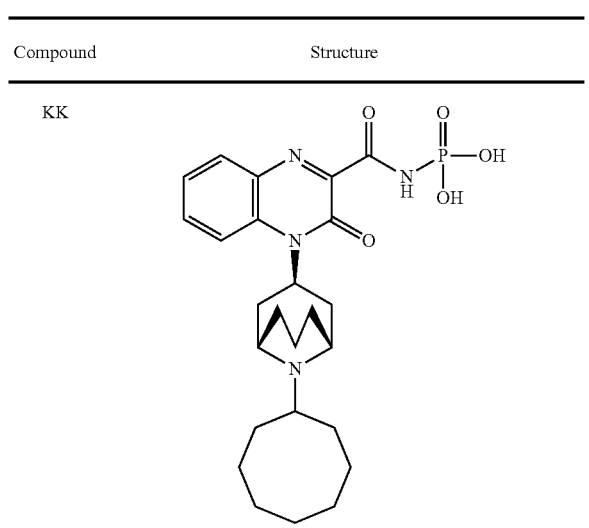 |
| LL | 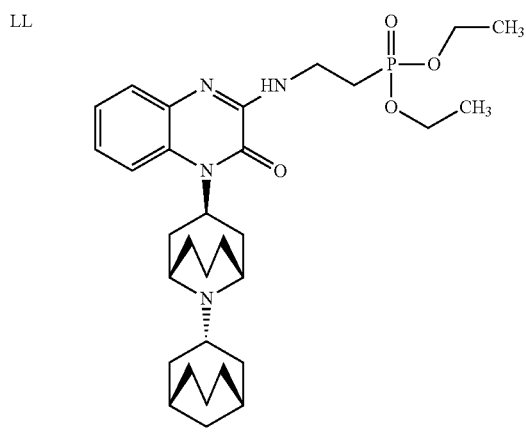 |
| MM | 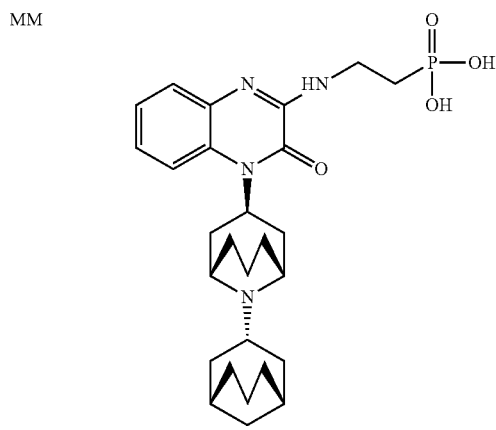 |
| NN | 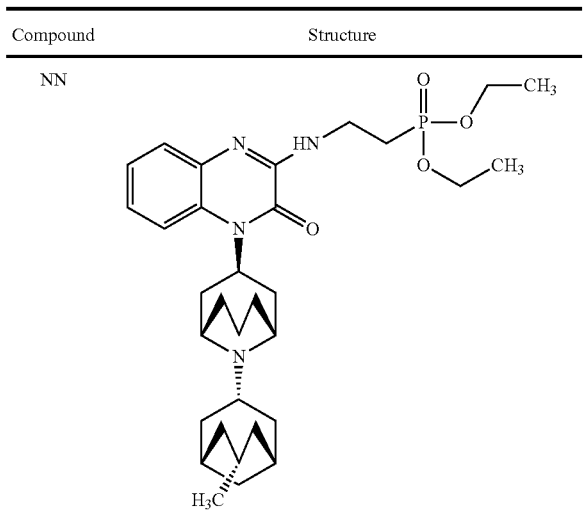 |
| OO | 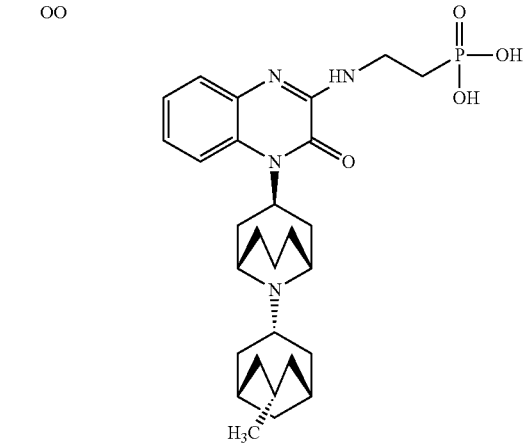 |
| PP | 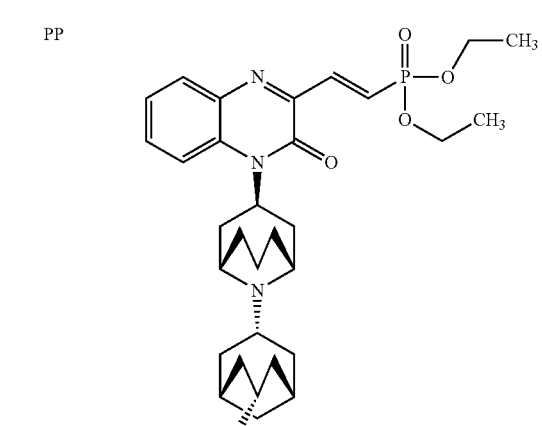 |

TABLE 2-continued

| Compound | Structure |
|---|---|
| QQ | (vinylphosphonic acid quinoxalinone with diazabicyclic-methylbicycloheptyl substituent) |
| RR | (diethyl phosphonate dihydroquinoxalinone with diazabicyclic-methylbicycloheptyl substituent) |
| SS | (diethyl phosphonate ethyl quinoxalinone with diazabicyclic-methylbicycloheptyl substituent) |
| TT | (ethylphosphonic acid quinoxalinone with diazabicyclic-methylbicycloheptyl substituent) |
| UU | (diethyl phosphonate quinoxalinone with diazabicyclic-N-ethyl-dimethylbicycloheptyl substituent) |
| VV | (phosphonic acid quinoxalinone with diazabicyclic-N-ethyl-dimethylbicycloheptyl substituent) |

TABLE 2-continued

| Compound | Structure |
|---|---|
| WW | (structure shown) |
| XX | (structure shown) |

4.2 Definitions

As used in connection with the Phosphorus-Substituted Quinoxaline-Type Piperidine Compounds herein, the terms used herein having following meaning:

"—($C_1$-$C_{10}$)alkyl" means a straight chain or branched non-cyclic hydrocarbon having 1, 2, 3, 4, 5, 6, 7, 8, 9, or 10 carbon atoms. Representative straight chain —($C_1$-$C_{10}$)alkyls include -methyl, -ethyl, -n-propyl, -n-butyl, -n-pentyl, -n-hexyl, -n-heptyl, -n-octyl, -n-nonyl, and -n-decyl. A branched alkyl means that one or more straight chain —($C_1$-$C_8$)alkyl groups, such as methyl, ethyl or propyl, replace one or both hydrogens in a —$CH_2$— group of a straight chain alkyl. A branched non-cyclic hydrocarbon means that one or more straight chain —($C_1$-$C_{10}$)alkyl groups, such as methyl, ethyl or propyl, replace one or both hydrogens in a —$CH_2$— group of a straight chain non-cyclic hydrocarbon. Representative branched —($C_1$-$C_{10}$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1-dimethylbutyl, 1,2-dimethylbutyl, 1,3-dimethylbutyl, 2,2-dimethylbutyl, 2,3-dimethylbutyl, 3,3-dimethylbutyl, 1-methylhexyl, 2-methylhexyl, 3-methylhexyl, 4-methylhexyl, 5-methylhexyl, 1,2-dimethylpentyl, 1,3-dimethylpentyl, 1,2-dimethylhexyl, 1,3-dimethylhexyl, 3,3-dimethylhexyl, 1,2-dimethylheptyl, 1,3-dimethylheptyl, and 3,3-dimethylheptyl.

In connection with a $U_1$, $U_3$, $U_5$, $U_7$, and/or Z group, "—($C_1$-$C_{10}$)alkyl-" means a straight chain or branched non-cyclic hydrocarbon moiety having 1, 2, 3, 4, 5, 6, 7, 8, 9, or 10 carbon atoms where two hydrogen atoms on the same or a different carbon atom of the moiety are each figuratively removed and replaced by a bond to one of the two adjoining groups. Representative —($C_1$-$C_{10}$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, n-deca-1,1-diyl, n-deca-1,2-diyl, n-deca-1,3-diyl, n-deca-1,4-diyl, n-deca-1,5-diyl, n-deca-1,6-diyl, n-deca-1,7-diyl, n-deca-1,8-diyl, n-deca-1,9-diyl, n-deca-1,10-diyl, and the like.

"—($C_1$-$C_6$)alkyl" means a straight chain or branched non-cyclic hydrocarbon having 1, 2, 3, 4, 5, or 6 carbon atoms. Representative straight chain —($C_1$-$C_6$)alkyls include -methyl, -ethyl, -n-propyl, -n-butyl, -n-pentyl, and -n-hexyl. Representative branched —($C_1$-$C_6$)alkyls include -iso-propyl, -sec-butyl, -iso-butyl, -tert-butyl, -iso-pentyl, -neopentyl, 1-methylbutyl, 2-methylbutyl, 3-methylbutyl, 1,1-dimethylpropyl, 1,2-dimethylpropyl, 1-methylpentyl, 2-methylpentyl, 3-methylpentyl, 4-methylpentyl, 1-ethylbutyl, 2-ethylbutyl, 3-ethylbutyl, 1,1 dimethtylbutyl 1,1-dimethylbutyl, 1,2-dimethylbutyl, 1,3-dimethylbutyl, 2,2-dimethylbutyl, 2,3-dimethylbutyl, and 3,3-dimethylbutyl.

In connection with a $U_1$, $U_3$, $U_5$, $U_7$, and/or Z group, "—($C_1$-$C_6$)alkyl-" means a straight chain or branched non-cyclic hydrocarbon moiety having 1, 2, 3, 4, 5, or 6 carbon atoms where two hydrogen atoms on the same or a different carbon atom of the moiety are each figuratively removed and replaced by a bond to one of the two adjoining groups. Representative —($C_1$-$C_6$)alkyl- moieties include meth-1,1-diyl, eth-1,1-diyl, eth-1,2-diyl, n-prop-1,1-diyl, n-prop-1,2-diyl, n-prop-1,3-diyl, n-but-1,1-diyl, n-but-1,2-diyl, n-but-1,3-diyl, n-but-1,4-diyl, iso-but-1,1-diyl, iso-but-1,2-diyl, iso-but-1,3-diyl, and the like.

"—($C_1$-$C_4$)alkyl" means a straight chain or branched non-cyclic hydrocarbon having 1, 2, 3, or 4 carbon atoms. Representative straight chain —($C_1$-$C_4$)alkyls include -methyl, -ethyl, -n-propyl, and -n-butyl. Representative branched —($C_1$-$C_4$)alkyls include -iso-propyl, -sec-butyl, -iso-butyl, and -tert-butyl.

"—($C_1$-$C_3$)alkyl" means a straight chain or branched non-cyclic hydrocarbon having 1, 2, or 3 carbon atoms. Representative straight chain —($C_1$-$C_3$)alkyls include -methyl, -ethyl, and -n-propyl. Representative branched —($C_1$-$C_3$)alkyls include -iso-propyl.

In connection with a $U_1$, $U_3$, $U_5$, $U_7$, and/or Z group, "—($C_1$-$C_3$)alkyl-" means a straight chain or branched non-cyclic hydrocarbon moiety having 1, 2, or 3 carbon atoms where two hydrogen atoms on the same or a different carbon atom of the moiety are each figuratively removed and replaced by a bond to one of the two adjoining groups. Representative —($C_1$-$C_3$)alkyl- moieties include meth-1,1-diyl, eth-1,1-diyl, eth-1,2-diyl, n-prop-1,1-diyl, n-prop-1,2-diyl, n-prop-1,3-diyl, and the like.

"—($C_1$-$C_2$)alkyl" means a straight chain non-cyclic hydrocarbon having 1 or 2 carbon atoms. Representative —($C_1$-$C_2$)alkyls include -methyl and -ethyl.

In connection with a $U_1$, $U_3$, $U_5$, $U_7$, and/or Z group, "—($C_1$-$C_2$)alkyl-" means a straight chain non-cyclic hydrocarbon moiety having 1 or 2 carbon atoms where two hydrogen atoms on the same or a different carbon atom of the moiety are each figuratively removed and replaced by a bond to one of the two adjoining groups. Representative —($C_1$-$C_2$)alkyl- moieties include meth-1,1-diyl, eth-1,1-diyl, and eth-1,2-diyl.

"—($C_2$-$C_{10}$)alkenyl" means a straight chain or branched non-cyclic hydrocarbon having 2, 3, 4, 5, 6, 7, 8, 9, or 10 carbon atoms and including at least one carbon-carbon double bond. A branched alkenyl means that one or more straight chain —($C_1$-$C_8$)alkyl groups, such as methyl, ethyl or propyl, replace one or both hydrogens in a —$CH_2$— or —CH= group of a straight chain alkenyl. Representative straight chain and branched ($C_2$-$C_{10}$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, -1-heptenyl, -2-heptenyl, -3-heptenyl, -1-octenyl, -2-octenyl, -3-octenyl, -1-nonenyl, -2-nonenyl, -3-nonenyl, -1-decenyl, -2-decenyl, -3-decenyl, and the like.

In connection with a $U_1$, $U_3$, $U_5$, $U_7$, and/or Z group, "—($C_2$-$C_{10}$)alkenyl-" means a straight chain or branched non-cyclic hydrocarbon moiety having 2, 3, 4, 5, 6, 7, 8, 9, or 10 carbon atoms and including at least one carbon-carbon double bond where two hydrogen atoms on the same or a different carbon atom of the moiety are each figuratively removed and replaced by a bond to one of the two adjoining groups. Representative —($C_2$-$C_{10}$)alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, prop-2-en-1,3-diyl, 2-methylprop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—($C_2$-$C_6$)alkenyl" means a straight chain or branched non-cyclic hydrocarbon having 2, 3, 4, 5, or 6 carbon atoms and including at least one carbon-carbon double bond. Representative straight chain and branched ($C_2$-$C_6$)alkenyls include -vinyl, -allyl, -1-butenyl, -2-butenyl, -iso-butylenyl, -1-pentenyl, -2-pentenyl, -3-methyl-1-butenyl, -2-methyl-2-butenyl, -2,3-dimethyl-2-butenyl, -1-hexenyl, -2-hexenyl, -3-hexenyl, and the like.

In connection with a $U_1$, $U_3$, $U_5$, $U_7$, and/or Z group, "—($C_2$-$C_6$)alkenyl-" means a straight chain or branched non-cyclic hydrocarbon moiety having 2, 3, 4, 5, or 6 carbon atoms and including at least one carbon-carbon double bond where two hydrogen atoms on the same or a different carbon atom of the moiety are each figuratively removed and replaced by a bond to one of the two adjoining groups. Representative —($C_2$-$C_6$)alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, prop-2-en-1,3-diyl, 2-methylprop-1-en-3,3-diyl, but-2-en-1,1-diyl, but-1-en-4,4-diyl, but-1-en-1,4-diyl, but-2-en-1,4-diyl, but-3-en-1,4-diyl, but-1-en-1,3-diyl, and the like.

"—($C_2$-$C_3$)alkenyl" means a straight chain non-cyclic hydrocarbon having 2 or 3 carbon atoms and including at least one carbon-carbon double bond. Representative ($C_2$-$C_3$)alkenyls include -vinyl, -allyl, and 1-prop-1-enyl.

In connection with a $U_1$, $U_3$, $U_5$, $U_7$, and/or Z group, "—($C_2$-$C_3$)alkenyl-" means a straight chain or branched non-cyclic hydrocarbon moiety having 2 or 3 carbon atoms and including at least one carbon-carbon double bond where two hydrogen atoms on the same or a different carbon atom of the moiety are each figuratively removed and replaced by a bond to one of the two adjoining groups. Representative —($C_2$-$C_3$)alkenyl- moieties include vin-1,1-diyl, vin-1,2-diyl, prop-1-en-1,1-diyl, prop-1-en-1,2-diyl, prop-1-en-1,3-diyl, prop-2-en-1,1-diyl, and prop-2-en-1,3-diyl.

"—($C_2$-$C_{10}$)alkynyl" means a straight chain or branched non-cyclic hydrocarbon having 2, 3, 4, 5, 6, 7, 8, 9, or 10 carbon atoms and including at least one carbon-carbon triple bond. A branched alkynyl means that one or more straight chain —($C_1$-$C_8$)alkyl groups, such as methyl, ethyl or propyl, replace one or both hydrogens in a —$CH_2$— group of a straight chain alkynyl. Representative straight chain and branched —($C_2$-$C_{10}$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, -1-heptynyl, -2-heptynyl, -6-heptynyl, -1-octynyl, -2-octynyl, -7-octynyl, -1-nonynyl, -2-nonynyl, -8-nonynyl, -1-decynyl, -2-decynyl, -9-decynyl, and the like.

"—($C_2$-$C_6$)alkynyl" means a straight chain or branched non-cyclic hydrocarbon having 2, 3, 4, 5, or 6 carbon atoms and including at least one carbon-carbon triple bond. Representative straight chain and branched ($C_2$-$C_6$)alkynyls include -acetylenyl, -propynyl, -1-butynyl, -2-butynyl, -1-pentynyl, -2-pentynyl, -3-methyl-1-butynyl, -4-pentynyl, -1-hexynyl, -2-hexynyl, -5-hexynyl, and the like.

"—($C_1$-$C_6$)alkoxy" means a straight chain or branched non-cyclic hydrocarbon having one or more ether groups and 1, 2, 3, 4, 5, or 6 carbon atoms. Representative straight chain and branched ($C_1$-$C_6$)alkoxys include -methoxy, -ethoxy, -methoxymethyl, -2-methoxyethyl, -5-methoxypentyl, -3-ethoxybutyl, (methoxymethoxy)methyl-, 1-(methoxy)-1-methoxyethyl-, trimethoxymethyl-, 2-((methoxy)methoxy)-2-methylpropyl-, 3-(1,1,1-trimethoxypropane), (methoxy)trimethoxymethyl-, (2,2,2-trimethoxyethoxy)-, and the like.

"—($C_1$-$C_4$)alkoxy" means a straight chain or branched non-cyclic hydrocarbon having one or more ether groups and 1, 2, 3, or 4 carbon atoms. Representative straight chain and branched ($C_1$-$C_4$)alkoxys include -methoxy, -ethoxy, -methoxymethyl, -2-methoxyethyl, (methoxymethoxy)methyl-, 1-(methoxy)-1-methoxyethyl-, trimethoxymethyl-, and the like.

"—($C_3$-$C_{14}$)cycloalkyl" means a saturated monocyclic hydrocarbon having 3, 4, 5, 6, 7, 8, 9, 10, 11, 12, 13, or 14 carbon atoms. Representative ($C_3$-$C_{14}$)cycloalkyls are -cyclopropyl, -cyclobutyl, -cyclopentyl, -cyclohexyl, -cycloheptyl, -cyclooctyl, -cyclononyl, -cyclodecyl, cycloundecyl, -cyclododecyl, and -cyclotetradecyl.

"—($C_3$-$C_{12}$)cycloalkyl" means a saturated monocyclic hydrocarbon having 3, 4, 5, 6, 7, 8, 9, 10, 11, or 12 carbon atoms. Representative ($C_3$-$C_{12}$)cycloalkyls are -cyclopropyl, -cyclobutyl, -cyclopentyl, -cyclohexyl, -cycloheptyl, -cyclooctyl, -cyclononyl, -cyclodecyl, -cycloundecyl, and -cyclododecyl.

"—($C_6$-$C_{12}$)cycloalkyl" means a saturated monocyclic hydrocarbon having 6, 7, 8, 9, 10, 11, or 12 carbon atoms. Representative ($C_6$-$C_{12}$)cycloalkyls are -cyclohexyl, -cycloheptyl, -cyclooctyl, -cyclononyl, -cyclodecyl, -cycloundecyl, and -cyclododecyl.

In connection with a $U_1$, $U_3$, $U_5$, $U_7$, and/or Z group, "—($C_6$-$C_{12}$)cycloalkyl-" means a saturated monocyclic hydrocarbon having 6, 7, 8, 9, 10, 11, or 12 carbon atoms where two hydrogen atoms on the same or a different atom of the ring are each figuratively removed and replaced by a bond to one of the two adjoining groups. Representative —($C_6$-$C_{12}$)cycloalkyl- include those described in the previous paragraph.

"—($C_4$-$C_8$)cycloalkyl" or "4- to 8-member cycloalkyl ring" means a saturated monocyclic hydrocarbon having 4, 5, 6, 7, or 8 carbon atoms. Representative —($C_4$-$C_8$)cycloalkyls are -cyclobutyl, -cyclopentyl, -cyclohexyl, -cycloheptyl, and -cyclooctyl.

"—($C_3$-$C_8$)cycloalkyl" means a saturated monocyclic hydrocarbon having 3, 4, 5, 6, 7, or 8 carbon atoms. Representative ($C_3$-$C_8$)cycloalkyls include -cyclopropyl, -cyclobutyl, -cyclopentyl, -cyclohexyl, -cycloheptyl, and -cyclooctyl.

"—($C_3$-$C_7$)cycloalkyl" means a saturated monocyclic hydrocarbon having 3, 4, 5, 6, or 7 carbon atoms. Representative ($C_3$-$C_7$)cycloalkyls include cyclopropyl, -cyclobutyl, -cyclopentyl, -cyclohexyl, and -cycloheptyl.

"—($C_6$-$C_{14}$)bicycloalkyl" means a bicyclic hydrocarbon ring system having 6, 7, 8, 9, 10, 11, 12, 13, or 14 carbon atoms and at least one saturated cyclic alkyl ring. Representative —($C_6$-$C_{14}$)bicycloalkyls include -indanyl, -norbornyl, -1,2,3,4-tetrahydronaphthalenyl, -5,6,7,8-tetrahydronaphthalenyl, -perhydronaphthalenyl, -bicyclo[2.2.1]hexyl, bicyclo[2.2.1.]heptyl, -bicyclo[2.2.2]octyl, -bicyclo[3.3.1]heptyl, -bicyclo[3.2.1]octyl, -bicyclo[3.3.1]nonyl, -bicyclo[3.3.2]decyl, -bicyclo[3.3.3]undecyl, -bicyclo[4.2.2]decyl, -bicyclo[4.3.2]undecyl, -bicyclo[4.3.1]decyl, and the like.

In connection with a $U_1$, $U_3$, $U_5$, $U_7$, and/or Z group, "—($C_6$-$C_{14}$)bicycloalkyl-" means a bicyclic hydrocarbon ring system having 6, 7, 8, 9, 10, 11, 12, 13, or 14 carbon atoms where two hydrogen atoms on the same or a different atom of the same or a different ring are each figuratively removed and replaced by a bond to one of the two adjoining groups. Representative —($C_6$-$C_{14}$)bicycloalkyl- include those described in the previous paragraph.

"—($C_8$-$C_{20}$)tricycloalkyl" means a tri-cyclic hydrocarbon ring system having 8, 9, 10, 11, 12, 13, 14, 15, 16, 17, 18, 19, or 20 carbon atoms and at least one saturated cyclic alkyl ring. Representative —($C_8$-$C_{20}$)tricycloalkyls include -pyrenyl, -adamantyl, -noradamantyl, -1,2,3,4-tetrahydroanthracenyl, -perhydroanthracenyl-aceanthrenyl, -1,2,3,4-tetrahydropenanthrenyl, -5,6,7,8-tetrahydrophenanthrenyl, -perhydrophenanthrenyl, -tetradecahydro-1H-cyclohepta[a]naphthalenyl, -tetradecahydro-1H-cycloocta[e]indenyl, -tetradecahydro-1H-cyclohepta[e]azulenyl, -hexadecahydrocycloocta[b]naphthalenyl, -hexadecahydrocyclohepta[a]heptalenyl, -tricyclo-pentadecanyl, -tricyclo-octadecanyl, -tricyclo-nonadecanyl, -tricyclo-icosanyl, and the like.

"—($C_3$-$C_{14}$)cycloalkenyl" means a cyclic non-aromatic hydrocarbon having at least one carbon-carbon double bond in the cyclic system and 3, 4, 5, 6, 7, 8, 9, 10, 11, 12, 13, or 14 carbon atoms. Representative ($C_3$-$C_{14}$)cycloalkenyls include -cyclopropenyl, -cyclobutenyl, -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, -cyclotetradecenyl, -cyclododecadienyl, and the like.

"—($C_5$-$C_{14}$)cycloalkenyl" means a cyclic non-aromatic hydrocarbon having at least one carbon-carbon double bond in the cyclic system and 5, 6, 7, 8, 9, 10, 11, 12, 13, or 14 carbon atoms. Representative ($C_5$-$C_{14}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclononatrienyl, -cyclodecenyl, -cyclodecadienyl, -cyclotetradecenyl, -cyclododecadienyl, and the like.

In connection with a $U_1$, $U_3$, $U_5$, $U_7$, and/or Z group, "—($C_5$-$C_{14}$)cycloalkenyl-" means a cyclic non-aromatic hydrocarbon having at least one carbon-carbon double bond in the cyclic system and 5, 6, 7, 8, 9, 10, 11, 12, 13, or 14 carbon atoms where two hydrogen atoms on the same or a different atom of the ring are each figuratively removed and replaced by a bond to one of the two adjoining groups. Representative —($C_5$-$C_{14}$)cycloalkenyls- include those described in the previous paragraph.

"—($C_6$-$C_{12}$)cycloalkenyl" means a cyclic non-aromatic hydrocarbon having at least one carbon-carbon double bond in the cyclic system and 6, 7, 8, 9, 10, 11, or 12 carbon atoms. Representative ($C_6$-$C_{12}$)cycloalkenyls include -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, -cyclododecadienyl, and the like.

"—($C_5$-$C_{10}$)cycloalkenyl" means a cyclic non-aromatic hydrocarbon having at least one carbon-carbon double bond in the cyclic system and 5, 6, 7, 8, 9, or 10 carbon atoms. Representative ($C_5$-$C_{10}$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, -cyclononenyl, -cyclononadienyl, -cyclodecenyl, -cyclodecadienyl, and the like.

"—($C_5$-$C_8$)cycloalkenyl" means a cyclic non-aromatic hydrocarbon having at least one carbon-carbon double bond in the cyclic system and 5, 6, 7, or 8 carbon atoms. Representative ($C_5$-$C_8$)cycloalkenyls include -cyclopentenyl, -cyclopentadienyl, -cyclohexenyl, -cyclohexadienyl, -cycloheptenyl, -cycloheptadienyl, -cycloheptatrienyl, -cyclooctenyl, -cyclooctadienyl, -cyclooctatrienyl, -cyclooctatetraenyl, and the like.

"—($C_7$-$C_{14}$)bicycloalkenyl" means a bicyclic hydrocarbon ring system having at least one carbon-carbon double bond in each ring and 7, 8, 9, 10, 11, 12, 13, or 14 carbon atoms. Representative —($C_7$-$C_{14}$)bicycloalkenyls include -bicyclo[3.2.0]hept-2-enyl, -indenyl, -pentalenyl, -naphthalenyl, -azulenyl, -heptalenyl, -1,2,7,8-tetrahydronaphthalenyl, -norbornenyl, and the like.

In connection with a $U_1$, $U_3$, $U_5$, $U_7$, and/or Z group, "—($C_7$-$C_{14}$)bicycloalkenyl-" means a bicyclic hydrocarbon ring system having at least one carbon-carbon double bond in each ring and 7, 8, 9, 10, 11, 12, 13, or 14 carbon atoms where two hydrogen atoms on the same or a different atom of the same or a different ring are each figuratively removed and replaced by a bond to one of the two adjoining groups. Representative —($C_7$-$C_{14}$)bicycloalkenyls- include those described in the previous paragraph.

"—($C_8$-$C_{20}$)tricycloalkenyl" means a tricyclic hydrocarbon ring system having at least one carbon-carbon double bond in each ring and 8, 9, 10, 11, 12, 13, 14, 15, 16, 17, 18, 19, or 20 carbon atoms. Representative —($C_8$-$C_{20}$)tricycloalkenyls include -anthracenyl, -phenanthrenyl, -phenalenyl, -acenaphthalenyl, -as-indacenyl, -s-indacenyl, -2,3,6,7,8,9,10,11-octahydro-1H-cycloocta[e]indenyl, 2,3,4,7,8,9,10,11-octahydro-1H-cyclohepta[a]naphthalenyl, -8,9,10,11-tetrahydro-7H-cyclohepta[a]naphthalenyl, -2,3,4,5,6,7,8,9,10,11,12,13-dodecahydro-1H-cyclohepta[a]heptalenyl, -1,2,3,4,5,6,7,8,9,10,11,12,13,14-tetradecahydro-dicyclohepta[a,c]cyclooctenyl, -2,3,4,5,6,7,8,9,10,11,12,13-dodecahydro-1H-dibenzo[a,d]cyclononenyl, and the like.

"-(3- to 7-membered)heterocycle" or "-(3- to 7-membered)heterocyclo" means a 3- to 7-membered monocyclic heterocyclic ring which is either saturated, unsaturated non-aromatic, or aromatic. A 3-membered heterocycle contains 1 heteroatom, a 4-membered heterocycle can contain 1 or 2 heteroatoms, a 5-membered heterocycle can contain 1, 2, 3, or 4 heteroatoms, a 6-membered heterocycle can contain 1, 2, 3, or 4 heteroatoms, and a 7-membered heterocycle can contain 1, 2, 3, 4, or 5 heteroatoms. Each heteroatom is independently selected from nitrogen, which can be quaternized; oxygen; and sulfur, including sulfoxide and sulfone. The -(3- to 7-membered)heterocycle can be attached via a nitrogen or carbon atom. Representative -(3- to 7-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, oxiranyl, oxetanyl, tetrahydrofuranyl, tetrahydropyranyl, dihydropyridinyl, tetrahydropyridinyl, tetrahydropyrimidinyl, tetrahydrothiophenyl, tetrahydrothiopyranyl, and the like.

"-(5- or 6-membered)heterocycle" or "-(5- or 6-membered)heterocyclo" means a 5- or 6-membered monocyclic heterocyclic ring which is either saturated, unsaturated non-aromatic, or aromatic. A 5-membered heterocycle can contain 1, 2, 3, or 4 heteroatoms and a 6-membered heterocycle can contain 1, 2, 3, or 4 heteroatoms. Each heteroatom is independently selected from nitrogen, which can be quaternized; oxygen; and sulfur, including sulfoxide and sulfone. The -(5- or 6-membered)heterocycle can be attached via a nitrogen or carbon atom. Representative -(5- or 6-membered)heterocycles include pyridyl, furyl, thiophenyl, pyrrolyl, oxazolyl, imidazolyl, thiazolidinyl, thiadiazolyl, thiazolyl, isoxazolyl, pyrazolyl, isothiazolyl, pyridazinyl, pyrimidinyl, triazinyl, morpholinyl, pyrrolidinonyl, pyrrolidinyl, piperidinyl, piperazinyl, 2,3-dihydrofuranyl, dihydropyranyl, hydantoinyl, valerolactamyl, tetrahydrofuranyl, tetrahydropyranyl, dihydropyridinyl, tetrahydropyridinyl, tetrahydropyrimidinyl, tetrahydrothiophenyl, tetrahydrothiopyranyl, tetrazolyl, and the like.

In connection with a $U_1$, $U_3$, $U_5$, $U_7$, and/or Z group, "-(5- or 6-membered)heterocycle-" or "-(5- or 6-membered)heterocyclo-" means a 5- or 6-membered monocyclic heterocyclic ring which is either saturated, unsaturated non-aromatic, or aromatic as described in the previous paragraph, where two hydrogen atoms on the same or a different atom of the ring, either carbon or nitrogen, are each figuratively removed and replaced by a bond to one of the two adjoining groups. Representative -(5- or 6-membered)heterocycle-rings include those described in the previous paragraph.

"-(7- to 10-membered)bicycloheterocycle" or "-(7- to 10-membered)bicycloheterocyclo" means a 7- to 10-membered bicyclic, heterocyclic ring which is either saturated, unsaturated non-aromatic, or aromatic. A -(7- to 10-membered)bicycloheterocycle contains 1, 2, 3, or 4 heteroatoms independently selected from nitrogen, which can be quaternized; oxygen; and sulfur, including sulfoxide and sulfone. The -(7- to 10-membered)bicycloheterocycle can be attached via a nitrogen or carbon atom. Representative -(7- to 10-membered)bicycloheterocycles include -quinolinyl, -isoquinolinyl, -chromonyl, -coumarinyl, -indolyl, -indolizinyl, -benzo[b]furanyl, -benzo[b]thiophenyl, -indazolyl, -purinyl, -4H-quinolizinyl, -isoquinolyl, -quinolyl, -phthalazinyl, -naphthyridinyl, -carbazolyl, -β-carbolinyl, -indolinyl, -isoindolinyl, -1,2,3,4-tetrahydroquinolinyl, -1,2,3,4-tetrahydroisoquinolinyl, -pyrrolopyrrolyl and the like.

"—$(C_3$-$C_{12})$cycloalkoxy" means a saturated monocyclic hydrocarbon having 3, 4, 5, 6, 7, 8, 9, 10, 11, or 12 carbon atoms where at least one of the carbon atoms is replaced by an oxygen atom. Representative $(C_3$-$C_{12})$cycloalkoxy are -oxiranyl, -oxetanyl, -tetrahydrofuranyl, -tetrahydro-2H-pyranyl, -1,4-dioxanyl, -oxepanyl, -1,4-dioxepanyl, -oxocanyl, -1,5-dioxocanyl, -1,3,5-trioxocanyl, -oxonanyl, -1,5-dioxonanyl, -1,4,7-trioxonanyl, -oxacyclododecanyl, -1,7-dioxacyclododecanyl, and -1,5,9-trioxacyclododecanyl.

"—$(C_3$-$C_7)$cycloalkoxy" means a saturated monocyclic hydrocarbon having 3, 4, 5, 6, or 7 carbon atoms where at least one of the carbon atoms is replaced by an oxygen atom. Representative $(C_3$-$C_7)$cycloalkoxy are -oxiranyl, -oxetanyl, -tetrahydrofuranyl, -tetrahydro-2H-pyranyl, -1,4-dioxanyl, -oxepanyl, and -1,4-dioxepanyl.

"—$(C_{14})$aryl" means a 14-membered aromatic carbocyclic moiety such as -anthryl or -phenanthryl.

"-(5- to 10-membered)heteroaryl" means an aromatic heterocycle ring of 5 to 10 members, including both mono- and bicyclic ring systems, where at least one carbon atom of one or both of the rings is replaced with a heteroatom independently selected from nitrogen, oxygen, and sulfur, or at least two carbon atoms of one or both of the rings are replaced with a heteroatom independently selected from nitrogen, oxygen, and sulfur. In one embodiment, one of the -(5- to 10-membered)heteroaryl's rings contain at least one carbon atom. In another embodiment, both of the -(5- to 10-membered)heteroaryl's rings contain at least one carbon atom. Representative -(5- to 10-membered)heteroaryls include pyridyl, furyl, benzofuranyl, thiophenyl, benzothiophenyl, quinolinyl, isoquinolinyl, pyrrolyl, indolyl, oxazolyl, benzoxazolyl, imidazolyl, benzimidazolyl, thiazolyl, benzothiazolyl, isoxazolyl, oxadiazolinyl, pyrazolyl, isothiazolyl, pyridazinyl, pyrimidyl, pyrimidinyl, pyrazinyl, thiadiazolyl, triazinyl, thienyl, cinnolinyl, phthalazinyl, and quinazolinyl.

"-(5- or 6-membered)heteroaryl" means a monocyclic aromatic heterocycle ring of 5 or 6 members where at least one carbon atom is replaced with a heteroatom independently selected from nitrogen, oxygen, and sulfur. In one embodiment, one of the -(5- or 6-membered)heteroaryl's ring contains at least one carbon atom. Representative -(5- or 6-membered)heteroaryls include pyridyl, furyl, pyrrolyl, oxazolyl, imidazolyl, thiazolyl, isoxazolyl, 1,2,3-oxadiazolyl, 1,3,4-oxadiazolyl, 1,2,5-oxadiazolyl, 1,2,3-triazolyl, pyrazolyl, isothiazolyl, pyridazinyl, pyrimidyl, pyrazinyl, 1,2,3-thiadiazolyl, 1,3,4-thiadiazolyl, 1,2,5-thiadiazolyl, 1,3,5-triazinyl, and thiophenyl.

"—$CH_2$(halo)" means a methyl group where one of the hydrogens of the methyl group has been replaced with a halogen. Representative —$CH_2$(halo) groups include —$CH_2F$, —$CH_2Cl$, —$CH_2Br$, and —$CH_2I$.

"—$CH(halo)_2$" means a methyl group where two of the hydrogens of the methyl group have been replaced with a halogen. Representative —$CH(halo)_2$ groups include —$CHF_2$, —$CHCl_2$, —$CHBr_2$, —$CHBrCl$, —$CHClI$, and —$CHI_2$.

"—$C(halo)_3$" means a methyl group where each of the hydrogens of the methyl group has been replaced with a halogen. Representative —$C(halo)_3$ groups include —$CF_3$, —$CCl_3$, —$CBr_3$, and —$CI_3$.

"-Halogen" or "-halo" means —F, —Cl, —Br, or —I.

"Oxo", "=O", and the like as used herein mean an oxygen atom doubly bonded to carbon or another element.

"Thiooxo", "thioxo", "=S", and the like as used herein mean a sulfur atom doubly bonded to carbon or another element.

In connection with a $U_1$, $U_2$, $U_3$, $U_4$, $U_5$, $U_6$, and/or $U_7$ group, when each such group is selected as a "bond" or a "single bond," the adjacent groups are directly connected by that bond. For example, when $U_2$ is a single bond then $U_1$ and $U_3$ are directly connected as follows: —$U_1$—$U_3$—.

In connection with a $U_1$, $U_2$, $U_3$, $U_4$, $U_5$, $U_6$, and/or $U_7$ group, when each such group is absent then the adjacent groups are directly connected. For example, when $U_2$ is absent then $U_1$ and $U_3$ are directly connected as follows: —$U_1$—$U_3$—. As another example, when $U_5$ and $U_6$ are each absent then $U_4$ and $U_7$ are directly connected as follows: —$U_4$—$U_7$—.

"$(C_2-C_6)$bridge" as used herein means a hydrocarbon chain containing 2 to 6 carbon atoms joining two atoms of the piperidine ring of Formula (I) to form a fused bicyclic ring system. For example, compounds of the disclosure can comprise a $(C_2-C_6)$bridge joining positions 2 and 6 of the piperidine ring (A-B can together form a $(C_2-C_6)$bridge). Exemplary compounds of the disclosure include those with an unsubstituted $(C_2)$bridge, —$CH_2$—$CH_2$—, joining positions 2 and 6 of the piperidine ring (A-B can together form a $(C_2)$bridge); an unsubstituted $(C_3)$bridge, —$CH_2$—$CH_2$—$CH_2$—, joining positions 2 and 6 of the piperidine ring (A-B can together form a $(C_3)$bridge); an unsubstituted $(C_4)$ bridge, —$CH_2$—$CH_2$—$CH_2$—$CH_2$—, joining positions 2 and 6 of the piperidine ring (A-B can together form a $(C_4)$bridge); an unsubstituted $(C_5)$bridge, —$CH_2$—$CH_2$—$CH_2$—$CH_2$—$CH_2$—, joining positions 2 and 6 of the piperidine ring (A-B can together form a $(C_5)$bridge); or an unsubstituted $(C_6)$bridge, —$CH_2$—$CH_2$—$CH_2$—$CH_2$—$CH_2$—$CH_2$—, joining positions 2 and 6 of the piperidine ring (A-B can together form a $(C_6)$bridge). Examples of compounds where A-B can together form a $(C_2-C_6)$bridge include compounds comprising the following ring systems: 8-aza-bicyclo[3.2.1]octane; 9-aza-bicyclo[3.3.1]nonane; 10-aza-bicyclo[4.3.1]decane; 11-aza-bicyclo[5.3.1]undecane; and 12-aza-bicyclo[6.3.1]dodecane. Examples of a $(C_2-C_6)$bridge which contains —HC=CH— within the $(C_2-C_6)$bridge include —HC=CH—, —$CH_2$—HC=CH—, —HC=CH—$CH_2$—, —$CH_2$—HC=CH—$CH_2$—, and the like. Examples of a $(C_2-C_6)$bridge which contains —O— within the $(C_2-C_6)$bridge include —$CH_2$—O—$CH_2$— (containing 2 carbon atoms), —$CH_2$—O—$CH_2$—$CH_2$— and —$CH_2$—$CH_2$—O—$CH_2$— (each containing 3 carbon atoms), —$CH_2$—$CH_2$—O—$CH_2$—$CH_2$—, —$CH_2$—O—$CH_2$—$CH_2$—$CH_2$— and —$CH_2$—$CH_2$—$CH_2$—O—$CH_2$— (each containing 4 carbon atoms), and the like.

In compounds of the disclosure comprising a bridge joining positions 2 and 6 of the piperidine ring (e.g., A-B can together form a $(C_2-C_6)$bridge), for, e.g., a compound of Formula (I), the exemplary endo bridge:

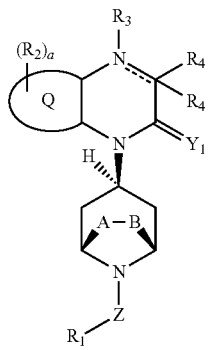

is equivalent to

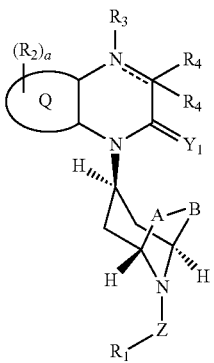

In compounds of the disclosure comprising a bridge joining positions 2 and 6 of the piperidine ring (e.g., A-B can together form a $(C_2-C_6)$bridge), for, e.g., a compound of Formula (I), the exemplary exo bridge:

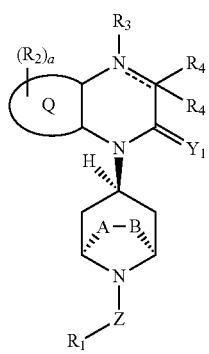

is equivalent to

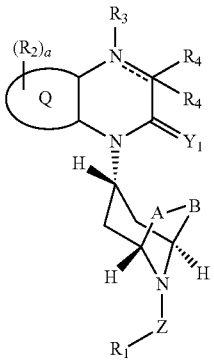

In compounds of the disclosure where the —Z—$R_1$ group comprises a bicyclic group, that bicyclic group can have two orientations. For example, for a —Z—$R_1$ group that is a —$(C_6-C_{14})$bicycloalkyl, e.g., bicyclo[3.3.1]nonanyl, attached directly to the piperidine ring nitrogen, the following orientations are possible:

Endo:

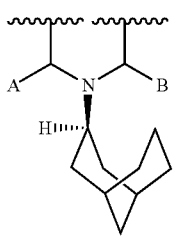

or

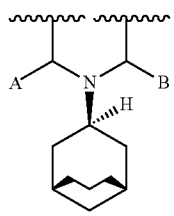

Exo:

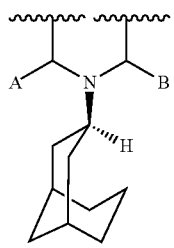

or

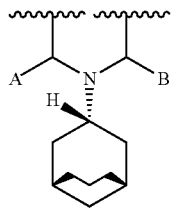

As used herein in connection with Formula (I), when the dashed line in the 6-membered, nitrogen-containing ring that is fused to the Q group is absent, then Formula (I) is understood to appear as follows:

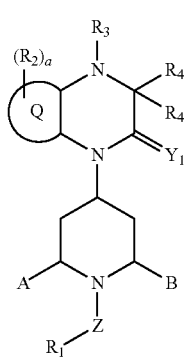

(I)

i.e., the 6-membered, nitrogen-containing ring that is fused to the Q group contains a single bond between the ring-carbon to which the $R_4$ groups are attached and the adjacent ring-nitrogen.

As used herein in connection with Formula (I), when the dashed line in the 6-membered, nitrogen-containing ring that is fused to the Q group indicates the presence of a bond to provide one bond of a double bond, then Formula (I) is understood to appear as follows:

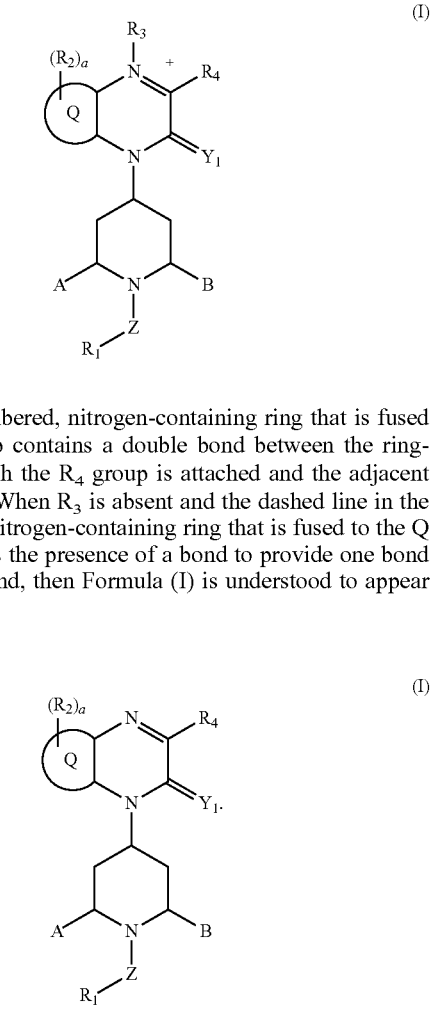

(I)

i.e., the 6-membered, nitrogen-containing ring that is fused to the Q group contains a double bond between the ring-carbon to which the $R_4$ group is attached and the adjacent ring-nitrogen. When $R_3$ is absent and the dashed line in the 6-membered, nitrogen-containing ring that is fused to the Q group indicates the presence of a bond to provide one bond of a double bond, then Formula (I) is understood to appear as follows:

(I)

"—[($C_1$-$C_{10}$)alkyl optionally substituted by $R_1$]$_h$—" as used herein in connection with Z means that, when h is 0, Z is a single bond. Also in connection with "—[($C_1$-$C_{10}$)alkyl optionally substituted by $R_1$]$_h$—", when h is 1 means that the Z—$R_1$ bonded to the piperidine ring bearing A and B substituents is understood to appear as follows:

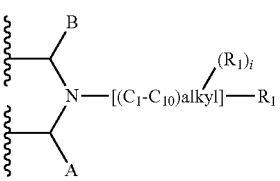

where, when i is 0, the —$(C_1$-$C_{10})$alkyl- is unsubstituted by a $R_1$ group at any position other than at the carbon atom furthest removed from the piperidine ring bearing A and B substituents; and, when i is 1, the —$(C_1$-$C_{10})$alkyl- is substituted by a $R_1$ group at the carbon atom furthest removed from the piperidine ring bearing A and B substituents and substituted by another independently selected $R_1$ group at any carbon atom of the —$(C_1$-$C_{10})$alkyl- including at the carbon atom furthest removed from the piperidine ring bearing A and B substituents. In one embodiment, the another independently selected $R_1$ group is selected from:

(a) —H, -halo, —CN, —OH, —$CH_2OH$, —$CH_2CH_2OH$, —$NO_2$, —$N(R_6)_2$, —$S(=O)NH_2$, —$S(=O)_2NH_2$, —$C(=O)OV_1$, and —$C(=O)CN$; and (b) —$(C_1$-$C_{10})$alkyl, —$(C_2$-$C_{10})$alkenyl, —$(C_2$-$C_{10})$alkynyl, —$O(C_1$-$C_6)$alkyl, —$(C_3$-$C_7)$cycloalkoxy, —$(C_5$-$C_{10})$cycloalkenyl, and -(3- to 7-membered)heterocycle, each of which is unsubstituted or substituted with 1, 2, 3, or 4 independently selected $R_8$ groups; and (c)

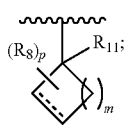

(i)

and (d) -phenyl and -(5- to 10-membered)heteroaryl, each of which is unsubstituted or substituted with a $R_7$ group.

In another embodiment, the another independently selected $R_1$ group is selected from:

(a) —H, -halo, —OH, —$CH_2OH$, —$CH_2CH_2OH$, —$N(R_6)_2$, and —$C(=O)OV_1$; and (b) —$(C_1$-$C_{10})$alkyl, —$(C_2$-$C_{10})$alkenyl, —$O(C_1$-$C_6)$alkyl, —$(C_5$-$C_{10})$cycloalkenyl, and -(5- or 6-membered)heterocycle, each of which is unsubstituted or substituted with 1, 2, 3, or 4 independently selected $R_8$ groups; and (c)

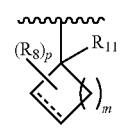

(i)

wherein $R_{11}$ is —H and m is an integer selected from 2, 3, 4, 5, 6, and 7;

(d) -phenyl and -(5- or 6-membered)heteroaryl, each of which is unsubstituted or substituted with a $R_7$ group.

In another embodiment, the another independently selected $R_1$ group is selected from:

(a) —H, -halo, —OH, —$CH_2OH$, —$CH_2CH_2OH$, —$N(R_6)_2$, and —$C(=O)OV_1$; and (b) —$(C_1$-$C_6)$alkyl, —$(C_2$-$C_6)$alkenyl, —$O(C_1$-$C_4)$alkyl, and -(5- or 6-membered)heterocycle, each of which is unsubstituted or substituted with 1, 2, or 3 independently selected $R_8$ groups; and (c)

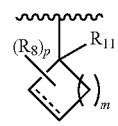

(i)

wherein $R_{11}$ is —H and m is an integer selected from 2, 3, 4, 5, 6, and 7;

(d) -phenyl and -(5- or 6-membered)heteroaryl, each of which is unsubstituted or substituted with a $R_7$ group.

"—[$(C_2$-$C_{10})$alkenyl optionally substituted by $R_1$]—" as used herein in connection with Z—$R_1$ means that the Z—$R_1$ bonded to the piperidine ring bearing A and B substituents is understood to appear as follows:

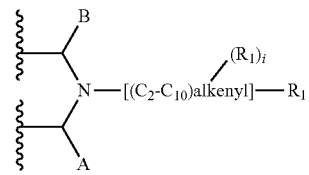

where, when i is 0, the —$(C_2$-$C_{10})$alkenyl- is unsubstituted by a $R_1$ group at any position other than at the carbon atom furthest removed from the piperidine ring bearing A and B substituents; and, when i is 1, the —$(C_2$-$C_{10})$alkenyl- is substituted by a $R_1$ group at the carbon atom furthest removed from the piperidine ring bearing A and B substituents and substituted by another independently selected $R_1$ group at any carbon atom of the —$(C_2$-$C_{10})$alkenyl- including at the carbon atom furthest removed from the piperidine ring bearing A and B substituents.

As used herein in connection with formula (i) of $R_1$, when the dashed line is present as a bond to provide one bond of a double bond, then formula (i) is understood to appear as follows

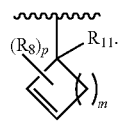

(i)

As used herein in connection with formula (i) of $R_1$, when the dashed line is absent, then formula (i) is understood to appear as follows

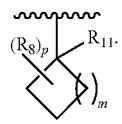

(i)

The phrase "benzo," "benzo group" and the like, when used in connection with the Q group, means

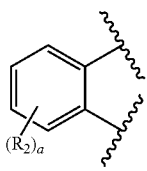

where R₂, and a are defined above for the Phosphorus-Substituted Quinoxaline-Type Piperidine Compounds of Formula (I).

The phrase "pyridino," "pyridino group" and the like, when used in connection with the Q group, means

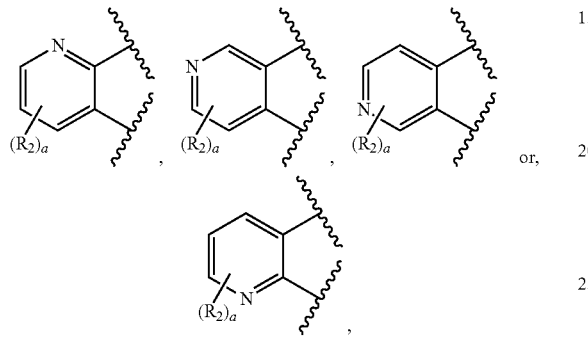

where R₂, and a are defined above for the Phosphorus-Substituted Quinoxaline-Type Piperidine Compounds of Formula (I). In one embodiment, the optionally-substituted pyridino Q group is

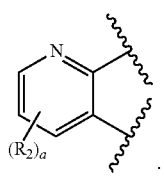

In another embodiment, the optionally-substituted pyridino Q group is

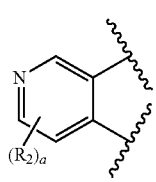

In another embodiment, the optionally-substituted pyridino Q group is

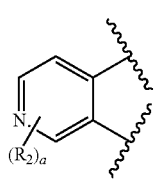

In another embodiment, the optionally-substituted pyridino Q group is

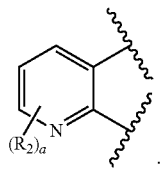

The phrase "pyrimidino", "pyrimidino group" and the like, when used in connection with the optionally-substituted Q group, means

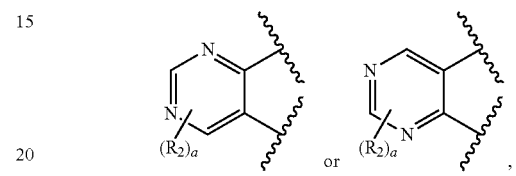

where R₂ and a are defined above for the Phosphorus-Substituted Quinoxaline-Type Piperidine Compounds of Formula (I). In one embodiment, the optionally-substituted pyrimidino Q group is

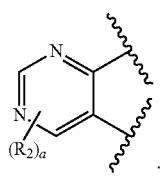

In another embodiment, the optionally-substituted pyrimidino Q group is

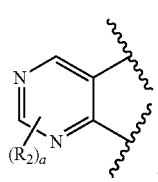

The phrase "pyrazino", "pyrazino group" and the like, when used in connection with the optionally-substituted Q group, means

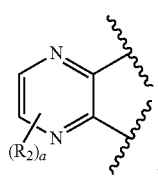

where R₂ and a are defined above for the Phosphorus-Substituted Quinoxaline-Type Piperidine Compounds of Formula (I).

The phrase "pyridazino", "pyridazino group" and the like, when used in connection with the optionally-substituted Q group, means

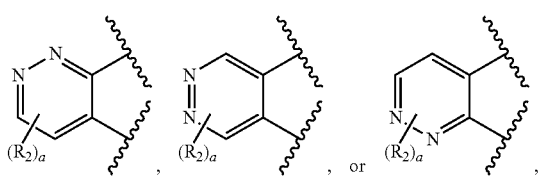

where $R_2$ and a are defined above for the Phosphorus-Substituted Quinoxaline-Type Piperidine Compounds of Formula (I). In one embodiment, the optionally-substituted pyridazino Q group is

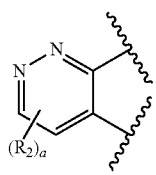

In another embodiment, the optionally-substituted pyridazino Q group is

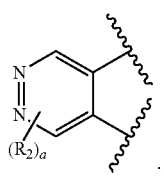

In another embodiment, the optionally-substituted pyridazino Q group is

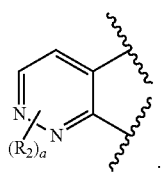

The phrase "pyrrolino", "pyrrolino group" and the like, when used in connection with the optionally-substituted Q group, means

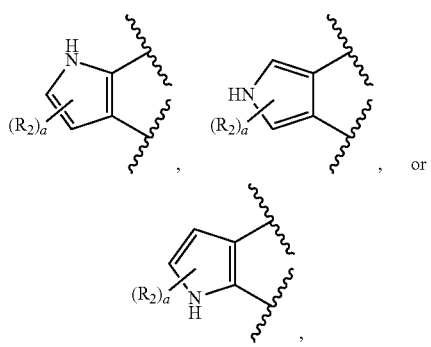

where $R_2$ and a are defined above for the Phosphorus-Substituted Quinoxaline-Type Piperidine Compounds of Formula (I). In one embodiment, the optionally-substituted pyrrolino Q group is

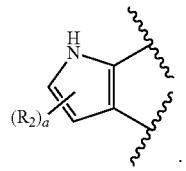

In another embodiment, the optionally-substituted pyrrolino Q group is

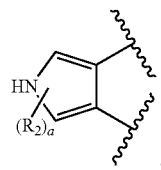

In another embodiment, the optionally-substituted pyrrolino Q group is

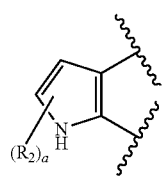

The phrase "imidazolino", "imidazolino group" and the like, when used in connection with the optionally-substituted Q group, means

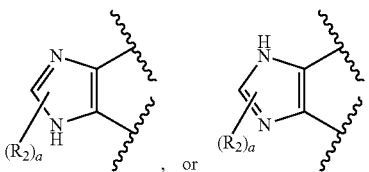

where $R_2$ and a are defined above for the Phosphorus-Substituted Quinoxaline-Type Piperidine Compounds of Formula (I). In one embodiment, the optionally-substituted imidazolino Q group is

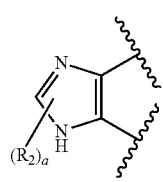

In another embodiment, the optionally-substituted imidazolino Q group is

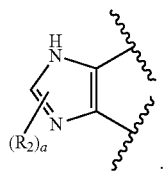

The phrase "pyrazolino", "pyrazolino group" and the like, when used in connection with the optionally-substituted Q group, means

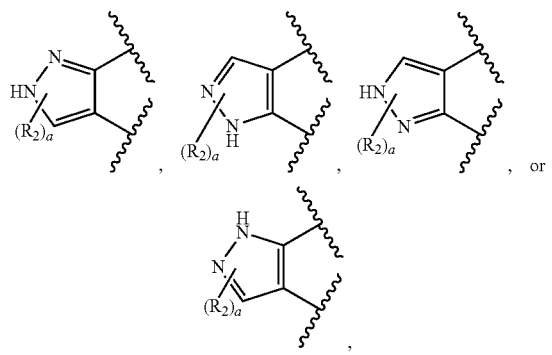

where $R_2$ and a are defined above for the Phosphorus-Substituted Quinoxaline-Type Piperidine Compounds of Formula (I). In one embodiment, the optionally-substituted pyrazolino Q group is

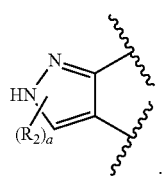

In another embodiment, the optionally-substituted pyrazolino Q group is

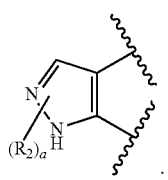

In another embodiment, the optionally-substituted pyrazolino Q group is

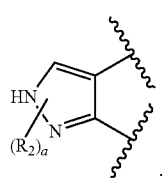

In another embodiment, the optionally-substituted pyrazolino Q group is

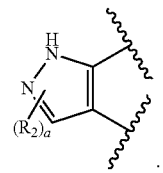

The phrase "triazolino", "triazolino group" and the like, when used in connection with the optionally-substituted Q group, means

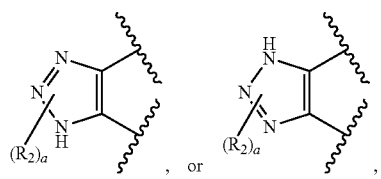

where $R_2$ and a are defined above for the Phosphorus-Substituted Quinoxaline-Type Piperidine Compounds of Formula (I). In one embodiment, the optionally-substituted triazolino Q group is

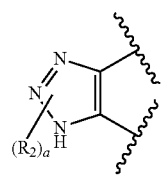

In another embodiment, the optionally-substituted triazolino Q group is

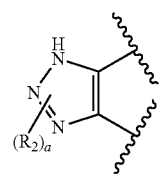

The phrase "furano", "furano group" and the like, when used in connection with the optionally-substituted Q group, means

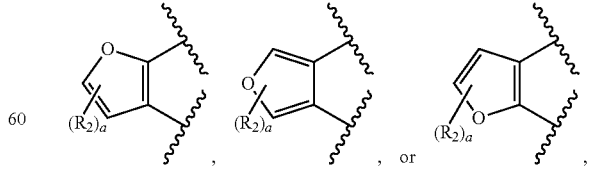

where $R_2$ and a are defined above for the Phosphorus-Substituted Quinoxaline-Type Piperidine Compounds of Formula (I). In one embodiment, the optionally-substituted furano Q group is

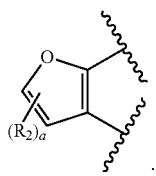

In another embodiment, the optionally-substituted furano Q group is

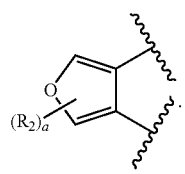

In another embodiment, the optionally-substituted furano Q group is

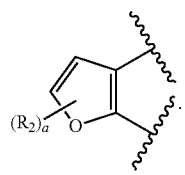

The phrase "oxazolino", "oxazolino group" and the like, when used in connection with the optionally-substituted Q group, means

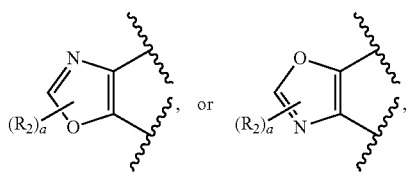

where $R_2$ and a are defined above for the Phosphorus-Substituted Quinoxaline-Type Piperidine Compounds of Formula (I). In one embodiment, the optionally-substituted oxazolino Q group is

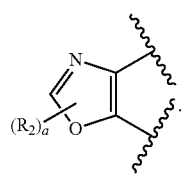

In another embodiment, the optionally-substituted oxazolino Q group is

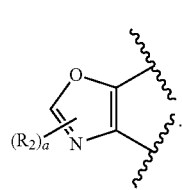

The phrase "isoxazolino", "isoxazolino group" and the like, when used in connection with the optionally-substituted Q group, means

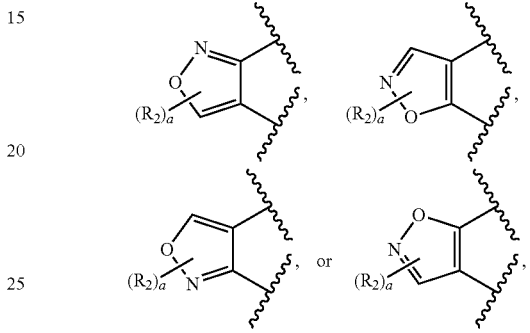

where $R_2$ and a are defined above for the Phosphorus-Substituted Quinoxaline-Type Piperidine Compounds of Formula (I). In one embodiment, the optionally-substituted isoxazolino Q group is

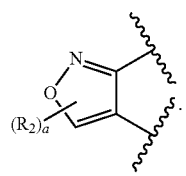

In another embodiment, the optionally-substituted isoxazolino Q group is

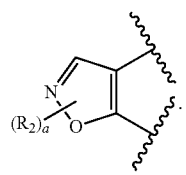

In another embodiment, the optionally-substituted isoxazolino Q group is

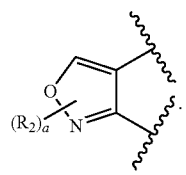

In another embodiment, the optionally-substituted isoxazolino Q group is

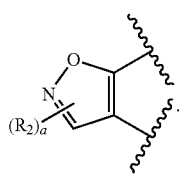

The phrase "oxadiazolino", "oxadiazolino group" and the like, when used in connection with the optionally-substituted Q group, means

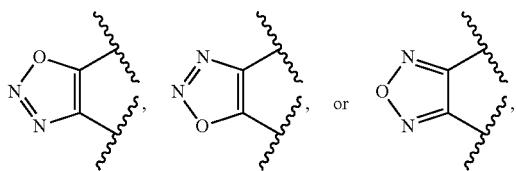

where $R_2$ and a are defined above for the Phosphorus-Substituted Quinoxaline-Type Piperidine Compounds of Formula (I). In one embodiment, the optionally-substituted oxadiazolino Q group is

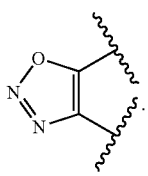 [SMILES: *c1nnoc1*]

In another embodiment, the optionally-substituted oxadiazolino Q group is

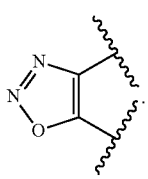 [SMILES: *c1nnoc1*]

In another embodiment, the optionally-substituted oxadiazolino Q group is

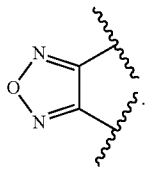 [SMILES: *c1nonc1*]

The phrase "thiopheno", "thiopheno group" and the like, when used in connection with the optionally-substituted Q group, means

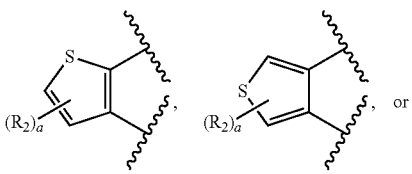

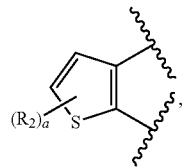

where $R_2$ and a are defined above for the Phosphorus-Substituted Quinoxaline-Type Piperidine Compounds of Formula (I). In one embodiment, the optionally-substituted thiopheno Q group is

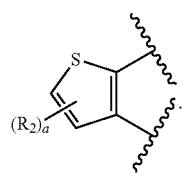

In another embodiment, the optionally-substituted thiopheno Q group is

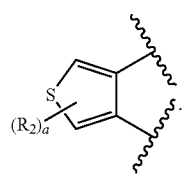

In another embodiment, the optionally-substituted thiopheno Q group is

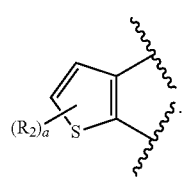

The phrase "thiazolino", "thiazolino group" and the like, when used in connection with the optionally-substituted Q group, means

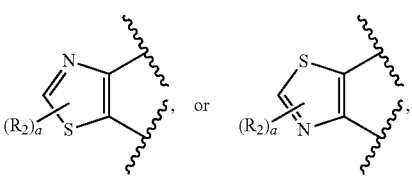

where $R_2$ and a are defined above for the Phosphorus-Substituted Quinoxaline-Type Piperidine Compounds of Formula (I). In one embodiment, the optionally-substituted thiazolino Q group is

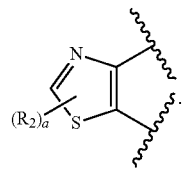

In another embodiment, the optionally-substituted thiazolino Q group is

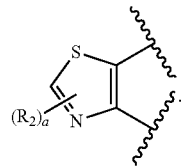

The phrase "isothiazolino", "isothiazolino group" and the like, when used in connection with the optionally-substituted Q group, means

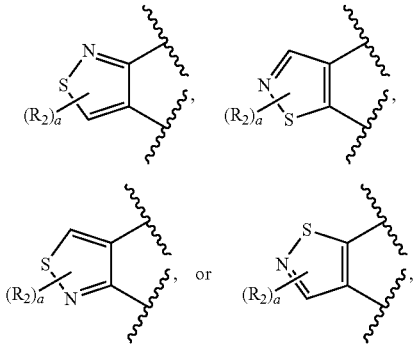

where $R_2$ and a are defined above for the Phosphorus-Substituted Quinoxaline-Type Piperidine Compounds of Formula (I). In one embodiment, the optionally-substituted isothiazolino Q group is

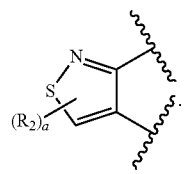

In another embodiment, the optionally-substituted isothiazolino Q group is

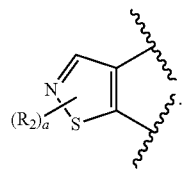

In another embodiment, the optionally-substituted isothiazolino Q group is

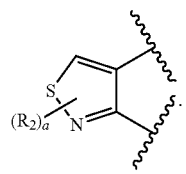

In another embodiment, the optionally-substituted isothiazolino Q group is

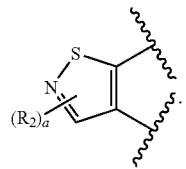

The phrase "thiadiazolino", "thiadiazolino group" and the like, when used in connection with the optionally-substituted Q group, means

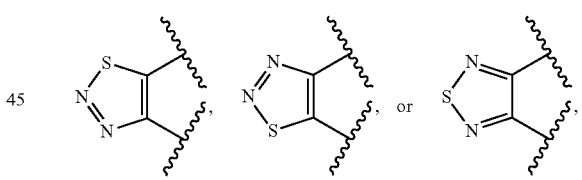

where $R_2$ and a are defined above for the Phosphorus-Substituted Quinoxaline-Type Piperidine Compounds of Formula (I). In one embodiment, the optionally-substituted thiadiazolino Q group is

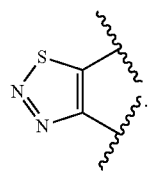

In another embodiment, the optionally-substituted thiadiazolino Q group is

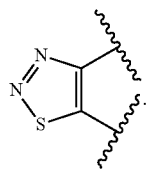

In another embodiment, the optionally-substituted thiadiazolino Q group is

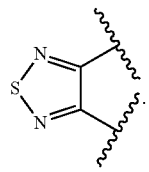 [SMILES: *c1nsnc1*]

The phrase "3,3-diphenylpropyl-" and the like, when used in connection with the —Z—R$_1$ group, means

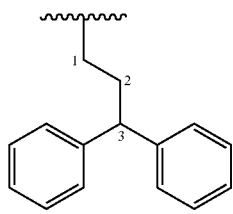 [SMILES: *CCC(c1ccccc1)c1ccccc1]

where the 3 carbon of the propyl is indicated by the number 3 in the structure above.

In one embodiment, the phrase "optionally substituted bicyclo[3.3.1]nonyl" and the like when used in connection with the optionally-substituted R$_1$ group is understood to refer to one of the structures below:

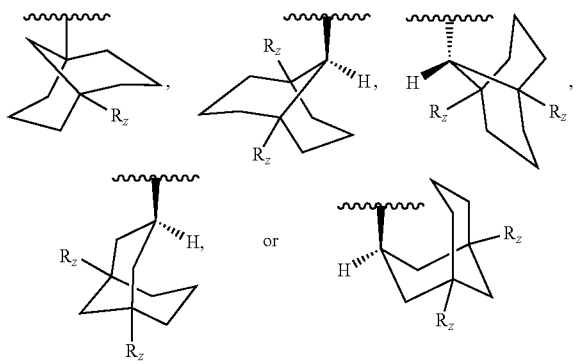

where the substituents are as defined above for the Phosphorus-Substituted Quinoxaline-Type Piperidine Compounds of Formula (I); and where in one or more embodiments, the optionally substituted R$_1$ group comprises one or more of the above-recited optionally substituted bicycle[3.3.1]nonyl structures.

In one embodiment, the phrase "optionally substituted —(C$_6$-C$_{14}$)bicycloalkyl" means

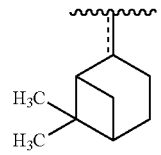

where the dashed line denotes the presence or absence of a bond. When the dashed line is present as a bond to provide one bond of a double bond, then the group above is understood to appear as follows

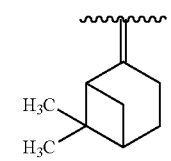

and when the dashed line is absent, then the optionally substituted —(C$_6$-C$_{14}$)bicycloalkyl group above is understood to appear as follows

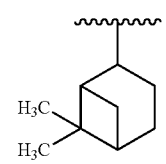

The phrase "tetrazolyl group" means

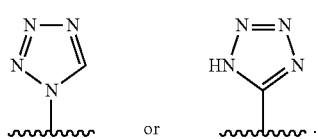 [SMILES: *n1cnnn1 ; *c1nnn[nH]1]

In one embodiment, the tetrazolyl group is

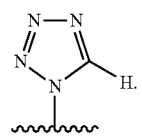

In another embodiment, the tetrazolyl group is

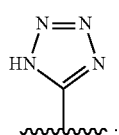

When a first group is "substituted with one or more" second groups, one or more hydrogen atoms of the first group is replaced with a corresponding number of second groups. When the number of second groups is two or greater, each second group can be the same or different. In one embodiment, a first group is substituted with up to three second groups. In another embodiment, a first group is substituted with one or two second groups. In another embodiment, a first group is substituted with two second groups. In another embodiment, a first group is substituted with two second groups and each second group is identical. In another embodiment, a first group is substituted with only one second group.

The term "animal" includes, but is not limited to, a human or a non-human animal, such as a companion animal or livestock, e.g., a cow, monkey, baboon, chimpanzee, horse, sheep, pig, chicken, turkey, quail, cat, dog, mouse, rat, rabbit or guinea pig.

The phrase "pharmaceutically acceptable derivative", as used herein, includes any pharmaceutically acceptable salt, solvate, prodrug, radiolabeled form, stereoisomer, enantiomer, diastereomer, other stereoisomeric form, racemic mixture, geometric isomer, and/or tautomer, e.g., of a Phosphorus-Substituted Quinoxaline-Type Piperidine Compound of the disclosure.

In one embodiment, the pharmaceutically acceptable derivative is a pharmaceutically acceptable salt, solvate, prodrug, radiolabeled form, stereoisomer, enantiomer, diastereomer, other stereoisomeric form, racemic mixture, geometric isomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, solvate, radiolabeled form, stereoisomer, enantiomer, diastereomer, other stereoisomeric form, racemic mixture, geometric isomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, radiolabeled form, stereoisomer, enantiomer, diastereomer, other stereoisomeric form, racemic mixture, geometric isomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, radiolabeled form, stereoisomer, geometric isomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, solvate, stereoisomer, enantiomer, diastereomer, other stereoisomeric form, racemic mixture, geometric isomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, solvate, stereoisomer, geometric isomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, stereoisomer, geometric isomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, stereoisomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, stereoisomer, and/or tautomer, e.g., of a Phosphorus-Substituted Quinoxaline-Type Piperidine Compound of the disclosure. In another embodiment, the pharmaceutically acceptable derivative is a pharmaceutically acceptable salt, e.g., of a Phosphorus-Substituted Quinoxaline-Type Piperidine Compound of the disclosure. In another embodiment, the pharmaceutically acceptable derivative is a solvate, e.g., of a Phosphorus-Substituted Quinoxaline-Type Piperidine Compound of the disclosure. In another embodiment, the pharmaceutically acceptable derivative is a prodrug, e.g., of a Phosphorus-Substituted Quinoxaline-Type Piperidine Compound of the disclosure. In another embodiment, the pharmaceutically acceptable derivative is a radiolabeled form, e.g., of a Phosphorus-Substituted Quinoxaline-Type Piperidine Compound of the disclosure. In another embodiment, the pharmaceutically acceptable derivative is a stereoisomer, e.g., of a Phosphorus-Substituted Quinoxaline-Type Piperidine Compound of the disclosure. In another embodiment, the pharmaceutically acceptable derivative is an enantiomer, e.g., of a Phosphorus-Substituted Quinoxaline-Type Piperidine Compound of the disclosure. In another embodiment, the pharmaceutically acceptable derivative is a diastereomer, e.g., of a Phosphorus-Substituted Quinoxaline-Type Piperidine Compound of the disclosure. In another embodiment, the pharmaceutically acceptable derivative is a stereoisomeric form other than a stereoisomer, an enantiomer and a diastereomer, e.g., of a Phosphorus-Substituted Quinoxaline-Type Piperidine Compound of the disclosure. In another embodiment, the pharmaceutically acceptable derivative is a racemic mixture, e.g., of a Phosphorus-Substituted Quinoxaline-Type Piperidine Compound of the disclosure. In another embodiment, the pharmaceutically acceptable derivative is a geometric isomer, e.g., of a Phosphorus-Substituted Quinoxaline-Type Piperidine Compound of the disclosure. In another embodiment, the pharmaceutically acceptable derivative is a tautomer, e.g., of a Phosphorus-Substituted Quinoxaline-Type Piperidine Compound of the disclosure.

The phrase "pharmaceutically acceptable salt", as used herein, is any pharmaceutically acceptable salt that can be prepared from a Phosphorus-Substituted Quinoxaline-Type Piperidine Compound including a salt formed from an acid and a basic functional group, such as a nitrogen group, of a Phosphorus-Substituted Quinoxaline-Type Piperidine Compound. Illustrative salts include, but are not limited, to sulfate, citrate, acetate, trifluoroacetate, oxalate, chloride, bromide, iodide, nitrate, bisulfate, phosphate, acid phosphate, isonicotinate, lactate, salicylate, acid citrate, tartrate, oleate, tannate, pantothenate, bitartrate, ascorbate, succinate, maleate, gentisinate, fumarate, gluconate, glucoronate, saccharate, formate, benzoate, glutamate, methanesulfonate, ethanesulfonate, benzenesulfonate, p-toluenesulfonate, and pamoate (i.e., 1,1'-methylene-bis-(2-hydroxy-3-naphthoate)) salts. The term "pharmaceutically acceptable salt" also includes a salt prepared from a Phosphorus-Substituted Quinoxaline-Type Piperidine Compound having an acidic functional group, such as a carboxylic acid functional group, and a pharmaceutically acceptable inorganic or organic base. Suitable bases include, but are not limited to, hydroxides of alkali metals such as sodium, potassium, cesium, and lithium; hydroxides of alkaline earth metal such as calcium and magnesium; hydroxides of other metals, such as aluminum and zinc; ammonia and organic amines, such as unsubstituted or hydroxy-substituted mono-, di-, or trialkylamines; dicyclohexylamine; tributyl amine; pyridine; picoline; N-methyl-N-ethylamine; diethylamine; triethylamine; mono-, bis-, or tris-(2-hydroxy-($C_1$-$C_3$)alkyl amines), such as mono-, bis-, or tris-(2-hydroxyethyl)amine, 2-hydroxy-tert-butylamine, or tris-(hydroxymethyl)methylamine, N,N-di-[($C_1$-$C_3$)alkyl]-N-(hydroxy-($C_1$-$C_3$)alkyl)-amines, such as N,N-dimethyl-N-(2-hydroxyethyl)amine, or tri-(2-hydroxyethyl)amine; N-methyl-D-glucamine; and amino acids such as arginine, lysine, and the like. In one embodiment, the pharmaceutically acceptable salt is a hydrochloride-salt, a sulfate-salt, a sodium-salt, a potassium-salt, a benzene sulfonic acid-salt, a para-toluenesulfonic acid-salt, or a fumaric acid-salt. In another embodiment, the pharmaceutically acceptable salt is a hydrochloride-salt or a sulfate-salt. In another embodiment, the pharmaceutically acceptable salt is a hydrochloride-salt. In another embodiment, the pharmaceutically acceptable salt is a sulfate-salt. In another embodiment, the pharmaceutically acceptable salt is a sodium-salt. In another embodiment, the pharmaceutically acceptable salt is a potassium-salt. In another embodiment, the pharmaceutically acceptable salt is a para-toluenesulfonic acid-salt. In another embodiment, the pharmaceutically acceptable salt is a fumaric acid-salt. In another embodiment, the pharmaceutically acceptable fumaric acid-salt contains about one equivalent of a Phosphorus-Substituted Quinoxaline-Type Piperidine Compound and about 0.5 equivalents of fumaric acid, e.g., from about 0.3 to about 0.7 equivalents of fumaric acid in one embodiment, from about 0.4 to about 0.6 equivalents of fumaric acid in another embodiment, from about 0.44 to about 0.56 equivalents of fumaric acid in another embodiment, or from about 0.47 to about 0.53 equivalents of fumaric acid in another embodiment. In another embodiment, the pharmaceutically acceptable fumaric acid-salt contains one equivalent of a Phosphorus-Substituted Quinoxaline-Type Piperidine Compound and 0.5 equivalents of fumaric acid. One skilled in the art will recognize that, e.g., acid addition salts, of a Phosphorus-Substituted Quinoxaline-Type Piperidine Compound can be prepared by reaction of the compounds with the appropriate acid by a variety of known methods.

The compounds of the disclosure provided herein also encompass all solvates of the Phosphorus-Substituted Quinoxaline-Type Piperidine Compounds. "Solvates" are known in the art and are considered to be a combination, physical association and/or solvation of a Phosphorus-Substituted Quinoxaline-Type Piperidine Compound with a solvent molecule, e.g., a disolvate, monosolvate or hemisolvate when the solvent molecule:Phosphorus-Substituted Quinoxaline-Type Piperidine Compound molecule molar ratio is 2:1, 1:1 or 1:2, respectively. This physical association involves varying degrees of ionic and covalent bonding, including hydrogen bonding. In certain instances, the solvate can be isolated, for example when one or more solvent molecules are incorporated into the crystal lattice of a crystalline solid. Thus, "solvate", as used herein, encompasses both solution-phase and isolatable solvates. A Phosphorus-Substituted Quinoxaline-Type Piperidine Compound of the disclosure can be present as a solvated form with a pharmaceutically acceptable solvent, such as water, methanol, ethanol, and the like, and it is intended that the disclosure include both solvated and unsolvated Phosphorus-Substituted Quinoxaline-Type Piperidine Compound forms. As "hydrate" relates to a particular subgroup of solvates, i.e., where the solvent molecule is water, hydrates are included within the solvates of the disclosure.

Preparation of solvates is known in the art. For example, Caira et al., "Preparation and Crystal Characterization of a Polymorph, a Monohydrate, and an Ethyl Acetate Solvate of the Antifungal Fluconazole," *J. Pharmaceut. Sci.,* 93(3): 601-611 (2004), describes the preparation of solvates of fluconazole with ethyl acetate and with water. Similar preparations of solvates, hemisolvate, hydrates, and the like are described by Van Tonder et al., "Preparation and Physicochemical Characterization of 5 Niclosamide Solvates and 1 Hemisolvate," *AAPS Pharm. Sci. Tech.,* 5(1):Article 12 (2004), and Bingham et al., "Over one hundred solvates of sulfathiazole," *Chem. Comm.,* pp. 603-604 (2001). In one embodiment, a non-limiting, process involves dissolving the Phosphorus-Substituted Quinoxaline-Type Piperidine Compound in a desired amount of the desired solvent (organic, water or mixtures thereof) at temperatures above about 20° C. to about 25° C., cooling the solution at a rate sufficient to form crystals, and isolating the crystals by known methods, e.g., filtration. Analytical techniques, for example, infrared spectroscopy, can be used to show the presence of the solvent in a crystal of the solvate.

The compounds disclosed herein also comprise all prodrugs of the Phosphorus-Substituted Quinoxaline-Type Piperidine Compounds. "Prodrugs" are known in the art and, while not necessarily possessing any pharmaceutical activity as such, are considered to be any covalently bonded carrier(s) that releases the active parent drug in vivo. In general, such prodrugs will be a functional derivative of a Phosphorus-Substituted Quinoxaline-Type Piperidine Compound of Formula (I) which is readily convertible in vivo, e.g., by being metabolized, into the required Phosphorus-Substituted Quinoxaline-Type Piperidine Compound of Formula (I). Conventional procedures for the selection and preparation of suitable prodrug derivatives are described in, for example, Bundgaard, ed., *Design of Prodrugs,* Elsevier, Amsterdam (1985); Colowick et al., "Drug and Enzyme Targeting, Part A," Widder et al., eds., *Methods in Enzymology,* Vol. 112, Academic Press (1985); Bundgaard, "Design and Application of Prodrugs," *A Textbook of Drug Design and Development,* Krogsgaard-Larsen and Bundgaard, eds., Harwood Academic Publishers, Chapter 5, pp. 113-191 (1991); Bundgaard et al., "(C) Means to Enhance Penetration (1) Prodrugs as a means to improve the delivery of peptide drugs," *Adv. Drug Delivery Revs.* 8:1-38 (1992); Bundgaard et al., "Glycolamide Esters as Biolabile Prodrugs of Carboxylic Acid Agents: Synthesis, Stability, Bioconversion, and Physicochemical Properties," *J. Pharmaceut. Sci.* 77(4):285-298 (1988); and Kakeya et al., "Studies on Prodrugs of Cephalosporins. I. Synthesis and Biological Properties of Glycyloxygenzoyloxymethyl and Glycylaminobenzoyloxymethyl Esters of 7β-[2-(2-Aminothiazol-4-yl)-(Z)-2-methoxyiminoacetamido]3-methyl-3-cephem-4-carboxylic Acid," *Chem. Pharm. Bull.* 32:692-698 (1984).

In addition, one or more hydrogen, carbon or other atoms of a Phosphorus-Substituted Quinoxaline-Type Piperidine Compound can be replaced by a radioactive isotope of the hydrogen, carbon or other atoms. Such a "radiolabeled", "radiolabeled form", and the like of a Phosphorus-Substituted Quinoxaline-Type Piperidine Compound, each of which is encompassed by the disclosure, is useful as a research and/or diagnostic tool in metabolism pharmacokinetic studies and in binding assays. "Radioactive", as used herein with respect to an atom, means an atom that comprises a radioactive atom and therefore the specific radioactivity thereof is above the background level of radioactivity. Examples of radioactive isotopes that can be incorporated into a Phosphorus-Substituted Quinoxaline- Type Piperidine Compound of the disclosure include isotopes of hydrogen, carbon, nitrogen, oxygen, phosphorous, sulfur, fluorine, chlorine, bromine, and iodine, such as $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I, respectively. In one embodiment, a radiolabeled Phosphorus-Substituted Quinoxaline-Type Piperidine Compound contains 1, 2, 3, 4, or more radioactive isotopes, each of which is independently selected from hydrogen, carbon, nitrogen, oxygen, phosphorous, sulfur, fluorine, chlorine, bromine, and iodine. In another embodiment, a radiolabeled Phosphorus-Substituted Quinoxaline-Type Piperidine Compound contains 1 or 2 radioactive isotopes, each of which is independently selected from hydrogen, carbon, nitrogen, oxygen, phosphorous, sulfur, fluorine, chlorine, bromine, and iodine. In another embodiment, a radiolabeled Phosphorus-Substituted Quinoxaline-Type Piperidine Compound contains 1 radioactive isotope which is selected from hydrogen; carbon, nitrogen, oxygen, phosphorous, sulfur, fluorine, chlorine, bromine, and iodine. In another embodiment, a radiolabeled Phosphorus-Substituted Quinoxaline-Type Piperidine Compound contains 1, 2, 3, 4, or more radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Phosphorus-Substituted Quinoxaline-Type Piperidine Compound contains 1 or 2 radioactive isotopes, each of which is independently selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Phosphorus-Substituted Quinoxaline-Type Piperidine Compound contains 1 radioactive isotope which is selected from $^2$H, $^3$H, $^{11}$C, $^{13}$C, $^{14}$C, $^{15}$N, $^{17}$O, $^{18}$O, $^{31}$P, $^{32}$P, $^{35}$S, $^{18}$F, $^{19}$F, $^{36}$Cl, $^{37}$Cl, $^{76}$Br, $^{77}$Br, $^{81}$Br, $^{123}$I, $^{124}$I, $^{125}$I, and $^{131}$I. In another embodiment, a radiolabeled Phosphorus-Substituted Quinoxaline-Type Piperidine Compound contains 1, 2, 3, 4, or more radioactive isotopes, each of which is independently selected from $^2$H, $^3$H, $^{13}$C, $^{14}$C, $^{15}$N, $^{18}$O, $^{32}$P, and $^{125}$I. In another embodiment, a radiolabeled Phosphorus-Substituted Quinoxaline-Type Piperidine Compound contains 1 or 2 radioactive isotopes, each of which is independently selected from $^3$H, $^{14}$C, $^{15}$N, $^{18}$O, $^{32}$P, and $^{125}$I. In another embodiment, a radiolabeled Phosphorus-Substituted Quinoxaline-Type Piperidine Compound contains 1 radioactive isotope which is selected from $^3$H, $^{14}$C, $^{15}$N, $^{18}$O, $^{32}$P, and $^{125}$I.

Radiolabeled compounds of the disclosure can be prepared by methods known in the art. For example, tritiated Phosphorus-Substituted Quinoxaline-Type Piperidine Compounds can be prepared by introducing tritium into the particular Phosphorus-Substituted Quinoxaline-Type Piperidine Compound, for example, by catalytic dehalogenation with tritium. This method can include reacting a suitably halogen-substituted precursor of a Phosphorus-Substituted Quinoxaline-Type Piperidine Compound with tritium gas in the presence of a suitable catalyst, for example, Pd/C, in the presence or absence of a base. Other suitable methods for preparing tritiated compounds can be found in Filer, "The Preparation and Characterization of Tritiated Neurochemicals," *Isotopes in the Physical and Biomedical Sciences, Vol. 1, Labeled Compounds (Part A)*, E. Buncel et al, eds., Chapter 6, pp. 155-192 (1987). $^{14}$C-labeled compounds can be prepared by employing starting materials having a $^{14}$C carbon. Compounds containing piperazine isotopically enriched with $^{13}$C and/or $^{15}$N can be prepared as described in, e.g., FIG. 5A and the associated description, of U.S. Pat. No. 7,355,045 B2. Radiolabeled compounds containing $^{18}$F at the 6-position of an aniline ring can be prepared as described in column 27 of U.S. Pat. No. 6,562,319 B2.

A Phosphorus-Substituted Quinoxaline-Type Piperidine Compound can contain one or more asymmetric centers and can thus give rise to enantiomers, diastereomers, and other stereoisomeric forms. Unless specifically otherwise indicated, the disclosure encompasses compounds with all such possible forms as well as their racemic and resolved forms or any mixture thereof. The art recognizes that a geometric isomer is encompassed by a stereoisomer (See, e.g., the definitions of "stereoisomers" and "cis-trans isomers" appearing in the IUPAC Compendium of Chemical Terminology, $2^{nd}$ Ed. (the "Gold Book"), McNaught et al., eds., Blackwell Scientific Publications, Oxford (1997)). When a Phosphorus-Substituted Quinoxaline-Type Piperidine Compound contains an olefinic double bond or other center of geometric asymmetry, and unless specifically otherwise indicated, it is intended to include all "geometric isomers", e.g., both E and Z geometric isomers. Unless specifically otherwise indicated, all "tautomers", e.g., ketone-enol, amide-imidic acid, lactam-lactim, enamine-imine, amine-imine, and enamine-enimine tautomers, are intended to be encompassed by the disclosure as well.

As used herein, the terms "stereoisomer", "stereoisomeric form", and the like are general terms for all isomers of individual molecules that differ only in the orientation of their atoms in space. It includes enantiomers and isomers of compounds with more than one chiral center that are not mirror images of one another ("diastereomers").

The term "chiral center" refers to a carbon atom to which four different groups are attached.

The term "enantiomer" or "enantiomeric" refers to a molecule that is nonsuperimposeable on its mirror image and hence optically active where the enantiomer rotates the plane of polarized light in one direction and its mirror image rotates the plane of polarized light in the opposite direction.

The term "racemic" refers to a mixture of equal parts of enantiomers which is optically inactive.

The term "resolution" refers to the separation or concentration or depletion of one of the two enantiomeric forms of a molecule. Optical isomers of a Phosphorus-Substituted Quinoxaline-Type Piperidine Compound can be obtained by known techniques such as chiral chromatography or formation of diastereomeric salts from an optically active acid or base.

Optical purity can be stated in terms of enantiomeric excess (% ee), which is determined by the formula:

$$\% \ ee = \left[ \frac{\text{major enantiomer(mol)} - \text{minor enantiomer(mol)}}{\text{major enantiomer(mol)} + \text{minor enantiomer(mol)}} \right] \times 100\%.$$

The term "MeOH" means methanol, i.e., methyl alcohol. The term "EtOH" means ethanol, i.e., ethyl alcohol. The term "Et$_2$O" means diethyl ether, i.e., ethoxyethane. The term "THF" means tetrahydrofuran. The term "DMF" means N,N-dimethylformamide. The term "DCM" means methylene chloride, i.e., dichloromethane or $CH_2Cl_2$. The term "DCE" means 1,2-dichloroethane. The term "EtOAc" means ethyl acetate. The term "MeCN" means acetonitrile. The term "DMSO" means dimethylsulfoxide, i.e., methylsulfinylmethane. The term "MTBE" means tert-butyl methyl ether, i.e., 2-methoxy-2-methylpropane. The term "AcOH" means acetic acid. The term "TEA" means triethylamine. The term "DIEA" means N,N-di-iso-propylethylamine or N-ethyl-N-iso-propylpropan-2-amine. The term "TMSBr" means trimethylsilyl bromide, i.e., bromotrimethylsilane. The term "TMSCl" means trimethylsilylchloride or $(CH_3)_3SiCl$. The term "Bn" means benzyl, i.e.:

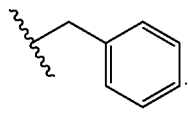 [SMILES: *Cc1ccccc1]

The term "BOC" means tert-butyloxycarbonyl, i.e.:

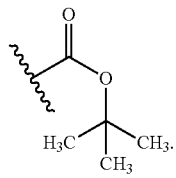 [SMILES: *C(=O)OC(C)(C)C]

The term "mesylate" means:

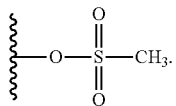

The term "tosylate" means:

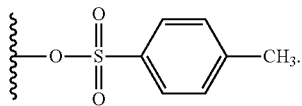 [SMILES: *OS(=O)(=O)c1ccc(C)cc1]

The term "IBD" means inflammatory-bowel disease. The term "IBS" means irritable-bowel syndrome. The term "ALS" means amyotrophic lateral sclerosis.

The phrase "effective amount", when used in connection with a Phosphorus-Substituted Quinoxaline-Type Piperidine Compound, means an amount effective for: (a) treating or preventing a Condition or symptom thereof; (b) detectably inhibiting ORL-1 receptor function in a cell; or (c) detectably activating ORL-1 receptor function in a cell.

The phrase "effective amount", when used in connection with a second therapeutic agent means an amount for providing the therapeutic effect of the second therapeutic agent.

The terms "modulate", "modulating", and the like as used herein with respect to the ORL-1 receptor mean the mediation of a pharmacodynamic response (e.g., analgesia) in an animal from (i) inhibiting or activating the receptor, or (ii) directly or indirectly affecting the normal regulation of the receptor activity. Compounds that modulate the receptor activity include agonists, partial agonists, antagonists, mixed agonists/antagonists, mixed partial agonists/antagonists and compounds which directly or indirectly affect regulation of the receptor activity.

As used herein, a compound that binds to a receptor and mimics the regulatory effect(s) of an endogenous ligand is defined as an "agonist". As used herein, a compound that binds to a receptor and is only partly effective as an agonist is defined as a "partial agonist". As used herein, a compound that binds to a receptor but produces no regulatory effect, but rather blocks binding of another agent to the receptor is defined as an "antagonist". (See Ross et al., "Pharmacodynamics: Mechanisms of Drug Action and the Relationship Between Drug Concentration and Effect," in *Goodman & Gilman's The Pharmacological Basis of Therapeutics* pp. 31-43 (Goodman et al., eds., 10th ed., McGraw-Hill, New York 2001)).

The phrases "treatment of", "treating", and the like include the amelioration or cessation of a Condition or a symptom thereof. In one embodiment, treating includes inhibiting, for example, decreasing the overall frequency of episodes of a Condition or a symptom thereof.

The phrases "prevention of", "preventing", and the like include the avoidance of the onset of a Condition or a symptom thereof.

A "disorder" includes, but is not limited to, the Conditions defined above.

In the event of doubt as to the agreement of a depicted chemical structure and a chemical name, the depicted chemical structure governs.

It is appreciated that various features of the disclosure which are, for clarity, described in the context of separate embodiments, can also be provided in combination in a single embodiment unless otherwise specifically herein excluded. Conversely, various features of the disclosure which are, for brevity, described in the context of a single embodiment, can also be provided separately and/or in any suitable subcombination unless otherwise specifically herein excluded.

4.3 Methods for Making the Phosphorus-Substituted Quinoxaline-Type Piperidine Compounds The Phosphorus-Substituted Quinoxaline-Type Piperidine Compounds can be made using conventional organic synthesis, in view of the present disclosure, and including the following illustrative methods shown in the schemes below where $R_1$, $R_2$, $R_3$, $R_4$, $R_9$, Q, $Y_1$, Y, Z, A, B, a, x, and the dashed line are defined above, L is a halogen leaving group such as Br or I, L' is F or Cl, R is —$(C_1$-$C_4)$alkyl or —$CF_3$, and R' is —$(C_1$-$C_4)$alkyl. For simplicity, in the following schemes the exemplary Q group is benzo which is sometimes unsubstituted with $R_2$; however, the schemes are also applicable to substituted benzo and any of the (5- or 6-membered)heteroaryl Q groups, whether unsubstituted or optionally substituted.

Scheme A

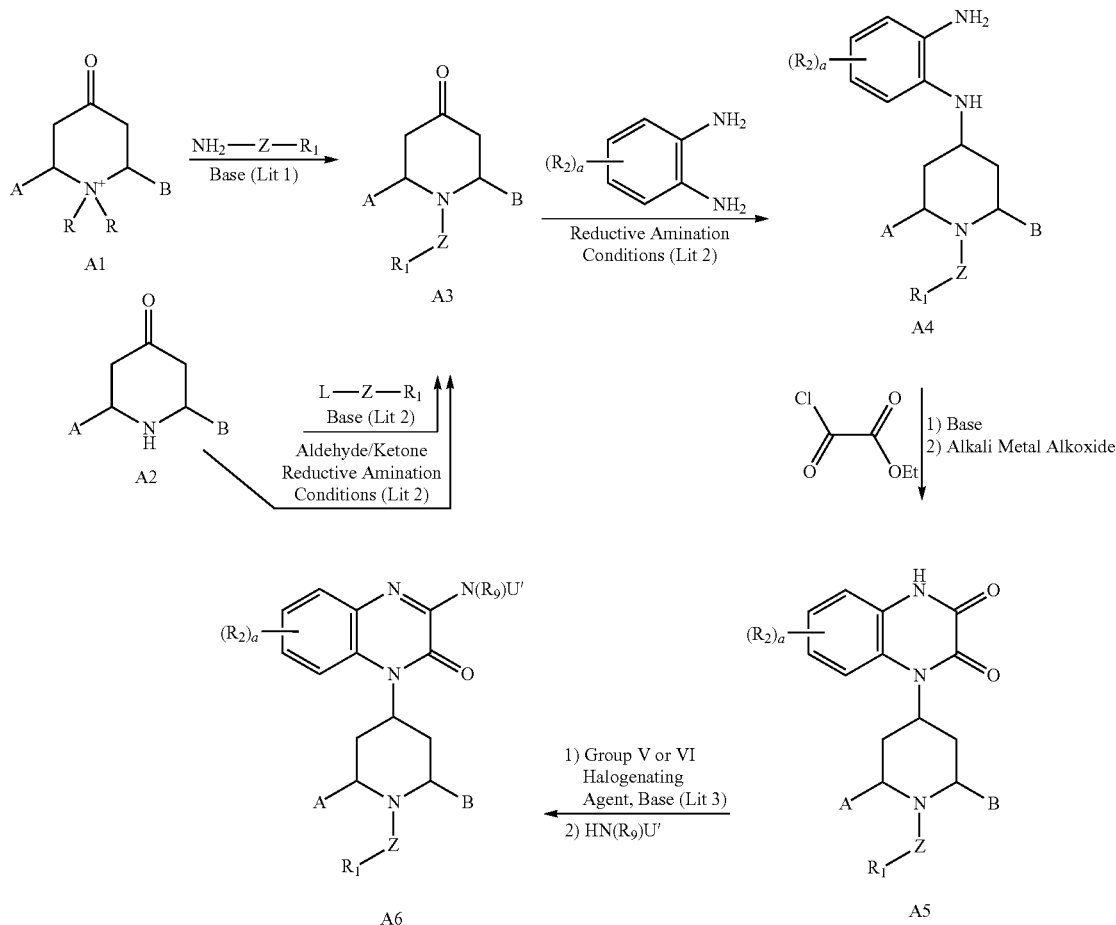

In Scheme A and the other schemes, "Lit 1" refers to the procedures described in the publications Tortolani et al., "A Convenient Synthesis to N-Aryl-Substituted 4-Piperidones," Org. Lett. 1:1261-1262 (1999) and/or International PCT Publication No. WO 2005/075459 A1 of Euro-Celtique S. A., "Lit 2" refers to the procedures described in U.S. Pat. No. 6,635,653 by Goehring et al., and "Lit 3" refers to the procedures described in the publication Dudash et al., "Synthesis and evaluation of 3-anilino-quinoxalinones as glycogen phosphorylase inhibitors," Bioorg. Med. Chem. Lett., 15(21):4790-4793 (2005).

Compounds of formula A1 and A2 are commercially available or can be prepared by methods known to the art.

A piperidinium salt of structure A1 can be reacted with a primary amine in a suitable solvent such as ethanol under reflux conditions in the presence of a base such as potassium carbonate as described in reference "Lit 1" to provide the 1-(substituted)piperidine-4-one Compound A3. As described in reference "Lit 2," Compound A3 can also be prepared by alkylation of a piperidine-4-one of structure A2 with an alkyl bromide or alkyl iodide in a suitable solvent such as dimethyl formamide, acetonitrile or dimethyl sulfoxide in the presence of an inorganic base such as potassium carbonate or an organic base such as diisopropylethylamine. As described in reference "Lit 2," Compound A3 can also be prepared by reductive amination of Compound A2 with an aldehyde or ketone using either sodium triacetoxyborohydride or sodium cyanoborohydride in a suitable solvent such as dichloromethane or methanol, respectively. Compound A3 can then be reductively aminated with a substituted or unsubstituted 1,2-phenylenediamine using sodium triacetoxyborohydride or sodium cyanoborohydride in a suitable solvent such as dichloromethane or methanol, respectively, to provide Compound A4, as described in reference "Lit 2." Compound A4 can be dissolved in a suitable solvent such as toluene and reacted with ethyl 2-chloro-2-oxoacetate in the presence of a base such as TEA followed by treatment with an alkali metal alkoxide such as sodium ethoxide in a suitable solvent such as methanol or ethanol to provide Compound A5. Compound A5 can be dissolved in a suitable solvent such as toluene and, as described in reference "Lit 3," reacted with a group V or VI halogenating agent, such as thionyl chloride, phosphorus oxychloride or phosphorus pentachloride, and a base such as diisopropylethylamine in which an intermediate, believed to comprise a 3-chloroquinoxalin-2-one, is formed then reacted with the desired amine, e.g., $HN(R_9)U'$, to provide Compound A6, as shown in Scheme A, where U' is —$U_3$—$U_4$—$U_5$—$U_6$—$U_7$—U, —$U_4$—$U_5$—$U_6$—$U_7$—U, —$U_5$—$U_6$—$U_7$—U, —$U_6$—$U_7$—U, —$U_7$—U, or —U.

Scheme B

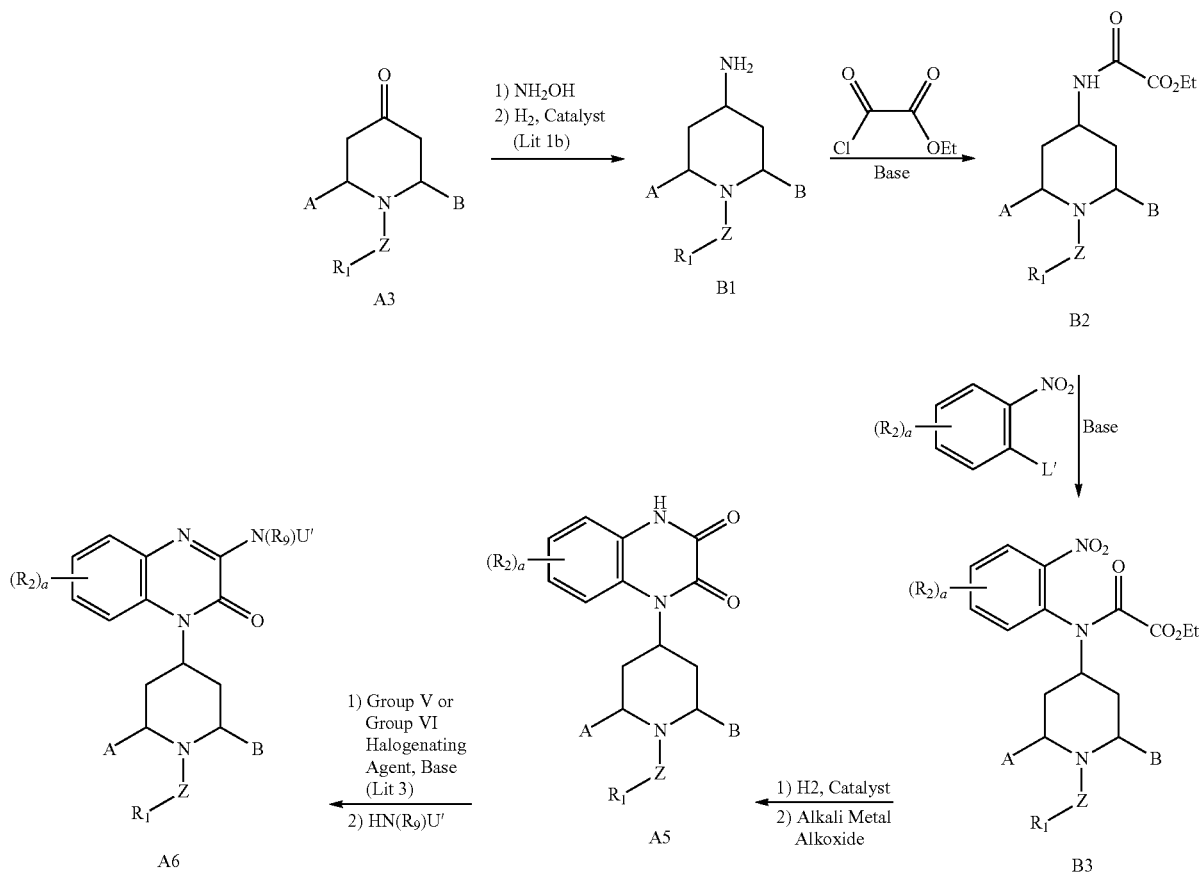

In Scheme B and the other schemes, "Lit 1b" refers to the procedures described in International PCT Publication No. WO 2005/075459 A1 of Euro-Celtique S.A.

As described in reference "Lit 1b," Compound A3 can be reacted with 50% aqueous hydroxylamine in a suitable solvent such as hexanes to provide an intermediate hydroxylamine which can be converted to an oxime by dehydration in a suitable solvent such as toluene under reflux conditions using a Dean-Stark apparatus. The oxime intermediate can be reduced to the primary amine Compound B1 by catalytic hydrogenation using a catalyst such as rhodium on alumina in a suitable solvent such as ethanol under a hydrogen atmosphere at a pressure of 1 atm or greater in a suitable apparatus such as a Parr Hydrogenator according to reference "Lit 1b." Compound B1 can be reacted with ethyl 2-chloro-2-oxoacetate in the presence of a base such as TEA to provide Compound B2. Compound B2 can be reacted with a substituted or unsubstituted 2-halo-1-nitrobenzene (where the halo is fluoride or chloride) in the presence of a base such as potassium carbonate in a suitable solvent such as acetonitrile under reflux conditions to provide Compound B3. Compound B3 can be treated with a hydrogenation catalyst such as Raney nickel in a suitable solvent such as ethanol under a hydrogen atmosphere, and the product immediately treated with an alkali metal alkoxide such as sodium ethoxide in a suitable solvent such as methanol or ethanol to provide Compound A5, which can be converted to Compound A6 as described in Scheme A.

Scheme C

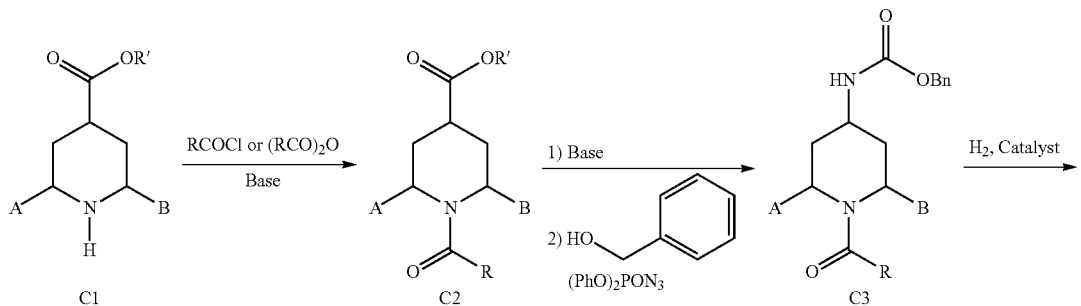

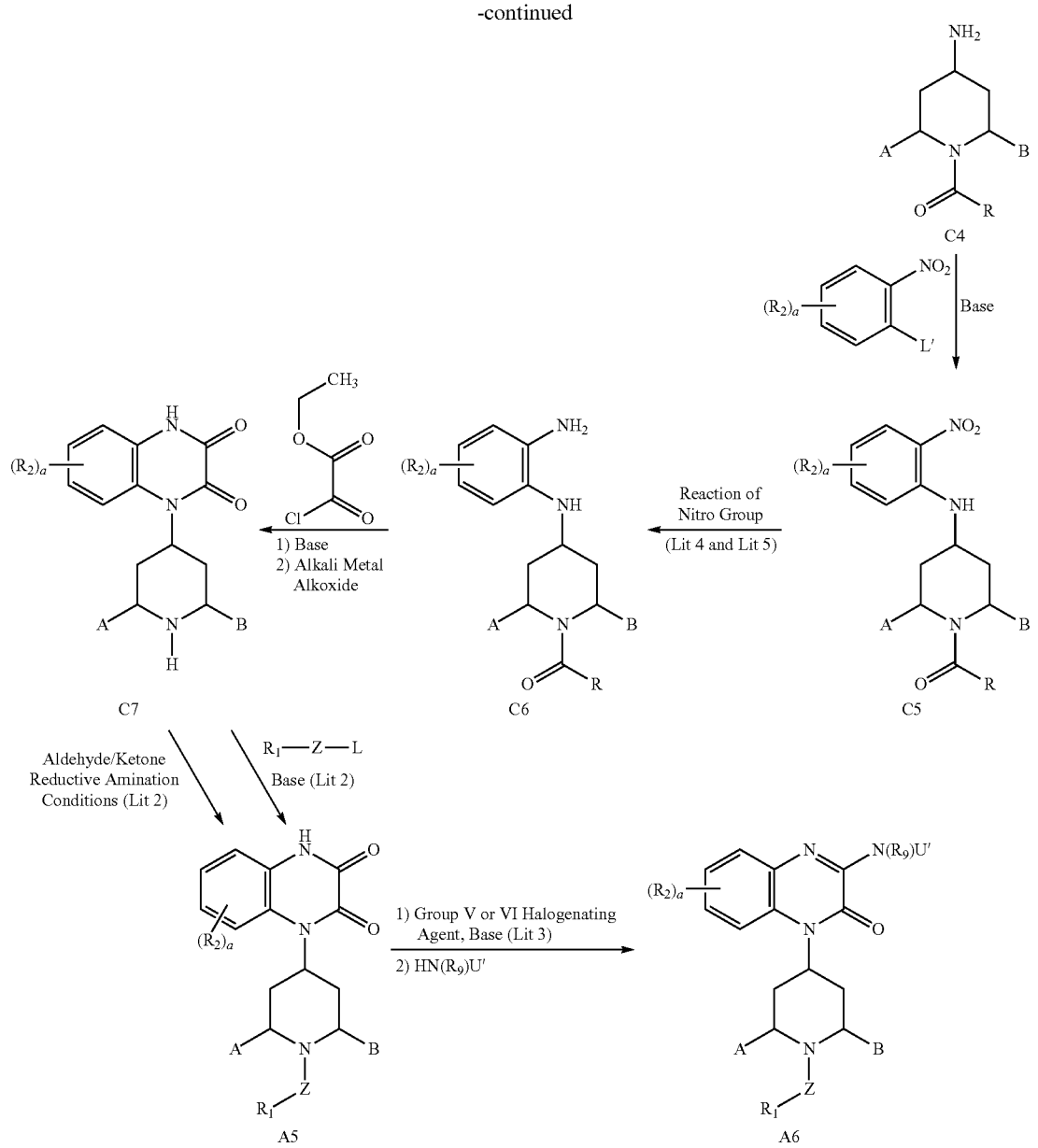

In Scheme C and the other schemes, "Lit 4" refers to the reference Rylander, "Hydrogenation of Nitro Compounds," in *Hydrogenation Methods* pp. 104-116 (Academic Press, London, 1985), which provides a review of the methods available for the reduction of nitro groups, and "Lit 5" refers to the Zinin reduction procedures described in the reference Porter, "The Zinin Reduction of Nitroarenes," *Org. Reactions,* 20:455-481 (1973).

Compound C1 is commercially available or can be prepared by methods known to the art. Compound C1 can be reacted with an acid chloride RC(=O)Cl, such as 2,2,2-trifluoroacetyl chloride, or anhydride (RC(=O))$_2$O, such as 2,2,2-trifluoroacetic anhydride, and a base such as TEA in a suitable solvent such as dichloromethane or tetrahydrofuran to provide Compound C2. Compound C2 can be converted to Compound C3 in a two step procedure by hydrolysis of the ester to the carboxylic acid using an appropriate base such as aqueous NaOH, followed by treatment with diphenyl phosphorazidate ("(PhO)$_2$P(=O)N$_3$") and phenylmethanol ("BnOH") under Curtius rearrangement conditions. The benzyloxycarbonyl group of Compound C3 can then be removed under hydrogenolysis conditions using a noble metal catalyst, e.g., palladium on carbon, under a hydrogen atmosphere, to provide Compound C4. Compound C4 can be reacted with a substituted or unsubstituted 2-halo-1-nitrobenzene (where the halo is fluoride or chloride) (similar to steps described in Scheme B) to provide Compound C5. In the next step, Compound C5 can be converted to Compound C6 using a catalyst such as Raney nickel in a suitable solvent such as ethanol under a hydrogen atmosphere as described in reference "Lit 4." Compound C5 can also be converted to Compound C6 by chemical means, such as with Zn, Sn(II) chloride or Fe, or using sulfides or polysulfides by the Zinin Reduction as described in reference "Lit 5." Compound C6 can then be treated with ethyl 2-chloro-2-oxoacetate and a base such as TEA in a suitable solvent such as toluene, followed by treatment with an alkali metal alkoxide such as sodium ethoxide in a suitable solvent such as ethanol to provide Compound C7. Compound A5 can be prepared by alkylation of Compound C7 with an alkyl bromide or alkyl iodide or by reductive amination of Compound C7 with an aldehyde or ketone, each as described in Scheme A. Thereafter, Compound A5 can be converted to Compound A6 as described in Scheme A.

such as ethanol under a hydrogen atmosphere, or by chemical means using a reducing agent such as Zn, Sn(II) chloride or Fe, or using sulfide or polysulfides by the Zinin Reduction as described in Scheme C. Thereafter (similar to steps described in Scheme A), Compound D4 can be treated with ethyl 2-chloro-2-oxoacetate in the presence of a base such as TEA followed by treatment with an alkali metal alkoxide such as sodium ethoxide in a suitable solvent such as ethanol

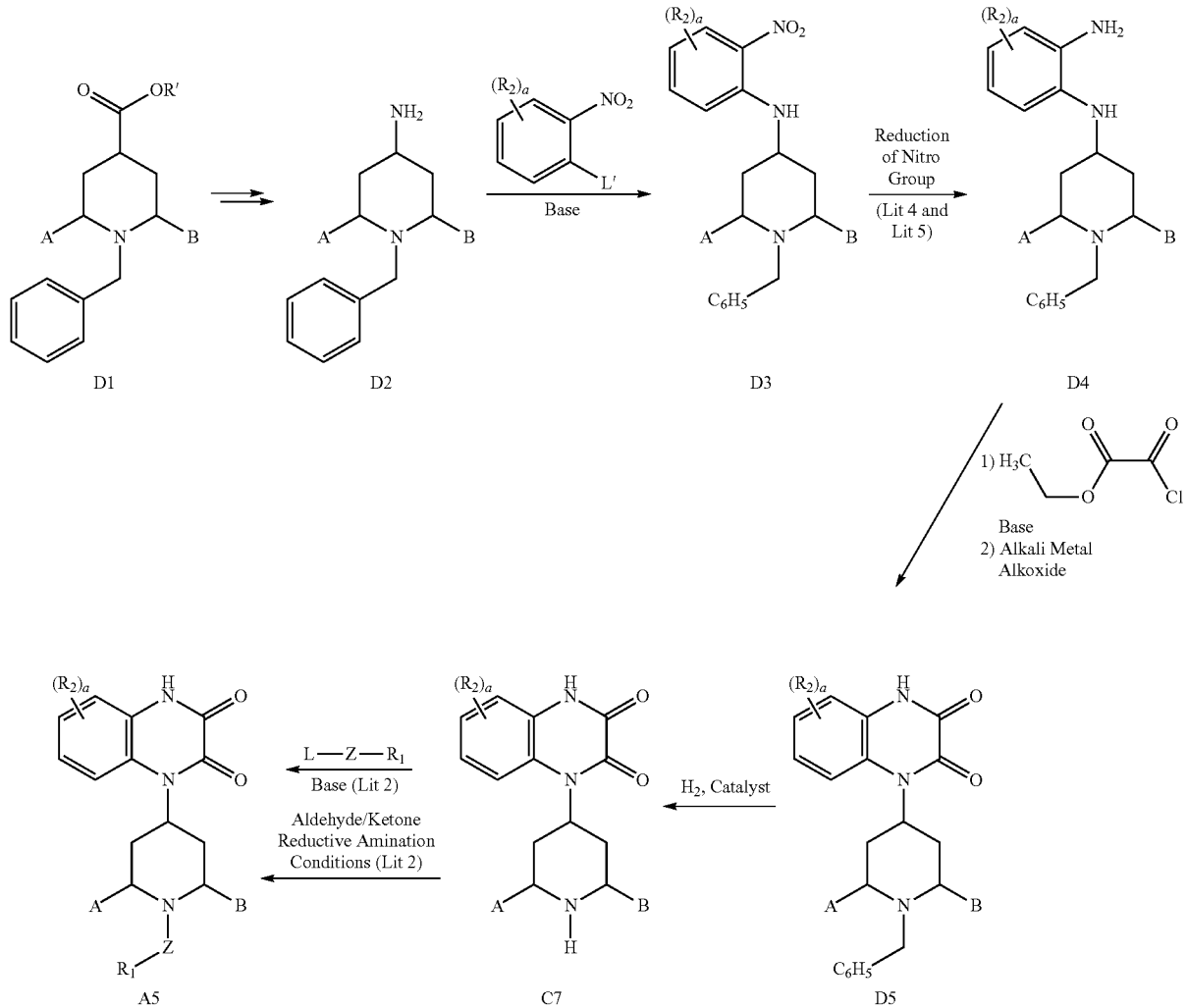

Scheme D

Compound D1 is commercially available or can be prepared from Compound C1 by methods known to the art. Compound D2 can be prepared from Compound D1 in a similar manner to the preparation of Compound C4 from Compound C1 in Scheme C. Compound D2 can be reacted with a substituted or unsubstituted 2-halo-1-nitrobenzene (where the halo is fluoride or chloride) (similar to steps described in Scheme B) to provide Compound D3. In the next step (similar to steps described in Scheme B), Compound D3 can be converted to Compound D4 by treatment with a hydrogenation catalyst such as Raney nickel in a suitable solvent to provide Compound D5. Compound D5 can be hydrogenolyzed using a noble metal catalyst, e.g., palladium on carbon, in a suitable solvent such as methanol or ethanol under a hydrogen atmosphere to provide Compound C7. Compound A5 can be prepared by alkylation of Compound C7 with an alkyl bromide or alkyl iodide or by reductive amination of Compound C7 with an aldehyde or ketone (similar to steps described in Scheme A). Thereafter, Compound A5 can be converted to Compound A6 as described in Scheme A.

Scheme E

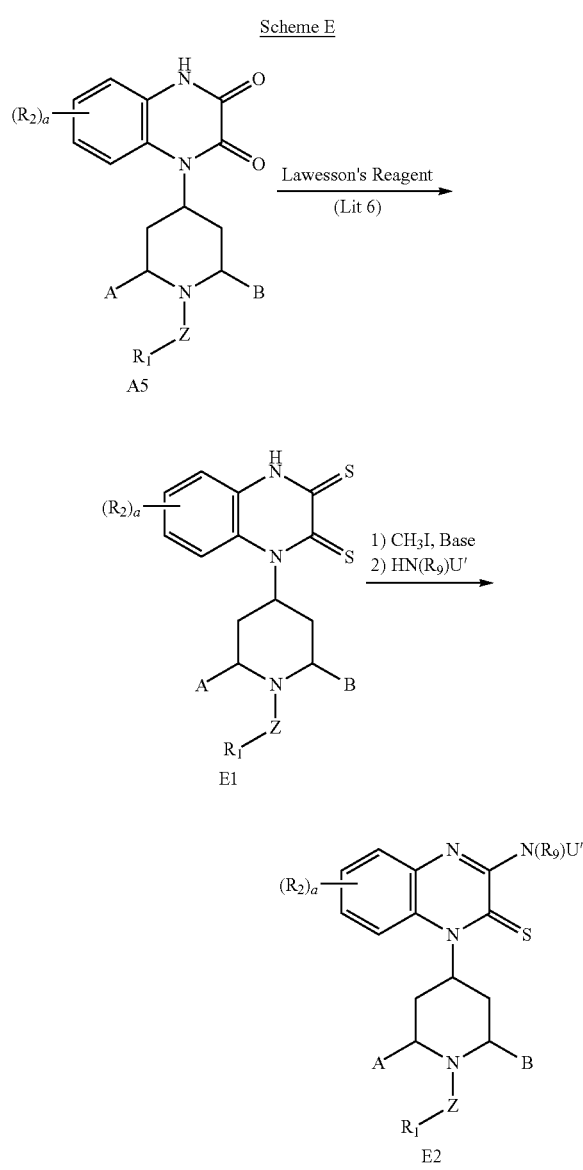

Scheme F

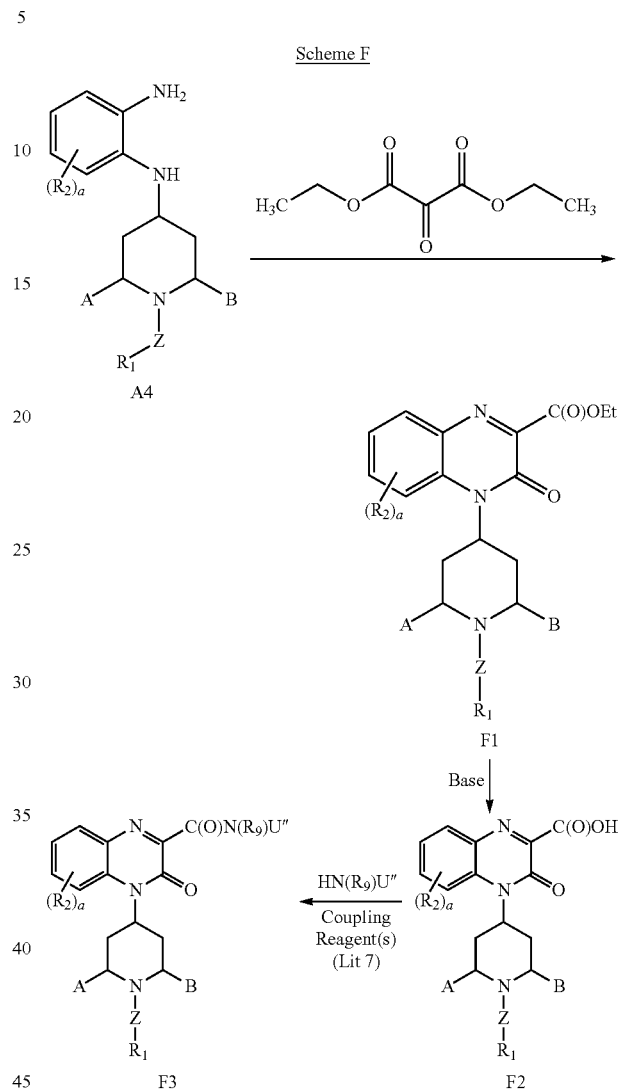

described in Scheme A for obtaining Compound A6 from Compound A5 except that methyl iodide is used in place of the group V or VI halogenating agent.

In Scheme E and the other schemes, "Lit 6" refers to the reference Perregaard et al., "Studies on Organophosphorus Compounds XVIII*. Oxidation of Tertiary Alicyclic Amines with Elemental Sulfur in Hexa-methylphosphoric Triamide (HMPA). Oxidative Rearrangements of Hexahy-Droazepines and Octahydroazocines to bis(3-Pyrrolyl)Polysulfides.," *Bull. Soc. Chim. Belg.* 86:679-691 (1977).

Compound E1, comprising a quinoxaline-2,3(1H,4H)-dithione, can be made by, e.g., reacting Compound A5 (i.e., comprising a quinoxaline-2,3(1H,4H)-dione) with Lawesson's reagent (i.e., 2,4-bis(4-methoxyphenyl)-1,3-dithia-2,4-diphosphetane-2,4-disulfide) according to the procedure described in reference "Lit 6." In one embodiment, Compound E1 can be made by reacting Compound A5 with Lawesson's reagent in a nonpolar solvent such as THF or toluene at a temperature of about 100° C. for about 2-3 hours, as shown above. Thereafter, Compound E2 can be obtained from Compound E1 in an analogous manner as In Scheme F and the other schemes, "Lit 7" refers to the references Sweet et al., "Synthesis of an Affinity Chromatography Column Designed for Recovery of Labile Proteins," *Biochem. Biophys. Res. Comm.* 63(1):99-105 (1975) and/or Keeton et al., "Specific and Sensitive Radioimmunoassay for 3-Methoxy-4-hydroxyphenylethyleneglycol (MOPEG)," *Science* 211:586-588 (1981).

Compound A4 and diethyl 2-oxomalonate can be dissolved in a solvent with a high boiling point, such as toluene or xylene, and heated under reflux conditions with azeotropic removal of water to provide Compound F1. Compound F1 can be hydrolyzed to the carboxylic acid F2 by treatment with a base, such as aqueous NaOH, in a solvent under appropriate conditions, such as methanol or ethanol at a temperature from about 0° C. to about 25° C. Upon completion of hydrolysis, the reaction mixture is neutralized, e.g., with dilute HCl, to provide Compound F2. Compound F2 can be converted to amide derivative F3 by treatment with a coupling agent, such as N-(3,3-dimethylaminopropyl)-N'-ethylcarbodiimide and TEA, and the desired amine, e.g., HN(R_9)U" shown in the scheme where U" is —$U_5$—$U_6$—$U_7$—U, —$U_6$—$U_7$—U, —$U_7$—U, or —U, in a solvent, such as DMF, to provide Compound F3, e.g., according to the procedure described in reference "Lit 7."

Compound G1 can be obtained, for example, by chlorinating Compound A5, e.g., by adding a group V or VI halogenating agent such as thionyl chloride, phosphorus oxychloride or phosphorus pentachloride, to a mixture of Compound A5, DMF, and a base such as TEA in a solvent with a high boiling point, such as toluene or xylene, under reflux conditions such as is described in reference "Lit 3." Compound G1 can be converted to Compound G2 by reacting the former with the desired U'O⁻ salt where U' is as defined above, e.g., a sodium alkoxide, in a solvent, such as tetrahydrofuran, DMF or an alcohol of the alkoxide, to provide Compound G2. In a similar manner but with the desired U'S⁻ salt, e.g., a sodium thioalkoxide, Compound G1 can be converted to Compound G3 in a suitable solvent.

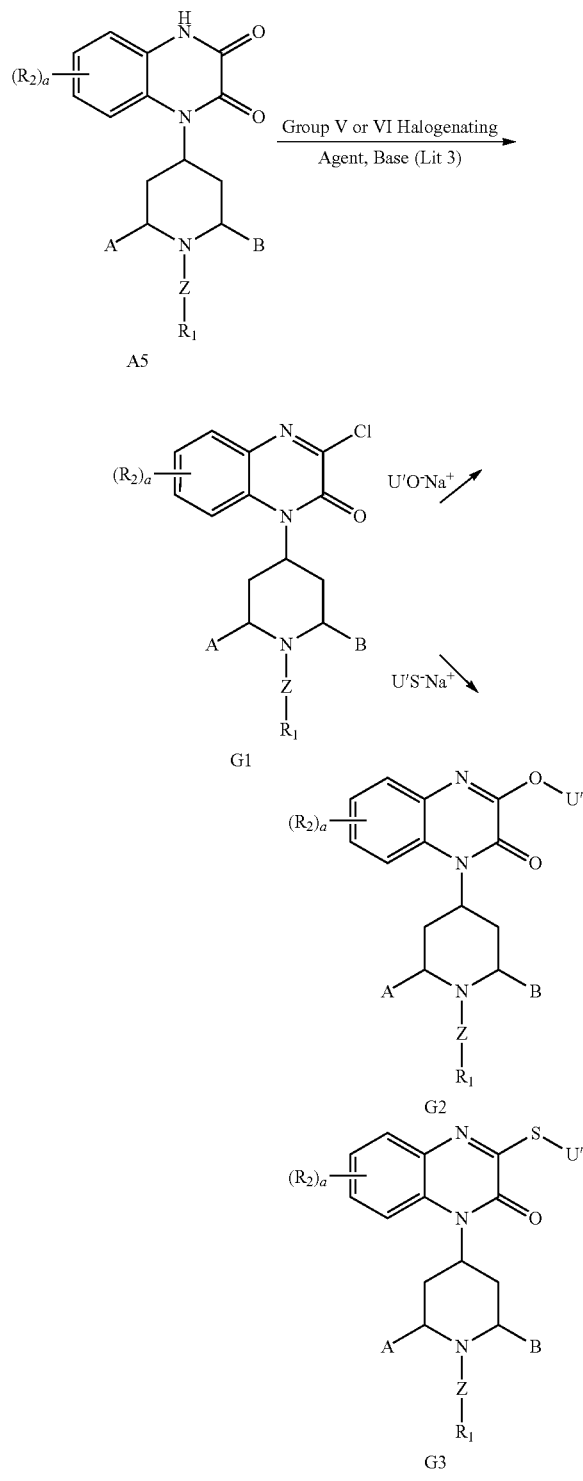

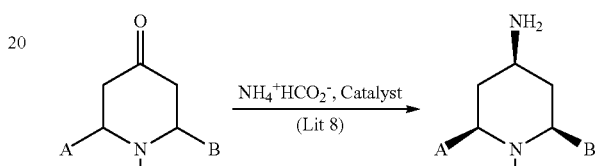

In Scheme H and the other schemes, "Lit 8" refers to Berdini et al., "A modified palladium catalysed reductive amination procedure," *Tetrahedron* 58:5669-5674 (2002) and "Lit 9" refers to Lewin et al., "Molecular Features Associated with Polyamine Modulation of NMDA Receptors," *J. Med. Chem.* 41:988-995 (1998).

Compound H1, wherein substituent groups A and B together form a bridge, e.g., a two carbon bridge, is commercially available or can be prepared by methods known to the art.

When substituent groups A and B together form a bridge, e.g., a two carbon bridge, Compound H1 can be converted to Compound H2, the "endo" isomer, under reductive amination conditions using, e.g., ammonium formate and a noble metal catalyst, e.g., palladium on carbon, in a solvent such as ethanol or methanol as described in reference "Lit 8." Similarly, where substituent groups A and B together form a bridge, e.g., a two carbon bridge, Compound H1 can be reacted with aqueous hydroxylamine in a solvent such as hexanes to form an intermediate hydroxylamine, which can be converted to its oxime by dehydration in a solvent with a high boiling point such as toluene, under Dean-stark conditions. The oxime intermediate can be converted to Compound H3, the "exo" isomer, by reduction using, e.g., sodium in propanol as described in reference "Lit 9."

Scheme I

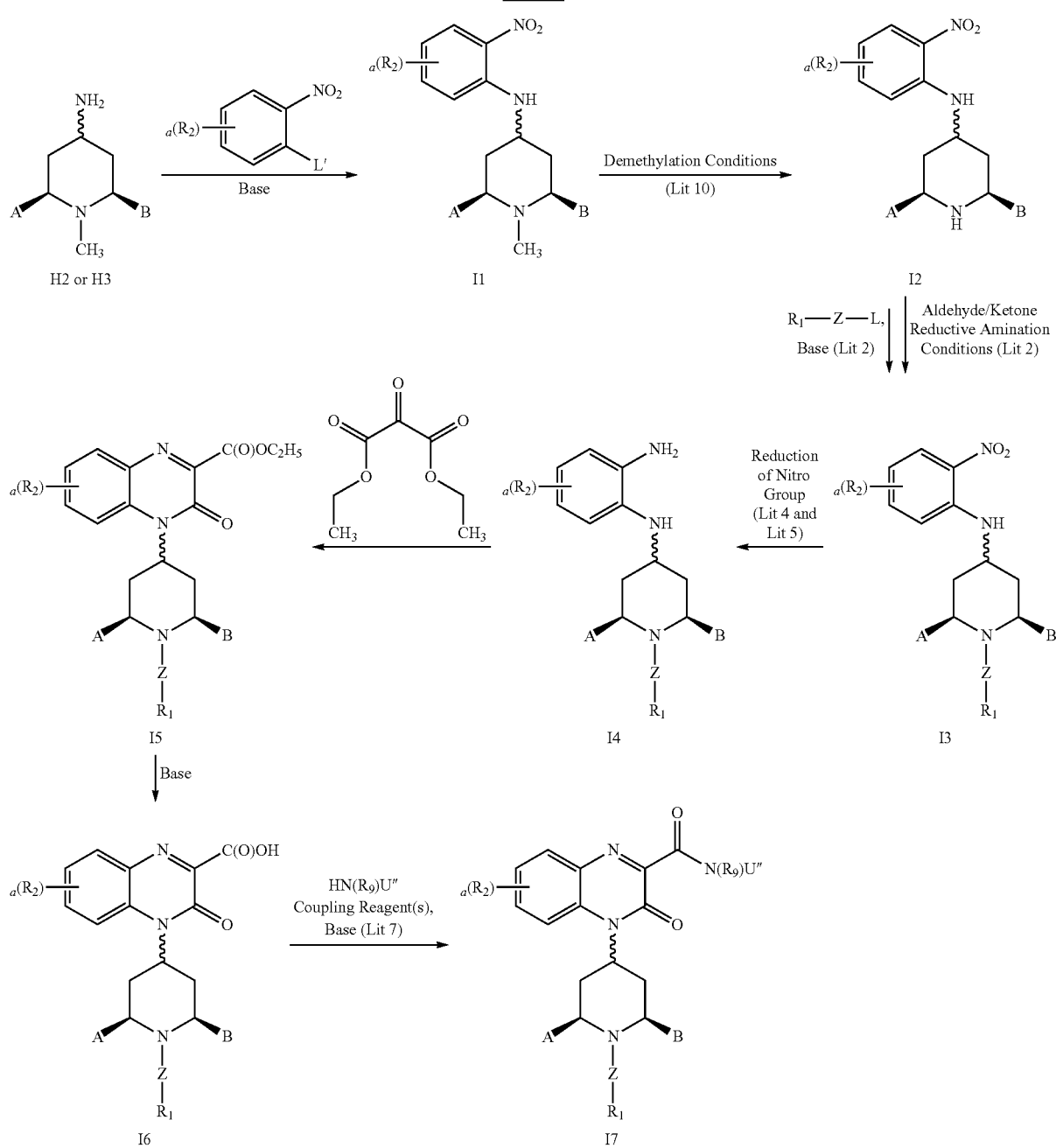

In Scheme I and the other schemes, "Lit 10" refers to the procedures described by Olofson et al., "A New Reagent for the Selective, High-Yield N-Dealkylation of Tertiary Amines: Improved Syntheses of Naltrexone and Nalbuphine," *J. Org. Chem.*, 49(11):2081-2082 (1984) and Olofson et al., "Value of the Vinyloxycarbonyl Unit in Hydroxyl Protection: Application to the Synthesis of Nalorphin," *Tetrahedron Lett.*, 18:1571-1574 (1977).

Compounds such as 16 and 17 where substituent groups A and B together form a bridge, e.g., a two carbon bridge, can be prepared as described in Scheme I. Compound H2 (the "endo" isomer) or H3 (the "exo" isomer) (where substituent groups A and B together form a bridge, e.g., a two carbon bridge) can be converted to Compound I1 by reaction with a substituted or unsubstituted 2-halo-1-nitrobenzene (where the halo is fluoride or chloride) and a base such as potassium carbonate, in a suitable solvent such as DMF or acetonitrile at a temperature from about 20° C. to about 100° C. Compound I1 can be demethylated to provide Compound I2 using, e.g., 1-chloromethylchloroformate in a solvent such as 1,2-dichloroethane, followed by treatment with methanol as described in "Lit 10." Compound I2 can be converted to Compound I3 (similar to steps described in reference "Lit 2" in Scheme A). Compound I3 can be converted to Compound I4 by hydrogenation using a catalyst under a hydrogen atmosphere or by chemical means using a reducing agent (similar to steps described in references "Lit 4" and "Lit 5" in Scheme C). Compound I4 can be converted to Compound I5 by reaction with diethyl 2-oxomalonate in a solvent with a high boiling point such as toluene or xylene under reflux conditions. Compound I5 can be converted to the carboxylic acid derivative I6 by hydrolysis using a base such as aqueous NaOH in a suitable solvent such as methanol or ethanol, followed by neutralization using an acid such as dilute HCl. Compound I6 can be converted to Compound I7 by a reaction employing a coupling agent (similar to steps described in reference "Lit 7" in Scheme F).

substituent groups A and B together form a bridge, e.g., a two carbon bridge, and Compound I4 may exist as either an "endo" isomer an "exo" isomer or a mixture of "endo/exo" isomers) can be converted to Compound J1, as shown in Scheme J, by reaction with ethyl 2-chloro-2-oxoacetate and a base such as TEA in a suitable solvent such as dichloromethane, followed by reaction with an alkali metal alkoxide, using the procedures described in Scheme A. These "endo" and "exo" isomers can be conveniently separated by flash column chromatography. Compound J1 can be converted to Compound J2 (similar to steps described previously in Scheme A).

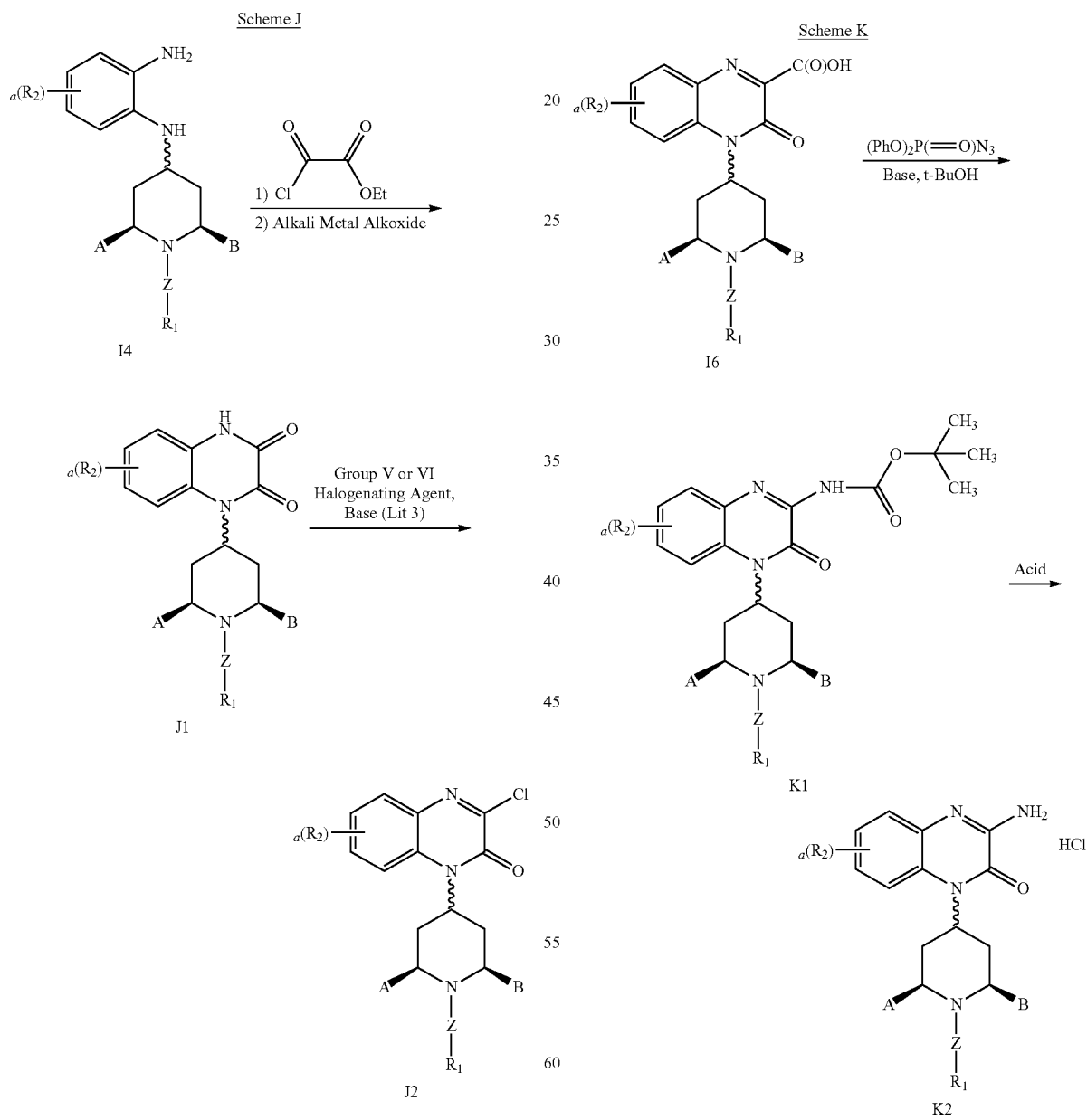

Compounds such as J2 where substituent groups A and B together form a bridge, e.g., a two carbon bridge, can be prepared as described in Scheme J. Compound I4 (where

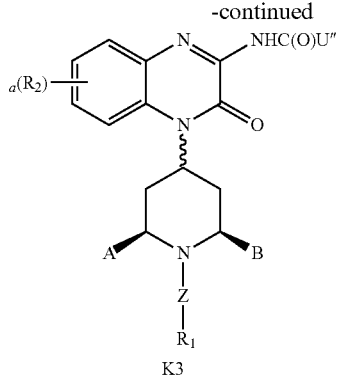

K3

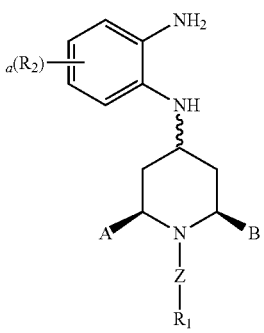

I4

Compound I4 can be prepared, as shown in Scheme L, from Compound A1 (similar to steps described in Scheme A). Where substituent groups A and B of Compound I4 form a bridge, e.g., a two carbon bridge, the two isomers, "exo" and "endo," can be separated by chromatography and can be separately converted to Compounds such as A5, A6, F2, F3, and the like as described earlier in Schemes A, B, and F.

Compounds such as K2 and K3 where substituent groups A and B together form a bridge, e.g., a two carbon bridge, can be prepared as described in Scheme K. Compound I6 (where substituent groups A and B together form a bridge, e.g., a two carbon bridge, and Compound I6 may exist as either an "endo" isomer an "exo" isomer or a mixture of "endo/exo" isomers) can be converted to Compound K1, as shown in Scheme K, using diphenylphosphoryl azide and t-butanol under Curtius Rearrangement Conditions (similar to steps described in Scheme C). The tert-butoxycarbonyl group in Compound K1 can be removed using acid conditions such as HCl in a solvent such as dioxane or ether to provide Compound K2 as the hydrochloride salt. Compound K2 can be converted to Compound K3 using an acid chloride U"C(O)Cl and a base, such as TEA, in a suitable solvent, such as dichloromethane or DMF, or using a carboxylic acid U"C(O)OH, a coupling reagent, such as N-(3,3-dimethyl-aminopropyl)-N'-ethylcarbodiimide, and a base, such as TEA, in a suitable solvent, such as DMF, as described in the literature references in Scheme F.

Scheme M

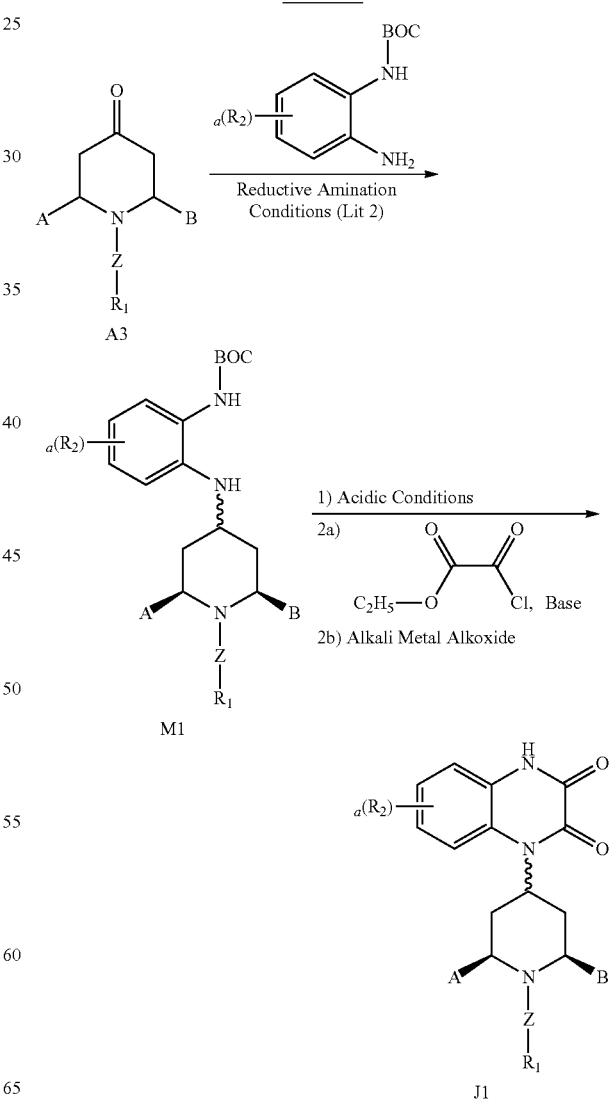

Scheme L

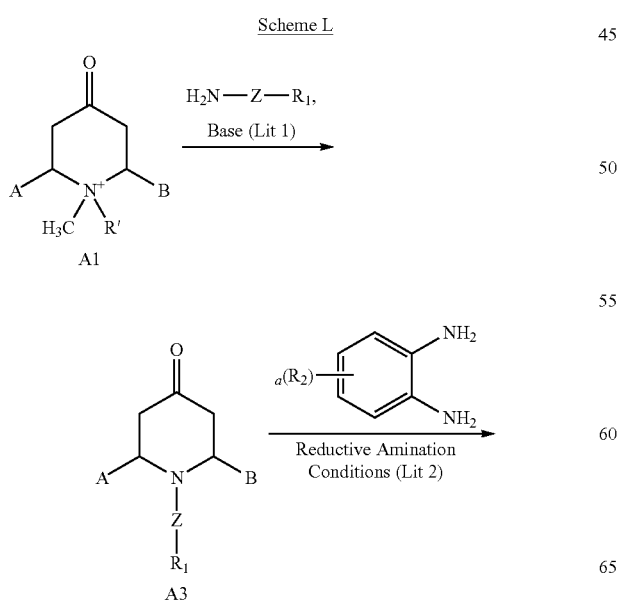

As shown in Scheme M, Compound A3 can be converted to Compound M1 under reductive amination conditions using a BOC protected, substituted or unsubstituted 1,2-phenylenediamine and a reducing agent such as sodium triacetoxyborohydride or sodium cyanoborohydride in a suitable solvent such as dichloromethane or methanol respectively as described in reference "Lit 2." The BOC protecting group can be removed using acidic conditions, such as using HCl or 2,2,2-trifluoroacetic acid, to provide an intermediate which can be converted to Compound J1 in a two step procedure using ethyl 2-chloro-2-oxoacetate and a base such as TEA, followed by reaction with an alkali metal alkoxide such as sodium ethoxide in a suitable solvent such as ethanol. Where substituent groups A and B together form a bridge, e.g., a two carbon bridge, the "exo" and "endo" isomers which result can be conveniently separated using flash column chromatography.

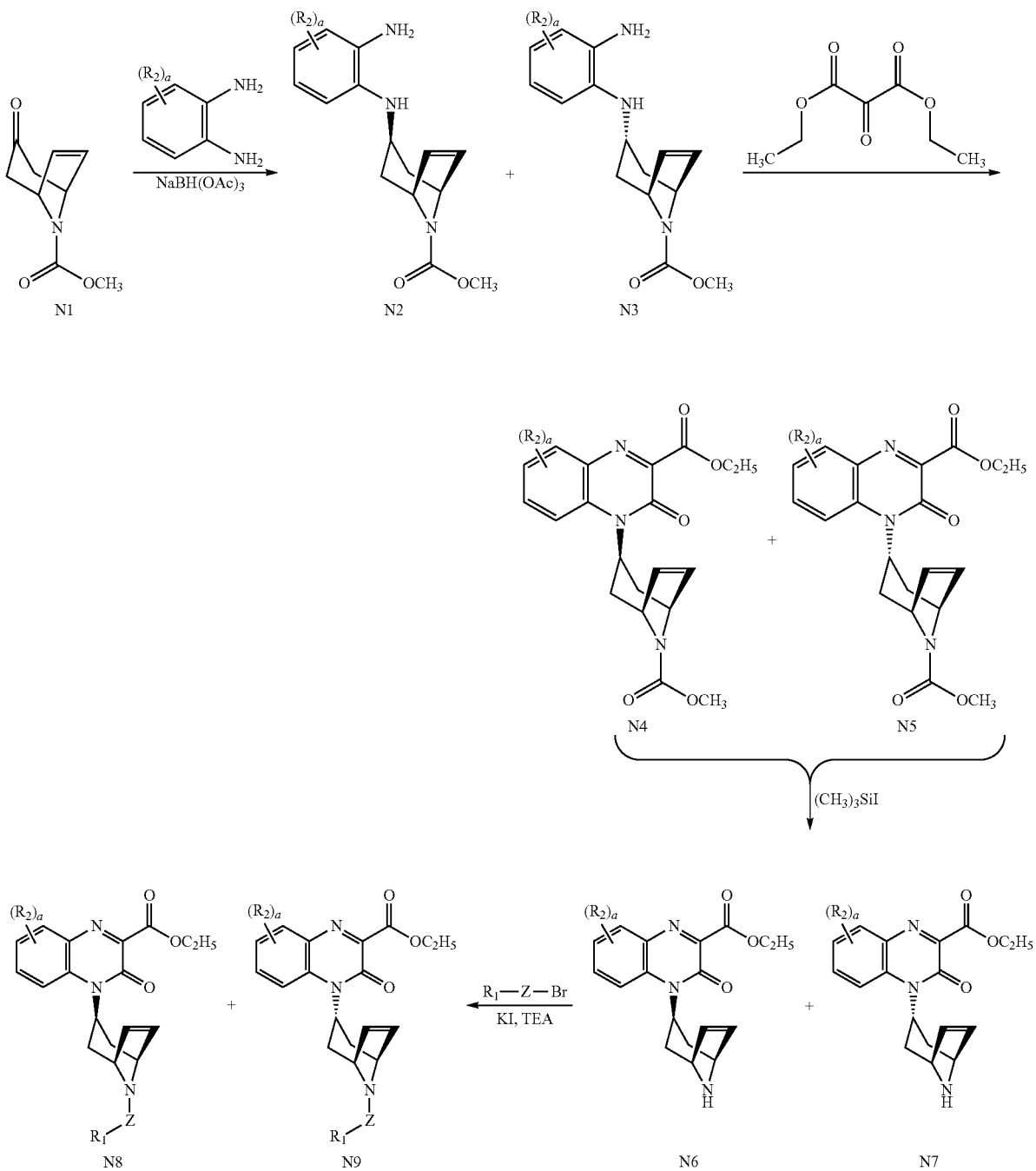

153

Scheme N shows the conversion of Compound N1 to Compounds N8 and N9, each comprising an A-B bridge containing —CH=CH—.

3-Oxo-8-aza-bicyclo[3.2.1]oct-6-ene-8-carboxylic acid methyl ester N1 can be prepared according to the literature procedure described in Cramer et al., "Enantioselective Desymmetrization of Tropinone Derivatives by Hydroboration," *Synlett*. 14:2175-2177 (2003).

Compound N1 can be reacted with a substituted or unsubstituted 1,2-phenylenediamine under reductive amination conditions using sodium triacetoxyborohydride in a solvent such as dichloromethane to provide the coupled products 3-(2-amino-phenylamino)-8-aza-bicyclo[3.2.1] oct-6-ene-8-carboxylic acid methyl esters N2 and N3 as a mixture of endo and exo isomers. Compounds N2 and N3 can be dissolved in a solvent such as toluene and acetic acid, diethyl 2-oxomalonate added, and the mixture heated under reflux. Column chromatography of the products can provide 4-(8-methoxycarbonyl-8-aza-bicyclo[3.2.1]oct-6-en-3-yl-3-oxo-3,4-dihydro-quinoxaline-2-carboxylic acid ethyl esters N4 and N5 as a mixture of endo and exo esters which can be further chromatographed if desired. The methyl carbamate group can be removed from Compounds N4 and N5 using iodo trimethylsilane in a solvent such as dichloromethane at a temperature of from about 25° C. to about 50° C. to provide 4-(8-aza-bicyclo[3.2.1]oct-6-en-3-yl)-3-oxo-3,4-dihydroquinoxaline-2-carboxylic acid ethyl esters N6 and N7 as a mixture of exo and endo isomers. Compound s N6 and N7 can be alkylated with various alkyl bromides or alkyl iodides such as 3-bromo-cyclooctene and a catalytic amount of potassium iodide and TEA in a solvent such as acetonitrile to provide isomers N8 and N9 which can be separated by column chromatography. Finally as shown in Scheme O below, hydrolysis of the ester group can be achieved using sodium hydroxide in aqueous ethanol to provide the carboxylic acids N10 and N11, each comprising an A-B bridge containing —CH=CH—.

Scheme O

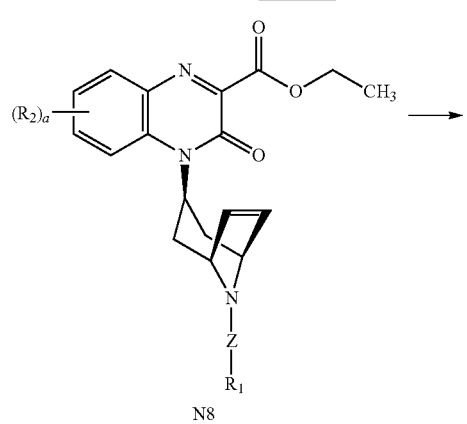

N8

154

-continued

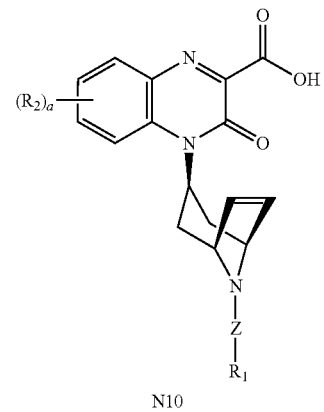

N10

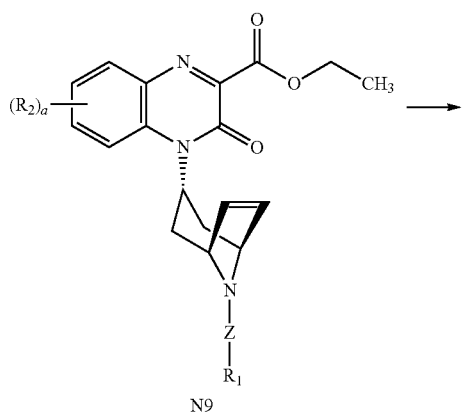

N9

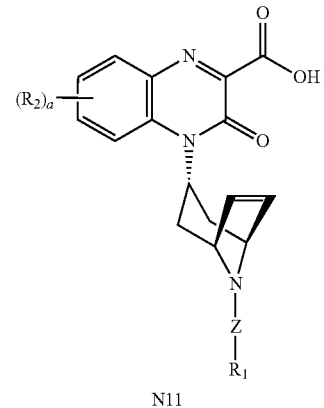

N11

Scheme P

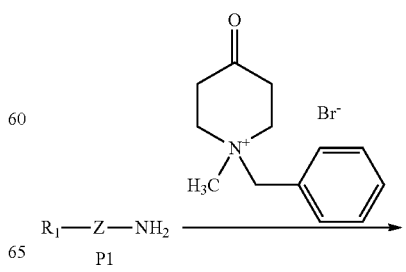

P1

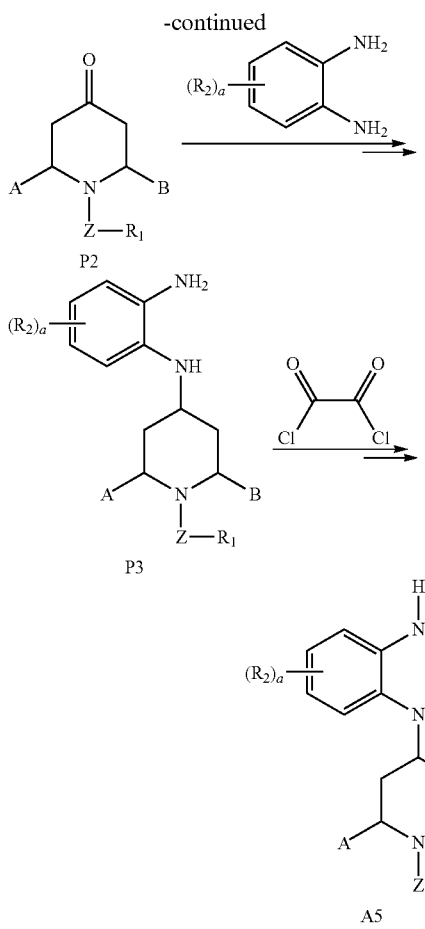

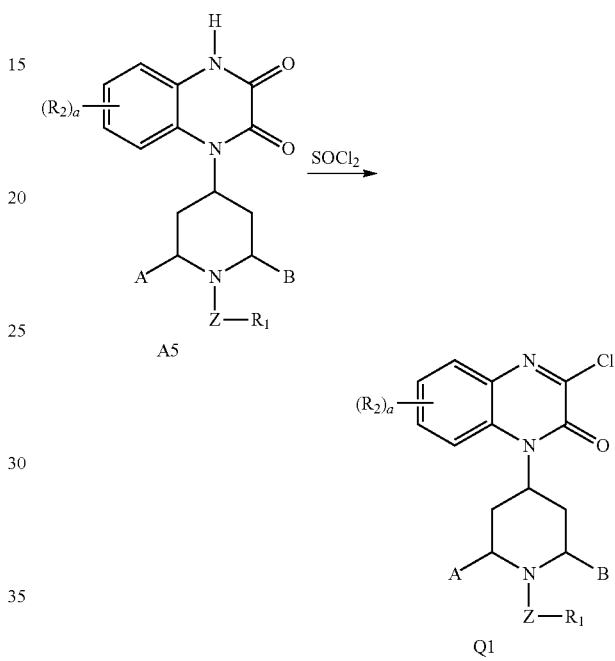

for from about 4 h to about 6 h to provide Compound P2. Compound P2 can be treated with a substituted or unsubstituted 1,2-phenylenediamine and acetic acid in a solvent, such as tetrahydrofuran or 1,2-dimethoxyethane, to provide an imine, which can be reduced with sodium triacetoxyborohydride to provide Compound P3. Compound P3 can be treated with oxalyl dichloride in a non-aqueous solvent, such as dichloromethane, and a base, such as TEA, to provide an amide which can be cyclized to a quinoxaline 2,3-dione A5 using potassium carbonate in a polar solvent, such as ethanol.

Alternatively to Scheme A, the quinoxaline 2,3-dione A5 can be prepared as described in U.S. Patent Application Publication US 2010/0022519 A1 for example, at paragraph [1364] and thereafter. Briefly, the primary amine P1, where —Z—R$_1$ can be cyclooctyl, adamantyl or noradamantyl, for example, can be treated with a piperidone salt in a polar solvent, such as ethanol or methanol containing water, and an inorganic base, such as potassium carbonate, under reflux Compound A5 can be converted to the 2-chloroquinoxaline Q1 using thionyl chloride in a solvent such as dichloromethane using the procedures described in, e.g., Pizey, "Thionyl Chloride," Ch. 4 in *Synthetic Reagents*, John Wiley & Sons, New York, Vol. 1, pp. 321-357 (1974).

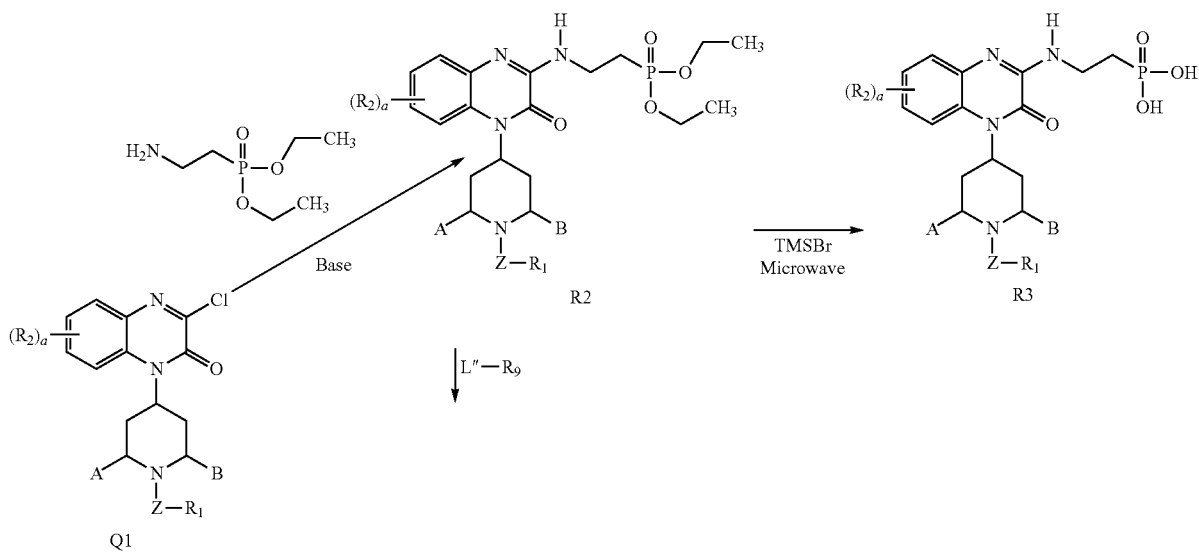

-continued

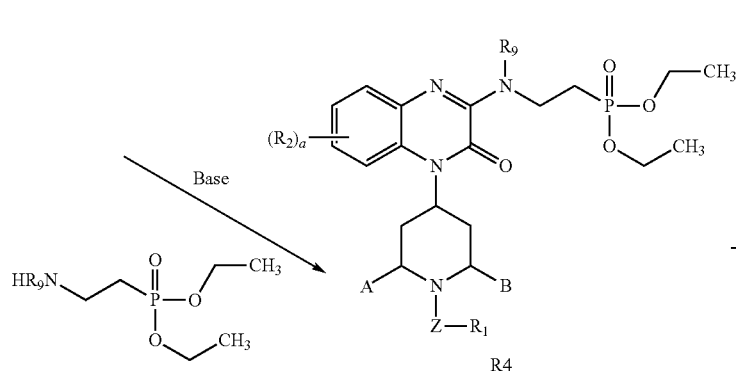

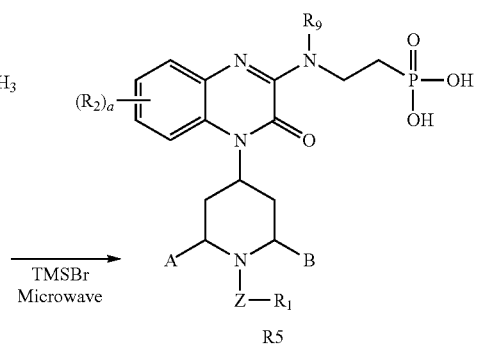

Compound Q1 can be converted to the amino-phosphonates R2 and R4 using diethyl 2-aminoethylphosphonate or diethyl 2-($R_9$-amino)ethylphosphonate, respectively, in a solvent, such as acetonitrile, and a base, such as TEA. Compound R2 can be converted to Compound R3 or Compound R4 can be converted to Compound R5 using triethylsilylbromide in a solvent, such as acetonitrile, in a microwave heating apparatus at a temperature of from about 60° C. to about 100° C. Compound R2 can be converted to Compound R4 using L"-$R_9$, where L" is mesylate, tosylate, or a halogen leaving group such as Cl, Br or I, in a solvent, such as THF, DCM, DCE or MeCN, at a temperature of from about 0° C. to about 100° C.

Scheme S

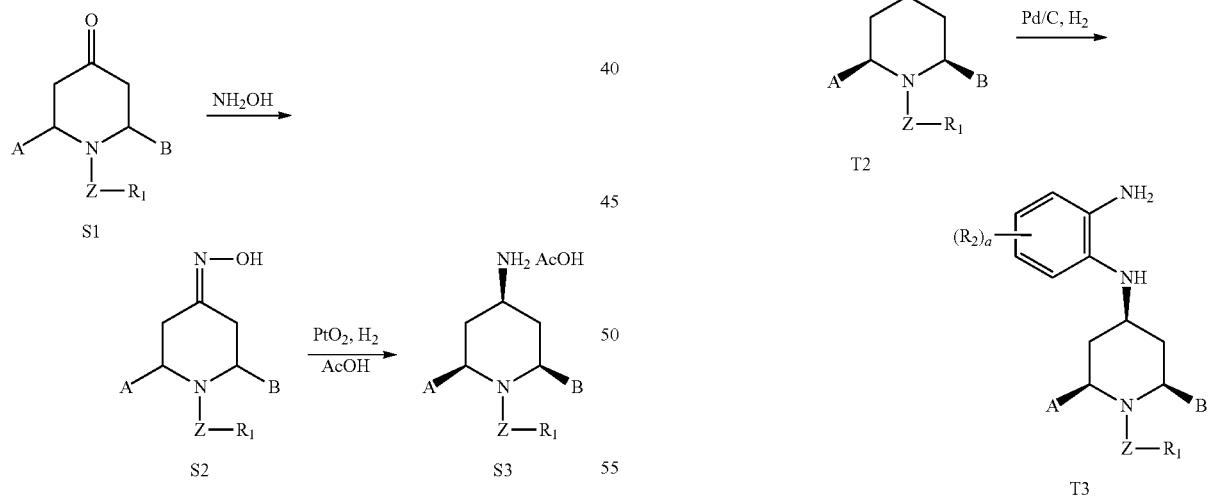

Compound S3 can be prepared according to the methods described in U.S. Patent Application Publication US 2010/0216726 A1 for example, at paragraph [1745] and thereafter. Briefly, Compound S1 can be converted to oxime Compound S2 using aqueous hydroxylamine in an acidic solvent, such as acetic acid. Compound S2 can be reduced to an endo amine Compound S3 by hydrogenation using a noble metal catalyst, such as platinum oxide, in a solvent, such as acetic acid.

Scheme T

Compound T3, a particular stereoisomer of Compound I4, can be prepared according to the methods described in U.S. Patent Application Publication US 2010/0216726 A1 for example, at paragraph [1745] and thereafter. Briefly, amine Compound S3 or its salt, such as the acetate, can be reacted with a substituted or unsubstituted 2-fluoronitrobenzene in a polar solvent, such as acetonitrile or DMF, and a base, such as TEA or potassium carbonate, to provide Compound T2. Compound T2 can be reduced to Compound T3 by hydrogenation using a noble metal catalyst, such as palladium on charcoal or Raney nickel, in a solvent, such as ethyl acetate or dichloromethane.

Scheme U

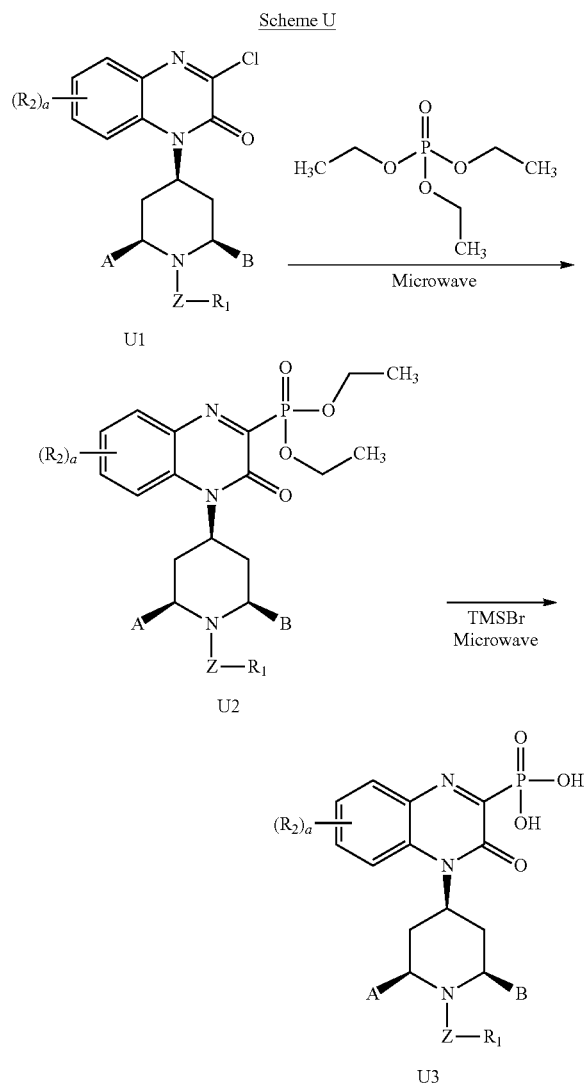

2-Chloro-quinoxaline U1 can be treated with triethylphosphate in a microwave heating apparatus at a temperature of about 100° C. to provide Compound U2. Compound U2 can be converted to Compound U3 using trimethylsilyl bromide in a solvent, such as acetonitrile, in a microwave heating apparatus at a temperature of about 60° C.

Scheme V

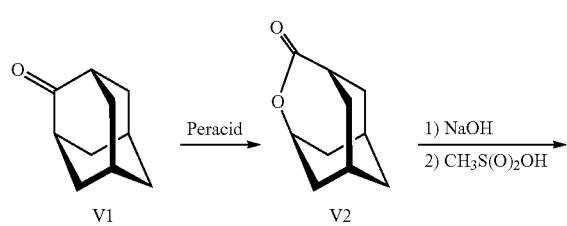

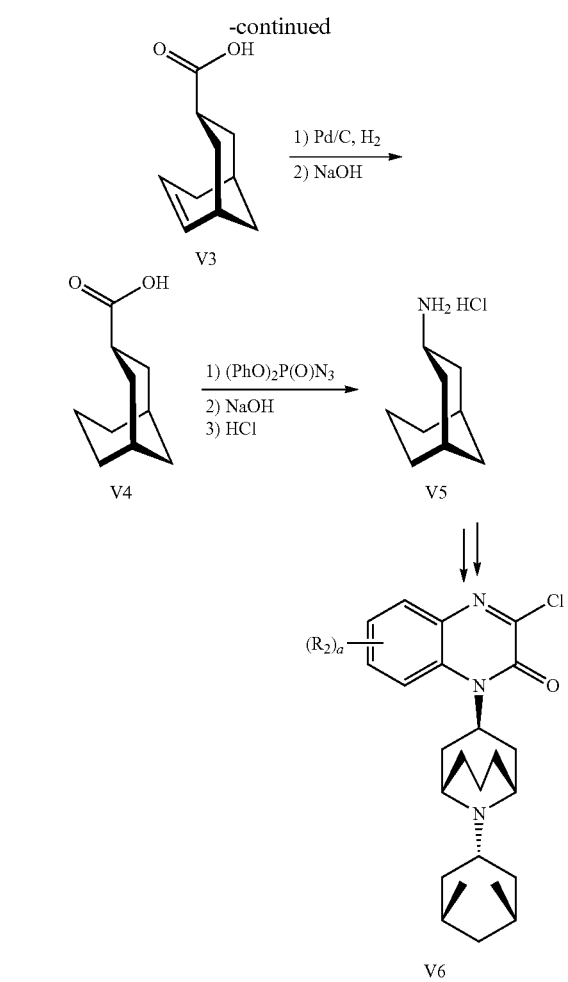

2-Adamantanone V1 can be dissolved in trifluoroacetic acid and treated with a peracid, such sodium percarbonate, at from about 20° C. to about 30° C. to provide a lactone Compound V2. Compound V2 can be hydrolyzed to a hydroxyl acid using sodium hydroxide in a solvent, such as methanol, under reflux. The stereochemistry of the acid epimerizes from endo to exo. The hydroxyl acid can be dehydrated to Compound V3 using an acid, such as methanesulfonic acid, in a solvent, such as toluene, by azeotropic drying. Compound V3 can be hydrogenated using a catalyst, such as palladium on charcoal, in a mixed solvent system, such as methanol and ethyl acetate, to provide a mixture of acid Compound V4 and its methyl ester (Compound V4', not shown). The mixture can be hydrolyzed to the acid Compound V4 using sodium hydroxide in aqueous methanol. Compound V4 can be converted to Compound V5 using di-phenyl phosphoryl azide and TEA in a solvent, such as toluene, in a Curtius type reaction to provide an isocyanate that can be hydrolyzed to the amine of Compound V5 using sodium hydroxide in aqueous tetrahydrofuran or another aprotic water miscible solvent. The isolated amine of Compound V5 can be converted to its hydrochloride salt by treatment with hydrochloric acid. Compound V5 can be converted to a 2-chloroquinoxaline Compound V6 according to the methods described in Schemes P and Q.

Scheme W

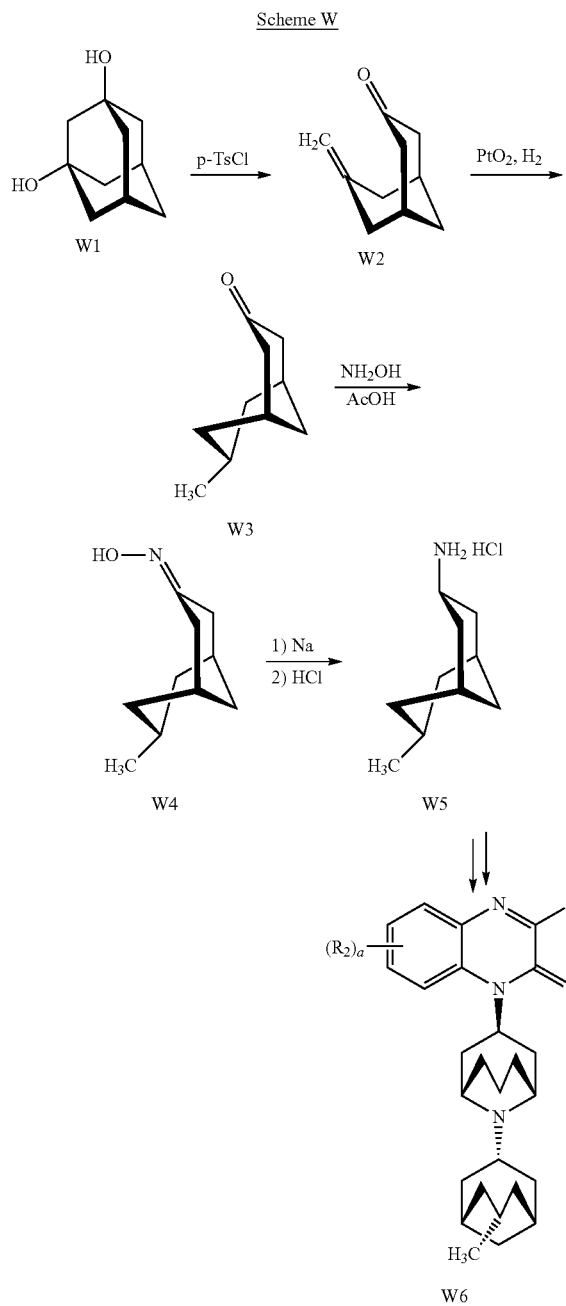

Scheme X1

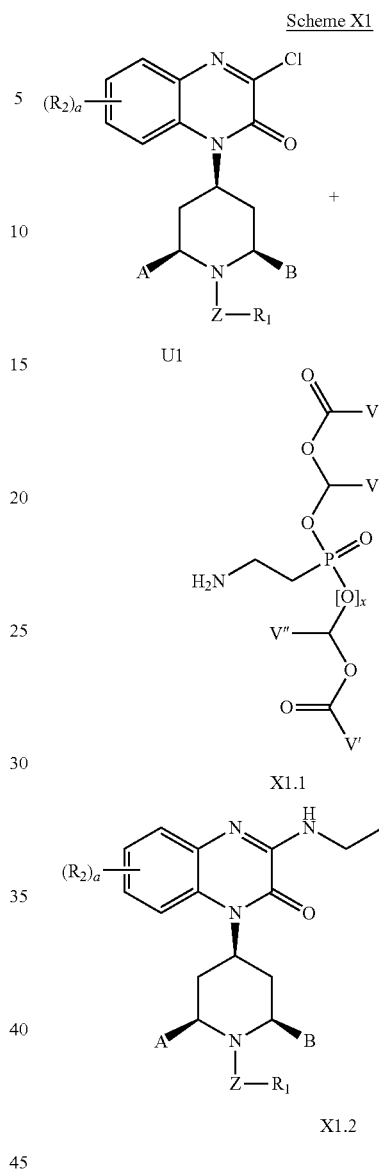

1,3-Dihydroxyadamantane W1 can be treated with p-toluenesulfonyl chloride in pyridine at a temperature of about 70° C. for from about 2 h to about 6 h to provide Compound W2. Compound W2 can be hydrogenated to Compound W3 using platinum oxide in a non-polar solvent, such as cyclohexane. Compound W3 can be converted to the oxime Compound W4 using hydroxylamine in acetic acid at a temperature from about 25° C. to about 40° C. Compound W4 can be reacted with sodium metal and isopropanol in a solvent, such as toluene, at a temperature of about 100° C. to provide the amine of Compound W5. The isolated amine of Compound W5 can be converted to its hydrochloride salt by treatment with hydrochloric acid in a solvent, such as diethyl ether. Compound W5 can be converted to Compound W6 according to the methods described in Schemes P and Q.

Compound U1 can be converted to Compound X1.2 according to the methods described in Scheme R using phosphonate X1.1. The chemical characteristics of desamino analogs of phosphonates of type X1.1 are described in Baudy et al., "Prodrugs of Perzinfotel with Improved Oral Bioavailability," *J. Med. Chem.* 52:771-778 (2009), herein "Lit 11." Exemplary substituents for the V' group in this scheme and the others that follow include methyl, ethyl, propyl, n-butyl, t-butyl, cyclohexyl, phenyl, hept-4-yl, 4-hexyl, and isopropyloxy. Exemplary substituents for the V" group in this scheme and the others that follow include hydrogen, methyl, ethyl, propyl, and butyl. Some exemplary combinations of the V' and V" substituents in this scheme and the others that follow include V'=phenyl, V"=H; V'=t-butyl, V"=H; V'=cyclohexyl, V"=H; V'=phenyl, V"=methyl; V'=cyclohexyl, V"=methyl; V'=hept-4-yl or 4-hexyl, V"=H; and V'=isopropyloxy, V"=H.

Scheme X2

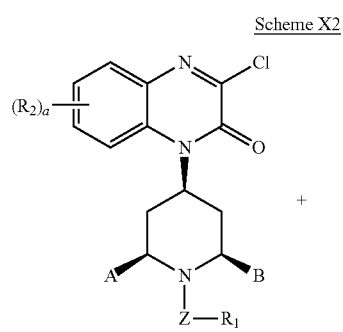

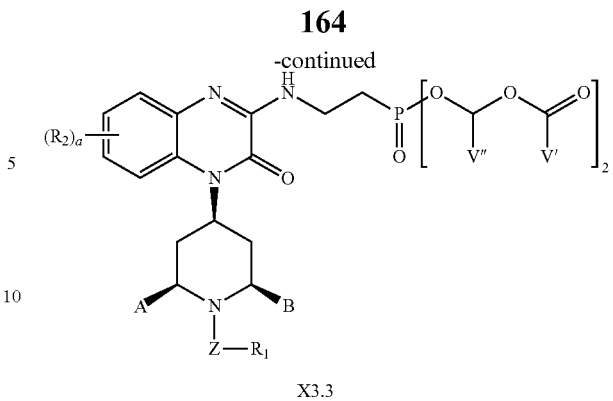

Compound U1 can be converted to Compound X2.2 according to the methods described in Scheme R using phosphonate X2.1. The chemical characteristics of deshydroxy analogs of phosphonates of type X2.1 are described in "Lit 11."

Scheme X3

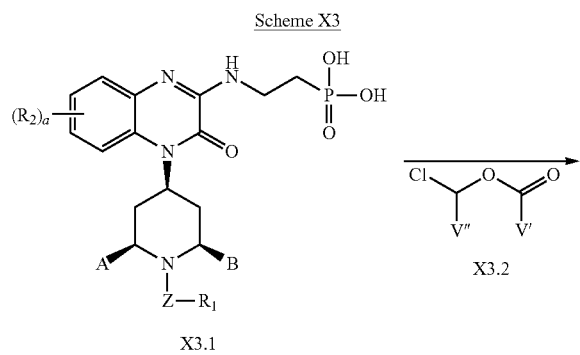

Compound X3.1 can be converted to Compound X3.3 using chloride X3.2 with a base, such as TEA or N,N-diisopropylethylamine, in a solvent, such as dimethylformamide, at an elevated temperature, such as at about 70° C., for from about 20 h to about 24 h. See, for example, "Lit 11."

Scheme X4

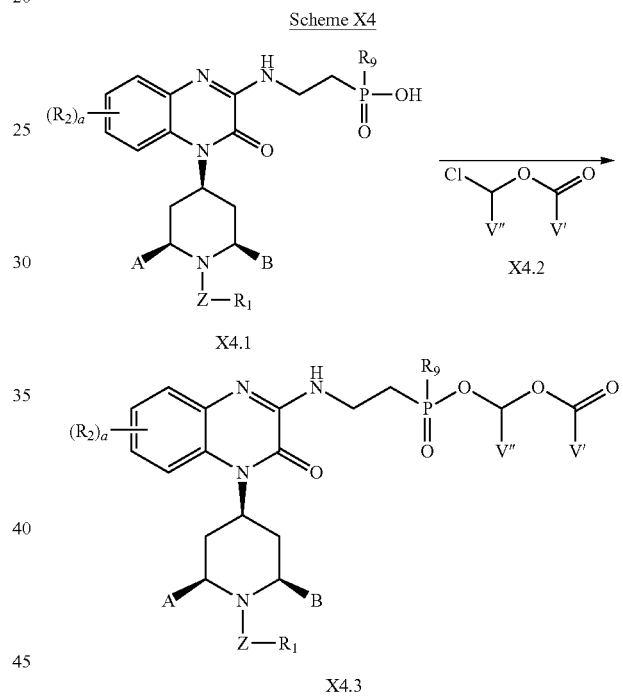

Compound X4.1 can be converted to Compound X4.3 using chloride X4.2 with a base, such as TEA or N,N-diisopropylethylamine, in a solvent, such as dimethylformamide, at an elevated temperature.

Scheme X5

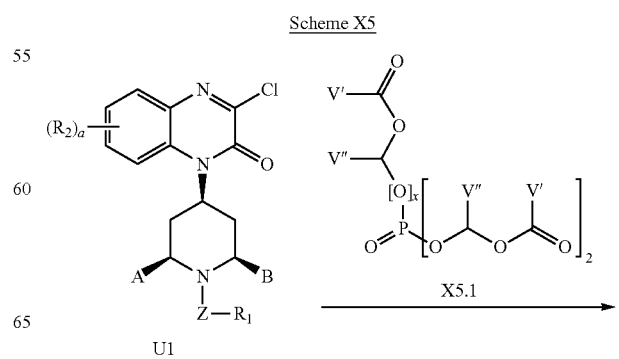

-continued

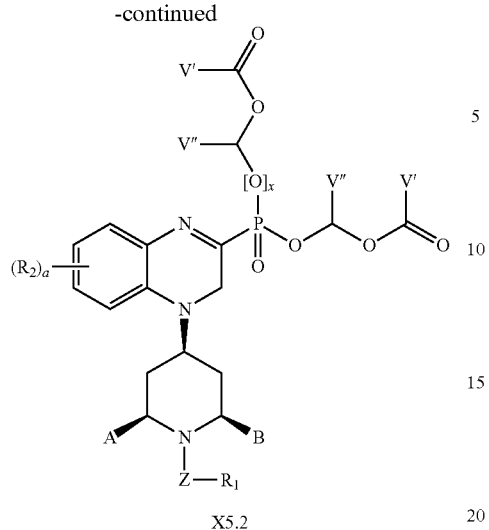

X5.2

Compound U1 can be converted to X5.2 using phosphate X5.1 under irradiation in a microwave heating apparatus.

Scheme X6

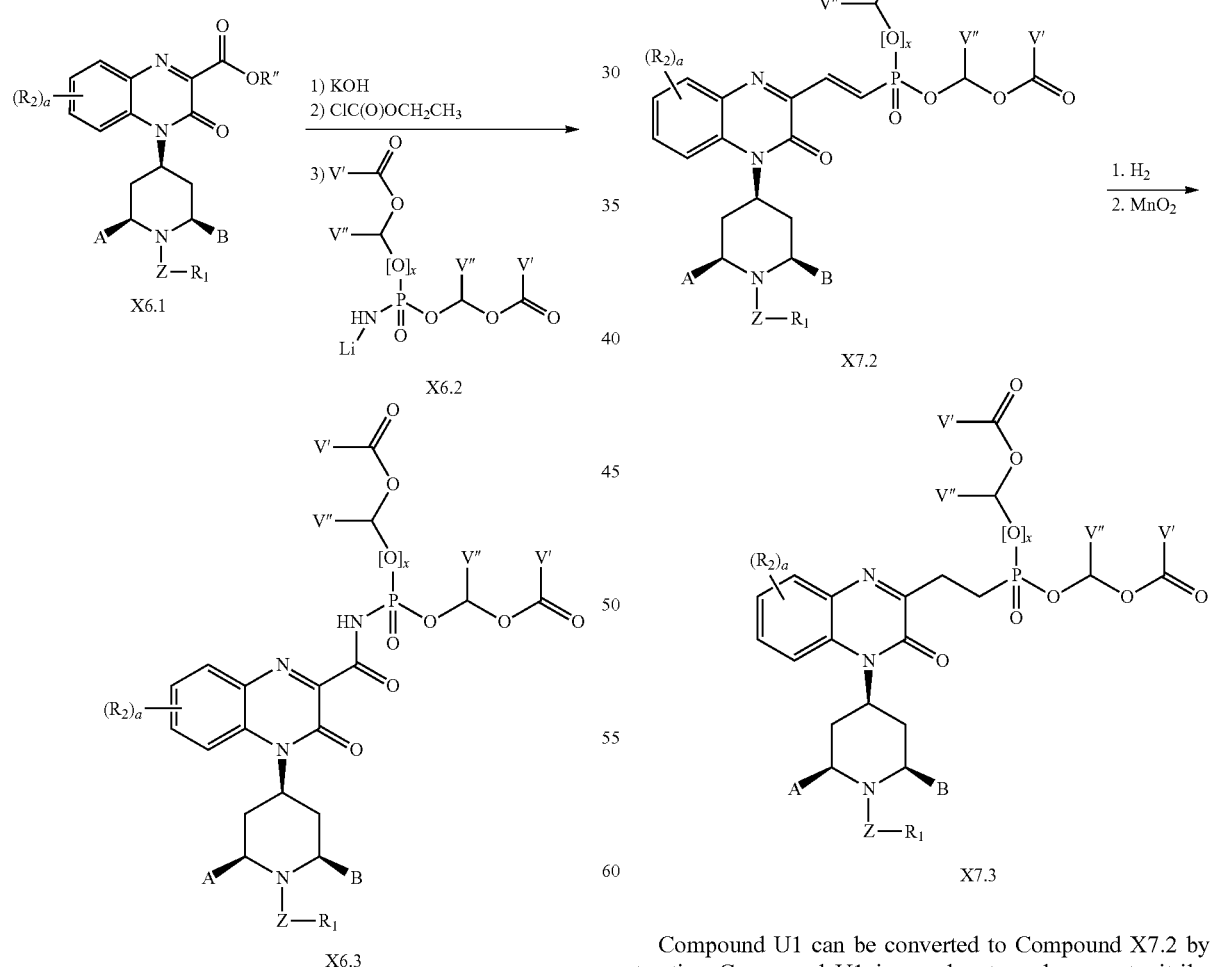

X6.1

X6.2

X6.3

Compound X6.1 can be converted to phosphoramidate X6.3 in a three step process. Compound X6.1, where R" is an alkyl group, e.g., —(C$_1$-C$_4$)alkyl, can be hydrolyzed to a potassium salt using potassium hydroxide and coupled with the chloridate to provide an activated compound which reacts with the lithium amide X6.2 to provide Compound X6.3.

Scheme X7

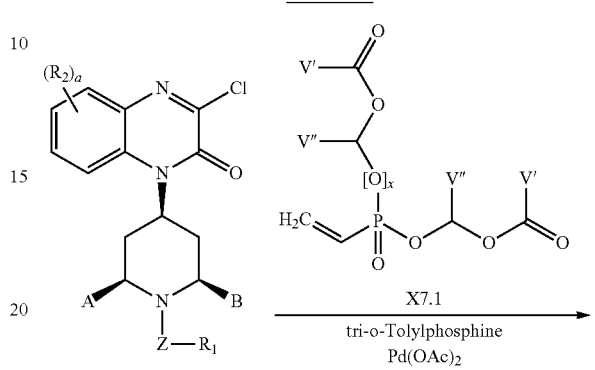

U1

X7.1

X7.2

X7.3

Compound U1 can be converted to Compound X7.2 by treating Compound U1 in a solvent, such as acetonitrile, with vinylphosphonate X7.1, a triphosphine, such as tri-o-tolylphosphine, a catalyst, such as palladium acetate, and a base, such as TEA. Compound X7.2 can be hydrogenated,

4.4 Therapeutic Uses of the Phosphorus-Substituted Quinoxaline-Type Piperidine Compounds In accordance with the disclosure, the Phosphorus-Substituted Quinoxaline-Type Piperidine Compounds are administered to an animal in need of treatment or prevention of a Condition.

In one embodiment, an effective amount of a Phosphorus-Substituted Quinoxaline-Type Piperidine Compound can be used to treat or prevent any condition treatable or preventable by inhibiting the activity of the ORL-1 receptor. Examples of Conditions that are treatable or preventable by inhibiting the activity of the ORL-1 receptor include, but are not limited to: pain (CNS effect), memory disorders, obesity, constipation, depression, dementia, and Parkinsonism.

In another embodiment, an effective amount of a Phosphorus-Substituted Quinoxaline-Type Piperidine Compound can be used to treat or prevent any condition treatable or preventable by activating the ORL-1 receptor. Examples of Conditions that are treatable or preventable by activating the ORL-1 receptor include, but are not limited to, pain (PNS effect), anxiety, cough, diarrhea, blood pressure disorder (via vasodilation and via diuresis), epilepsy, anorexia/cachexia, urinary incontinence, and drug abuse.

The Phosphorus-Substituted Quinoxaline-Type Piperidine Compounds can be used to treat or prevent acute or chronic pain. Examples of pain that can be treated or prevented using a Phosphorus-Substituted Quinoxaline-Type Piperidine Compound include, but are not limited to, cancer pain, neuropathic pain, labor pain, myocardial infarction pain, pancreatic pain, colic pain, post-operative pain, headache pain, muscle pain, arthritic pain, and pain associated with a periodontal disease, including gingivitis and periodontitis.

The Phosphorus-Substituted Quinoxaline-Type Piperidine Compounds can also be used to treat or prevent pain associated with inflammation or with an inflammatory disease in an animal. Such pain can arise where there is an inflammation of the body tissue which can be a local inflammatory response or a systemic inflammation. For example, a Phosphorus-Substituted Quinoxaline-Type Piperidine Compound can be used to treat or prevent pain associated with inflammatory diseases including, but not limited to, organ transplant rejection; reoxygenation injury resulting from organ transplantation (see Grupp et al., "Protection against Hypoxia-reoxygenation in the Absence of Poly (ADP-ribose) Synthetase in Isolated Working Hearts," *J. Mol. Cell Cardiol.* 31:297-303 (1999)) including, but not limited to, transplantation of the heart, lung, liver, or kidney; chronic inflammatory diseases of the joints, including arthritis, rheumatoid arthritis, osteoarthritis and bone diseases associated with increased bone resorption; inflammatory bowel diseases, such as ileitis, ulcerative colitis, Barrett's syndrome, and Crohn's disease; inflammatory lung diseases, such as asthma, adult respiratory distress syndrome, and chronic obstructive airway disease; inflammatory diseases of the eye, including corneal dystrophy, trachoma, onchocerciasis, uveitis, sympathetic ophthalmitis and endophthalmitis; chronic inflammatory disease of the gum, including gingivitis and periodontitis; tuberculosis; leprosy; inflammatory diseases of the kidney, including uremic complications, glomerulonephritis and nephrosis; inflammatory disease of the skin, including sclerodermatitis, psoriasis and eczema; inflammatory diseases of the central nervous system, including chronic demyelinating diseases of the nervous system, multiple sclerosis, AIDS-related neurodegeneration and Alzheimer's disease, infectious meningitis, encephalomyelitis, Parkinson's disease, Huntington's disease, amyotrophic lateral sclerosis and viral or autoimmune encephalitis; autoimmune diseases, including Type I and Type II diabetes mellitus; diabetic complications, including, but not limited to, diabetic cataract, glaucoma, retinopathy, nephropathy (such as microalbuminuria and progressive diabetic nephropathy), gangrene of the feet, atherosclerotic coronary arterial disease, peripheral arterial disease, nonketotic hyperglycemic-hyperosmolar coma, foot ulcers, joint problems, and a skin or mucous membrane complication (such as an infection, a shin spot, a candidal infection or necrobiosis lipoidica diabeticorum), immune-complex vasculitis, and systemic lupus erythematosus (SLE); inflammatory disease of the heart, such as cardiomyopathy, ischemic heart disease hypercholesterolemia, and artherosclerosis; as well as various other diseases that can have significant inflammatory components, including preeclampsia, chronic liver failure, brain and spinal cord trauma, and cancer. A Phosphorus-Substituted Quinoxaline-Type Piperidine Compound can also be used to treat or prevent pain associated with inflammatory disease that can, for example, be a systemic inflammation of the body, exemplified by gram-positive or gram negative shock, hemorrhagic or anaphylactic shock, or shock induced by cancer chemotherapy in response to pro-inflammatory cytokines, e.g., shock associated with pro-inflammatory cytokines. Such shock can be induced, e.g., by a chemotherapeutic agent that is administered as a treatment for cancer.

The Phosphorus-Substituted Quinoxaline-Type Piperidine Compounds can also be used to treat or prevent pain associated with nerve injury (i.e., neuropathic pain). Chronic neuropathic pain is a heterogenous disease state with an unclear etiology. In chronic neuropathic pain, the pain can be mediated by multiple mechanisms. This type of pain generally arises from injury to the peripheral or central nervous tissue. The syndromes include pain associated with spinal cord injury, multiple sclerosis, post-herpetic neuralgia, trigeminal neuralgia, phantom pain, causalgia, and reflex sympathetic dystrophy and lower back pain. The chronic pain is different from acute pain in that chronic neuropathic pain patients suffer the abnormal pain sensations that can be described as spontaneous pain, continuous superficial burning and/or deep aching pain. The pain can be evoked by heat-, cold-, and mechano-hyperalgesia, or by heat-, cold-, or mechano-allodynia.

Chronic neuropathic pain can be caused by injury or infection of peripheral sensory nerves. It includes, but is not limited to, pain from peripheral nerve trauma, herpes virus infection, diabetes mellitus, causalgia, plexus avulsion, neuroma, limb amputation, and vasculitis. Neuropathic pain can also be caused by nerve damage from chronic alcoholism, human immunodeficiency virus infection, hypothyroidism, uremia, or vitamin deficiencies. Stroke (spinal or brain) and spinal cord injury can also induce neuropathic pain. Cancer-related neuropathic pain results from tumor growth compression of adjacent nerves, brain, or spinal cord. In addition, cancer treatments, including chemotherapy and radiation therapy, can cause nerve injury. Neuropathic pain includes but is not limited to pain caused by nerve injury such as, for example, the pain from which diabetics suffer.

The Phosphorus-Substituted Quinoxaline-Type Piperidine Compounds can be used to treat or prevent a migraine including, but not limited to, migraine without aura ("common migraine"), migraine with aura ("classic migraine"), migraine without headache, basilar migraine, familial hemiplegic migraine, migrainous infarction, and migraine with prolonged aura.

According to the disclosure, some of the Phosphorus-Substituted Quinoxaline-Type Piperidine Compounds are agonists at the ORL-1 receptor, some of the Phosphorus-Substituted Quinoxaline-Type Piperidine Compounds are partial agonists at the ORL-1 receptor, and some of the Phosphorus-Substituted Quinoxaline-Type Piperidine Compounds are antagonists at the ORL-1 receptor. In another embodiment, a Phosphorus-Substituted Quinoxaline-Type Piperidine Compound is an agonist at the ORL-1 receptor and an agonist at a µ, κ and/or δ opioid receptor, particularly at a µ opioid receptor. In another embodiment, a Phosphorus-Substituted Quinoxaline-Type Piperidine Compound is a partial agonist at the ORL-1 receptor and an agonist at a µ, κ and/or δ opioid receptor, particularly at a µ opioid receptor. In another embodiment, a Phosphorus-Substituted Quinoxaline-Type Piperidine Compound is an antagonist at the ORL-1 receptor and an agonist at a µ, κ and/or δ opioid receptor, particularly at a µ opioid receptor. In another embodiment, a Phosphorus-Substituted Quinoxaline-Type Piperidine Compound is an agonist at the ORL-1 receptor and an antagonist at a µ, κ and/or δ opioid receptor, particularly at a µ opioid receptor. In another embodiment, a Phosphorus-Substituted Quinoxaline-Type Piperidine Compound is a partial agonist at the ORL-1 receptor and an antagonist at a µ, κ and/or δ opioid receptor, particularly at a µ opioid receptor. In another embodiment, a Phosphorus-Substituted Quinoxaline-Type Piperidine Compound is an antagonist at the ORL-1 receptor and an antagonist at a µ, κ and/or δ opioid receptor, particularly at a µ opioid receptor.

The disclosure also provides methods for inhibiting ORL-1 receptor function in a cell, comprising contacting a cell capable of expressing the ORL-1 receptor with an amount of a Phosphorus-Substituted Quinoxaline-Type Piperidine Compound effective to inhibit ORL-1 receptor function in the cell. This method can be adapted for use in vitro as part of an assay to select compounds that can be useful for treating or preventing a Condition in an animal. Alternatively, this method can be adapted for use in vivo, (i.e., in an animal such as a human) by contacting a cell in the animal with an effective amount of a Phosphorus-Substituted Quinoxaline-Type Piperidine Compound. In one embodiment, the method is useful for treating or preventing pain in an animal in need of such treatment or prevention. In another embodiment, the method is useful for treating or preventing a memory disorder, obesity, constipation, depression, dementia, or Parkinsonism in an animal in need of such treatment or prevention.

The disclosure also relates to methods for activating ORL-1 receptor function in a cell, comprising contacting a cell capable of expressing the ORL-1 receptor with an amount of a Phosphorus-Substituted Quinoxaline-Type Piperidine Compound effective to activate ORL-1 receptor function in the cell. This method can be adapted for use in vitro as part of an assay to select compounds useful for treating or preventing, pain, anxiety, cough, diarrhea, high blood pressure, epilepsy, anorexia/cachexia, urinary incontinence, or drug abuse. Alternatively, the method can be adapted for use in vivo (i.e., in an animal such as a human), by contacting a cell in the animal with an effective amount of a Phosphorus-Substituted Quinoxaline-Type Piperidine Compound. In one embodiment, the method is useful for treating or preventing pain in an animal in need of such treatment or prevention. In another embodiment, the method is useful for treating or preventing anxiety, cough, diarrhea, high blood pressure, epilepsy, anorexia/chachexia, urinary incontinence, or drug abuse in an animal in need of such treatment or prevention.

Examples of tissue comprising cells capable of expressing the ORL-1 receptor include but are not limited to brain, spinal cord, vas deferens, and gastrointestinal tract tissue. Methods for assaying cells that express the ORL-1 receptor are known in the art; for example, see Shimohigashi et al., "Sensitivity of Opioid Receptor-like Receptor ORL1 for Chemical Modification on Nociceptin, a Naturally Occurring Nociceptive Peptide," *J. Biol. Chem.* 271(39):23642-23645 (1996); Narita et al., "Identification of the G-protein Coupled ORL1 Receptor in the Mouse Spinal Cord by [$^{35}$S]-GTPγS Binding and Immunohistochemistry," *Brit. J. Pharmacol.* 128:1300-1306 (1999); Milligan, "Principles: Extending the Utility of [$^{35}$S]GTPγS Binding Assays," *TIPS* 24(2):87-90 (2003):and Lazareno, "Measurement of Agonist-stimulated [$^{35}$S]GTPγS Binding to Cell Membranes," *Methods in Molecular Biology* 106:231-245 (1999).

4.5 Therapeutic/Prophylactic Administration and Compositions of the Disclosure Due to their activity, the Phosphorus-Substituted Quinoxaline-Type Piperidine Compounds are advantageously useful in human and veterinary medicine. As described above, the Phosphorus-Substituted Quinoxaline-Type Piperidine Compounds are useful for treating or preventing a Condition in an animal in need thereof. The Phosphorus-Substituted Quinoxaline-Type Piperidine Compounds of the disclosure can be administered to any animal requiring modulation of the opioid and/or ORL-1 receptors.

When administered to an animal, a Phosphorus-Substituted Quinoxaline-Type Piperidine Compound can be administered as a component of a composition that comprises a pharmaceutically acceptable carrier or excipient. The compositions, which comprise a Phosphorus-Substituted Quinoxaline-Type Piperidine Compound, can be administered orally. A Phosphorus-Substituted Quinoxaline-Type Piperidine Compound can also be administered by any other convenient route, for example, by infusion or bolus injection, by absorption through epithelial or mucocutaneous linings (e.g., oral, rectal, and intestinal mucosa, etc.) and can be administered together with a second therapeutically active agent. Administration can be systemic or local. Various delivery systems are known, e.g., encapsulation in liposomes, microparticles, microcapsules, multiparticulates, capsules, etc., and can be used to administer a Phosphorus-Substituted Quinoxaline-Type Piperidine Compound.

Methods of administration include, but are not limited to, intradermal, intramuscular, intraperitoneal, parenteral, intravenous, subcutaneous, intranasal, epidural, oral, sublingual, intracerebral, intravaginal, transdermal, rectal, by inhalation, or topical, particularly to the ears, nose, eyes, or skin. The method of administration is left to the discretion of the practitioner. In most instances, administration will result in the release of a Phosphorus-Substituted Quinoxaline-Type Piperidine Compound into the bloodstream.

In specific embodiments, it can be desirable to administer a Phosphorus-Substituted Quinoxaline-Type Piperidine Compound locally. This can be achieved, for example and not by way of limitation, by local infusion during surgery, topical application, e.g., in conjunction with a wound dressing after surgery, by injection, by means of a catheter, by means of a suppository or enema, or by means of an implant, said implant being of a porous, non-porous, or gelatinous material, including membranes, such as sialastic membranes, or fibers.

In certain embodiments, it can be desirable to introduce a Phosphorus-Substituted Quinoxaline-Type Piperidine Compound into the central nervous system or gastrointestinal tract by any suitable route, including intraventricular, intrathecal, and epidural injection, and enema. Intraventricular injection can be facilitated by an intraventricular catheter, for example, attached to a reservoir, such as an Ommaya reservoir.

Pulmonary administration can also be employed, e.g., by use of an inhaler or nebulizer, and formulation with an aerosolizing agent, or via perfusion in a fluorocarbon or synthetic pulmonary surfactant. In certain embodiments, a Phosphorus-Substituted Quinoxaline-Type Piperidine Compound can be formulated as a suppository, with traditional binders and excipients such as triglycerides.

When a Phosphorus-Substituted Quinoxaline-Type Piperidine Compound of the disclosure is incorporated for parenteral administration by injection (e.g., continuous infusion or bolus injection), the formulation for parenteral administration can be in the form of a suspension, solution, emulsion in an oily or aqueous vehicle, and such formulations can further comprise pharmaceutically necessary additives such as one or more stabilizing agents, suspending agents, dispersing agents, and the like. A Phosphorus-Substituted Quinoxaline-Type Piperidine Compound of the disclosure can also be in the form of a powder for reconstitution as an injectable formulation.

In another embodiment, a Phosphorus-Substituted Quinoxaline-Type Piperidine Compound can be delivered in a vesicle, in particular a liposome (see Langer, "New Methods of Drug Delivery," Science 249:1527-1533 (1990); and Treat et al., "Liposome Encapsulated Doxorubicin Preliminary Results of Phase I and Phase II Trials," pp. 317-327 and 353-365 in Liposomes in the Therapy of Infectious Disease and Cancer (1989)).

In yet another embodiment, a Phosphorus-Substituted Quinoxaline-Type Piperidine Compound can be delivered in a controlled-release system or sustained-release system (see, e.g., Goodson, "Dental Applications," in Medical Applications of Controlled Release, Vol. 2, Applications and Evaluation, Langer and Wise, eds., CRC Press, Chapter 6, pp. 115-138 (1984), hereafter "Goodson"). Other controlled- or sustained-release systems discussed in the review by Langer, Science 249:1527-1533 (1990) can be used. In one embodiment, a pump can be used (Langer, Science 249:1527-1533 (1990); Sefton, "Implantable Pumps," in CRC Crit. Rev. Biomed. Eng. 14(3):201-240 (1987); Buchwald et al., "Long-term, Continuous Intravenous Heparin Administration by an Implantable Infusion Pump in Ambulatory Patients with Recurrent Venous Thrombosis," Surgery 88:507-516 (1980); and Saudek et al., "A Preliminary Trial of the Programmable Implantable Medication System for Insulin Delivery," New Engl. J. Med. 321:574-579 (1989)). In another embodiment, polymeric materials can be used (see Goodson; Smolen et al., "Drug Product Design and Performance," Controlled Drug Bioavailability Vol. 1, John Wiley & Sons, New York (1984); Langer et al., "Chemical and Physical Structure of Polymers as Carriers for Controlled Release of Bioactive Agents: A Review," J. Macromol. Sci. Rev. Macromol. Chem. C23(1):61-126 (1983); Levy et al., "Inhibition of Calcification of Bioprosthetic Heart Valves by Local Controlled-Release Diphosphonate," Science 228:190-192 (1985); During et al., "Controlled Release of Dopamine from a Polymeric Brain Implant: In Vivo Characterization," Ann. Neurol. 25:351-356 (1989); and Howard et al., "Intracerebral drug delivery in rats with lesion-induced memory deficits," J. Neurosurg. 71:105-112 (1989)). In yet another embodiment, a controlled- or sustained-release system can be placed in proximity of a target of a Phosphorus-Substituted Quinoxaline-Type Piperidine Compound, e.g., the spinal column, brain, or gastrointestinal tract, thus requiring only a fraction of the systemic dose.

The compositions can optionally comprise a suitable amount of a pharmaceutically acceptable excipient so as to provide the form for proper administration to the animal. Such a pharmaceutical excipient can be a diluent, suspending agent, solubilizer, binder, disintegrant, preservative, coloring agent, lubricant, and the like. The pharmaceutical excipient can be a liquid, such as water or an oil, including those of petroleum, animal, vegetable, or synthetic origin, such as peanut oil, soybean oil, mineral oil, sesame oil, and the like. The pharmaceutical excipient can be saline, gum acacia, gelatin, starch paste, talc, keratin, colloidal silica, urea, and the like. In addition, auxiliary, stabilizing, thickening, lubricating, and coloring agents can be used. In one embodiment, the pharmaceutically acceptable excipient is sterile when administered to an animal. Water is a particularly useful excipient when a Phosphorus-Substituted Quinoxaline-Type Piperidine Compound is administered intravenously. Saline solutions and aqueous dextrose and glycerol solutions can also be employed as liquid excipients, particularly for injectable solutions. Suitable pharmaceutical excipients also include starch, glucose, lactose, sucrose, gelatin, malt, rice, flour, chalk, silica gel, sodium stearate, glycerol monostearate, talc, sodium chloride, dried skim milk, glycerol, propylene glycol, water, ethanol, and the like. The compositions, if desired, can also contain minor amounts of wetting or emulsifying agents, or pH buffering agents. Specific examples of pharmaceutically acceptable carriers and excipients that can be used to formulate oral dosage forms are described in the Handbook of Pharmaceutical Excipients, (Amer. Pharmaceutical Ass'n, Washington, D.C., 1986), incorporated herein by reference.

The compositions can take the form of solutions, suspensions, emulsions, tablets, pills, pellets, capsules, capsules containing liquids, powders, sustained-release formulations, suppositories, emulsions, aerosols, sprays, suspensions, or any other form suitable for use. In one embodiment, the composition is in the form of a capsule (see, e.g., U.S. Pat. No. 5,698,155). Other examples of suitable pharmaceutical excipients are described by Radebough et al., "Preformulation," pp. 1447-1676 in Remington's Pharmaceutical Sciences Vol. 2 (Gennaro, ed., $19^{th}$ ed., Mack Publishing, Easton, Pa., 1995), incorporated herein by reference.

In one embodiment, the Phosphorus-Substituted Quinoxaline-Type Piperidine Compounds are formulated in accordance with routine procedures as a composition adapted for oral administration to human beings. A Phosphorus-Substituted Quinoxaline-Type Piperidine Compound to be orally delivered can be in the form of tablets, capsules, gelcaps, caplets, lozenges, aqueous or oily solutions, suspensions, granules, powders, emulsions, syrups, or elixirs, for example. When a Phosphorus-Substituted Quinoxaline-Type Piperidine Compound is incorporated into oral tablets, such tablets can be compressed, tablet triturates, enteric-coated, sugar-coated, film-coated, multiply compressed or multiply layered. Techniques and compositions for making solid oral dosage forms are described in Pharmaceutical Dosage Forms: Tablets (Lieberman et al., eds., $2^{nd}$ ed., Marcel Dekker, Inc., 1989 & 1990). Techniques and compositions for making tablets (compressed and molded), capsules (hard and soft gelatin) and pills are also described by King, "Tablets, Capsules, and Pills," pp. 1553-1593 in *Remington's Pharmaceutical Sciences* (Osol, ed., 16th ed., Mack Publishing, Easton, Pa., 1980).

Liquid oral dosage forms include aqueous and nonaqueous solutions, emulsions, suspensions, and solutions and/or suspensions reconstituted from non-effervescent granules, optionally containing one or more suitable solvents, preservatives, emulsifying agents, suspending agents, diluents, sweeteners, coloring agents, flavoring agents, and the like. Techniques and composition for making liquid oral dosage forms are described in *Pharmaceutical Dosage Forms: Disperse Systems* (Lieberman et al., eds., 2nd ed., Marcel Dekker, Inc., 1996 & 1998).

When a Phosphorus-Substituted Quinoxaline-Type Piperidine Compound is to be injected parenterally, it can be, e.g., in the form of an isotonic sterile solution. Alternatively, when a Phosphorus-Substituted Quinoxaline-Type Piperidine Compound is to be inhaled, it can be formulated into a dry aerosol or can be formulated into an aqueous or partially aqueous solution.

An orally administered Phosphorus-Substituted Quinoxaline-Type Piperidine Compound can contain one or more agents, for example, sweetening agents such as fructose, aspartame or saccharin; flavoring agents such as peppermint, oil of wintergreen, or cherry; coloring agents; and preserving agents, to provide a pharmaceutically palatable preparation. Moreover, where in tablet or pill form, the compositions can be coated to delay disintegration and absorption in the gastrointestinal tract thereby providing a sustained action over an extended period of time. Selectively permeable membranes surrounding an osmotically active driving compound are also suitable for orally administered compositions. In these latter platforms, fluid from the environment surrounding the capsule is imbibed by the driving compound, which swells to displace the agent or agent composition through an aperture. These delivery platforms can provide an essentially zero order delivery profile as opposed to the spiked profiles of immediate release formulations. A time-delay material such as glycerol monostearate or glycerol stearate can also be used. Oral compositions can include standard excipients such as mannitol, lactose, starch, magnesium stearate, sodium saccharin, cellulose, and magnesium carbonate. In one embodiment, the excipients are of pharmaceutical grade.

In another embodiment, the Phosphorus-Substituted Quinoxaline-Type Piperidine Compounds can be formulated for intravenous administration. In certain embodiments, compositions for intravenous administration comprise sterile isotonic aqueous buffer. Where necessary, the compositions can also include a solubilizing agent. A Phosphorus-Substituted Quinoxaline-Type Piperidine Compound for intravenous administration can optionally include a local anesthetic such as benzocaine or prilocaine to lessen pain at the site of the injection. Generally, the ingredients are supplied either separately or mixed together in unit dosage form, for example, as a dry lyophilized powder or water free concentrate in a hermetically sealed container such as an ampule or sachette indicating the quantity of active agent. Where a Phosphorus-Substituted Quinoxaline-Type Piperidine Compound is to be administered by infusion, it can be dispensed, for example, with an infusion bottle containing sterile pharmaceutical grade water or saline. Where a Phosphorus-Substituted Quinoxaline-Type Piperidine Compound is administered by injection, an ampule of sterile water for injection or saline can be provided so that the ingredients can be mixed prior to administration.

A Phosphorus-Substituted Quinoxaline-Type Piperidine Compound can be administered by controlled-release or sustained-release means or by delivery devices that are known to those in the art. Examples include, but are not limited to, those described in U.S. Pat. Nos. 3,845,770, 3,916,899, 3,536,809, 3,598,123, 4,008,719, 5,674,533, 5,059,595, 5,591,767, 5,120,548, 5,073,543, 5,639,476, 5,354,556, and 5,733,566, each of which is incorporated herein by reference. Such dosage forms can be used to provide controlled- or sustained-release of one or more active ingredients using, for example, hydropropylmethyl cellulose, ethylcellulose, other polymer matrices, gels, permeable membranes, osmotic systems, multilayer coatings, microparticles, multiparticulates, liposomes, microspheres, or a combination thereof to provide the desired release profile in varying proportions. Suitable controlled- or sustained-release formulations known to those in the art, including those described herein, can be readily selected for use with the active ingredients of the disclosure. The disclosure thus encompasses single unit dosage forms suitable for oral administration such as, but not limited to, tablets, capsules, gelcaps, and caplets that are adapted for controlled- or sustained-release.

Controlled- or sustained-release pharmaceutical compositions can have a common goal of improving drug therapy over that achieved by their non-controlled or non-sustained-release counterparts. In one embodiment, a controlled- or sustained-release composition comprises a minimal amount of a Phosphorus-Substituted Quinoxaline-Type Piperidine Compound to treat or prevent the Condition or a symptom thereof in a minimum amount of time. Advantages of controlled- or sustained-release compositions include extended activity of the drug, reduced dosage frequency, and increased compliance. In addition, controlled- or sustained-release compositions can favorably affect the time of onset of action or other characteristics, such as blood levels of the Phosphorus-Substituted Quinoxaline-Type Piperidine Compound, and can thus reduce the occurrence of adverse side effects.

Controlled- or sustained-release compositions can initially release an amount of a Phosphorus-Substituted Quinoxaline-Type Piperidine Compound that promptly produces the desired therapeutic or prophylactic effect, and gradually and continually release other amounts of the Phosphorus-Substituted Quinoxaline-Type Piperidine Compound to maintain this level of therapeutic or prophylactic effect over an extended period of time. To maintain a constant level of the Phosphorus-Substituted Quinoxaline-Type Piperidine Compound in the body, the Phosphorus-Substituted Quinoxaline-Type Piperidine Compound can be released from the dosage form at a rate that will replace the amount of Phosphorus-Substituted Quinoxaline-Type Piperidine Compound being metabolized and excreted from the body. Controlled- or sustained-release of an active ingredient can be stimulated by various conditions, including but not limited to, changes in pH, changes in temperature, concentration or availability of enzymes, concentration or availability of water, or other physiological conditions or compounds.

The amount of the Phosphorus-Substituted Quinoxaline-Type Piperidine Compound that is effective for the treatment or prevention of a Condition can be determined by standard clinical techniques. In addition, in vitro and/or in vivo assays can optionally be employed to help identify optimal dosage ranges. The precise dose to be employed will also depend on, e.g., the route of administration and the seriousness of the Condition, and can be decided according to the judgment of a practitioner and/or each animal's circumstances. In other examples thereof, variations will necessarily occur depending upon the weight and physical condition (e.g., hepatic and renal function) of the animal being treated, the affliction to be treated, the severity of the symptoms, the frequency of the dosage interval, the presence of any deleterious side-effects, and the particular compound utilized, among other things.

Suitable effective dosage amounts, however, range from about 0.01 mg/kg of body weight to about 3000 mg/kg of body weight of the animal per day, although they are, in certain embodiments, from about 0.01 mg/kg of body weight to about 2500 mg/kg of body weight of the animal per day or from about 0.01 mg/kg of body weight to about 1000 mg/kg of body weight of the animal per day. In another embodiment, the effective dosage amount is about 100 mg/kg of body weight of the animal per day or less. In another embodiment, the effective dosage amount ranges from about 0.01 mg/kg of body weight to about 100 mg/kg of body weight of the animal per day of a Phosphorus-Substituted Quinoxaline-Type Piperidine Compound, in another embodiment, about 0.02 mg/kg of body weight to about 50 mg/kg of body weight of the animal per day, and in another embodiment, about 0.025 mg/kg of body weight to about 20 mg/kg of body weight of the animal per day.

Administration can be as a single dose or as a divided dose. In one embodiment, an effective dosage amount is administered about every 24 hr until the Condition is abated. In another embodiment, an effective dosage amount is administered about every 12 hr until the Condition is abated. In another embodiment, an effective dosage amount is administered about every 8 hr until the Condition is abated. In another embodiment, an effective dosage amount is administered about every 6 hr until the Condition is abated. In another embodiment, an effective dosage amount is administered about every 4 hr until the Condition is abated. The effective dosage amounts described herein refer to total amounts administered; that is, if more than one Phosphorus-Substituted Quinoxaline-Type Piperidine Compound is administered, the effective dosage amounts correspond to the total amount administered.

Where a cell capable of expressing the ORL-1 receptor, the μ-opioid receptor, the κ-opioid receptor and/or the δ-opioid receptor is contacted with a Phosphorus-Substituted Quinoxaline-Type Piperidine Compound in vitro, the amount effective for inhibiting or activating that receptor function in a cell will, in certain embodiments, range from about $10^{-12}$ mol/L to about $10^{-4}$ mol/L, in one embodiment, from about $10^{-12}$ mol/L to about $10^{-5}$ mol/L, in another embodiment, from about $10^{-12}$ mol/L to about $10^{-6}$ mol/L, and in another embodiment, from about $10^{-12}$ mol/L to about $10^{-9}$ mol/L of a solution or suspension of a pharmaceutically acceptable carrier or excipient. In one embodiment, the volume of solution or suspension comprising the Phosphorus-Substituted Quinoxaline-Type Piperidine Compound will be from about 0.01 μL to about 1 mL. In another embodiment, the volume of solution or suspension will be about 200 μL.

The Phosphorus-Substituted Quinoxaline-Type Piperidine Compounds will have a binding affinity ($K_i$) for the human ORL-1 receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment. The binding affinity $K_i$ can be measured in ways known to the art, e.g., by an assay utilizing membranes from recombinant HEK-293 cells expressing the ORL-1 receptor.

In certain embodiments, the Phosphorus-Substituted Quinoxaline-Type Piperidine Compounds will have a Ki (nM) of about 300 or less for binding to ORL-1 receptors. In one embodiment, the Phosphorus-Substituted Quinoxaline-Type Piperidine Compounds of the disclosure will have a $K_i$ (nM) of about 100 or less. In another embodiment, the Phosphorus-Substituted Quinoxaline-Type Piperidine Compounds of the disclosure will have a $K_i$ (nM) of about 35 or less. In another embodiment, the Phosphorus-Substituted Quinoxaline-Type Piperidine Compounds of the disclosure will have a $K_i$ (nM) of about 20 or less. In another embodiment, the Phosphorus-Substituted Quinoxaline-Type Piperidine Compounds of the disclosure will have a $K_i$ (nM) of about 15 or less. In another embodiment, the Phosphorus-Substituted Quinoxaline-Type Piperidine Compounds of the disclosure will have a $K_i$ (nM) of about 10 or less. In another embodiment, the Phosphorus-Substituted Quinoxaline-Type Piperidine Compounds of the disclosure will have a $K_i$ (nM) of about 4 or less. In another embodiment, the Phosphorus-Substituted Quinoxaline-Type Piperidine Compounds of the disclosure will have a $K_i$ (nM) of about 1 or less. In another embodiment, the Phosphorus-Substituted Quinoxaline-Type Piperidine Compounds of the disclosure will have a $K_i$ (nM) of about 0.4 or less. In another embodiment, the Phosphorus-Substituted Quinoxaline-Type Piperidine Compounds of the disclosure will have a $K_i$ (nM) of about 0.1 or less.

ORL-1 GTP $EC_{50}$ is the concentration of a compound providing 50% of the maximal response for the compound at an ORL-1 receptor. In one embodiment, the Phosphorus-Substituted Quinoxaline-Type Piperidine Compounds will have an ORL-1 GTP $EC_{50}$ (nM) of about 5000 or less to stimulate ORL-1 receptor function. In another embodiment, a Phosphorus-Substituted Quinoxaline-Type Piperidine Compound of the disclosure will have an ORL-1 GTP $EC_{50}$ (nM) of about 1000 or less. In another embodiment, the Phosphorus-Substituted Quinoxaline-Type Piperidine Compounds of the disclosure will have an ORL-1 GTP $EC_{50}$ (nM) of about 100 or less. In another embodiment, the Phosphorus-Substituted Quinoxaline-Type Piperidine Compounds of the disclosure will have an ORL-1 GTP $EC_{50}$ (nM) of about 80 or less. In another embodiment, the Phosphorus-Substituted Quinoxaline-Type Piperidine Compounds of the disclosure will have an ORL-1 GTP $EC_{50}$ (nM) of about 50 or less. In another embodiment, the Phosphorus-Substituted Quinoxaline-Type Piperidine Compounds of the disclosure will have an ORL-1 GTP $EC_{50}$ (nM) of about 35 or less. In another embodiment, the Phosphorus-Substituted Quinoxaline-Type Piperidine Compounds of the disclosure will have an ORL-1 GTP $EC_{50}$ (nM) of about 15 or less. In another embodiment, the Phosphorus-Substituted Quinoxaline-Type Piperidine Compounds will have an ORL-1 GTP $EC_{50}$ (nM) of about 10 or less. In another embodiment, the Phosphorus-Substituted Quinoxaline-Type Piperidine Compounds will have an ORL-1 GTP $EC_{50}$ (nM) of about 4 or less. In another embodiment, the Phosphorus-Substituted Quinoxaline-Type Piperidine Compounds will have an ORL-1 GTP $EC_{50}$ (nM) of about 1 or less. In another embodiment, the Phosphorus-Substituted Quinoxaline-Type Piperidine Compounds will have an ORL-1 GTP $EC_{50}$ (nM) of about 0.4 or less. In another embodiment, the Phosphorus-Substituted Quinoxaline-Type Piperidine Compounds will have an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In certain embodiments, a Phosphorus-Substituted Quinoxaline-Type Piperidine Compound of the disclosure acting as an agonist will have an ORL-1 GTP Emax (%) of about 50% or greater. In one embodiment, agonist Phosphorus-Substituted Quinoxaline-Type Piperidine Compounds will have an ORL-1 GTP Emax (%) of about 75% or greater. In another embodiment, agonist Phosphorus-Substituted Quinoxaline-Type Piperidine Compounds will have an ORL-1 GTP Emax (%) of about 85% or greater. In another embodiment, agonist Phosphorus-Substituted Quinoxaline-Type Piperidine Compounds will have an ORL-1 GTP Emax (%) of about 95% or greater. In another embodiment, agonist Phosphorus-Substituted Quinoxaline-Type Piperidine Compounds will have an ORL-1 GTP Emax (%) of about 100% or greater. In certain embodiments, a Phosphorus-Substituted Quinoxaline-Type Piperidine Compound of the disclosure acting as a partial agonist will have an ORL-1 GTP Emax (%) of less than about 10%. In one embodiment, partial agonist Phosphorus-Substituted Quinoxaline-Type Piperidine Compounds will have an ORL-1 GTP Emax (%) of less than about 20%. In another embodiment, partial agonist Phosphorus-Substituted Quinoxaline-Type Piperidine Compounds will have an ORL-1 GTP Emax (%) of less than about 30%. In another embodiment, partial agonist Phosphorus-Substituted Quinoxaline-Type Piperidine Compounds will have an ORL-1 GTP Emax (%) of less than about 40%. In another embodiment, partial agonist Phosphorus-Substituted Quinoxaline-Type Piperidine Compounds will have an ORL-1 GTP Emax (%) of less than about 50%.

In certain embodiments, a Phosphorus-Substituted Quinoxaline-Type Piperidine Compound will have a binding affinity ($K_i$) for the human μ-opioid receptor of about 1000 nM or less in one embodiment, or about 500 nM or less in another embodiment, about 100 nM or less in another embodiment, about 50 nM or less in another embodiment, or about 20 nM or less in another embodiment, or about 5 nM or less in another embodiment.

In certain embodiments, a Phosphorus-Substituted Quinoxaline-Type Piperidine Compound will have a $K_i$ (nM) for the human μ-opioid receptor of about 3000 or less for binding to a human μ-opioid receptor, or about 1000 or less, or about 650 or less, or about 525 or less, or about 250 or less, or about 100 or less, or about 10 or less, or about 1 or less. In one embodiment, a Phosphorus-Substituted Quinoxaline-Type Piperidine Compound will have substantially no activity.

μ GTP $EC_{50}$ is the concentration of a compound providing 50% of the maximal response for the compound at a human μ-opioid receptor. In certain embodiments, the Phosphorus-Substituted Quinoxaline-Type Piperidine Compounds will have a μ GTP $EC_{50}$ (nM) of about 20,000 or less to stimulate human μ-opioid receptor function, or about 10,000 or less. In other embodiments, the Phosphorus-Substituted Quinoxaline-Type Piperidine Compounds will have a g GTP $EC_{50}$ (nM) of about 5000 or less to stimulate human μ-opioid receptor function, or about 4100 or less, or about 3100 or less, or about 2000 or less, or about 1000 or less, or about 100 or less, or about 10 or less, or about 1 or less, or about 0.4 or less.

μ GTP Emax (%) is the maximal effect elicited by a compound relative to the effect elicited by DAMGO, a standard μ agonist. In certain embodiments, the Phosphorus-Substituted Quinoxaline-Type Piperidine Compounds will have at GTP Emax (%) of about 10% or greater, or about 20% or greater, or about 50% or greater, or about 65% or greater, or about 75% or greater, or about 88% or greater. In other embodiments, the Phosphorus-Substituted Quinoxaline-Type Piperidine Compounds will have a μ GTP Emax (%) of about 10% or less, or about 5% or less, or about 2% or less.

In one embodiment, a Phosphorus-Substituted Quinoxaline-Type Piperidine Compound will have a $K_i$ (nM) of about 20,000 or less for binding to a human κ-opioid receptor. In another embodiment, a Phosphorus-Substituted Quinoxaline-Type Piperidine Compound will have substantially no activity. In certain embodiments, the Phosphorus-Substituted Quinoxaline-Type Piperidine Compounds that bind to the human κ-opioid receptor will have a $K_i$ (nM) of about 10,000 or less, or about 5000 or less, or about 1000 or less, or about 500 or less, or about 300 or less, or about 100 or less, or about 50 or less, or about 20 or less, or about 15 or less.

κ GTP $EC_{50}$ is the concentration of a compound providing 50% of the maximal response for the compound at a human κ-opioid receptor. In certain embodiments, the Phosphorus-Substituted Quinoxaline-Type Piperidine Compounds will have a κ GTP $EC_{50}$ (nM) of about 20,000 or less to stimulate human κ-opioid receptor function, or about 10,000 or less, or about 5000 or less, or about 2000 or less, or about 1500 or less, or about 800 or less, or about 500 or less, or about 300 or less, or about 100 or less, or about 50 or less, or about 25 or less.

κ GTP Emax (%) is the maximal effect elicited by a compound relative to the effect elicited by U69,593. In certain embodiments, the Phosphorus-Substituted Quinoxaline-Type Piperidine Compounds will have a κ GTP Emax (%) of about 10% or greater, or about 15% or greater, or about 30% or greater, or about 40% or greater, or about 45% or greater, or about 75% or greater, or about 90% or greater. In other embodiments, the Phosphorus-Substituted Quinoxaline-Type Piperidine Compounds will have a κ GTP Emax (%) of about 10% or less, or about 5% or less, or about 2% or less.

In one embodiment, a Phosphorus-Substituted Quinoxaline-Type Piperidine Compound will have a $K_i$ (nM) of about 20,000 or less for binding to a human δ-opioid receptor. In another embodiment, a Phosphorus-Substituted Quinoxaline-Type Piperidine Compound will have substantially no activity. In other embodiments, a Phosphorus-Substituted Quinoxaline-Type Piperidine Compound that binds to the human δ-opioid receptor will have a $K_i$ (nM) of about 10,000 or less, or about 9000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less.

δ GTP $EC_{50}$ is the concentration of a compound providing 50% of the maximal response for the compound at a human δ-opioid receptor. In certain embodiments, the Phosphorus-Substituted Quinoxaline-Type Piperidine Compounds will have a δ GTP $EC_{50}$ (nM) of about 20,000 or less to stimulate human δ-opioid receptor function, or about 10,000 or less, or about 1000 or less, or about 100 or less, or about 90 or less, or about 50 or less, or about 25 or less or less.

δ GTP Emax (%) is the maximal effect elicited by a compound relative to the effect elicited by met-enkephalin. In certain embodiments, the Phosphorus-Substituted Quinoxaline-Type Piperidine Compounds will have a δ GTP Emax (%) of about 10% or greater, or about 30% or greater, or about 50% or greater, or about 75% or greater, or about 90% or greater, or about 100% or greater. In other embodiments, the Phosphorus-Substituted Quinoxaline-Type Piperidine Compounds will have a δ GTP Emax (%) of about 10% or less, or about 5% or less, or about 2% or less.

The Phosphorus-Substituted Quinoxaline-Type Piperidine Compounds can be assayed in vitro or in vivo for the desired therapeutic or prophylactic activity prior to use in humans. Animal model systems can be used to demonstrate safety and efficacy.

The methods for treating or preventing a Condition in an animal in need thereof can further comprise co-administering to the animal being administered a Phosphorus-Substituted Quinoxaline-Type Piperidine Compound (i.e., a first therapeutic agent) a second therapeutic agent. In one embodiment, the second therapeutic agent is administered in an effective amount.

An effective amount of the second therapeutic agent will be known to those skilled the art depending on the agent. However, it is well within the skilled artisan's purview to determine the second therapeutic agent's optimal effective-amount range. A Phosphorus-Substituted Quinoxaline-Type Piperidine Compound and the second therapeutic agent combined can act either additively or synergistically to treat the same Condition, or they may act independently of each other such that the Phosphorus-Substituted Quinoxaline-Type Piperidine Compound treats or prevents a first Condition and the second therapeutic agent treats or prevents a second disorder, which can be the same as the first Condition or another disorder. In one embodiment of the disclosure, where a second therapeutic agent is administered to an animal for treatment of a Condition (e.g., pain), the minimal effective amount of the Phosphorus-Substituted Quinoxaline-Type Piperidine Compound will be less than its minimal effective amount would be where the second therapeutic agent is not administered. In this embodiment, the Phosphorus-Substituted Quinoxaline-Type Piperidine Compound and the second therapeutic agent can act synergistically to treat or prevent a Condition. In one embodiment, a Phosphorus-Substituted Quinoxaline-Type Piperidine Compound is administered concurrently with a second therapeutic agent as a single composition comprising an effective amount of a Phosphorus-Substituted Quinoxaline-Type Piperidine Compound and an effective amount of the second therapeutic agent. Alternatively, a composition comprising an effective amount of a Phosphorus-Substituted Quinoxaline-Type Piperidine Compound and a second composition comprising an effective amount of the second therapeutic agent are concurrently administered. In another embodiment, an effective amount of a Phosphorus-Substituted Quinoxaline-Type Piperidine Compound is administered prior or subsequent to administration of an effective amount of the second therapeutic agent. In this embodiment, the Phosphorus-Substituted Quinoxaline-Type Piperidine Compound is administered while the second therapeutic agent exerts its therapeutic effect, or the second therapeutic agent is administered while the Phosphorus-Substituted Quinoxaline-Type Piperidine Compound exerts its therapeutic effect for treating or preventing a Condition.

The second therapeutic agent can be, but is not limited to, an opioid agonist, a non-opioid analgesic, a non-steroidal anti-inflammatory agent, an antimigraine agent, a Cox-II inhibitor, a 5-lipoxygenase inhibitor, an anti-emetic, a β-adrenergic blocker, an anticonvulsant, an antidepressant, a $Ca^{2+}$-channel blocker, an anti-cancer agent, an agent for treating or preventing UI, an agent for treating or preventing anxiety, an agent for treating or preventing a memory disorder, an agent for treating or preventing obesity, an agent for treating or preventing constipation, an agent for treating or preventing cough, an agent for treating or preventing diarrhea, an agent for treating or preventing high blood pressure, an agent for treating or preventing epilepsy, an agent for treating or preventing anorexia/cachexia, an agent for treating or preventing drug abuse, an agent for treating or preventing an ulcer, an agent for treating or preventing IBD, an agent for treating or preventing IBS, an agent for treating or preventing addictive disorder, an agent for treating or preventing Parkinson's disease and parkinsonism, an agent for treating or preventing a stroke, an agent for treating or preventing a seizure, an agent for treating or preventing a pruritic condition, an agent for treating or preventing psychosis, an agent for treating or preventing Huntington's chorea, an agent for treating or preventing ALS, an agent for treating or preventing a cognitive disorder, an agent for treating or preventing a migraine, an agent for inhibiting vomiting, an agent for treating or preventing dyskinesia, an agent for treating or preventing depression, or any mixture thereof.

Examples of useful opioid agonists include, but are not limited to, alfentanil, allylprodine, alphaprodine, anileridine, benzylmorphine, bezitramide, buprenorphine, butorphanol, clonitazene, codeine, desomorphine, dextromoramide, dezocine, diampromide, diamorphone, dihydrocodeine, dihydromorphine, dimenoxadol, dimepheptanol, dimethylthiambutene, dioxaphetyl butyrate, dipipanone, eptazocine, ethoheptazine, ethylmethylthiambutene, ethylmorphine, etonitazene, fentanyl, heroin, hydrocodone, hydromorphone, hydroxypethidine, isomethadone, ketobemidone, levorphanol, levophenacylmorphan, lofentanil, meperidine, meptazinol, metazocine, methadone, metopon, morphine, myrophine, nalbuphine, narceine, nicomorphine, norlevorphanol, normethadone, nalorphine, normorphine, norpipanone, opium, oxycodone, oxymorphone, papaveretum, pentazocine, phenadoxone, phenomorphan, phenazocine, phenoperidine, piminodine, piritramide, proheptazine, promedol, properidine, propiram, propoxyphene, sufentanil, tilidine, tramadol, pharmaceutically acceptable derivatives thereof, or any mixture thereof.

In certain embodiments, the opioid agonist is codeine, hydromorphone, hydrocodone, oxycodone, dihydrocodeine, dihydromorphine, morphine, tramadol, oxymorphone, pharmaceutically acceptable derivatives thereof, or any mixture thereof.

Examples of useful non-opioid analgesics include, but are not limited to, non-steroidal anti-inflammatory agents, such as aspirin, ibuprofen, diclofenac, naproxen, benoxaprofen, flurbiprofen, fenoprofen, flubufen, ketoprofen, indoprofen, piroprofen, carprofen, oxaprozin, pramoprofen, muroprofen, trioxaprofen, suprofen, aminoprofen, tiaprofenic acid, fluprofen, bucloxic acid, indomethacin, sulindac, tolmetin, zomepirac, tiopinac, zidometacin, acemetacin, fentiazac, clidanac, oxpinac, mefenamic acid, meclofenamic acid, flufenamic acid, niflumic acid, tolfenamic acid, diflurisal, flufenisal, piroxicam, sudoxicam, isoxicam, a pharmaceutically acceptable derivative thereof, or any mixture thereof. Other suitable non-opioid analgesics include the following, non-limiting, chemical classes of analgesic, antipyretic, non-steroidal anti-inflammatory drugs: salicylic acid derivatives, including aspirin, sodium salicylate, choline magnesium trisalicylate, salsalate, diflunisal, salicylsalicylic acid, sulfasalazine, and olsalazin; para-aminophenol derivatives including acetaminophen and phenacetin; indole and indene acetic acids, including indomethacin, sulindac, and etodolac; heteroaryl acetic acids, including tolmetin, diclofenac, and ketorolac; anthranilic acids (fenamates), including mefenamic acid and meclofenamic acid; enolic acids, including oxicams (piroxicam, tenoxicam), and pyrazolidinediones (phenylbutazone, oxyphenthartazone); alkanones, including nabumetone; a pharmaceutically acceptable derivative thereof; or any mixture thereof. For a more detailed description of the NSAIDs, see Insel, "Analgesic-Antipyretic and Anti-inflammatory Agents and Drugs Employed in the Treatment of Gout," pp. 617-657 in *Goodman & Gilman's The Pharmacological Basis of Therapeutics* (Goodman et al., Eds., 9$^{th}$ Ed., McGraw-Hill, New York 1996), and Hanson, "Analgesic, Antipyretic and Anti-Inflammatory Drugs," pp. 1196-1221 in *Remington: The Science and Practice of Pharmacy Vol. II* (Gennaro, ed., 19$^{th}$ ed., Mack Publishing, Easton, Pa., 1995), which are hereby incorporated by reference in their entireties.

Examples of useful Cox-II inhibitors and 5-lipoxygenase inhibitors, as well as combinations thereof, are described in U.S. Pat. No. 6,136,839, which is hereby incorporated by reference in its entirety. Examples of useful Cox-II inhibitors include, but are not limited to, celecoxib, DUP-697, flosulide, meloxicam, 6-MNA, L-745337, rofecoxib, nabumetone, nimesulide, NS-398, SC-5766, T-614, L-768277, GR-253035, JTE-522, RS-57067-000, SC-58125, SC-078, PD-138387, NS-398, flosulide, D-1367, SC-5766, PD-164387, etoricoxib, valdecoxib, parecoxib, a pharmaceutically acceptable derivative thereof, or any mixture thereof.

Examples of useful antimigraine agents include, but are not limited to, alpiropride, bromocriptine, dihydroergotamine, dolasetron, ergocornine, ergocorninine, ergocryptine, ergonovine, ergot, ergotamine, flumedroxone acetate, fonazine, ketanserin, lisuride, lomerizine, methylergonovine, methysergide, metoprolol, naratriptan, oxetorone, pizotyline, propranolol, risperidone, rizatriptan, sumatriptan, timolol, trazodone, zolmitriptan, a pharmaceutically acceptable derivative thereof, or any mixture thereof.

Examples of useful anticonvulsants include, but are not limited to, acetylpheneturide, albutoin, aloxidone, aminoglutethimide, 4-amino-3-hydroxybutyric acid, atrolactamide, beclamide, buramate, calcium bromide, carbamazepine, cinromide, clomethiazole, clonazepam, decimemide, diethadione, dimethadione, doxenitroin, eterobarb, ethadione, ethosuximide, ethotoin, felbamate, fluoresone, gabapentin, 5-hydroxytryptophan, lamotrigine, magnesium bromide, magnesium sulfate, mephenytoin, mephobarbital, metharbital, methetoin, methsuximide, 5-methyl-5-(3-phenanthryl)-hydantoin, 3-methyl-5-phenyl-hydantoin, narcobarbital, nimetazepam, nitrazepam, oxcarbazepine, paramethadione, phenacemide, phenetharbital, pheneturide, phenobarbital, phensuximide, phenylmethylbarbituric acid, phenytoin, phethenylate sodium, potassium bromide, pregabaline, primidone, progabide, sodium bromide, solanum, strontium bromide, suclofenide, sulthiame, tetrantoin, tiagabine, topiramate, trimethadione, valproic acid, valpromide, vigabairin, zonisamide, a pharmaceutically acceptable derivative thereof, or any mixture thereof.

Examples of useful Ca$^{2+}$-channel blockers include, but are not limited to, bepridil, clentiazem, diltiazem, fendiline, gallopamil, mibefradil, prenylamine, semotiadil, terodiline, verapamil, amlodipine, aranidipine, barnidipine, benidipine, cilnidipine, efonidipine, elgodipine, felodipine, isradipine, lacidipine, lercanidipine, manidipine, nicardipine, nifedipine, nilvadipine, nimodipine, nisoldipine, nitrendipine, cinnarizine, flunarizine, lidoflazine, lomerizine, bencyclane, etafenone, fantofarone, perhexyline, a pharmaceutically acceptable derivative thereof, or any mixture thereof.

Examples of useful therapeutic agents for treating or preventing UI include, but are not limited to, propantheline, imipramine, hyoscyamine, oxybutynin, dicyclomine, a pharmaceutically acceptable derivative thereof, or any mixture thereof.

Examples of useful therapeutic agents for treating or preventing anxiety include, but are not limited to, benzodiazepines, such as alprazolam, brotizolam, chlordiazepoxide, clobazam, clonazepam, clorazepate, demoxepam, diazepam, estazolam, flumazenil, flurazepam, halazepam, lorazepam, midazolam, nitrazepam, nordazepam, oxazepam, prazepam, quazepam, temazepam, and triazolam; non-benzodiazepine agents, such as buspirone, gepirone, ipsapirone, tiospirone, zolpicone, zolpidem, and zaleplon; tranquilizers, such as barbituates, e.g., amobarbital, aprobarbital, butabarbital, butalbital, mephobarbital, methohexital, pentobarbital, phenobarbital, secobarbital, and thiopental; propanediol carbamates, such as meprobamate and tybamate; a pharmaceutically acceptable derivative thereof; or any mixture thereof.

Examples of useful therapeutic agents for treating or preventing diarrhea include, but are not limited to, diphenoxylate, loperamide, a pharmaceutically acceptable derivative thereof, or any mixture thereof.

Examples of useful therapeutic agents for treating or preventing epilepsy include, but are not limited to, carbamazepine, ethosuximide, gabapentin, lamotrigine, phenobarbital, phenyloin, primidone, valproic acid, trimethadione, benzodiazepines, γ vinyl GABA, acetazolamide, felbamate, a pharmaceutically acceptable derivative thereof, or any mixture thereof.

Examples of useful therapeutic agents for treating or preventing drug abuse include, but are not limited to, methadone, desipramine, amantadine, fluoxetine, buprenorphine, an opiate agonist, 3-phenoxypyridine, levomethadyl acetate hydrochloride, serotonin antagonists, a pharmaceutically acceptable derivative thereof, or any mixture thereof.

Examples of non-steroidal anti-inflammatory agents, 5-lipoxygenase inhibitors, anti-emetics, β-adrenergic blockers, antidepressants, and anti-cancer agents are known in the art and can be selected by those skilled in the art. Examples of useful therapeutic agents for treating or preventing memory disorder, obesity, constipation, cough, high blood pressure, anorexia/cachexia, an ulcer, IBD, IBS, addictive disorder, Parkinson's disease and parkinsonism, a stroke, a seizure, a pruritic condition, psychosis, Huntington's chorea, ALS, a cognitive disorder, a migraine, dyskinesia, depression, and/or treating, preventing or inhibiting vomiting include those that are known in the art and can be selected by those skilled in the art.

A composition of the disclosure is prepared by a method comprising admixing a Phosphorus-Substituted Quinoxaline-Type Piperidine Compound or a pharmaceutically acceptable derivative thereof with a pharmaceutically acceptable carrier or excipient. Admixing can be accomplished using methods known for admixing a compound (or derivative) and a pharmaceutically acceptable carrier or excipient. In one embodiment, the Phosphorus-Substituted Quinoxaline-Type Piperidine Compound is present in the composition in an effective amount.

4.6 Kits

The disclosure further provides kits that can simplify the handling and administration of a Phosphorus-Substituted Quinoxaline-Type Piperidine Compound to an animal.

A typical kit of the disclosure comprises a unit dosage form of a Phosphorus-Substituted Quinoxaline-Type Piperidine Compound. In one embodiment, the unit dosage form comprises a first container, which can be sterile, containing an effective amount of a Phosphorus-Substituted Quinoxaline-Type Piperidine Compound and a pharmaceutically acceptable carrier or excipient. The kit can further comprise a label or printed instructions instructing the use of the Phosphorus-Substituted Quinoxaline-Type Piperidine Compound to treat or prevent a Condition. The kit can further comprise a unit dosage form of a second therapeutic agent, for example, a second container containing an effective amount of the second therapeutic agent and a pharmaceutically acceptable carrier or excipient. In another embodiment, the kit comprises a container containing an effective amount of a Phosphorus-Substituted Quinoxaline-Type Piperidine Compound, an effective amount of a second therapeutic agent and a pharmaceutically acceptable carrier or excipient. Examples of second therapeutic agents include, but are not limited to, those listed above.

Kits of the disclosure can further comprise a device that is useful for administering the unit dosage forms. Examples of such a device include, but are not limited to, a syringe, a drip bag, a patch, an inhaler, and an enema bag.

The following examples are set forth to assist in understanding the invention and should not be construed as specifically limiting the invention described and claimed herein. Such variations of the invention, including the substitution of all equivalents now known or later developed, that would be within the purview of those skilled in the art, and changes in formulation or changes in experimental design, are to be considered to fall within the scope of the invention incorporated herein.

5. EXAMPLES

Certain Examples below relate to the synthesis of illustrative Phosphorus-Substituted Quinoxaline-Type Piperidine Compounds.

5.1 Example 1

Synthesis of Phosphorus-Substituted Quinoxaline-Type Piperidine Compounds AA and BB

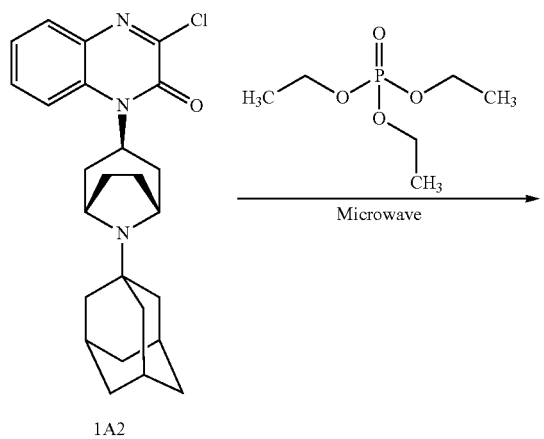

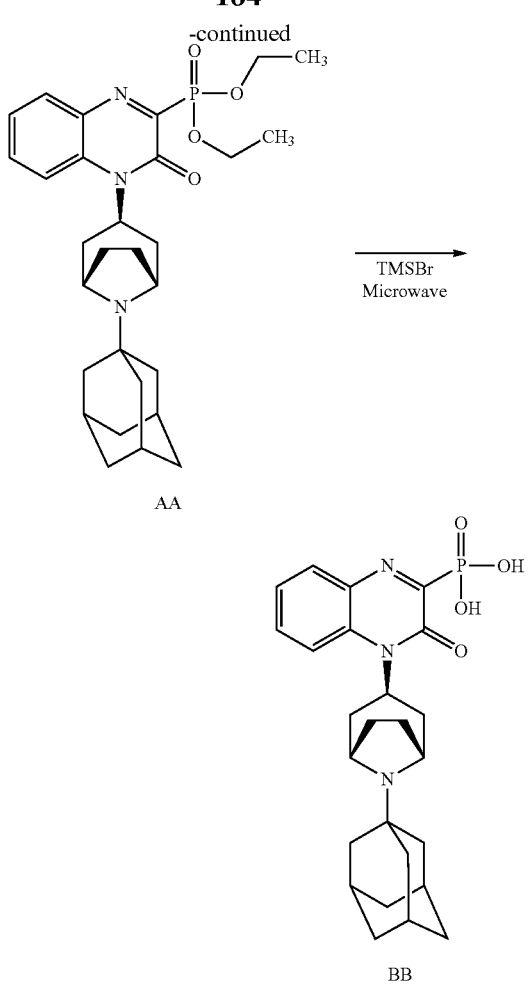

Compound 1A2,3-chloro-1-((1R,3R,5S)-8-((2R,3aS,5S,6aS)-octahydro-2,5-methanopentalen-3a-yl)-8-azabicyclo[3.2.1]octan-3-yl)quinoxalin-2(1H)-one, is commercially available or can be prepared, inter alia, as described in Example 14 of U.S. Patent Application Publication US 2010/0216726 A1 (preparation of Substituted-Quinoxaline-Type Piperidine Compound 347) except using 3-noradamantamine hydrochloride (see Example 36 therein) in place of the compound of formula EE (8-cyclooctyl-8-azabicyclo[3.2.1]octan-3-one) therein.

Compound 1A2 (0.24 mmol) was introduced into a 10 mL glass vial equipped with a small magnetic stirring bar. To this was added triethyl phosphate (6 mL, Sigma-Aldrich, St. Louis, Mo.), and the vial was tightly sealed with an aluminum and TEFLON crimped top. The reaction mixture was then irradiated for 1.5 h at 120° C. using a Biotage Initiator 2.5 high-powered, focused microwave heating apparatus (Uppsala, Sweden) operating at 2.45 GHz and 150 Watts. Thereafter, the mixture was cooled to a temperature of about 25° C. before the vial was opened. After the removal of volatiles by distillation on a "KUGELROHR" short-path reduced pressure distillation apparatus at 80° C., the residue was chromatographed on a flash column eluted with a gradient of from 50:50 EtOAc:hexane to 70:30 EtOAc:hexane. The fractions containing the product were combined and, under reduced pressure at 75° C., evaporated and dried to provide Phosphorus-Substituted Quinoxaline-Type Piperidine Compound AA, diethyl (4-((1R,3R,5S)-8-((2R,3aS,5S,6aS)-octahydro-2,5-methanopentalen-3a-yl)-8-azabicyclo[3.2.1]octan-3-yl)-3-oxo-3,4-dihydroquinoxalin-2-yl)phosphonate, as a white powder (yield 15%).

The identity of Phosphorus-Substituted Quinoxaline-Type Piperidine Compound AA was confirmed using ¹H NMR and MS.

Phosphorus-Substituted Quinoxaline-Type Piperidine Compound AA: ¹H NMR: $\delta_H$ (ppm, CD₃OD): 7.87-7.82 (m, 1H), 7.68-7.58 (m, 2H), 7.33 (t, J=8.1 Hz, 1H), 5.19 (br, 1H), 4.32-4.24 (m, 4H), 3.54 (s, 2H), 2.32-2.24 (m, 2H), 2.18 (s, 2H), 2.09-2.02 (m, 3H), 1.91-1.77 (m, 6H), 1.73-1.68 (m, 2H), 1.64-1.57 (m, 6H), 1.53-1.39 (m, 6H); MS: m/z=512.2 [M+1].

In a microwave vial, Phosphorus-Substituted Quinoxaline-Type Piperidine Compound AA (100 mg) was dissolved in MeCN (20 mL). TMSBr (286 mg, 1.87 mmol, Sigma-Aldrich) was added. The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound BB, (4-((1R,3R,5S)-8-((2R,3as,5S,6aS)-octahydro-2,5-methanopentalen-3a-yl)-8-azabicyclo[3.2.1]octan-3-yl)-3-oxo-3,4-dihydroquinoxalin-2-yl)phosphonic acid (yield 30%).

The identity of Phosphorus-Substituted Quinoxaline-Type Piperidine Compound BB was confirmed using ¹H NMR and MS.

Phosphorus-Substituted Quinoxaline-Type Piperidine Compound BB: ¹H NMR: $\delta_H$ (ppm, CD₃OD): 7.99 (d, J=8.0 Hz, 1H), 7.70-7.61 (m, 2H), 7.42 (t, J=14.2 Hz, 1H), 5.54 (br, 1H), 4.22 (s, 2H), 2.89-2.81 (m, 2H), 2.65 (d, J=6.9 Hz, 3H), 2.42 (br, 4H), 2.16 (m, 6H), 1.76 (d, J=12.0, 3H), 1.63 (d, J=11.8 Hz, 1H), 1.31 (t, J=7 .Hz, 2H); MS: m/z=456.1 [M+1].

5.2 Example 2

Synthesis of Phosphorus-Substituted Quinoxaline-Type Piperidine Compounds CC and DD

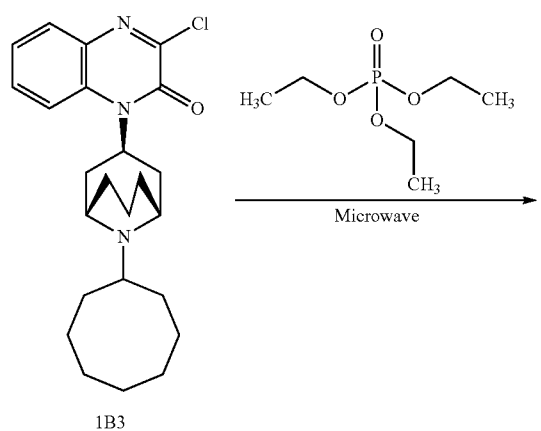

1B3

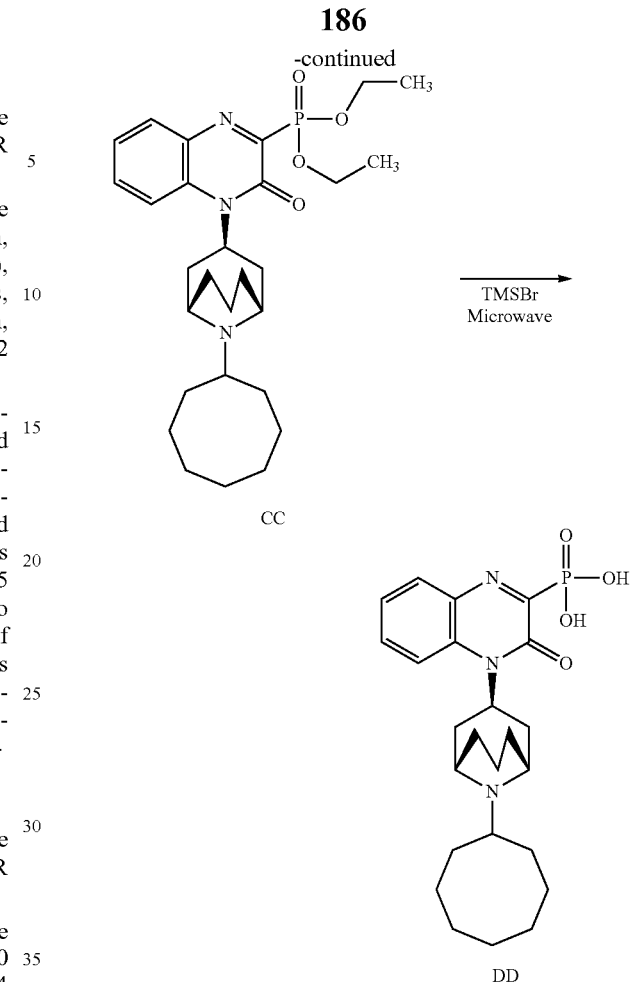

CC

DD

Compound 1B3,3-chloro-1-((1R,3R,5S)-9-cyclooctyl-9-azabicyclo[3.3.1]nonan-3-yl)quinoxalin-2(1H)-one, is commercially available or can be prepared, inter alia, as described in Example 14 of U.S. Patent Application Publication US 2010/0216726 A1 (preparation of Substituted-Quinoxaline-Type Piperidine Compound 347) except using the compound of formula LC (9-cyclooctyl-9-azabicyclo [3.3.1]nonan-3-one) from Example 35 therein in place of the compound of formula EE (8-cyclooctyl-8-azabicyclo[3.2.1] octan-3-one).

Compound 1B3 (0.34 mmol) was introduced into a 10 mL glass vial equipped with a small magnetic stirring bar. To this was added triethyl phosphate (6 mL, Sigma-Aldrich), and the vial was tightly sealed with an aluminum and TEFLON crimped top. The reaction mixture was then irradiated for 1.5 h at 120° C. using the microwave apparatus and conditions previously described. Thereafter, the mixture was cooled to a temperature of about 25° C. before the vial was opened. After the removal of volatiles by distillation on a "KUGELROHR" short-path reduced pressure distillation apparatus at 80° C., the residue was chromatographed on a flash column eluted with a gradient of from 50:50 EtOAc: hexane to 70:30 EtOAc:hexane. The fractions containing the product were combined and, under reduced pressure at 75° C., evaporated and dried to provide Phosphorus-Substituted Quinoxaline-Type Piperidine Compound CC, diethyl (4-((1R,3r,5S)-9-cyclooctyl-9-azabicyclo[3.3.1]nonan-3-yl)-3-oxo-3,4-dihydroquinoxalin-2-yl)phosphonate, as a white powder.

In a microwave vial, Phosphorus-Substituted Quinoxaline-Type Piperidine Compound CC (0.17 mmol), taken directly from the previous step, was dissolved in MeCN (20 mL). TMSBr (154 mg, 1.01 mmol) was added. The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound DD, (4-((1R,3R,5S)-9-cyclooctyl-9-azabicyclo[3.3.1]nonan-3-yl)-3-oxo-3,4-dihydroquinoxalin-2-yl)phosphonic acid (yield 33% from Compound 1B3).

The identity of Phosphorus-Substituted Quinoxaline-Type Piperidine Compound DD was confirmed using $^1$H NMR and MS.

Phosphorus-Substituted Quinoxaline-Type Piperidine Compound DD: $^1$H NMR: $\delta_H$ (ppm, CD$_3$OD): 7.88 (d, J=8.2 Hz, 1H), 7.76 (d, J=9.2 Hz, 1H), 7.62-7.58 (m, 1H), 7.32 (t, J=7.3 Hz, 1H), 5.32 (br, 1H), 4.08 (d, J=9.2 Hz, 2H), 3.75 (d, J=9.8 Hz, 2H), 3.04-2.98 (m, 3H), 2.65 (m, 1H), 2.35-2.20 (m, 2H), 2.02-1.92 (m, 4H), 1.80 (m, 2H), 1.70-1.52 (br, 10H), 1.45 (m, 1H); MS: m/z 460.2 [M+1] (Calc: 459.5).

5.3 Example 3

Synthesis of Phosphorus-Substituted Quinoxaline-Type Piperidine Compounds EE and FF

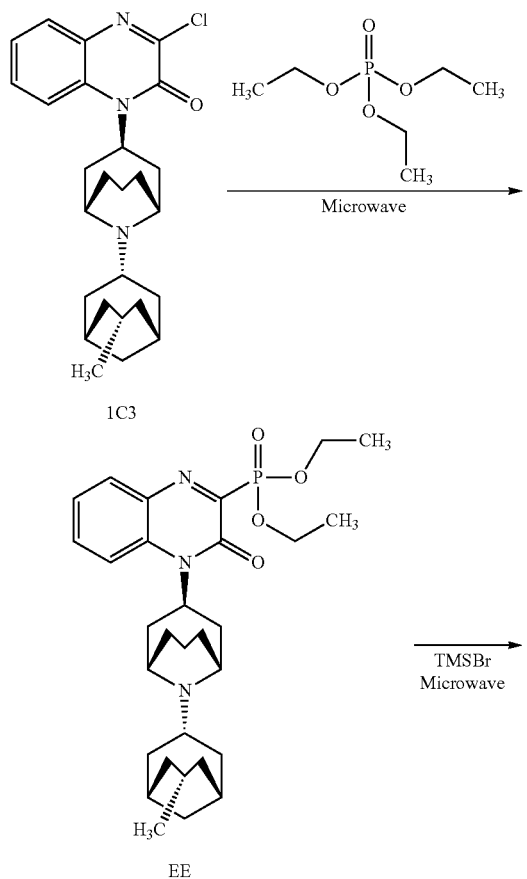

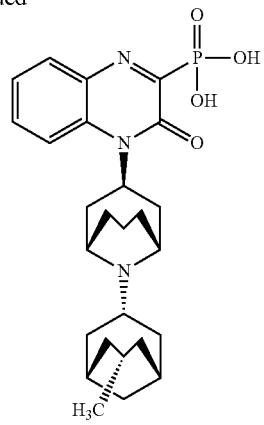

FF

Compound 1C3,3-chloro-1-((1R,1'R,3R,3'R,5S,5'S,7S)-7-methyl-9'-aza[3,9'-bi(bicyclo[3.3.1]nonan)]-3'-yl)quinoxalin-2(1H)-one, was prepared as described in Example 12 herein.

Compound 1C3 (0.23 mmol) was introduced into a 10 mL glass vial equipped with a small magnetic stirring bar. To this was added triethyl phosphate (6 mL), and the vial was tightly sealed with an aluminum and TEFLON crimped top. The reaction mixture was then irradiated for 1.5 h at 120° C. using the microwave apparatus and conditions previously described. Thereafter, the mixture was cooled to a temperature of about 25° C. before the vial was opened. After the removal of volatiles by distillation on a "KUGELROHR" short-path reduced pressure distillation apparatus at 80° C., the residue was chromatographed on a flash column eluted with a gradient of from 50:50 EtOAc:hexane to 70:30 EtOAc:hexane. The fractions containing the product were combined and, under reduced pressure at 75° C., evaporated and dried to provide Phosphorus-Substituted Quinoxaline-Type Piperidine Compound EE, diethyl (4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)phosphonate, as a white powder.

The identity of Phosphorus-Substituted Quinoxaline-Type Piperidine Compound EE was confirmed using MS.

Phosphorus-Substituted Quinoxaline-Type Piperidine Compound EE: MS: m/z=542.3 [M+1] (Calc: 541.3).

In a microwave vial, Phosphorus-Substituted Quinoxaline-Type Piperidine Compound EE (0.20 mmol) was dissolved in MeCN (20 mL). TMSBr (186 mg, 1.21 mmol) was added. The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound FF, (4-((1R,1'R,3R,3'R,5S,5'S,7S)-7-methyl-[3,9'-bi(9'-azabicyclo[3.3.1]nonan)]-3'-yl)-3-oxo-3,4-dihydroquinoxalin-2-yl)phosphonic acid (yield 14%).

The identity of Phosphorus-Substituted Quinoxaline-Type Piperidine Compound FF was confirmed using $^1$H NMR and MS.

Phosphorus-Substituted Quinoxaline-Type Piperidine Compound FF: $^1$H NMR: $\delta_H$ (ppm, DMSO): 8.02-7.89 (m, 2H), 7.78-7.64 (m, 1H), 7.48-7.38 (m, 1H), 5.49 (br, 1H), 4.10 (m, 5H), 3.87-3.76 (m, 4H), 2.87-2.75 (m, 4H), 2.35-2.12 (m, 5H), 2.08-1.88 (m, 4H), 1.78-1.38 (m, 2H) 1.27-0.98 (m, 3H) 0.90-0.70 (m, 2H); MS: m/z=486.2 [M+1] (Calc: 485.2).

5.4 Example 4

Synthesis of Phosphorus-Substituted Quinoxaline-Type Piperidine Compounds GG and HH

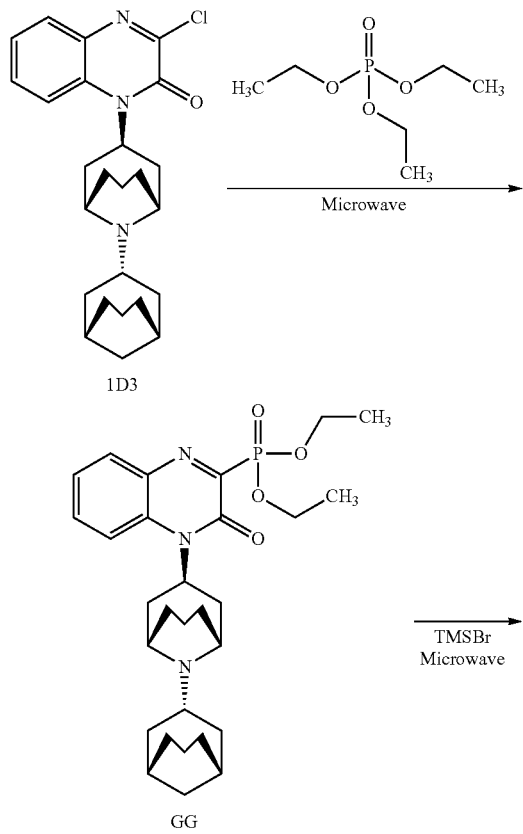

Compound 1D3, 1-((1R,1'R,3R,3'R,5S,5'S)-[3,9'-bi(9'-azabicyclo[3.3.1]nonan)]-3'-yl)-3-chloroquinoxalin-2(1H)-one, was prepared as described in Example 13 herein.

Compound 1D3, (0.32 mmol) was introduced into a 10 mL glass vial equipped with a small magnetic stirring bar. To this was added triethyl phosphate (6 mL), and the vial was tightly sealed with an aluminum and TEFLON crimped top. The reaction mixture was then irradiated for 1.5 h at 120° C. using the microwave apparatus and conditions previously described. Thereafter, the mixture was cooled to a temperature of about 25° C. before the vial was opened. After the removal of volatiles by distillation on a "KUGELROHR" short-path reduced pressure distillation apparatus at 80° C., the residue was chromatographed on a flash column eluted with a gradient of from 50:50 EtOAc:hexane to 70:30 EtOAc:hexane. The fractions containing the product were combined and, under reduced pressure at 75° C., evaporated and dried to provide Phosphorus-Substituted Quinoxaline-Type Piperidine Compound GG, diethyl (4-((1R,1'R,3R,3'R,5S,5'S)-[3,9'-bi(9'-azabicyclo[3.3.1]nonan)]-3'-yl)-3-oxo-3,4-dihydroquinoxalin-2-yl)phosphonate, as a white powder.

The identity of Phosphorus-Substituted Quinoxaline-Type Piperidine Compound GG was confirmed using MS.

Phosphorus-Substituted Quinoxaline-Type Piperidine Compound GG: MS: m/z=528.3 [M+1] (Calc: 527.3).

In a microwave vial, Phosphorus-Substituted Quinoxaline-Type Piperidine Compound GG (0.09 mmol) was dissolved in MeCN (20 mL). TMSBr (87 mg, 0.56 mmol) was added. The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound HH, (4-((R,1'R,3R,3'R,5S,5'S)-[3,9'-bi(9'-azabicyclo[3.3.1]nonan)]-3'-yl)-3-oxo-3,4-dihydroquinoxalin-2-yl)phosphonic acid (yield 22%).

The identity of Phosphorus-Substituted Quinoxaline-Type Piperidine Compound HH was confirmed using $^1$H NMR and MS.

Phosphorus-Substituted Quinoxaline-Type Piperidine Compound HH: $^1$H NMR: $\delta_H$ (ppm, CD$_3$OD): 8.15 (d, J=8.6 Hz, 1H), 8.02 (d, J=9.3 Hz, 1H), 7.77 (t, J=8.7 Hz, 1H), 7.47 (t, J=7.6 Hz, 1H), 5.74-5.63 (m, 1H), 4.43-4.35 (m, 1H), 4.23 (d, J=10.8 Hz, 2H), 3.12 (t, J=13.4 Hz, 2H), 2.87-2.73 (m, 1H), 2.45-2.37 (m, 2H), 2.28-2.19 (m, 4H), 2.18-2.08 (m, 4H), 1.85-1.73 (m, 7H), 1.70-1.62 (m, 4H); MS: m/z=472.1 [M+1] (Calc: 471.2).

5.5 Example 5

Synthesis of Phosphorus-Substituted Quinoxaline-Type Piperidine Compounds JJ and KK

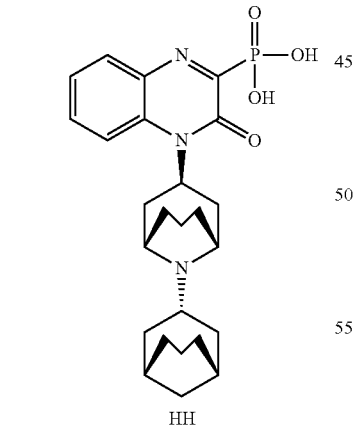

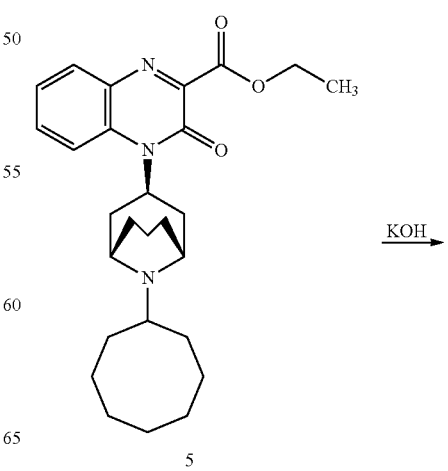

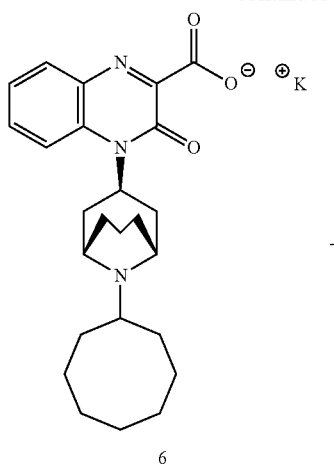

6

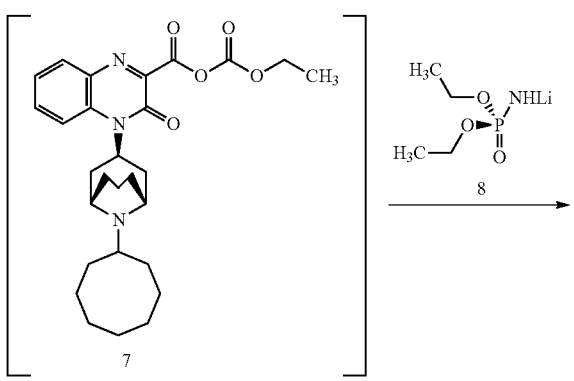

7

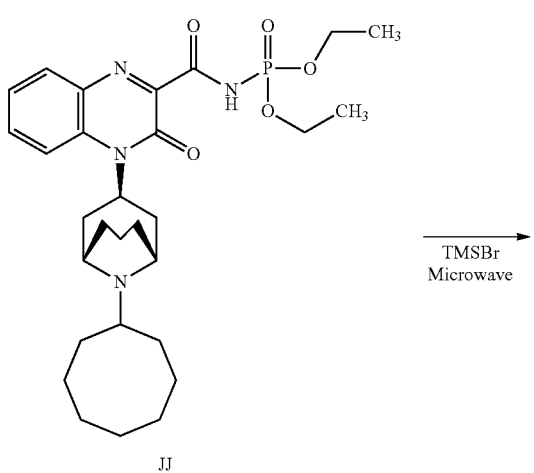

JJ

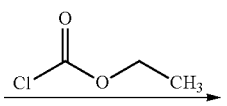

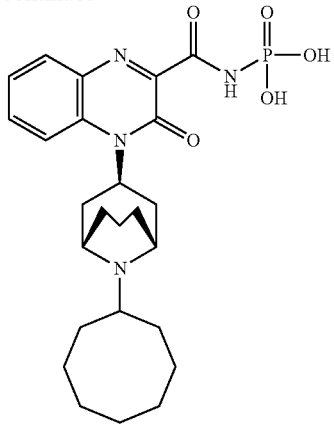

KK

Compound 5, ethyl 4-((1R,3R,5S)-9-cyclooctyl-9-azabicyclo[3.3.1]nonan-3-yl)-3-oxo-3,4-dihydroquinoxaline-2-carboxylate, is commercially available or can be prepared, inter alia, as described in Example 35 of U.S. Patent Application Publication US 2010/0216726 A1 (preparation of Substituted-Quinoxaline-Type Piperidine Compound 240).

Compound 5 (200 mg, 0.46 mmol) was added to 1M potassium hydroxide (0.5 mL) and MeCN (0.5 mL). The reaction mixture was stirred at a temperature of about 25° C. for 30 min. Volatiles were removed under reduced pressure and the remaining water was removed by azeotroping with toluene, ethyl acetate, then chloroform under reduced pressure to provide Compound 6, potassium 4-((1R,3R,5S)-9-cyclooctyl-9-azabicyclo[3.3.1]nonan-3-yl)-3-oxo-3,4-dihydroquinoxaline-2-carboxylate.

Compound 6 (200 mg, 0.43 mmol) was dissolved in anhydrous DCM (20 mL) in the presence of molecular sieves. Dropwise addition of ethyl carbonochloridate (346 μL, 3.65 mmol, Sigma-Aldrich) gave a pale yellow solution containing Compound 7; thereafter, the solution was stirred under a nitrogen atmosphere for 2 h.

Lithium (diethoxyphosphoryl)amide 8 was prepared as follows.

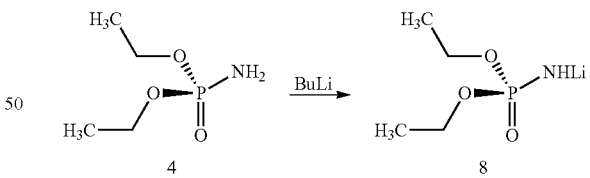

Diethyl phosphoroamidate (4, 368 mg, 2.41 mmol, Sigma-Aldrich) was dissolved in anhydrous DCM (5 mL) and stirred at −78° C. To this solution, butyl lithium (1.2 mL, 2M solution in hexane, Sigma-Aldrich) was added, which spontaneously precipitated the salt as a colorless solid. The mixture was stirred for 30 min at −78° C. then allowed to warm to a temperature of about 25° C. over 30 min with stirring.

The solution containing Compound 7 was cooled to −78° C., then the mixture containing Compound 8 was added. The reaction mixture was stirred for about 16 h at a temperature of about 25° C. The reaction was quenched by the addition of water (15 mL) then the mixture was acidified to pH 1 with aqueous 1M HCl. The organic layer was separated and washed with 80:20 EtOAc:hexane to provide Phosphorus-Substituted Quinoxaline-Type Piperidine Compound JJ, diethyl (4-((1R,3R,5S)-9-cyclooctyl-9-azabicyclo[3.3.1]nonan-3-yl)-3-oxo-3,4-dihydroquinoxaline-2-carbonyl)phosphoramidate (yield 20%).

The identity of Phosphorus-Substituted Quinoxaline-Type Piperidine Compound JJ was confirmed using MS.

Phosphorus-Substituted Quinoxaline-Type Piperidine Compound JJ: MS: m/z=559.5 [M+1] (Calc: 558.3).

Phosphorus-Substituted Quinoxaline-Type Piperidine Compound JJ (420 mg, 0.75 mmol) was dissolved in MeCN (20 mL). TMSBr (620 mg, 4.52 mmol) was added. The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound KK, (4-((1R,3R,5S)-9-cyclooctyl-9-azabicyclo[3.3.1]nonan-3-yl)-3-oxo-3,4-dihydroquinoxaline-2-carbonyl)phosphoramidic acid (yield 10%).

The identity of Phosphorus-Substituted Quinoxaline-Type Piperidine Compound KK was confirmed using $^1$H NMR and MS.

Phosphorus-Substituted Quinoxaline-Type Piperidine Compound KK: $^1$H NMR: $\delta_H$ (ppm, $CD_3OD$): 7.95 (d, J=8.0 Hz, 1H), 7.69-7.61 m, 2H), 7.41-7.34 m, 1H), 5.21-5.06 (m, 1H), 3.46 (d, J=9 Hz, 2H), 3.07-3.01 (m, 1H), 2.71-2.59 (m, 2H), 2.50-2.30 (m, 1H) 1.99-1.88 (m, 3H), 1.84-1.67 (m, 5H) 1.63-1.38 (m, 6H), 1.25-1.02 (m, 5H) 0.85-0.73 (m, 2H); MS: m/z=503.2 [M+1] (Calc: 502.2).

5.6 Example 6

Synthesis of Phosphorus-Substituted Quinoxaline-Type Piperidine Compounds LL and MM

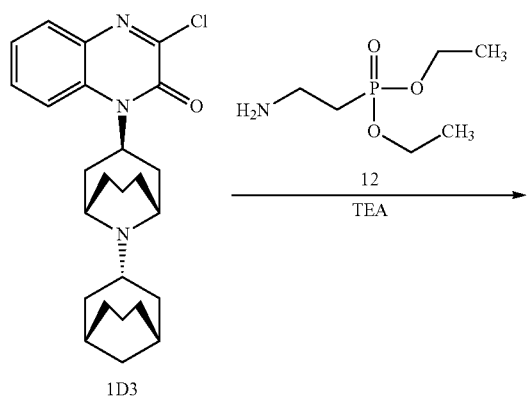

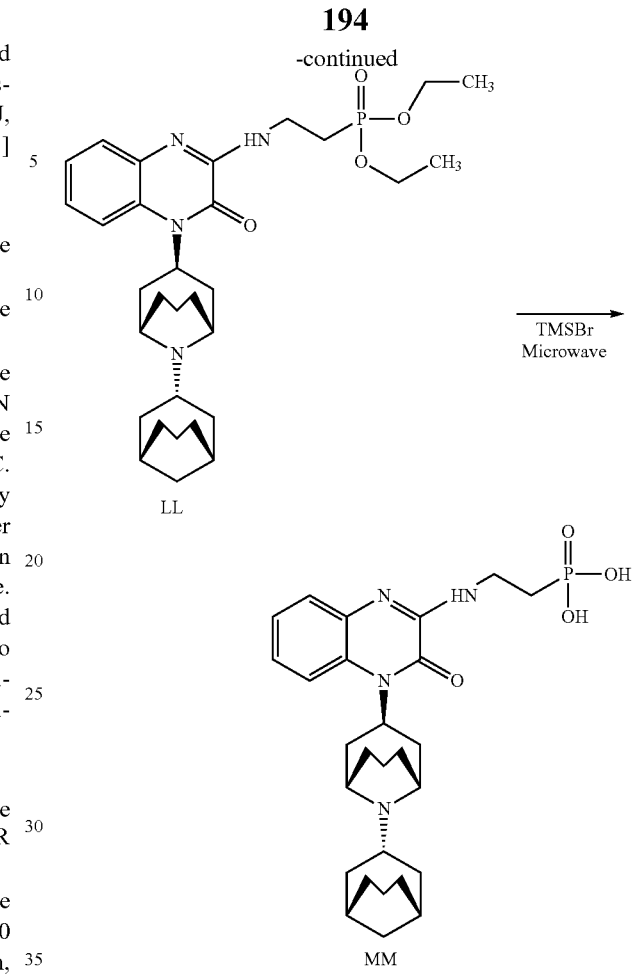

Compound 1D3 (100 mg, 0.23 mmol) was dissolved in DMF (5 mL). Diethyl 2-aminoethylphosphonate (12, 0.52 mmol, Sigma-Aldrich) was added followed by the addition of TEA (41 μL, 0.28 mmol, Sigma-Aldrich). The resulting reaction mixture was stirred for about 16 h at a temperature of about 25° C. Thereafter, the mixture was evaporated under reduced pressure. The residue was dissolved in DCM (20 mL) and washed with brine (20 mL). The organic layer was separated and dried over sodium sulfate. The filtrate was evaporated to provide Phosphorus-Substituted Quinoxaline-Type Piperidine Compound LL, diethyl (2-((4-((1R,1'R,3r,3'R,5S,5'S)-[3,9'-bi(9'-azabicyclo[3.3.1]nonan)]-3'-yl)-3-oxo-3,4-dihydroquinoxalin-2-yl)amino)ethyl)phosphonate.

Phosphorus-Substituted Quinoxaline-Type Piperidine Compound LL (110 mg, 0.19 mmol), taken directly from the previous step, and TMSBr (176 mg, 1.15 mmol) were added to MeCN (5 mL). The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound MM, (2-((4-((1R,1'R,3r,3'R,5S,5'S)-[3,9'-bi(9'-azabicyclo[3.3.1]nonan)]-3'-yl)-3-oxo-3,4-dihydroquinoxalin-2-yl)amino)ethyl)phosphonic acid (yield 6% from Compound 1D3).

The identity of Phosphorus-Substituted Quinoxaline-Type Piperidine Compound MM was confirmed using $^1$H NMR and MS.

Phosphorus-Substituted Quinoxaline-Type Piperidine Compound MM: $^1$H NMR: $\delta_H$ (ppm, $CD_3OD$): 7.73 (d, J=8.6 Hz, 1H), 7.60 (d, J=6.1 Hz, 1H), 7.39-7.29 (m, 2H), 5.49-5.36 (m, 1H), 4.42-4.30 (m, 2H), 3.90-3.75 (m, 2H), 3.15-3.03 (m, 2H), 2.79-2.65 (m, 1H), 2.51-2.37 (m, 2H), 2.31-2.07 (m, 8H), 1.98-1.88 (m, 3H), 1.85-1.73 (m, 6H), 1.71-1.61 (m, 5H); MS: m/z=515.2 [M+1] (Calc: 514.3).

5.7 Example 7

Synthesis of Phosphorus-Substituted Quinoxaline-Type Piperidine Compounds NN and OO

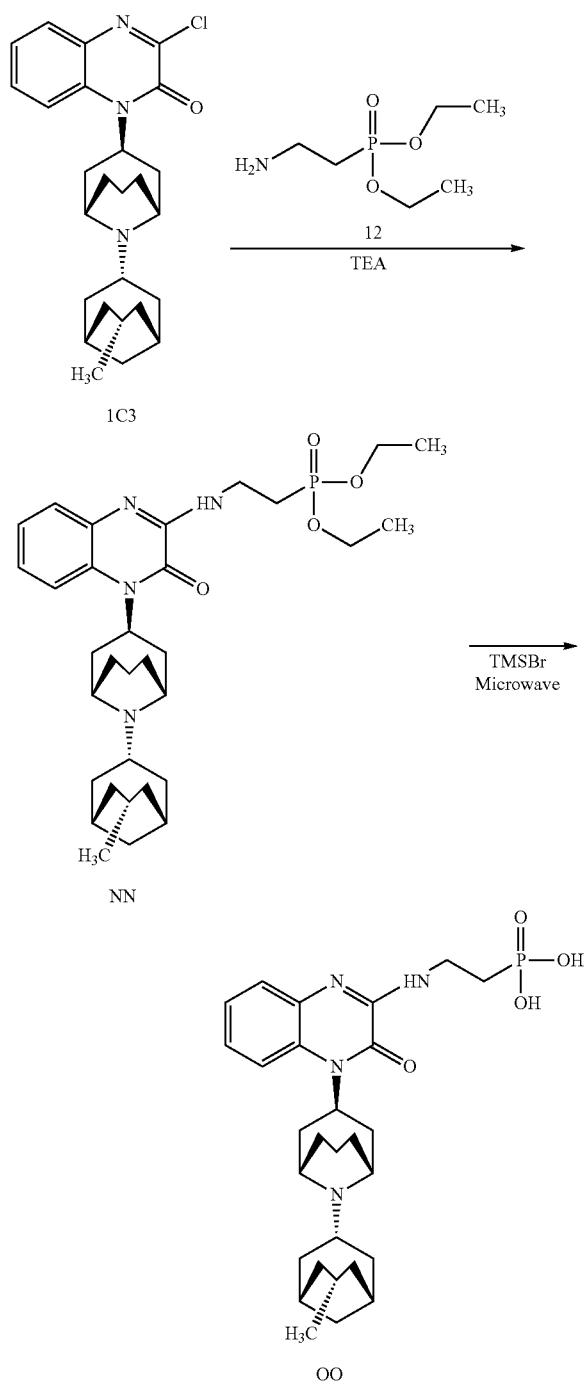

Compound 1C3 (300 mg, 0.68 mmol) was dissolved in (5 mL) of DMF. Compound 12 (277 mg, 1.53 mmol) was added followed by the addition of TEA (0.3 mL, 2.04 mmol). The mixture stirred for about 16 h at a temperature of about 25° C. Thereafter, the mixture was evaporated under reduced pressure. The residue was dissolved in DCM (20 mL) and washed with brine (20 mL). The organic layer was separated and dried over sodium sulfate. The filtrate was evaporated to provide Compound NN, diethyl (2-((4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)amino)ethyl)phosphonate:

The identity of Phosphorus-Substituted Quinoxaline-Type Piperidine Compound NN was confirmed using MS.

Phosphorus-Substituted Quinoxaline-Type Piperidine Compound NN: MS: m/z=585.5 [M+1] (Calc: 584.4).

Compound NN (120 mg, 0.21 mmol), taken directly from the previous step, and TMSBr (188 mg, 1.23 mmol) were added to MeCN (5 mL). The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound OO, (2-((4-((1R,1'R,3R,3'R,5S,5'S,7S)-7-methyl-[3,9'-bi(9'-azabicyclo[3.3.1]nonan)]-3'-yl)-3-oxo-3,4-dihydroquinoxalin-2-yl)amino)ethyl)phosphonic acid (yield 10%).

The identity of Phosphorus-Substituted Quinoxaline-Type Piperidine Compound OO was confirmed using $^1$H NMR and MS.

Phosphorus-Substituted Quinoxaline-Type Piperidine Compound OO: $^1$H NMR: $\delta_H$ (ppm, CD$_3$OD): 7.59 (br, 1H), 7.50 (m, 1H), 7.20 (m, 2H), 5.21 (br, 1H), 3.76 (m, 2H), 3.64 (m, 2H), 2.72 (m, 3H), 2.28-1.52 (m, 16H), 1.29 (m, 4H), 1.13 (d, J=11.4 Hz, 1H), 0.93 (d, J=6.3 Hz, 3H), 0.90 (m, 2H); MS: m/z=529.3 [M+1] (Calc: 528.3).

5.8 Example 8

Synthesis of Phosphorus-Substituted Quinoxaline-Type Piperidine Compounds PP and QQ

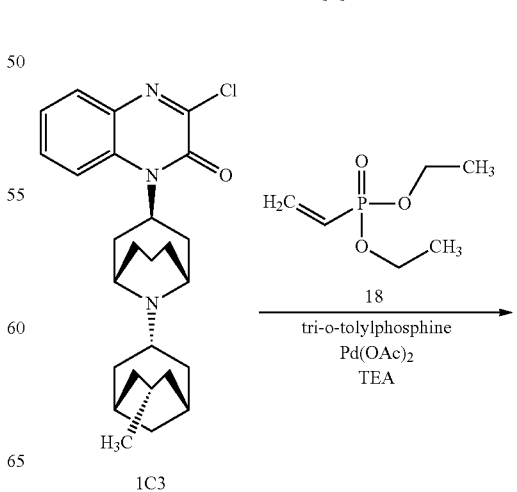

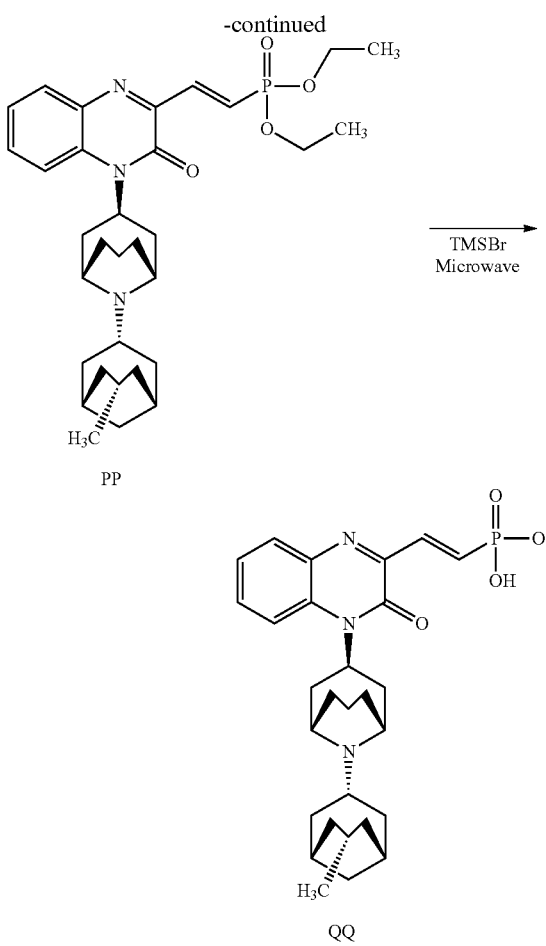

Compound 1C3 (1 g, 2.28 mmol) and diethyl vinylphosphonate (18, 2.28 mmol, Sigma-Aldrich) were dissolved in anhydrous MeCN. To this solution was added tri-o-tolylphosphine (55 mg, 0.18 mmol, Sigma-Aldrich) followed by Pd(OAc)$_2$ (31 mg, 0.14 mmol, Sigma-Aldrich). The reaction vial was sealed and the mixture was allowed to stir for about 16 h at 100° C. Progress of the reaction was monitored by LC/MS and when it was substantially complete the volatiles were evaporated under reduced pressure to provide a residue. To the residue was added Et$_2$O (20 mL). The resulting crystals were collected and filtered to provide Phosphorus-Substituted Quinoxaline-Type Piperidine Compound PP, diethyl ((E)-2-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)vinyl)phosphonate.

The identity of Phosphorus-Substituted Quinoxaline-Type Piperidine Compound PP was confirmed using $^1$H NMR and MS.

Phosphorus-Substituted Quinoxaline-Type Piperidine Compound PP: $^1$H NMR: $\delta_H$ (ppm, CD$_3$OD): 7.96 (m, 1H), 7.90 (d, J=5.2 Hz, 1H), 7.86 (m, 1H), 7.71 (m, 1H), 7.50 (m, 1H), 7.29 (dd, J=17.5, 20.8 Hz, 1H), 5.49 (br, 1H), 4.22 (m, 6H), 3.96 (m, 1H), 3.16 (m, 2H), 2.80 (m, 1H), 2.41 (m, 4H), 2.12 (m, 6H), 1.91 (m, 2H), 1.69 (m, 5H), 1.40 (t, J=7.0 Hz, 6H), 1.18 (d, J=3.5 Hz, 1H), 0.95 (d, J=6.4 Hz, 3H), 0.83 (m, 2H); MS: m/z=568.3 [M+1] (Calc: 567.3).

Phosphorus-Substituted Quinoxaline-Type Piperidine Compound PP (350 mg, 0.21 mmol), taken directly from the previous step, and TMSBr (796 mg, 5.21 mmol) were added to MeCN (5 mL). The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound QQ, ((E)-2-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)vinyl) phosphonic acid (yield 27%).

The identity of Phosphorus-Substituted Quinoxaline-Type Piperidine Compound QQ was confirmed using $^1$H NMR and MS.

Phosphorus-Substituted Quinoxaline-Type Piperidine Compound QQ: $^1$H NMR: $\delta_H$ (ppm, CD$_3$OD): 8.25 (m, 1H), 7.79 (m, 1H), 7.72 (d, J=5.0 Hz, 1H), 7.60 (m, 1H), 7.33 (m, 1H), 7.24 (dd, J=17.4, 20.0 Hz, 1H), 5.78 (br, 1H), 4.11 (m, 2H), 3.81 (m, 1H), 2.97 (m, 2H), 2.70 (m, 1H), 2.30 (m, 4H), 1.95 (m, 9H), 1.70 (m, 4H), 1.16 (m, 1H), 0.81 (d, J=6.4 Hz, 3H), 0.69 (m, 2H); MS: m/z=512.3 [M+1] (Calc: 511.3).

5.9 Example 9

Synthesis of Phosphorus-Substituted Quinoxaline-Type Piperidine Compounds RR, SS, and TT

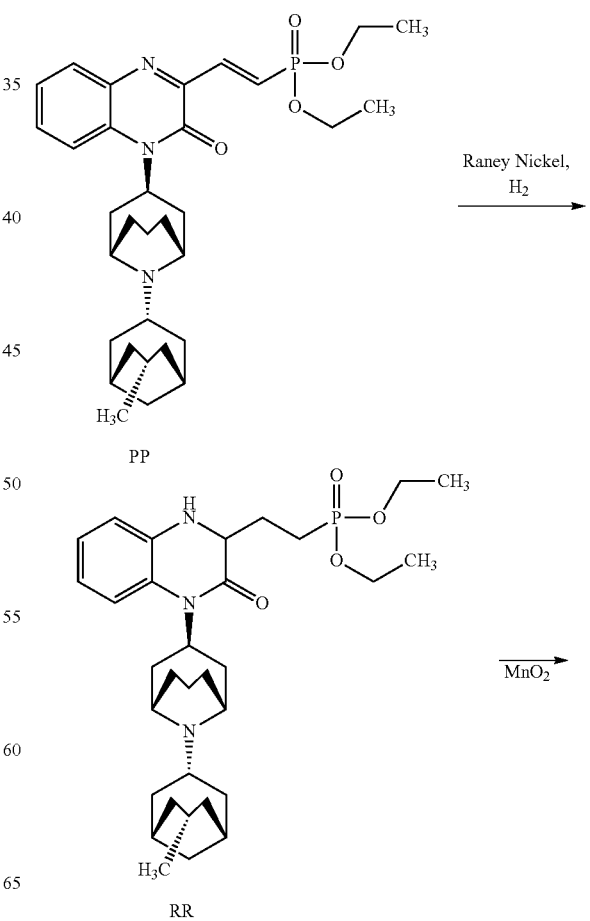

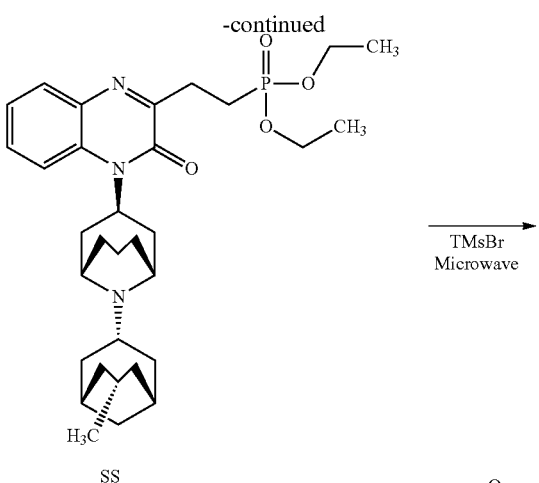

SS

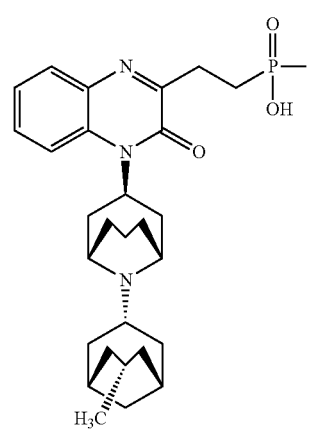

TMsBr, Microwave →

TT

A solution of Phosphorus-Substituted Quinoxaline-Type Piperidine Compound PP (300 mg, 0.53 mmol) in EtOH (10 mL) under a hydrogen atmosphere was reduced over 5% Raney-Nickel (100 mg, Sigma-Aldrich) at a temperature of about 25° C. using a hydrogen-filled balloon apparatus. Thereafter, the mixture was filtered through CELITE and concentrated under reduced pressure to provide Phosphorus-Substituted Quinoxaline-Type Piperidine Compound RR, diethyl (2-(4-((1R,1'R,3R,3'R,5S,5'S,7S)-7-methyl-[3,9'-bi(9'-azabicyclo[3.3.1]nonan)]-3'-yl)-3-oxo-1,2,3,4-tetrahydroquinoxalin-2-yl)ethyl)phosphonate.

The identity of Phosphorus-Substituted Quinoxaline-Type Piperidine Compound RR was confirmed using MS.

Phosphorus-Substituted Quinoxaline-Type Piperidine Compound RR: MS: m/z=572.3 [M+1] (Calc: 571.4).

Manganese dioxide (122 mg, 1.38 mmol, Sigma-Aldrich) was suspended in a solution of Phosphorus-Substituted Quinoxaline-Type Piperidine Compound RR (100 mg, 0.18 mmol) in toluene (5 mL). The reaction mixture was heated to reflux, a temperature of about 100° C., refluxed for 2 h, then the hot mixture was filtered through CELITE. Volatiles were removed under reduced pressure to provide Phosphorus-Substituted Quinoxaline-Type Piperidine Compound SS, diethyl (2-(4-((1R,1'R,3R,3'R,5S,5'S,7S)-7-methyl-[3,9'-bi(9'-azabicyclo[3.3.1]nonan)]-3'-yl)-3-oxo-3,4-dihydroquinoxalin-2-yl)ethyl)phosphonate.

The identity of Phosphorus-Substituted Quinoxaline-Type Piperidine Compound SS was confirmed using MS.

Phosphorus-Substituted Quinoxaline-Type Piperidine Compound SS: MS: m/z=570.4 [M+1] (Calc: 569.3).

Phosphorus-Substituted Quinoxaline-Type Piperidine Compound SS (100 mg, 0.17 mmol), taken directly from the previous step, and TMSBr (796 mg, 5.21 mmol) were added to MeCN (5 mL). The reaction mixture was then irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound TT, (2-(4-((1'R,3R,3'R,5S,5'S,7S)-7-methyl-[3,9'-bi(9'-azabicyclo[3.3.1]nonan)]-3'-yl)-3-oxo-3,4-dihydroquinoxalin-2-yl)ethyl)phosphonic acid (yield 15%).

The identity of Phosphorus-Substituted Quinoxaline-Type Piperidine Compound TT was confirmed using $^1$H NMR and MS.

Phosphorus-Substituted Quinoxaline-Type Piperidine Compound TT: $^1$H NMR: $\delta_H$ (ppm, CD$_3$OD): 7.86 (d, J=7.9 Hz, 2H), 7.61 (m, 1H), 7.41 (m, 1H), 5.50 (br, 1H), 4.24 (m, 2H), 3.95 (m, 1H), 3.16 (m, 3H), 2.79 (m, 1H), 2.46-1.62 (m, 20H), 1.18 (d, J=13.0 Hz, 1H), 0.94 (d, J=6.4 Hz, 3H), 0.84 (m, 2H); MS: m/z=514.3 [M+1] (Calc: 513.3).

5.10 Example 10

Synthesis of Phosphorus-Substituted Quinoxaline-Type Piperidine Compounds UU and VV

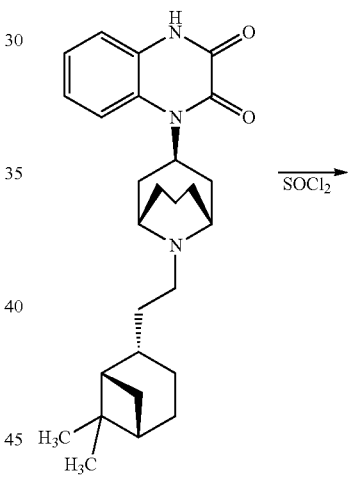

24

SOCl$_2$ →

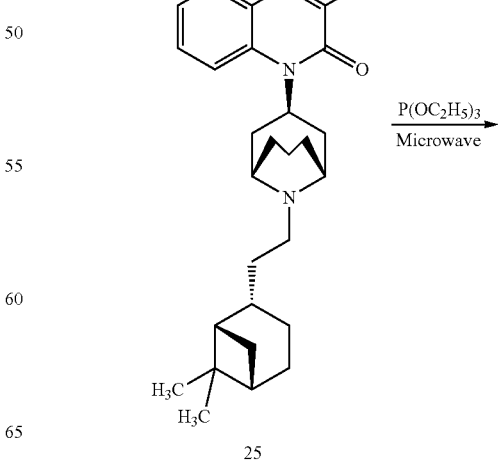

25

P(OC$_2$H$_5$)$_3$, Microwave →

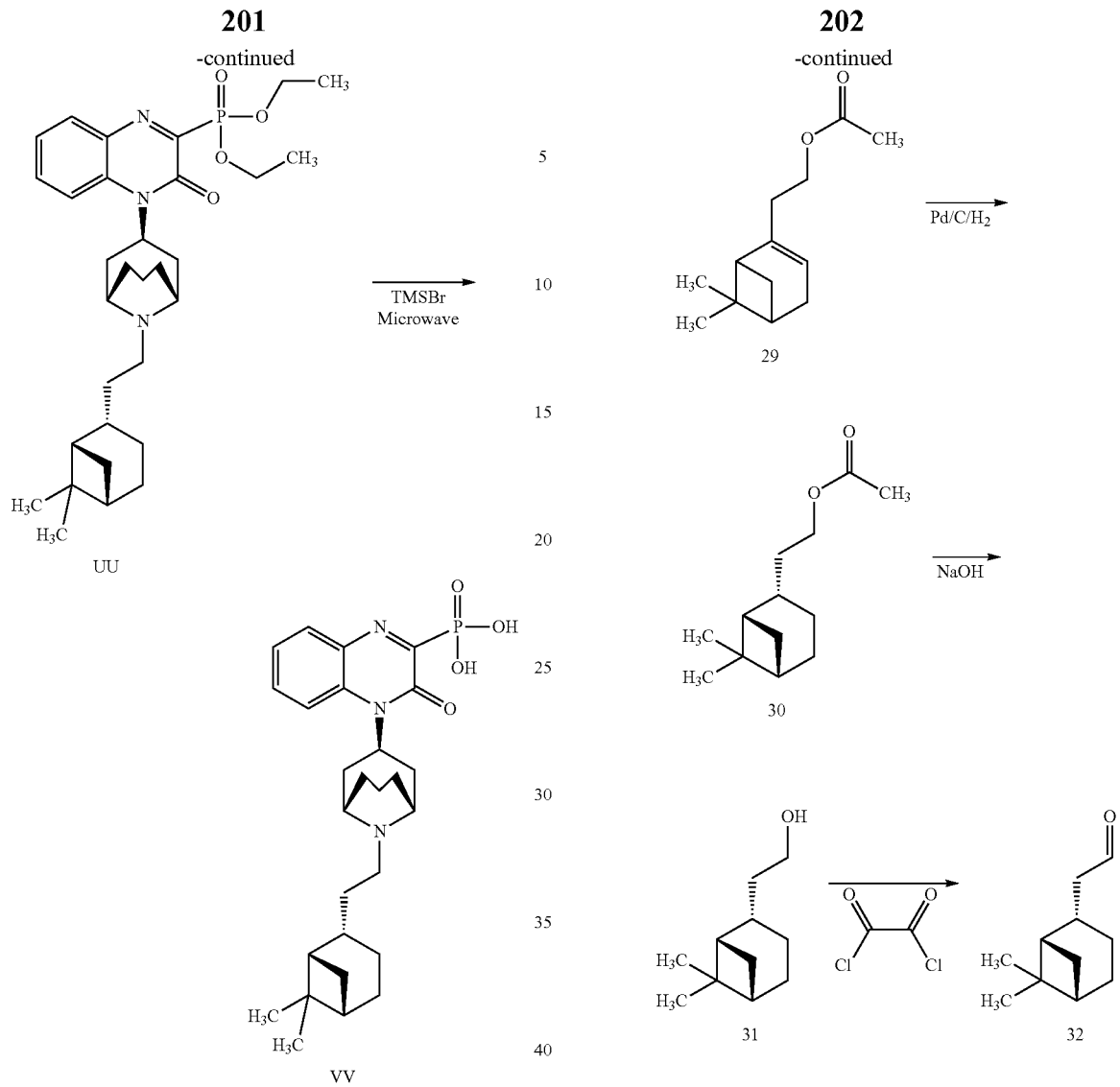

Compound 24, 1-((1R,3S,5S)-9-(2-((1S,2S,5S)-6,6-dimethylbicyclo[3.1.1]heptan-2-yl)ethyl)-9-azabicyclo[3.3.1]nonan-3-yl)quinoxaline-2,3(1H,4H)-dione, is commercially available or can be prepared, inter alia, as described in Scheme G of U.S. Patent Application Publication US 2010/0022519 A1 wherein a and q are each 0, C and D are each H, A and B together form a —(CH$_2$)$_3$— bridge, and the ketone is 2-((1S,2S,5S)-6,6-dimethylbicyclo[3.1.1]heptan-2-yl)acetaldehyde.

2-((1S,2S,5S)-6,6-Dimethylbicyclo[3.1.1]heptan-2-yl)acetaldehyde 32 was prepared as follows.

To a solution of Compound 28 (30 g, 0.2 mol, Nopol, i.e., 2-(6,6-dimethylbicyclo[3.1.1]hept-2-en-2-yl)ethanol, Sigma-Aldrich) and 45 mL TEA (0.33 mol) in DCM (200 mL) at a temperature in the range of 5-10° C. was slowly added acetyl chloride (17 g, Sigma-Aldrich). Thereafter, the reaction mixture was stirred for another 20 min at a temperature in the range of 5-10° C., allowed to warm to at a temperature of about 25° C., then poured into ice water (300 mL). The organic phase was separated and the aqueous phase was extracted with DCM (100 mL). The organic portions were combined and washed with brine. The volatiles were evaporated under reduced pressure to provide a residue. The residue was chromatographed with a silica column eluted with 1:3 Et$_2$O:hexanes to provide Compound 29, 2-(6,6-dimethylbicyclo[3.1.1]hept-2-en-2-yl)ethyl acetate, as a colorless oil (30 g). Compound 29 (10 g) was hydrogenated by shaking a mixture of it and 10% palladium on carbon (Pd/C, 1 g, Sigma-Aldrich) in EtOAc (100 mL) at a temperature of about 25° C. under a hydrogen pressure of 60 bar for 5 h. After the Pd/C was filtered off, the volatiles were evaporated under reduced pressure to provide Compound 30, 2-((1S,2S,5S)-6,6-dimethylbicyclo[3.1.1]heptan-2-yl)ethyl acetate, as colorless oil. To the oil was added a solution of NaOH (7 g) in 100 mL MeOH:10 mL water and the mixture was stirred for 2 h at a temperature of about 25° C. Thereafter, the mixture was concentrated under reduced pressure, diluted with water (40 mL), extracted twice with DCM (100 mL for each extraction), and again concentrated under reduced pressure to provide Compound 31, 2-((1S,2S,5S)-6,6-dimethylbicyclo[3.1.1]heptan-2-yl)ethanol, as colorless oil (6 g). At a temperature of −78° C., DMSO (4 mL) in DCM (50 mL) was slowly added to a 2N solution of oxalyl dichloride (Sigma-Aldrich) in DCM (25 mL). After 1 h at that temperature, Compound 31 (5 g) in DCM (50 mL) was added and the reaction mixture stirred for 2 h. Thereafter, TEA (20 mL) in DCM (40 mL) was added and the mixture was allowed to warm to a temperature of about 25° C. over about 16 h. The reaction mixture was then quenched by the addition of water. The organic layer was separated and the volatiles were evaporated therefrom under reduced pressure to provide Compound 32 as colorless oil.

Compound 24 (500 mg, 1.49 mmol) was dissolved in DCM (10 mL). To this solution at a temperature of about 25° C. was first added thionyl chloride (0.3 mL, 3.45 mmol, Sigma-Aldrich) dropwise followed by DMF (0.3 mL). After completion of the reaction in about 5 min, the mixture was evaporated under reduced pressure to provide Compound 25, 3-chloro-1-((1R,3S,5S)-9-(2-((1S,2S,5S)-6,6-dimethylbicyclo[3.1.1]heptan-2-yl)ethyl)-9-azabicyclo[3.3.1]nonan-3-yl)quinoxalin-2(1H)-one.

A solution of Compound 25 (200 mg, 0.44 mmol), taken directly from the previous step, in triethyl phosphate (6 mL) was introduced into a 10 mL glass vial equipped with a small magnetic stirring bar, and the vial was tightly sealed with an aluminum and TEFLON crimped top. The reaction mixture was then irradiated for 1.5 h at 120° C. using the microwave apparatus and conditions previously described. Thereafter, the mixture was cooled to a temperature of about 25° C. before the vial was opened. After the removal of volatiles by distillation on a "KUGELROHR" short-path reduced pressure distillation apparatus at 80° C., the residue was chromatographed on a flash column eluted with a gradient of from 50:50 EtOAc:hexane to 70:30 EtOAc:hexane. The fractions containing the product were combined and, under reduced pressure at 75° C., evaporated and dried to provide Phosphorus-Substituted Quinoxaline-Type Piperidine Compound UU, diethyl (4-((1R,3S,5S)-9-(2-((1S,2S,5S)-6,6-dimethylbicyclo[3.1.1]heptan-2-yl)ethyl)-9-azabicyclo[3.3.1]nonan-3-yl)-3-oxo-3,4-dihydroquinoxalin-2-yl)phosphonate, as a white powder.

A reaction mixture of Phosphorus-Substituted Quinoxaline-Type Piperidine Compound UU (180 mg, 0.32 mmol), taken directly from the previous step, and TMSBr (298 mg, 1.95 mmol) in MeCN was irradiated for 20 min at 60° C. using the microwave apparatus and conditions previously described. The resulting solution was concentrated under reduced pressure, washed with hexane (5 mL), and again concentrated under reduced pressure to provide a residue. The residue was dissolved in a mixture of MeCN (5 mL) and water (2.5 mL). The resulting crystals were collected to provide Phosphorus-Substituted Quinoxaline-Type Piperidine Compound VV, (4-((1R,3S,5S)-9-(2-((1S,2S,5S)-6,6-dimethylbicyclo[3.1.1]heptan-2-yl)ethyl)-9-azabicyclo[3.3.1]nonan-3-yl)-3-oxo-3,4-dihydroquinoxalin-2-yl)phosphonic acid (yield 8% from Compound 24).

The identity of Phosphorus-Substituted Quinoxaline-Type Piperidine Compound VV was confirmed using $^1$H NMR and MS.

Phosphorus-Substituted Quinoxaline-Type Piperidine Compound VV: $^1$H NMR: $\delta_H$ (ppm, CD$_3$OD): 8.13 (br, 1H), 7.91 (d, J=7.9 Hz, 1H), 7.70 (m, 1H), 7.36 (m, 1H), 5.63 (br, 1H), 3.82 (m, 2H), 2.96 (m, 2H), 2.66 (m, 1H), 2.33 (m, 3H), 2.20-1.81 (m, 11H), 1.65 (m, 1H), 1.54 (m, 2H), 1.20 (m, 2H), 1.15 (s, 3H), 1.04 (s, 3H), 0.88 (d, J=9.4 Hz, 1H); MS: m/z=500.2 [M+1] (Calc: 499.3).

5.11 Example 11

Synthesis of Phosphorus-Substituted Quinoxaline-Type Piperidine Compound WW

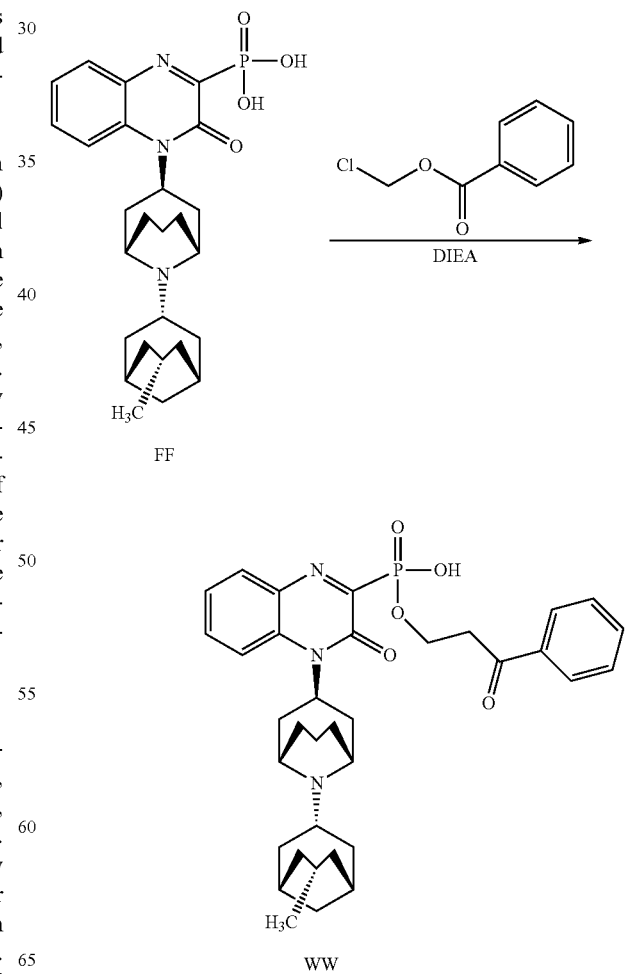

Phosphorus-Substituted Quinoxaline-Type Piperidine Compound FF (100 mg, 0.21 mmol) was dissolved in DMF (5 mL) and stirred at a temperature of about 25° C. DIEA (0.2 mL, 0.82 mmol, Sigma-Aldrich) and chloromethyl benzoate (119 mg, 0.70 mmol, Sigma-Aldrich) were added. The reaction mixture was heated to reflux, a temperature of about 70° C., and refluxed for about 16 h. After the mixture was cooled to a temperature of about 25° C., EtOAc (50 mL) was added. The mixture was washed with saturated aqueous NaHCO$_3$ solution (15 mL) followed by brine (10 mL). The organic layer was separated, dried (MgSO$_4$), filtered, and evaporated under reduced pressure to provide a residue. The residue was chromatographed on a reverse phase column eluted with MeCN:water to provide Phosphorus-Substituted Quinoxaline-Type Piperidine Compound WW, (((4-((1R,1'R,3R,3'R,5S,5'S)-[3,9'-bi(9'-azabicyclo[3.3.1]nonan)]-3'-yl)-3-oxo-3,4-dihydroquinoxalin-2-yl)(hydroxy)phosphoryl)oxy)methyl 2-phenylacetate (yield 38%).

The identity of Phosphorus-Substituted Quinoxaline-Type Piperidine Compound WW was confirmed using $^1$H NMR and MS.

Phosphorus-Substituted Quinoxaline-Type Piperidine Compound WW: $^1$H NMR: $\delta_H$ (ppm, CD$_3$OD): 8.33 (d, J=8.7 Hz, 1H), 8.08 (s, 1H), 7.86 (m, 2H), 7.76 (m, 1H), 7.56 (m, 1H), 7.42 (m, 1H), 7.34 (m, 2H), 6.08 (d, J=13.8 Hz, 2H), 5.82 (br, 1H), 4.15 (m, 2H), 3.90 (m, 1H), 2.92 (m, 2H), 2.73 (m, 1H), 2.37 (m, 2H), 2.24 (m, 2H), 2.05 (m, 7H), 1.80 (m, 3H), 1.49 (m, 2H), 1.40 (m, 1H), 1.24 (m, 1H), 0.92 (d, J=6.3 Hz, 3H), 0.79 (m, 2H); MS: m/z=620.2 [M+1] (Calc: 619.3).

5.12 Example 12

Synthesis of Compound 1C3

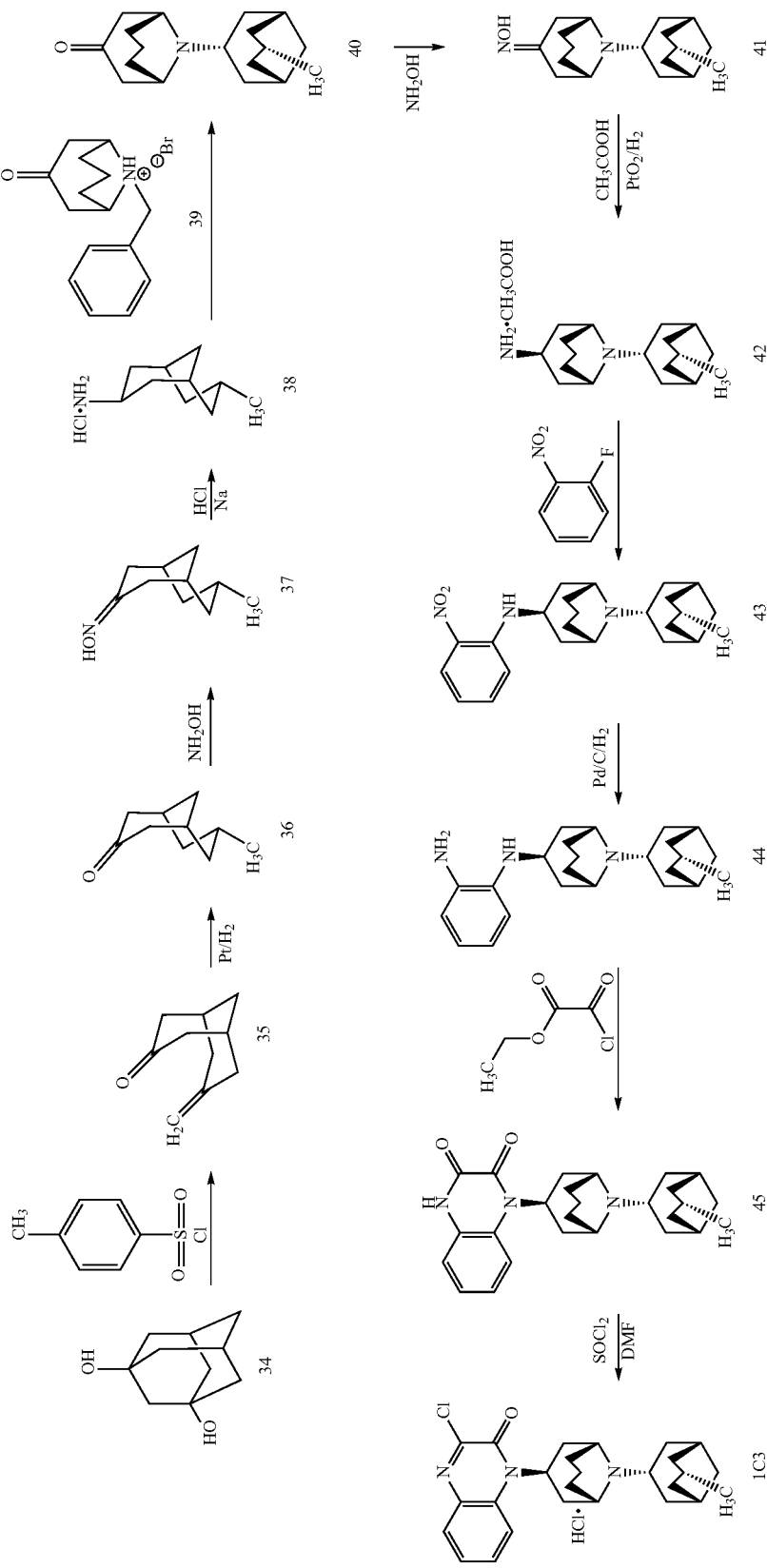

2-Adamantanediol (34, 500 g, 2.97 mol, Sigma-Aldrich), p-tosyl chloride (624 g, 3.27 mol, Sigma-Aldrich), and pyridine (1.5 L) were combined and stirred under an argon atmosphere. The reaction mixture was heated to a temperature in the range of 68-71° C. and remained at that temperature for 2.5 h. The reaction mixture was cooled to a temperature of about 25° C. and poured into saturated brine (6 L). The resulting mixture was extracted three times with MTBE (4 L for each extraction). The organic portions were combined, dried ($MgSO_4$), filtered, and concentrated onto 1 kg silica gel (pre-treated with hexanes:TEA). The adsorbed material was chromatographed on 1.5 kg silica eluted sequentially with 1:10 EtOAc:hexanes (5 L) then 2:10 EtOAc:hexanes (5 L). All product fractions were combined and evaporated under reduced pressure to provide a residue. The residue was suspended in deionized water (2 L), stirred for 10 min, and filtered under reduced pressure to remove any excess reactants. The remaining solids were taken up in MTBE (2 L), dried ($MgSO_4$), filtered, and evaporated under reduced pressure to provide 301 g of Compound 35, (1R, 5S)-7-methylenebicyclo[3.3.1]nonan-3-one, as a white crystalline solid (yield 67%).

The identity of Compound 35 was confirmed using $^1$H NMR and TLC.

Compound 35: $^1$H NMR: $\delta_H$ (400 MHz, $CDCl_3$): 4.79 (2H, s), 2.51 (8H, m), 2.29 (2H, m), 1.94 (2H, m), 1.60 (1H, m); TLC ($SiO_2$) 1:10 EtOAc:hexanes: $R_f$=0.25 (visualized with $KMnO_4$ spray reagent).

Compound 35 (250 g, 1.66 mol) was divided into five equal batches. Under a hydrogen atmosphere, the first batch was hydrogenated over platinum black (5 g, Sigma-Aldrich) at 50 psi in dry 99:1 cyclohexane:EtOAc (200 mL) for 2 h. The reaction mixture was decanted and the remaining catalyst washed with cyclohexane until no product remained as determined by TLC. The reaction flask was then recharged with the next batch of Compound 35, cyclohexane (200 mL), and hydrogen and the reaction mixture was hydrogenated at 50 psi for 2 h. This procedure was repeated until all batches were reacted. All filtrates were combined, filtered through CELITE, and concentrated at a temperature of about 25° C. to provide Compound 36, 7-methylbicyclo[3.3.1]nonan-3-one, as a colorless oil.

The identity of Compound 36 was confirmed using $^1$H NMR and TLC.

Compound 36: $^1$H NMR: $\delta_H$ (400 MHz, $CDCl_3$): 2.42 (4H, m), 2.26 (2H, m), 1.98-2.00 (3H, m), 1.65 (1H, m), 1.54 (1H, m), 0.80 (1H, m); TLC ($SiO_2$) 2:10 EtOAc:hexanes: $R_f$=0.30 (visualized with $KMnO_4$ spray reagent).

Compound 36, taken directly from the previous step, was taken up in AcOH (1 L). To this was added 50% aqueous $NH_2OH$ (100 mL, Sigma-Aldrich). With stirring, the reaction mixture was heated to a gentle reflux and refluxed for 1 h. The mixture was cooled to a temperature of about 25° C. and slowly poured into 2.5M $Na_2CO_3$ aqueous solution (5 L) with stirring. Thereafter, the mixture was stirred vigorously for 1 h. Deionized water (1 L) was added and the mixture was stirred for another 0.5 h. The precipitate that formed was collected by filtering under reduced pressure and washed with deionized water (2 L). The residue was taken up in DCM (1 L), dried ($MgSO_4$), filtered, and evaporated under reduced pressure to provide 231.5 g of Compound 37, 7-methylbicyclo[3.3.1]nonan-3-one oxime, as a white fluffy solid (85% yield from Compound 35).

The identity of Compound 37 was confirmed using $^1$H NMR.

Compound 37: $^1$H NMR: $\delta_H$ (400 MHz, $CDCl_3$): 3.21 (1H, d), 2.05-2.41 (4H, m), 1.73-2.11 (4H, m), 1.51-1.73 (2H, m), 1.33 (1H, d), 0.82 (4H, m), 0.63 (1H, t).

To a three neck 5 L round bottom flask equipped with an overhead stirrer, 1 L pressure equalizing dropping funnel, and temperature probe was added toluene (about 3 L) and Na metal (67.17 g, 2.8 mol, Sigma-Aldrich). Under an argon atmosphere, the mixture was heated to a gentle reflux until the Na metal became molten. A solution of a portion of Compound 37 (66.66 g, 0.40 mol) in dry isopropyl alcohol (230 mL) was then added dropwise via the dropping funnel over 1.5 h. With stirring, the resulting reaction mixture was heated to reflux and refluxed for 16 h. After cooling to a temperature of about 25° C., the following materials were added in sequential order: EtOH (164 mL) dropwise over 15 min, 1:1 EtOH:$H_2O$ (164 mL) dropwise over 15 min, and water (500 mL) dropwise over 30 min. The resulting mixture was stirred for 2 h. The mixture was poured into a 6 L separatory funnel and the organic layer was separated. The aqueous portion was extracted three times with $Et_2O$ (1 L for each extraction).

The process just described was repeated twice more with 66.66 g of Compound 37 being used each time. All organic portions were combined, dried ($MgSO_4$), and filtered into a 6 L Erlenmeyer flask. To the mixture was added 2M HCl in $Et_2O$ (1.5 L, 2.5 eq). The mixture was allowed to stir and cool in an ice:MeOH bath for 1 h. The solids that formed were filtered under reduced pressure and dried under reduced pressure at 50° C. for 18 h to provide 100.01 g of Compound 38, (3s,7s)-7-methylbicyclo[3.3.1]nonan-3-amine hydrochloride, as a white crystalline solid. The filtrate was evaporated under reduced pressure to provide a residue which was triturated with $Et_2O$ (2 L). The solids that remained were filtered and washed with $Et_2O$ (2 L) to provide 87.1 g of a second crop of Compound 38 after drying (overall yield 39%).

The identity of Compound 38 was confirmed using $^1$H NMR.

Compound 38: $^1$H NMR: $\delta_H$ (400 MHz, $CDCl_3$): 8.28 (3H, bs), 3.55 (1H, m), 2.25 (2H, m), 1.81-2.09 (4H, m), 1.85 (1H, m), 1.61 (3H, m) 1.08 (1H, d), 0.70-0.88 (5H, m).

Compound 38 (87.1 g, 0.463 mol), 9-benzyl-3-oxo-9-azoniabicyclo[3.3.1]nonane bromide (39, 165.20 g, 0.509 mol, Sigma-Aldrich), potassium carbonate (67.83 g, 0.491 mol), EtOH (1.07 L), and water (346 mL) were combined. The resulting reaction mixture was stirred for about 16 h at a temperature of about 25° C. The reaction mixture was then heated to reflux and refluxed for 3 h. Thereafter, the mixture was cooled to a temperature of about 25° C. then further cooled to 5° C. in an ice/MeOH bath and allowed to stir for 30 min at that temperature. The solids that formed were filtered under reduced pressure, washed with deionized water, and dried under reduced pressure to provide 102.1 g of Compound 40, (1R,3r,5S,7s)-7-methyl-9'-aza[3,9'-bi(bicyclo[3.3.1]nonan)]-3'-one, as an off-white crystalline solid (yield 80%).

The identity of Compound 40 was confirmed using $^1$H NMR.

Compound 40: $^1$H NMR: $\delta_H$ (400 MHz, $CDCl_3$): 3.68 (2H, m), 3.05 (1H, m), 2.61 (2H, m), 2.25 (4H, m), 1.98 (1H, m), 1.85 (4H, m), 1.49-1.78 (7H, m), 1.25 (2H, m), 1.07 (1H, d), 0.86 (3H, d), 0.78 (2H, t).

Compound 40 (67 g, 0.243 mol), THF (500 mL), and AcOH (41.78 mL, 0.730 mol) were combined. To this mixture was added 50% aqueous $NH_2OH$ (45 mL, 0.730 mol). With stirring, the resulting reaction mixture was heated to reflux and refluxed for 1 h. The mixture was cooled to a temperature of about 25° C. and deionized water was added (500 mL). Potassium carbonate (100 g, 0.730 mol) in deionized water (500 mL) was then added in one portion. The resulting mixture was stirred and cooled in an ice bath for 1 h. The solids that formed were filtered under reduced pressure and dried under reduced pressure at 60° C. to provide Compound 41, (1R,3r,5S,7s)-7-methyl-9'-aza[3,9'-bi(bicyclo[3.3.1]nonan)]-3'-one oxime (yield >99%).

The identity of Compound 41 was confirmed using $^1$H NMR.

Compound 41: $^1$H NMR: $\delta_H$ (400 MHz, CD$_3$OD): 3.76 (1H, m), 3.45 (2H, m), 3.18 (1H, m), 3.02 (1H, m), 2.62 (1H, m), 2.27 (4H, m), 1.78-2.08 (7H, m), 1.67 (1H, m), 1.58 (2H, m), 1.46 (1H, m), 1.22 (2H, t), 1.09 (1H, d), 0.85 (5H, m).

Compound 41 (70.01 g, 0.241 mol) was taken up in AcOH (400 mL). This mixture was divided into two batches. Under a hydrogen atmosphere, to each batch was added platinum (IV) oxide (5.98 g, 0.2 eq, Sigma-Aldrich) and each batch was then hydrogenated at 50 psi for 16 h to 18 h. The batches were combined and filtered through CELITE. The filter cake was washed with AcOH (500 mL). The filtrate was concentrated under reduced pressure at 70° C. to provide an oil. To the oil was added MTBE (6 L). The mixture was stirred and cooled to 0° C. for 1 h. The white precipitate that formed was filtered under reduced pressure, washed with Et$_2$O (2 L), and dried under reduced pressure to provide 76.2 g of Compound 42, (1R,1'R,3r,3'R,5S,5'S,7S)-7-methyl-9'-aza[3,9'-bi(bicyclo[3.3.1]nonan)]-3'-amine acetate, as a white solid (yield 94%).

The identity of Compound 42 was confirmed using $^1$H NMR and LC/MS.

Compound 42: $^1$H NMR: $\delta_H$ (400 MHz, CD$_3$OD): 3.73 (2H, m), 3.55 (1H, m), 2.46 (2H, m), 2.24 (2H, m), 1.75-2.12 (11H, m), 1.45-1.75 (4H, m), 1.28 (4H, m), 1.06 (1H, d), 0.89 (3H, d), 0.80 (2H, t); LC/MS (t$_r$=1.689 min): m/z=277.3 [M+H]$^+$ (Calc: 276.5).

Compound 42 (80.0 g, 0.23 mol), 1-fluoro-2-nitrobenzene (35.69 g, 0.253 mol, Sigma-Aldrich), and potassium carbonate (95.36 g, 0.69 mol) were combined in dry DMF (400 mL). The reaction mixture was heated to 110° C. under an argon atmosphere for 1 h then cooled to a temperature of about 25° C. Deionized water (2 L) was added and the mixture was stirred and cooled in an ice/MeOH bath for 1 h. The resulting solids were filtered under reduced pressure, washed with deionized water (4 L), and dried under reduced pressure to provide 66.81 g of Compound 43, (1R,1'R,3r,3'R,5S,5'S,7S)-7-methyl-N-(2-nitrophenyl)-9'-aza[3,9'-bi(bicyclo[3.3.1]nonan)]-3'-amine, as a orange solid (yield 73%).

The identity of Compound 43 was confirmed using $^1$H NMR and LC/MS.

Compound 43: $^1$H NMR: $\delta_H$ (400 MHz, CDCl$_3$): 8.17 (1H, d), 8.01 (1H, m), 7.43 (1H, t), 6.93 (1H, d), 6.61 (1H, t), 3.95 (1H, m), 3.45 (2H, m), 3.06 (1H, m), 2.48 (2H, m), 2.20 (2H, m), 1.87-2.08 (4H, m), 1.45-1.89 (6H, m), 1.35 (2H, t), 0.95-1.22 (5H, m), 0.87 (5H, m); LC/MS (t$_r$=2.732 min): m/z=398.4 [M+H]$^+$ (Calc: 397.6).

Compound 43 (30.0 g, 75.57 mmol) was taken up in DCM (100 mL). Under a hydrogen atmosphere, to this was added Pd/C (3 g) and, with stirring, the reaction mixture was hydrogenated at 50 psi for 2 h at a temperature of about 25° C. to provide Compound 44, N$^1$-((1R,1'R,3r,3'R,5S,5'S,7S)-7-methyl-[3,9'-bi(9'-azabicyclo[3.3.1]nonan)]-3'-yl)benzene-1,2-diamine.

The identity of Compound 44 was confirmed using LC/MS.

Compound 44: LC/MS (t$_r$=2.045 min): m/z=368.9 [M+H]$^+$ (Calc: 367.6).

The reaction mixture containing Compound 44, taken directly from the previous step, was filtered through CELITE. Ethyl 2-chloro-2-oxoacetate (12.65 mL, 113.36 mmol, Sigma-Aldrich) was added and the reaction mixture was stirred at a temperature of about 25° C. for 30 min. Thereafter, the mixture was evaporated under reduced pressure in a rotary evaporator to provide a residue. The residue was taken up in EtOH (800 mL) and potassium carbonate (31.33 g, 226.71 mmol) was added. The resulting mixture was heated to reflux, refluxed for 1 h, then cooled to a temperature of about 25° C. The solids that formed were filtered and washed with EtOH. The filtered solids were then triturated with deionized water and filtered under reduced pressure to provide 27.49 g of Compound 45, 1-((1R,1'R,3r,3'R,5S,5'S,7S)-7-methyl-[3,9'-bi(9'-azabicyclo[3.3.1]nonan)]-3'-yl)quinoxaline-2,3(1H,4H)-dione, as an off-white crystalline solid.

The identity of Compound 45 was confirmed using $^1$H NMR and LC/MS.

Compound 45: $^1$H NMR: $\delta_H$ (400 MHz, DMSO-d$_6$): 7.26 (1H, m), 7.05 (3H, m), 4.80 (1H, bs), 3.44 (2H, m), 3.08 (1H, m), 2.25-2.46 (3H, m), 2.05 (2H, m), 1.93 (4H, m), 1.82 (2H, m), 1.69 (4H, m), 1.54 (1H, m), 1.18 (4H, m), 1.01 (1H, m), 0.88 (5H, m); LC/MS (t$_r$=2.048 min): m/z=422.3 [M+H]$^+$ (Calc: 421.6).

Compound 45, taken directly from the previous step, was suspended in DCE (250 mL) and DMF (2.5 mL). Thionyl chloride (20 equivalents, Sigma-Aldrich) was added dropwise. The resulting reaction mixture was heated to reflux and refluxed for 2 h. The mixture was evaporated under reduced pressure to provide a residue which was triturated with MTBE. The residue was stirred for 1 h in MTBE then filtered under reduced pressure to provide 24.13 g of Compound 1C3 as the hydrochloride (82% yield from Compound 43).

The identity of Compound 1C3 was confirmed using $^1$H NMR and LC/MS.

Compound 1C3: $^1$H NMR: $\delta_H$ (400 MHz, CDCl$_3$): 11.05 (1H, bs), 8.79 (1H, d), 7.79 (2H, m), 7.43 (1H, t), 6.55 (1H, m), 4.10 (2H, m), 3.81 (1H, m), 3.00 (2H, t), 2.92 (1H, m), 2.47 (6H, m), 2.09 (4H, m), 1.50-1.93 (7H, m), 1.39 (1H, d), 0.92 (3H, d), 0.65 (2H, m); LC/MS (t$_r$=2.588 min): m/z=442.3 [M+H]$^+$ (Calc: 440.0).

5.13 Example 13

Synthesis of Compound 1D3

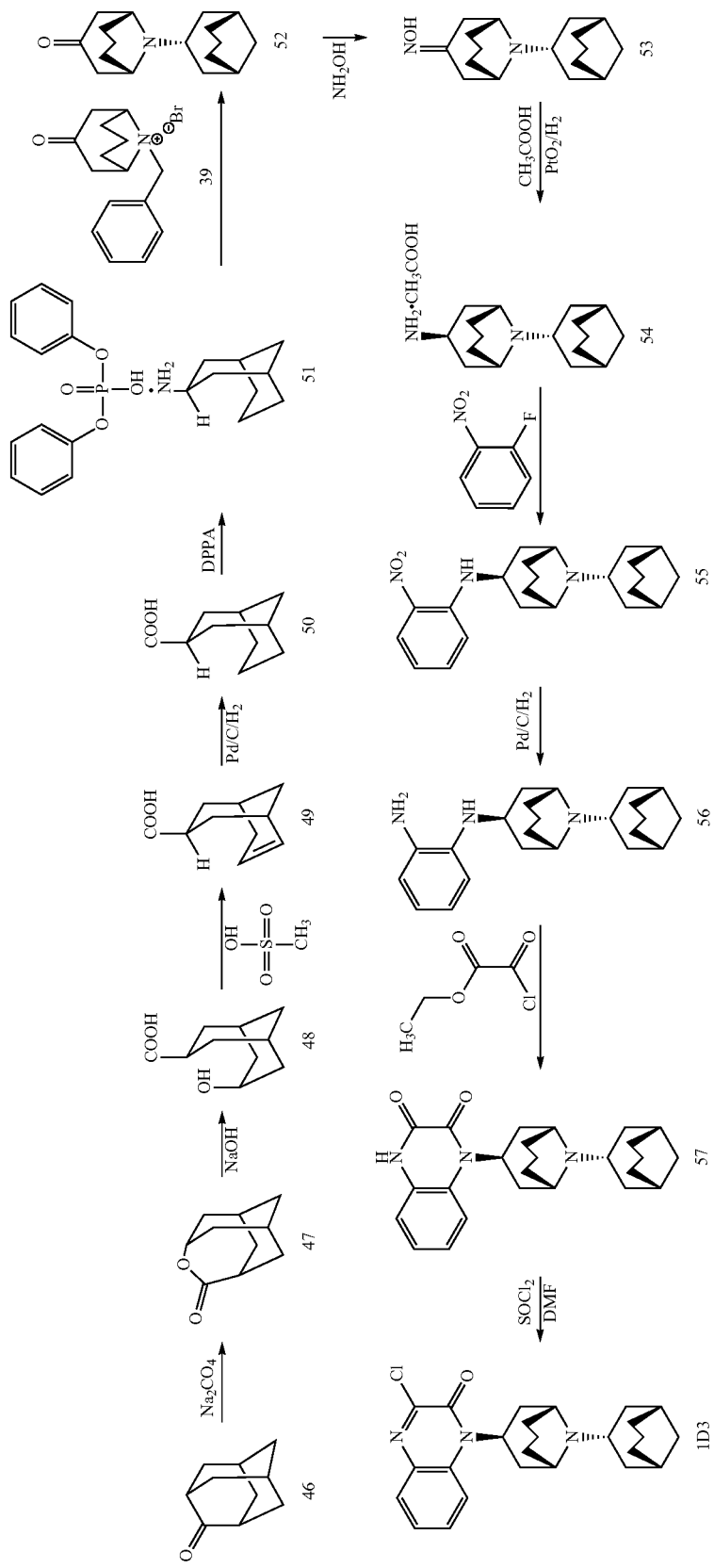

2-Adamantanone (46, 1000 g, 6.66 mol, Sigma-Aldrich) was dissolved in 2,2,2-trifluoroacetic acid (3 L, Sigma-Aldrich). To this mechanically stirred mixture surrounded by a cooling bath with a temperature maintained at 20° C. was added sodium percarbonate (1254.8 g, 7.99 mol, Sigma-Aldrich) portion-wise over 1 h; the temperature of the reaction mixture increased to 60° C. during the addition. After 2 h additional stirring, deionized water (4 L) was added followed by four extractions with DCM (2 L for each extraction). The organic portions were combined, dried (MgSO$_4$), filtered, and evaporated under reduced pressure to provide 1180 g of Compound 47, (1R,3r,6s,8S)-4-oxatricyclo[4.3.1.1$^{3,8}$]undecan-5-one, as a white crystalline solid (yield 97%).

The identity of Compound 47 was confirmed using $^1$H NMR and TLC.

Compound 47: $^1$H NMR: $\delta_H$ (400 MHz, CDCl$_3$): 4.48 (1H, s), 3.06 (1H, m), 2.09 (2H, m), 2.00 (3H, m), 1.95 (2H, m), 1.81 (2H, m), 1.70 (2H, m); TLC (SiO$_2$) 1:1 EtOAc:hexanes: R$_f$=0.8 (visualized with molybdenum blue spray reagent).

Compound 47 (1572.7 g, 9.46 mol) was taken up in MeOH (2 L). To this was added NaOH (2270 g, 56.7 mol) in deionized water (6 L); the temperature of the mixture increased from about 25° C. to 54° C. during the addition. With stirring, the resulting reaction mixture was heated to a gentle reflux and refluxed for 36 h. After cooling to a temperature of about 25° C., the MeOH was removed by vacuum distillation at 60° C. The resulting solution was stirred and acidified with concentrated HCl to a pH of about 2.5. The white precipitate that formed was allowed to stir for 18 h at a temperature of about 25° C. then filtered under reduced pressure to provide partially dried Compound 48, (1R,3r,5S,7r)-7-hydroxybicyclo[3.3.1]nonane-3-carboxylic acid.

The identity of Compound 48 was confirmed using $^1$H NMR and TLC.

Compound 48: $^1$H NMR: $\delta_H$ (400 MHz, DMSO-d$_6$): 11.88 (1H, s), 4.44 (1H, s), 3.73 (1H, m), 1.95 (4H, m), 1.63 (2H, m), 1.41 (3H, m), 1.22 (2H, m), 1.16 (1H, m); TLC (SiO$_2$) 2:1:0.1 EtOAc:hexanes:AcOH: R$_f$=0.3 (visualized with molybdenum blue spray reagent).

Compound 48, taken directly from the previous step, was suspended in toluene (8 L). To this was added methane sulfonic acid (367 mL, 4.73 mol, Sigma-Aldrich). With stirring, the resulting reaction mixture was heated to reflux and water removed azeotropically for 5 h. After cooling to a temperature of about 25° C., deionized water (4 L) was added with stirring. The organic layer was separated, dried (MgSO$_4$), filtered, and concentrated to provide Compound 49, (1R,3S,5S)-bicyclo[3.3.1]non-6-ene-3-carboxylic acid.

The identity of Compound 49 was confirmed using $^1$H NMR and TLC.

Compound 49: $^1$H NMR: $\delta_H$ (400 MHz, CDCl$_3$): 10.45 (1H, bs), 5.85 (1H, m), 5.70 (1H, m), 2.79 (1H, m), 2.37 (2H, m), 2.11 (1H, m), 1.81 (3H, m), 1.61 (4H, m); TLC (SiO$_2$) 1:1:0.1 EtOAc:hexanes:AcOH: R$_f$=0.8 (visualized with molybdenum blue spray reagent).

Compound 49, taken directly from the previous step, was taken up in MeOH (1 L). This was divided into six batches and to each, under a hydrogen atmosphere, was added 10% Pd/C (0.01 mol). The reaction mixtures were each hydrogenated at 50 psi until hydrogen uptake ceased (10 h to 15 h). The mixtures were combined, filtered through CELITE, and NaOH (1 kg) in deionized water (400 mL) was added. The mixture was stirred for 4 h at a temperature of about 25° C. The mixture was concentrated under reduced pressure and deionized water (4 L) was added. Concentrated HCl was added until a pH within the range of 3-4 was achieved. The white solid that formed was allowed to stir for 1 h at a temperature of about 25° C. and then was filtered under reduced pressure to provide 1.232 kg of Compound 50, (1R,3r,5S)-bicyclo[3.3.1]nonane-3-carboxylic acid, as an off-white crystalline solid (78% yield from Compound 47).

The identity of Compound 50 was confirmed using $^1$H NMR and TLC.

Compound 50: $^1$H NMR: $\delta_H$ (400 MHz, CDCl$_3$): 9.25 (1H, bs), 3.13 (1H, m), 1.97 (4H, m), 1.80 (2H, m), 1.70 (5H, m), 1.57 (3H, m); TLC (SiO$_2$) 1:1:0.1 EtOAc:hexanes:AcOH: R$_f$=0.8 (visualized with molybdenum blue spray reagent).

Compound 50 (1108.5 g, 6.59 mol) was taken up in toluene (5 L) in a 20 L reaction vessel. To this was added TEA (1013.3 mL, 7.26 mol). The resulting mixture was stirred and heated to 75° C. under a nitrogen atmosphere. The diphenyl phosphoryl azide (DPPA, 1564 mL, 7.26 mol, Sigma-Aldrich) was diluted with toluene to 2 L total volume and added slowly via addition funnel over 1.5 h; during this addition the temperature increased by about 10° C. to 15° C. The resulting reaction mixture was allowed to stir for 3 h at 75° C. The mixture was then concentrated to a brownish-yellow oil by vacuum distillation at 90° C. The oil was cooled to 5° C. and THF (2.5 L) was added. The mixture was allowed to stir and cool to 0° C. NaOH (792 g, 19.80 mol) in deionized water (3 L) was added over 1 h keeping the temperature below 5° C. The mixture was stirred for 18 h at 5° C. The resulting mixture was then extracted twice with Et$_2$O (4 L for each extraction). To the remaining aqueous mixture at 5° C. was slowly added concentrated HCl until a pH of about 6-7 was reached; no significant change in temperature occurred during this neutralization. The resulting white precipitate was allowed to stir for 2 h at 0° C. The precipitate was then filtered under reduced pressure and dried under reduced pressure at 50° C. to provide 1.875 kg of Compound 51, (1R,3r,5S)-bicyclo[3.3.1]nonan-3-amine diphenyl phosphate salt, as a white solid (yield 73.1%).

The identity of Compound 51 was confirmed using $^1$H NMR.

Compound 51: $^1$H NMR: $\delta_H$ (400 MHz, DMSO-d$_6$): 7.78 (2H, s), 7.22 (4H, t), 7.11 (4H, m), 6.93 (2H, t), 3.61 (1H, m), 3.31 (1H, s), 1.93 (4H, m), 1.33-1.60 (10H, m).

Compound 51 (1037.5 g, 2.67 mol) and Compound 39 (1000 g, 3.08 mol) were suspended in EtOH (6.2 L) and deionized water (2 L). To this stirred mixture was added potassium carbonate (390.72 g, 2.83 mol) in deionized water (800 mL). The resulting reaction mixture was stirred for 18 h at a temperature of about 25° C. The reaction mixture was then heated to reflux, about 81° C., and refluxed for 3 h. Thereafter, the mixture was allowed to cool slowly over 4 h to a temperature of about 25° C. with vigorous stirring during which time a white precipitate formed. The mixture was then cooled to 5° C. and allowed to stir for 2 h at that temperature. The white precipitate was filtered under reduced pressure, washed with deionized water (8 L), and dried under reduced pressure at 60° C. to provide 580.1 g of Compound 52, (1R,1'R,3r,5S,5'S)-9'-aza[3,9'-bi(bicyclo[3.3.1]nonan)]-3'-one, as a white crystalline solid (yield 83.1%).

The identity of Compound 52 was confirmed using $^1$H NMR and TLC.

Compound 52: $^1$H NMR: $\delta_H$ (400 MHz, CDCl$_3$): 3.69 (2H, s), 3.38 (1H, m), 2.62 (2H, m), 2.21 (2H, d), 2.12 (4H, m), 1.85 (2H, m), 1.41-1.78 (14H, m); TLC (SiO$_2$) 7:3 hexanes:EtOAc: R$_f$=0.4 (visualized with potassium iodoplatinate spray).

Compound 52 (580.1 g, 2.22 mol) and THF (4 L) were introduced into a reactor; the reactor temperature control was set to 18° C. 50% Aqueous NH$_2$OH (415 mL, 6.66 mol) was added followed by the slow addition of AcOH (381.25 mL, 6.66 mol). The temperature of the reaction mixture increased to 28° C. during the addition. The reaction mixture was stirred for 16 h at a temperature of about 25° C. then heated to a gentle reflux and refluxed for 1 h. The mixture was cooled to a temperature of about 25° C. and deionized water (4 L) and DCM (4 L) were added. With vigorous stirring, solid NaHCO$_3$ (560 g, 6.66 mol) was then slowly added over 30 min and the mixture was allowed to stir until effervescence ceased. The white precipitate that formed was filtered under reduced pressure, washed with deionized water (1 L), and dried under reduced pressure at 60° C. for 72 h to provide 432.5 g of Compound 53, (1R,1'R,3r,5S,5'S)-9'-aza[3,9'-bi(bicyclo[3.3.1]nonan)]-3'-one oxime, as a white solid (yield 70.6%). The filtrate was allowed to form layers and the organic layer was separated. The aqueous layer was washed three times with DCM (2 L for each wash). The organic portions were combined, dried (MgSO$_4$), filtered, and evaporated under reduced pressure to provide a pale yellow solid. The solid was triturated with 10:1 Et$_2$O: EtOAc (1 L), stirred for 1 h, and filtered under reduced pressure to provide a residue which was dried under reduced pressure at 60° C. for 72 h to provide an additional 138.4 g of Compound 53 as a white solid (yield 22.6%, overall yield 93.2%).

Compound 53 (570.9 g, 2.07 mol) was taken up in AcOH (3 L). This mixture, with a total dissolved volume of 3.3 L, was divided into ten 330 mL batches. Under a hydrogen atmosphere, to each batch was added platinum (IV) oxide (9.40 g, 0.041 mol) and each batch was then hydrogenated at 50 psi for 16 h to 18 h. The batches were combined and filtered through CELITE. The filter cake was washed with AcOH (500 mL). The filtrate was concentrated under reduced pressure at 70° C. to provide an oil. To the oil was added Et$_2$O (6 L). The mixture was stirred and cooled to 0° C. for 1 h. The white precipitate that formed was filtered under reduced pressure and washed with Et$_2$O (2 L) to provide 253.4 g of Compound 54, (1R,1'R,3r,3'R,5S,5'S)-9'-aza[3,9'-bi(bicyclo[3.3.1]nonan)]-3'-amine acetate (yield 35.3%). The filtrate was evaporated under reduced pressure to provide a residue which was subjected to the same treatment with Et$_2$O. A second crop of 213.7 g of Compound 54 was isolated (yield 32.1%). The filtrate was again evaporated under reduced pressure to provide 201.1 g of Compound 54 (yield 25.4%, overall yield 92.8%).

The identity of Compound 54 was confirmed using $^1$H NMR.

Compound 54: $^1$H NMR: $\delta_H$ (400 MHz, CD$_3$OD): 3.63 (3H, m), 3.42 (1H, m), 2.36 (2H, m), 2.01 (5H, m), 1.89 (5H, m), 1.39-1.78 (13H, m), 1.12 (2H, m).

In part 1, Compound 54 (439.0 g, 1.36 mol) and MeCN (4 L) were introduced into a reactor; the reactor temperature control was set to 25° C. To this mixture were added TEA (412.9 g, 4.08 mol, 3 eq) and 1-fluoro-2-nitrobenzene (194.2 g, 1.38 mol, 1 eq). The reaction mixture was heated to reflux, refluxed for 6 days, then cooled to 0° C. The yellow precipitate that formed was collected by filtration under reduced pressure. The filter cake was washed four times with DCM (2 L for each wash) and the filtrates were set aside. The remaining 91 g of solids, comprising recovered Compound 54, were dried and set aside.

In part 2, the reaction described in part 1 above was repeated using the recovered Compound 54 starting material except DMF (2 L) and K$_2$CO$_3$ (3 eq) were used. After stirring for 2 h at 110° C., the reaction mixture was cooled to a temperature of about 25° C. and poured into deionized water (4 L). This mixture was extracted six times with Et$_2$O (2 L for each extraction). The organic portions were combined and evaporated under reduced pressure to provide a residue.

The residue from part 2 and the filtrates from part 1 were combined and the resulting combination was evaporated under reduced pressure to provide an oil. The oil was triturated with deionized water (4 L). The solids that formed were filtered under reduced pressure and washed with further deionized water. The solids were then dried under reduced pressure at 60° C. for 48 h to provide 402 g of Compound 55, (1R,1'R,3r,3'R,5S,5'S)—N-(2-nitrophenyl)-9'-aza[3,9'-bi(bicyclo[3.3.1]nonan)]-3'-amine, as a bright yellow solid (yield 77%).

Compound 55 (402 g, 1.05 mol) was taken up in MeOH (2.5 L). This mixture was divided into ten batches. Under a hydrogen atmosphere, to each batch was added 10% Pd/C (0.04 mol) and, with stirring, each batch was hydrogenated at 50 psi for 3 h at a temperature of about 25° C. The batches were filtered through CELITE and the filter cake washed with MeOH. The filtrate was evaporated under reduced pressure to provide a residue which was triturated with Et$_2$O then filtered under reduced pressure to provide Compound 56, N$^1$-((1R,1'R,3r,3'R,5S,5'S)-[3,9'-bi(9'-azabicyclo[3.3.1] nonan)]-3'-yl)benzene-1,2-diamine, as a light brown solid (yield >99%).

Compound 57, 1-((1R,1'R,3r,3'R,5S,5'S)-[3,9'-bi(9'-azabicyclo[3.3.1]nonan)]-3'-yl)quinoxaline-2,3(1H,4H)-dione, was prepared from Compound 56 and ethyl 2-chloro-2-oxoacetate in a similar manner to the previously-described preparation of Compound 45 from Compound 44 (yield 95%).

The identity of Compound 57 was confirmed using $^1$H NMR.

Compound 57: $^1$H NMR: $\delta_H$ (400 MHz, CDCl$_3$): 7.74, (1H, d, J=8.7 Hz), 7.55 (2H, m), 7.30 (1H, dt, J=8.7, 1.5 Hz), 5.13 (1H, bs), 3.50-3.40 (3H, m), 2.65 (2H, bt), 2.40 (1H, m), 2.00-1.87 (6H, m), 1.86-1.30 (15H, m), 1.03 (2H, m).

Compound 57 (6.5 g, 15.95 mmol) was suspended in DCM (150 mL). Thionyl chloride (20 mL) was added followed by the addition of DMF (1 mL). The resulting reaction mixture was heated to reflux and refluxed for 1 h. The mixture was evaporated under reduced pressure to provide a residue which was triturated with MTBE (100 mL) to provide a light brown solid. The solid was partitioned between ice-water:aqueous sodium carbonate solution (400 mL) and DCM (400 mL). The organic layer was separated, dried (MgSO$_4$), and evaporated under reduced pressure to provide a yellow solid. The solid was triturated with Et$_2$O (150 mL) to provide 4.8 g of Compound 1D3 as a white solid (yield 71%).

The identity of Compound 1D3 was confirmed using $^1$H NMR and LC/MS.

Compound 1D3: $^1$H NMR: $\delta_H$ (400 MHz, CDCl$_3$): 8.82 (1H, d, J=7.4 Hz), 7.62 (2H, m), 7.37 (1H, m), 5.19 (1H, br), 3.55 (3H, m), 2.73 (2H, m), 2.47 (1H, m), 2.10-1.94 (5H, m), 1.90-1.50 (11H, m), 1.43 (3H, m), 1.10 (2H, d, J=13.0 Hz); LC/MS (t$_r$=2.925 min): m/z 426.1 [M+H]$^+$ (Calc: 425.2).

5.14 Example 14

Synthesis of Phosphorus-Substituted Quinoxaline-Type Piperidine Compound XX

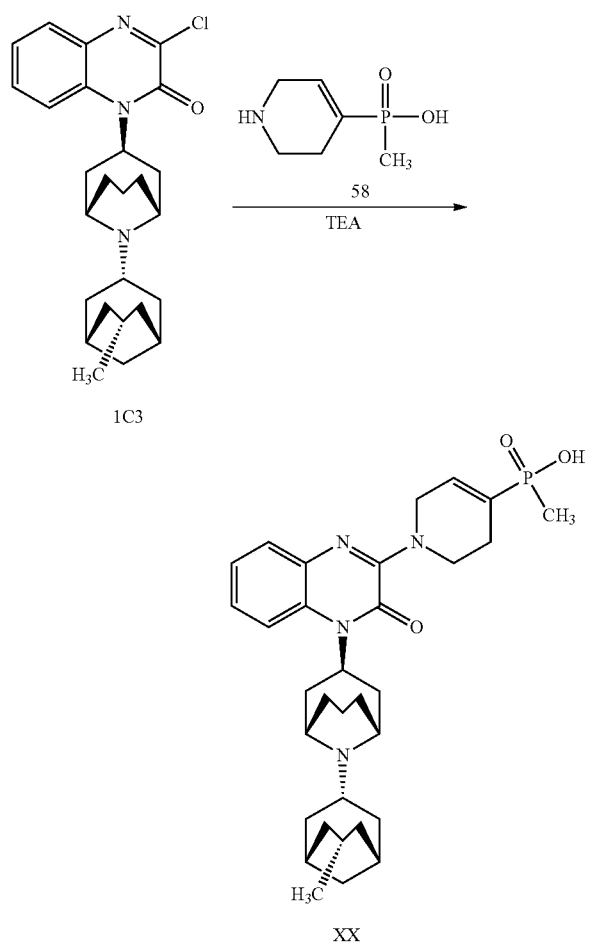

To a solution of Compound 1C3 (96 mg, 0.22 mmol) and methyl(1,2,3,6-tetrahydropyridin-4-yl)phosphinic acid (58, 35.0 mg, 0.22 mmol, Tocris Bioscience, Ellisville, Mo.) in DMSO (3 mL) in a reaction vial was added TEA (0.05 mL, 0.33 mmol). The resulting reaction mixture was sealed into the reaction vial and allowed to stir at 100° C. for 1.5 h. Thereafter, the mixture was evaporated to dryness to provide a residue. The residue was chromatographed on a flash column eluted with a gradient of from 15:85 MeOH(10% NH$_4$OH):DCM to 20:80 MeOH(10% NH$_4$OH):DCM. The fractions containing the product were combined and concentrated under reduced pressure to provide Phosphorus-Substituted Quinoxaline-Type Piperidine Compound XX, methyl(1-(4-((1R,1'R,3r,3'R,5S,5'S,7S)-7-methyl-[3,9'-bi(9'-azabicyclo[3.3.1]nonan)]-3'-yl)-3-oxo-3,4-dihydroquinoxalin-2-yl)-1,2,3,6-tetrahydropyridin-4-yl)phosphinic acid.

The identity of Phosphorus-Substituted Quinoxaline-Type Piperidine Compound XX was confirmed using $^1$H NMR and MS.

Phosphorus-Substituted Quinoxaline-Type Piperidine Compound XX: $^1$H NMR: $\delta_H$ (ppm, CD$_3$OD): 7.76-7.63 (1H, br), 7.57-7.41 (1H, d, J=8.1 Hz), 7.37-7.17 (2H, m), 6.55-6.38 (1H, d, J=17.9 Hz), 5.48-5.33 (1H, br), 4.42 (2H, s), 4.27-4.14 (2H, d, J=8.1 Hz), 4.05-3.90 (3H, m), 3.11-2.94 (2H, m), 2.88-2.70 (1H, m), 2.64-2.52 (2H, m), 2.49-2.30 (4H, m), 2.21-2.04 (6H, m), 1.95-1.61 (2H, m), 1.79-1.67 (4H, m), 1.37-1.29 (3H, d, J=13.6 Hz), 1.27-1.14 (1H, d, J=13.2 Hz), 1.00-0.91 (3H, m), 0.90-0.71 (2H, m); MS: m/z 565.3 [M+1].

5.15 Example 15

In Vitro ORL-1 Receptor Binding Assay

ORL-1 Receptor Binding Assay Procedures: Membranes from recombinant HEK-293 cells expressing the human opioid receptor-like receptor (ORL-1) (Receptor Biology) were prepared by lysing cells in ice-cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration 1-3 mg/mL. Protein concentrations were determined using the BioRad protein assay reagent with bovine serum albumen as a standard. Aliquots of the ORL-1 receptor membranes were stored at −80° C.

Radioligand binding assays (screening and dose-displacement) used 0.1 nM [$^3$H]-nociceptin (NEN; 87.7 Ci/mmole) with 10-20 µg membrane protein in a final volume of 500 µL binding buffer (10 mM MgCl$_2$, 1 mM EDTA, 5% DMSO, 50 mM HEPES, pH 7.4). Non-specific binding was determined in the presence of 10 nM unlabeled nociceptin (American Peptide Company). All reactions were performed in 96-deep well polypropylene plates for 1 h at about 25° C. Binding reactions were terminated by rapid filtration onto 96-well Unifilter GF/C filter plates (Packard) presoaked in 0.5% polyethylenimine (Sigma-Aldrich). Harvesting was performed using a 96-well tissue harvester (Packard) followed by three filtration washes with 500 µL ice-cold binding buffer. Filter plates were subsequently dried at 50° C. for 2-3 hours. Fifty µL/well scintillation cocktail (BetaScint; Wallac) was added and plates were counted in a Packard Top-Count for 1 min/well. The data from screening and dose-displacement experiments were analyzed using Microsoft Excel and the curve fitting functions in GraphPad PRISM™, v. 3.0, respectively, or an in-house function for one-site competition curve-fitting.

ORL-1 Receptor Binding Data: The Phosphorus-Substituted Quinoxaline-Type Piperidine Compounds will have a binding affinity (K$_i$) for the human ORL-1 receptor of about 1000 nM or less in one embodiment, or about 500 nM or less in another embodiment. In certain embodiments, the Phosphorus-Substituted Quinoxaline-Type Piperidine Compounds will have a K$_i$ (nM) of about 300 or less for binding to ORL-1 receptors. In one embodiment, the Phosphorus-Substituted Quinoxaline-Type Piperidine Compounds will have a K$_i$ (nM) of about 100 or less. In another embodiment, the Phosphorus-Substituted Quinoxaline-Type Piperidine Compounds of the disclosure will have a K$_i$ (nM) of about 35 or less. In another embodiment, the Phosphorus-Substituted Quinoxaline-Type Piperidine Compounds of the disclosure will have a K$_i$ (nM) of about 20 or less. In another embodiment, the Phosphorus-Substituted Quinoxaline-Type Piperidine Compounds of the disclosure will have a K$_i$ (nM) of about 15 or less. In another embodiment, the Phosphorus-Substituted Quinoxaline-Type Piperidine Compounds of the disclosure will have a K$_i$ (nM) of about 10 or less. In another embodiment, the Phosphorus-Substituted Quinoxaline-Type Piperidine Compounds of the disclosure will have a $K_i$ (nM) of about 4 or less. In another embodiment, the Phosphorus-Substituted Quinoxaline-Type Piperidine Compounds of the disclosure will have a $K_i$ (nM) of about 1 or less. In another embodiment, the Phosphorus-Substituted Quinoxaline-Type Piperidine Compounds of the disclosure will have a $K_i$ (nM) of about 0.4 or less. In another embodiment, the Phosphorus-Substituted Quinoxaline-Type Piperidine Compounds of the disclosure will have a $K_i$ (nM) of about 0.1 or less.

5.16 Example 16

In Vitro ORL-1 Receptor Functional Assay

ORL-1 Receptor [$^{35}$S]GTPγS Binding Assay Procedures: Membranes from recombinant HEK-293 cells expressing the human opioid receptor-like (ORL-1) (Receptor Biology) were prepared by lysing cells in ice-cold hypotonic buffer (2.5 mM $MgCl_2$, 50 mM HEPES, pH 7.4) (10 mL/10 cm dish) followed by homogenization with a tissue grinder/ Teflon pestle. Membranes were collected by centrifugation at 30,000×g for 15 min at 4° C., and pellets resuspended in hypotonic buffer to a final concentration of 1-3 mg/mL. Protein concentrations were determined using the BioRad protein assay reagent with bovine serum albumen as a standard. Aliquots of the ORL-1 receptor membranes were stored at −80° C.

Functional binding assays were conducted as follows. ORL-1 membrane solution was prepared by sequentially adding final concentrations of 0.066 μg/L ORL-1 membrane protein, 10 μg/mL saponin, 3 μM GDP and 0.20 nM [35S] GTPγS to binding buffer (100 mM NaCl, 10 mM $MgCl_2$, 20 mM HEPES, pH 7.4) on ice. The prepared membrane solution (190 μL/well) was transferred to 96-shallow well polypropylene plates containing 10 μL of 20× concentrated stock solutions of agonist/nociceptin prepared in DMSO. Plates were incubated for 30 min at about 25° C. with shaking. Reactions were terminated by rapid filtration onto 96-well Unifilter GF/B filter plates (Packard) using a 96-well tissue harvester (Packard) and followed by three filtration washes with 200 μL ice-cold binding buffer (10 mM $NaH_2PO_4$, 10 mM $Na_2HPO_4$, pH 7.4). Filter plates were subsequently dried at 50° C. for 2-3 hours. Fifty μL/well scintillation cocktail (BetaScint; Wallac) was added and plates were counted in Packard Top-Count for 1 min/ well. Data are analyzed using the sigmoidal dose-response curve fitting functions in GraphPad PRISM v. 3.0, or an in-house function for non-linear, sigmoidal dose-response curve-fitting.

ORL-1 Receptor Functional Data: ORL-1 GTP $EC_{50}$ is the concentration of a compound providing 50% of the maximal response for the compound at an ORL-1 receptor. In one embodiment, a Phosphorus-Substituted Quinoxaline-Type Piperidine Compound will have an ORL-1 GTP $EC_{50}$ (nM) of about 5000 or less to stimulate ORL-1 receptor function. In another embodiment, the Phosphorus-Substituted Quinoxaline-Type Piperidine Compounds will have an ORL-1 GTP $EC_{50}$ (nM) of about 1000 or less. In another embodiment, the Phosphorus-Substituted Quinoxaline-Type Piperidine Compounds will have an ORL-1 GTP $EC_{50}$ (nM) of about 100 or less. In another embodiment, the Phosphorus-Substituted Quinoxaline-Type Piperidine Compounds will have an ORL-1 GTP $EC_{50}$ (nM) of about 80 or less. In another embodiment, the Phosphorus-Substituted Quinoxaline-Type Piperidine Compounds will have an ORL-1 GTP $EC_{50}$ (nM) of about 50 or less. In another embodiment, the Phosphorus-Substituted Quinoxaline-Type Piperidine Compounds will have an ORL-1 GTP $EC_{50}$ (nM) of about 35 or less. In another embodiment, the Phosphorus-Substituted Quinoxaline-Type Piperidine Compounds will have an ORL-1 GTP $EC_{50}$ (nM) of about 15 or less. In another embodiment, the Phosphorus-Substituted Quinoxaline-Type Piperidine Compounds will have an ORL-1 GTP $EC_{50}$ (nM) of about 10 or less. In another embodiment, the Phosphorus-Substituted Quinoxaline-Type Piperidine Compounds will have an ORL-1 GTP $EC_{50}$ (nM) of about 4 or less. In another embodiment, the Phosphorus-Substituted Quinoxaline-Type Piperidine Compounds will have an ORL-1 GTP $EC_{50}$ (nM) of about 1 or less. In another embodiment, the Phosphorus-Substituted Quinoxaline-Type Piperidine Compounds will have an ORL-1 GTP $EC_{50}$ (nM) of about 0.4 or less. In another embodiment, the Phosphorus-Substituted Quinoxaline-Type Piperidine Compounds will have an ORL-1 GTP $EC_{50}$ (nM) of about 0.1 or less.

ORL-1 GTP Emax (%) is the maximal effect elicited by a compound relative to the effect elicited by nociceptin, a standard ORL-1 agonist. In one embodiment, a Phosphorus-Substituted Quinoxaline-Type Piperidine Compound will have an ORL-1 GTP Emax (%) of about 50% or greater. In another embodiment, the Phosphorus-Substituted Quinoxaline-Type Piperidine Compounds will have an ORL-1 GTP Emax (%) of about 75% or greater. In another embodiment, the Phosphorus-Substituted Quinoxaline-Type Piperidine Compounds will have an ORL-1 GTP Emax (%) of about 85% or greater. In another embodiment, the Phosphorus-Substituted Quinoxaline-Type Piperidine Compounds will have an ORL-1 GTP Emax (%) of about 95% or greater. In another embodiment, the Phosphorus-Substituted Quinoxaline-Type Piperidine Compounds will have an ORL-1 GTP Emax (%) of about 100% or greater. In another embodiment, the Phosphorus-Substituted Quinoxaline-Type Piperidine Compounds will have an ORL-1 GTP Emax (%) of about 110% or greater. In certain embodiments, a Phosphorus-Substituted Quinoxaline-Type Piperidine Compound acting as a partial agonist will have an ORL-1 GTP Emax (%) of less than about 10%. In one embodiment, partial agonist Phosphorus-Substituted Quinoxaline-Type Piperidine Compounds will have an ORL-1 GTP Emax (%) of less than about 20%. In another embodiment, partial agonist Phosphorus-Substituted Quinoxaline-Type Piperidine Compounds will have an ORL-1 GTP Emax (%) of less than about 30%. In another embodiment, partial agonist Phosphorus-Substituted Quinoxaline-Type Piperidine Compounds will have an ORL-1 GTP Emax (%) of less than about 40%. In another embodiment, partial agonist Phosphorus-Substituted Quinoxaline-Type Piperidine Compounds will have an ORL-1 GTP Emax (%) of less than about 50%.

5.17 Example 17

In Vitro Mu-Opioid Receptor Binding Assays

μ-Opioid Receptor Binding Assay Procedures: Radioligand binding assays were conducted using freshly thawed membranes expressing human μ-receptors (Perkin Elmer, Shelton, Conn.). Radioligand dose-displacement binding assays for human μ-opioid receptors used 0.2 nM[$^3$H]-diprenorphine (NEN, Boston, Mass.), with 5-20 mg membrane protein/well in a final volume of 500 μL binding buffer (10 mM $MgCl_2$, 1 mM EDTA, 5% DMSO, 50 mM HEPES, pH 7.4). Reactions were carried out in the absence or presence of increasing concentrations of unlabeled naloxone. All reactions were conducted in 96-deep well polypropylene plates for 1-2 hr at about 25° C. Binding reactions were terminated by rapid filtration onto 96-well Unifilter GF/C filter plates (Packard, Meriden, Conn.) presoaked in 0.5% polyethylenimine using a 96-well tissue harvester (Brandel, Gaithersburg, Md.) followed by performing three filtration washes with 500 µL of ice-cold binding buffer. Filter plates were subsequently dried at 50° C. for 2-3 hours. BetaScint scintillation cocktail (Wallac, Turku, Finland) was added (50 µL/well), and plates were counted using a Packard Top-Count for 1 min/well. The data were analyzed using the one-site competition curve fitting functions in GraphPad PRISM v. 3.0 (San Diego, Calif.), or an in-house function for one-site competition curve-fitting.

µ-Opioid Receptor Binding Data: In certain embodiments, the Phosphorus-Substituted Quinoxaline-Type Piperidine Compounds will have a $K_i$ (nM) of about 3000 or less for binding to µ-opioid receptors, or about 1000 or less, or about 650 or less, or about 525 or less, or about 250 or less, or about 100 or less, or about 10 or less, or about 1 or less, or about 0.1 or less.

5.18 Example 18

In Vitro Mu-Opioid Receptor Functional Assays

µ-Opioid Receptor Functional Assay Procedures: [$^{35}$S] GTPγS functional assays were conducted using freshly thawed membranes expressing human µ-receptors. Assay reactions were prepared by sequentially adding the following reagents to binding buffer (100 mM NaCl, 10 mM MgCl$_2$, 20 mM HEPES, pH 7.4) on ice (final concentrations indicated): membrane protein (0.026 mg/mL), saponin (10 mg/mL), GDP (3 mM) and [$^{35}$S]GTPγS (0.20 nM; NEN). The prepared membrane solution (190 µL/well) was transferred to 96-shallow well polypropylene plates containing 10 µL of 20× concentrated stock solutions of the agonist DAMGO ([D-Ala2, N-methyl-Phe4 Gly-ol5]-enkephalin) prepared in dimethyl sulfoxide (DMSO). Plates were incubated for 30 min at about 25° C. with shaking. Reactions were terminated by rapid filtration onto 96-well Unifilter GF/B filter plates (Packard, Meriden, Conn.) using a 96-well tissue harvester (Brandel, Gaithersburg, Md.) followed by three filtration washes with 200 µL of ice-cold wash buffer (10 mM NaH$_2$PO$_4$, 10 mM Na$_2$HPO$_4$, pH 7.4). Filter plates were subsequently dried at 50° C. for 2-3 hr. BetaScint scintillation cocktail (Wallac, Turku, Finland) was added (50 µL/well) and plates were counted using a Packard Top-Count for 1 min/well. Data were analyzed using the sigmoidal dose-response curve fitting functions in GraphPad PRISM v. 3.0, or an in-house function for non-linear, sigmoidal dose-response curve-fitting.

µ-Opioid Receptor Functional Data: µ GTP $EC_{50}$ is the concentration of a compound providing 50% of the maximal response for the compound at a µ-opioid receptor. In certain embodiments, the Phosphorus-Substituted Quinoxaline-Type Piperidine Compounds will have a µ GTP $EC_{50}$ (nM) of about 5000 or less, or about 4100 or less, or about 3100 or less, or about 2000 or less, or about 1000 or less, or about 100 or less, or about 10 or less, or about 1 or less, or about 0.4 or less, or about 0.1 or less.

µ GTP Emax (%) is the maximal effect elicited by a compound relative to the effect elicited by DAMGO, a standard µ agonist. In certain embodiments, the Phosphorus-Substituted Quinoxaline-Type Piperidine Compounds will have a µ GTP Emax (%) of about 10% or greater, or about 20% or greater, or about 50% or greater, or about 65% or greater, or about 75% or greater, or about 88% or greater, or about 100% or greater. In other embodiments, the Phosphorus-Substituted Quinoxaline-Type Piperidine Compounds will have a µ GTP Emax (%) of about 10% or less, or about 5% or less, or about 2% or less.

5.19 Example 19

In Vitro Kappa-Opioid Receptor Binding Assays

κ-Opioid Receptor Binding Assay Procedures: Membranes from recombinant HEK-293 cells expressing the human kappa opioid receptor (kappa) (cloned in house) were prepared by lysing cells in ice cold hypotonic buffer (2.5 mM MgCl$_2$, 50 mM HEPES, pH 7.4) (10 mL/10 cm dish) followed by homogenization with a tissue grinder/Teflon pestle. Membranes were collected by centrifugation at 30,000×g for 15 min at 4° C. and pellets resuspended in hypotonic buffer to a final concentration of 1-3 mg/mL. Protein concentrations were determined using the BioRad protein assay reagent with bovine serum albumen as a standard. Aliquots of kappa receptor membranes were stored at −80° C.

Radioligand dose displacement assays used 0.4-0.8 nM [$^3$H]-U69,593 (NEN; 40 Ci/mmole) with 10-20 µg membrane protein (recombinant kappa opioid receptor expressed in HEK 293 cells; in-house prep) in a final volume of 200 L binding buffer (5% DMSO, 50 mM Trizma base, pH 7.4). Non-specific binding was determined in the presence of 10 µM unlabeled naloxone or U69,593. All reactions were performed in 96-well polypropylene plates for 1 h at a temperature of about 25° C. Binding reactions were determined by rapid filtration onto 96-well Unifilter GF/C filter plates (Packard) presoaked in 0.5% polyethylenimine (Sigma-Aldrich). Harvesting was performed using a 96-well tissue harvester (Packard) followed by five filtration washes with 200 µL ice-cold binding buffer. Filter plates were subsequently dried at 50° C. for 1-2 hours. Fifty µL/well scintillation cocktail (MicroScint20, Packard) was added and plates were counted in a Packard Top-Count for 1 min/well.

κ-Opioid Receptor Binding Data: In one embodiment, the Phosphorus-Substituted Quinoxaline-Type Piperidine Compounds will have substantially no activity at a κ-opioid receptor. In certain embodiments, the Phosphorus-Substituted Quinoxaline-Type Piperidine Compounds will have a Ki (nM) of about 20,000 or less, or about 10,000 or less, or about 5000 or less, or about 500 or less, or about 300 or less, or about 100 or less, or about 50 or less, or about 20 or less, or about 15 or less, or about 10 or less.

5.20 Example 20

In Vitro Kappa-Opioid Receptor Functional Assays

κ-Opioid Receptor Functional Assay Procedures: Functional [$^{35}$S]GTPγS binding assays were conducted as follows. Kappa opioid receptor membrane solution was prepared by sequentially adding final concentrations of 0.026 µg/µL kappa membrane protein (in-house), 10 g/mL saponin, 3 µM GDP and 0.20 nM [$^{35}$S]GTPγS to binding buffer (100 mM NaCl, 10 mM MgCl$_2$, 20 mM HEPES, pH 7.4) on ice. The prepared membrane solution (190 L/well) was transferred to 96-shallow well polypropylene plates containing 10 µL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 µL ice-cold binding buffer (10 mM $NaH_2PO_4$, 10 mM $Na_2HPO_4$, pH 7.4). Filter plates were subsequently dried at 50° C. for 2-3 hours. Fifty µL/well scintillation cocktail (MicroScint20, Packard) was added and plates were counted in a Packard Top-Count for 1 min/well.

κ-Opioid Receptor Functional Data: κ GTP $EC_{50}$ is the concentration of a compound providing 50% of the maximal response for the compound at a κ-opioid receptor. In certain embodiments, the Phosphorus-Substituted Quinoxaline-Type Piperidine Compounds will have a κ GTP $EC_{50}$ (nM) of about 20,000 or less, or about 10,000 or less, or about 5000 or less, or about 2000 or less, or about 1500 or less, or about 800 or less, or about 500 or less, or about 300 or less, or about 100 or less, or about 50 or less, or about 10 or less.

κ GTP Emax (%) is the maximal effect elicited by a compound relative to the effect elicited by U69,593. In certain embodiments, the Phosphorus-Substituted Quinoxaline-Type Piperidine Compounds will have a κ GTP Emax (%) of about 10% or greater, or about 15% or greater, or about 30% or greater, or about 40% or greater, or about 45% or greater, or about 75% or greater, or about 90% or greater, or about 100% or greater. In other embodiments, the Phosphorus-Substituted Quinoxaline-Type Piperidine Compounds will have a κ GTP Emax (%) of about 10% or less, or about 5% or less, or about 2% or less.

5.21 Example 21

In Vitro Delta-Opioid Receptor Binding Assays

δ-Opioid Receptor Binding Assay Procedures: Radioligand dose-displacement assays used 0.2 nM [$^3$H]-Naltrindole (NEN; 33.0 Ci/mmole) with 10-20 µg membrane protein (recombinant delta opioid receptor expressed in CHO-K1 cells; Perkin Elmer) in a final volume of 500 µL binding buffer (5 mM $MgCl_2$, 5% DMSO, 50 mM Trizma base, pH 7.4). Non-specific binding was determined in the presence of 25 µM unlabeled naloxone. All reactions were performed in 96-deep well polypropylene plates for 1 h at a temperature of about 25° C. Binding reactions were determined by rapid filtration onto 96-well Unifilter GF/C filter plates (Packard) presoaked in 0.5% polyethylenimine (Sigma-Aldrich). Harvesting was performed using a 96-well tissue harvester (Packard) followed by five filtration washes with 500 µL ice-cold binding buffer. Filter plates were subsequently dried at 50° C. for 1-2 hours. Fifty µL/well scintillation cocktail (MicroScint20, Packard) was added and plates were counted in a Packard Top-Count for 1 min/well.

δ-Opioid Receptor Binding Data: In one embodiment, a Phosphorus-Substituted Quinoxaline-Type Piperidine Compound will have substantially no activity at a δ-opioid receptor. In certain embodiments, the Phosphorus-Substituted Quinoxaline-Type Piperidine Compounds will have a Ki (nM) of about 20,000 or less, or about 10,000 or less, or about 7500 or less, or about 6500 or less, or about 5000 or less, or about 3000 or less, or about 2500 or less, or about 1000 or less, or about 500 or less, or about 350 or less, or about 250 or less, or about 100 or less, or about 10 or less.

5.22 Example 22

In Vitro Delta-Opioid Receptor Functional Assays

δ-Opioid Receptor Functional Assay Procedures: Functional [$^{35}$S]GTPγS binding assays were conducted as follows using membranes expressing human δ-opioid receptors. Delta opioid receptor membrane solution was prepared by sequentially adding final concentrations of 0.026 µg/µL delta membrane protein (Perkin Elmer), 10 µg/mL saponin, 3 µM GDP and 0.20 nM [$^{35}$S]GTPγS to binding buffer (100 mM NaCl, 10 mM $MgCl_2$, 20 mM HEPES, pH 7.4) on ice. The prepared membrane solution (190 µL/well) was transferred to 96-shallow well polypropylene plates containing 10 µL of 20× concentrated stock solutions of agonist prepared in DMSO. Plates were incubated for 30 min at a temperature of about 25° C. with shaking. Reactions were terminated by rapid filtration onto 96-well Unifilter GF/B filter plates (Packard) using a 96-well tissue harvester (Packard) and followed by three filtration washes with 200 µL ice-cold binding buffer (10 mM $NaH_2PO_4$, 10 mM $Na_2HPO_4$, pH 7.4). Filter plates were subsequently dried at 50° C. for 1-2 hours. Fifty µL/well scintillation cocktail (MicroScint20, Packard) was added and plates were counted in a Packard Top-count for 1 min/well.

δ-Opioid Receptor Functional Data: δ GTP $EC_{50}$ is the concentration of a compound providing 50% of the maximal response for the compound at a δ receptor. In certain embodiments, the Phosphorus-Substituted Quinoxaline-Type Piperidine Compounds will have a δ GTP $EC_{50}$ (nM) of about 20,000 or less, or about 10,000 or less, or about 100 or less, or about 1000 or less, or about 90 or less, or about 50 or less, or about 25 or less, or about 10 or less.

δ GTP Emax (%) is the maximal effect elicited by a compound relative to the effect elicited by met-enkephalin. In certain embodiments, the Phosphorus-Substituted Quinoxaline-Type Piperidine Compounds will have a δ GTP Emax (%) of about 10% or greater, or about 30% or greater, or about 50% or greater, or about 75% or greater, or about 90% or greater, or about 100% or greater, or about 110% or greater. In other embodiments, the Phosphorus-Substituted Quinoxaline-Type Piperidine Compounds will have a δ GTP Emax (%) of about 10% or less, or about 5% or less, or about 2% or less.

5.23 Example 23

Efficacy of Receptor Binding and Activity Response

The following Tables provide results on the efficacy of binding and activity response of several Phosphorus-Substituted Quinoxaline-Type Piperidine Compounds to the ORL-1 receptor and, for certain Phosphorus-Substituted Quinoxaline-Type Piperidine Compounds, the mu-opioid receptor, the kappa-opioid receptor, and/or the delta-opioid receptor.

In Table 3, binding efficacy to the ORL-1 receptor was determined by the procedure in Example 15. Binding efficacy to the mu-opioid receptor was determined by the procedure in Example 17. Binding efficacy to the kappa-opioid receptor was determined by the procedure in Example 19. Binding efficacy to the delta-opioid receptor was determined by the procedure in Example 21.

In Table 4, activity response to the ORL-1 receptor was determined by the procedure in Example 16. Activity response to the mu-opioid receptor was determined by the procedure in Example 18. Activity response to the kappa-opioid receptor was determined by the procedure in Example 20. Activity response to the delta-opioid receptor can be determined by the procedure in Example 22.

TABLE 3
Efficacy of Receptor Binding of Phosphorus-Substituted Quinoxaline-Type Piperidine Compounds
| Ref No. | Compound | $K_i$ [Average ± Std Deviation] (nM) | | | |
| --- | --- | --- | --- | --- | --- |
| | | | Opioid Receptor | | |
| | | ORL-1 | Mu | Kappa | Delta |
| AA | 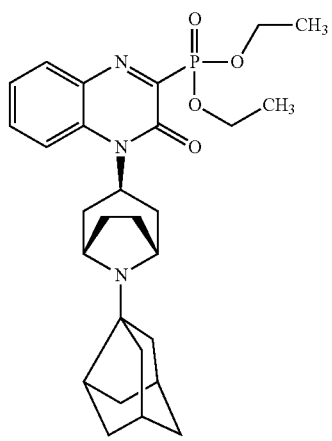 [SMILES: CCOP(=O)(OCC)c1nc2ccccc2n([C@H]2C[C@H]3CC[C@@H](C2)N3C23CC4CC(CC2C4)C3)c1=O] | 48.1 ± 4.4 | 429 ± 40 | 31.5 ± 3.6 | >20,000 |
| BB | 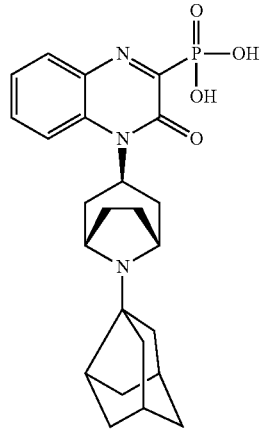 [SMILES: O=c1c(P(=O)(O)O)nc2ccccc2n1[C@H]1C[C@H]2CC[C@@H](C1)N2C12CC3CC(CC1C3)C2] | 58.5 ± 5.4 | 660 ± 115 | 3957 ± 291 | >20,000 |
| DD | 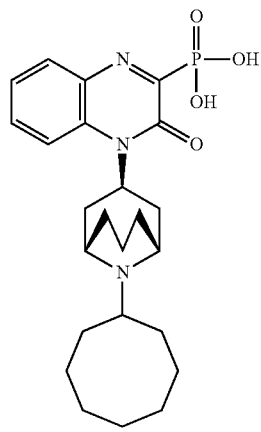 [SMILES: O=c1c(P(=O)(O)O)nc2ccccc2n1[C@H]1C[C@H]2CCC[C@@H](C1)N2C1CCCCCCC1] | 29.28 ± 6.02 | 2154 ± 127 | 1420 ± 105 | >20,000 |

TABLE 3-continued
Efficacy of Receptor Binding of Phosphorus-Substituted Quinoxaline-Type Piperidine Compounds
| | | $K_i$ [Average ± Std Deviation] (nM) | | | |
| --- | --- | --- | --- | --- | --- |
| | | | Opioid Receptor | | |
| Ref No. | Compound | ORL-1 | Mu | Kappa | Delta |
| FF | 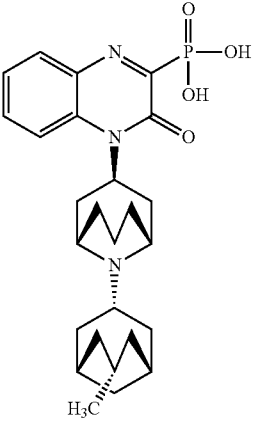 [SMILES: C[C@@H]1C[C@@H]2C[C@H](C1)C[C@@H](N1[C@@H]3CCC[C@H]1C[C@@H](n1c(=O)c(P(=O)(O)O)nc4ccccc41)C3)C2] | 1.0 ± 0.1 | 28.3 ± 4.1 | 267.4 ± 4.2 | 2040 ± 313 |
| HH | 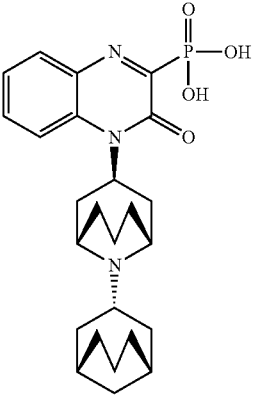 [SMILES: O=c1c(P(=O)(O)O)nc2ccccc2n1[C@H]1C[C@H]2CCC[C@@H](C1)N2[C@H]1C[C@@H]2CCC[C@@H](C2)C1] | 7.51 ± 0.63 | — | — | — |
| KK | 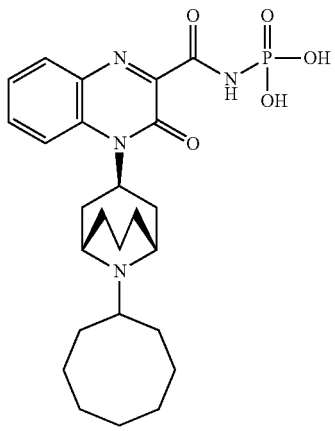 [SMILES: O=C(NP(=O)(O)O)c1nc2ccccc2n([C@H]2C[C@H]3CCC[C@@H](C2)N3C2CCCCCCC2)c1=O] | 175 ± 17 | 20,000 | 7406 ± 609 | >20,000 |

TABLE 3-continued
Efficacy of Receptor Binding of Phosphorus-Substituted Quinoxaline-Type Piperidine Compounds
| Ref No. | Compound | $K_i$ [Average ± Std Deviation] (nM) ||||
| | | ORL-1 | Opioid Receptor |||
| | | | Mu | Kappa | Delta |
|---|---|---|---|---|---|
| MM | 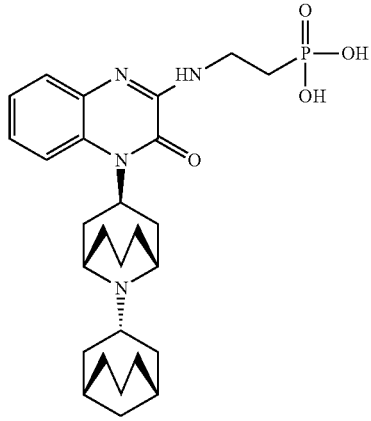 [SMILES: O=c1c(NCCP(=O)(O)O)nc2ccccc2n1[C@H]1C[C@H]2CCC[C@@H](C1)N2[C@H]1C[C@@H]2CCC[C@@H](C2)C1] | 24.1 ± 1.5 | — | — | — |
| OO | 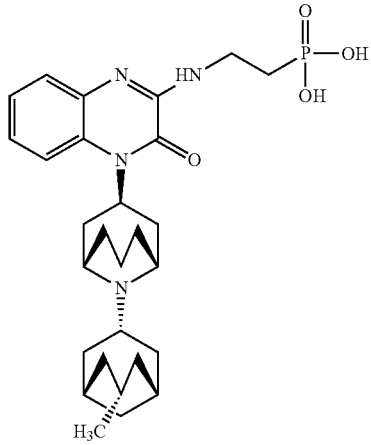 [SMILES: C[C@@H]1C[C@@H]2C[C@H](C1)C[C@@H](N1[C@@H]3CCC[C@H]1C[C@@H](n1c(=O)c(NCCP(=O)(O)O)nc4ccccc41)C3)C2] | 2.92 ± 0.41 | — | — | — |
| PP | 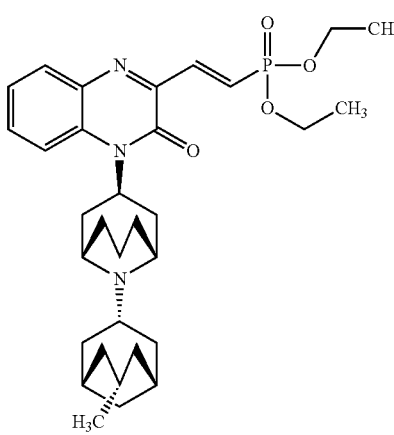 [SMILES: CCOP(=O)(/C=C/c1nc2ccccc2n([C@H]2C[C@H]3CCC[C@@H](C2)N3[C@H]2C[C@@H]3C[C@@H](C)C[C@@H](C3)C2)c1=O)OCC] | 2.62 ± 0.42 | 29.8 ± 3.4 | 2.50 ± 0.28 | 3982 ± 995 |

TABLE 3-continued

Efficacy of Receptor Binding of Phosphorus-Substituted Quinoxaline-Type Piperidine Compounds

| | | $K_i$ [Average ± Std Deviation] (nM) | | | |
|---|---|---|---|---|---|
| | | | Opioid Receptor | | |
| Ref No. | Compound | ORL-1 | Mu | Kappa | Delta |
| QQ | (structure) | 5.49 ± 1.08 | 505 ± 140 | 403 ± 75 | 5589 ± 575 |
| TT | (structure) | 3.40 ± 0.48 | 129 ± 13 | 78 ± 15 | 5908 ± 465 |
| VV | (structure) | 11.1 ± 1.3 | >20,000 | 43.7 ± 15.9 | >20,000 |

TABLE 3-continued

Efficacy of Receptor Binding of Phosphorus-Substituted Quinoxaline-Type Piperidine Compounds

| Ref No. | Compound | $K_i$ [Average ± Std Deviation] (nM) Opioid Receptor | | | |
|---|---|---|---|---|---|
| | | ORL-1 | Mu | Kappa | Delta |
| WW | (structure) | 12.2 ± 1.7 | 396 ± 101 | 37.9 ± 7.6 | 5295 ± 1506 |
| XX | (structure) | 6.34 ± 0.24 | — | — | — |

TABLE 4

Activity Response of Phosphorus-Substituted Quinoxaline-Type Piperidine Compounds

| | GTPγS (EC$_{50}$: nM, Emax: %) [mean ± SEM] | | | | |
|---|---|---|---|---|---|
| | Opioid Receptor | | | | |
| | ORL-1 | | Mu | | Kappa |
| Ref No. | EC$_{50}$ | E$_{max}$ | EC$_{50}$ | E$_{max}$ | EC$_{50}$ |
| AA | 184 ± 9 | 61.7 ± 2.0 | >20,000 | −0.33 ± 0.67 | >20,000 |
| BB | 197 ± 19 | 81.7 ± 5.8 | >20,000 | 6.7 ± 5.7 | — |
| DD | 174 ± 18 | 130 ± 7 | — | — | — |
| FF | 2.49 ± 0.32 | 55.0 ± 1.2 | >20,000 | — | >20,000 |
| HH | 19.3 ± 2.4 | 21 ± 1 | — | — | — |
| KK | 658 ± 132 | 105 ± 12 | — | — | — |
| MM | 10.8 ± 2.2 | 11.6 ± 0.6 | — | — | — |
| OO | 2.92 ± 0.41 | 18.5 ± 1.4 | — | — | — |
| PP | 2.32 ± 0.21 | 62 ± 5 | >20,000 | — | >20,000 |
| QQ | 8.9 ± 0.8 | 33.3 ± 0.8 | >20,000 | — | >20,000 |
| TT | 3.94 ± 0.87 | 34.8 ± 1.8 | >20,000 | 0.33 ± 0.67 | >20,000 |
| VV | 15.0 ± 1.7 | 40 ± 3 | — | — | >20,000 |
| WW | 13.8 ± 1.4 | 34.3 ± 0.7 | >20,000 | — | >20,000 |
| XX | 26.6 ± 3.1 | 21.7 ± 3.7 | — | — | — |

5.24 Example 24

In Vivo Assays for Prevention or Treatment of Pain

Test Animals: Each experiment uses rats weighing between 200-260 g at the start of the experiment. The rats are group-housed and have free access to food and water at all times, except prior to oral administration of a Phosphorus-Substituted Quinoxaline-Type Piperidine Compound when food is removed for 16 hours before dosing. A control group acts as a comparison to rats treated with a Phosphorus-Substituted Quinoxaline-Type Piperidine Compound. The control group is administered the carrier for the Phosphorus-Substituted Quinoxaline-Type Piperidine Compound. The volume of carrier administered to the control group is the same as the volume of carrier and Phosphorus-Substituted Quinoxaline-Type Piperidine Compound administered to the test group.

Acute Pain: To assess the actions of a Phosphorus-Substituted Quinoxaline-Type Piperidine Compound for the treatment or prevention of acute pain, the rat tail flick test can be used. Rats are gently restrained by hand and the tail exposed to a focused beam of radiant heat at a point 5 cm from the tip using a tail flick unit (Model 7360, commercially available from Ugo Basile of Italy). Tail flick latencies are defined as the interval between the onset of the thermal stimulus and the flick of the tail. Animals not responding within 20 seconds are removed from the tail flick unit and assigned a withdrawal latency of 20 seconds. Tail flick latencies are measured immediately before (pre-treatment) and 1, 3, and 5 hours following administration of a Phosphorus-Substituted Quinoxaline-Type Piperidine Compound. Data are expressed as tail flick latency(s) and the percentage of the maximal possible effect (% MPE), i.e., 20 seconds, is calculated as follows:

$$\% \, MPE = \frac{[(\text{post administration latency}) - (\text{pre-administration latency})]}{(20 \, \text{s pre-administration latency})} \times 100$$

The rat tail flick test is described in D'Amour et al., "A Method for Determining Loss of Pain Sensation," *J. Pharmacol. Exp. Ther.* 72:74-79 (1941).

Inflammatory Pain: To assess the actions of a Phosphorus-Substituted Quinoxaline-Type Piperidine Compound for the treatment or prevention of inflammatory pain, the Freund's complete adjuvant ("FCA") model of inflammatory pain can be used. FCA-induced inflammation of the rat hind paw is associated with the development of persistent inflammatory mechanical hyperalgesia and provides reliable prediction of the anti-hyperalgesic action of clinically useful analgesic drugs (Bartho et al., "Involvement of capsaicin-sensitive neurons in hyperalgesia and enhanced opioid antinociception in inflammation," *Naunyn-Schmiedeberg's Archives of Pharmacol.* 342:666-670 (1990)). The left hind paw of each animal is administered a 50 L intraplantar injection of 50% FCA. 24 hour post injection, the animal is assessed for response to noxious mechanical stimuli by determining the PWT, as described below. Rats are then administered a single injection of 1, 3, 10 or 30 mg/kg of either a Phosphorus-Substituted Quinoxaline-Type Piperidine Compound; 30 mg/kg of a control selected from Celebrex, indomethacin, and naproxen; or carrier. Responses to noxious mechanical stimuli are then determined 1, 3, 5 and 24 hours post administration. Percentage reversal of hyperalgesia for each animal is defined as:

$$\% \, \text{Reversal} = \frac{[(\text{post administration} \, PWT) - (\text{pre-administration} \, PWT)]}{[(\text{baseline} \, PWT) - (\text{pre-administration} \, PWT)]} \times 100$$

Neuropathic Pain: To assess the actions of a Phosphorus-Substituted Quinoxaline-Type Piperidine Compound for the treatment or prevention of neuropathic pain, either the Seltzer model or the Chung model can be used.

In the Seltzer model, the partial sciatic nerve ligation model of neuropathic pain is used to produce neuropathic hyperalgesia in rats (Seltzer et al., "A Novel Behavioral Model of Neuropathic Pain Disorders Produced in Rats by Partial Sciatic Nerve Injury," *Pain* 43:205-218 (1990)). Partial ligation of the left sciatic nerve is performed under isoflurane/$O_2$ inhalation anaesthesia. Following induction of anesthesia, the left thigh of the rat is shaved and the sciatic nerve exposed at high thigh level through a small incision and is carefully cleared of surrounding connective tissues at a site near the trocanther just distal to the point at which the posterior biceps semitendinosus nerve branches off of the common sciatic nerve. A 7-0 silk suture is inserted into the nerve with a ⅜ curved, reversed-cutting mini-needle and tightly ligated so that the dorsal ⅓ to ½ of the nerve thickness is held within the ligature. The wound is closed with a single muscle suture (4-0 nylon (Vicryl)) and vetbond tissue glue. Following surgery, the wound area is dusted with antibiotic powder. Sham-treated rats undergo an identical surgical procedure except that the sciatic nerve is not manipulated. Following surgery, animals are weighed and placed on a warm pad until they recover from anesthesia. Animals are then returned to their home cages until behavioral testing begins. The animal is assessed for response to noxious mechanical stimuli by determining PWT, as described below, prior to surgery (baseline), then immediately prior to and 1, 3, and 5 hours after drug administration for rear paw of the animal. Percentage reversal of neuropathic hyperalgesia is defined as:

$$\% \, \text{Reversal} = \frac{[(\text{post administration} \, PWT) - (\text{pre-administration} \, PWT)]}{[(\text{baseline} \, PWT) - (\text{pre-administration} \, PWT)]} \times 100$$

In the Chung model, the spinal nerve ligation model of neuropathic pain is used to produce mechanical hyperalgesia, thermal hyperalgesia and tactile allodynia in rats. Surgery is performed under isoflurane/$O_2$ inhalation anaesthesia. Following induction of anaesthesia, a 3 cm incision is made and the left paraspinal muscles are separated from the spinous process at the $L_4$-$S_2$ levels. The $L_6$ transverse process is carefully removed with a pair of small rongeurs to identify visually the $L_4$-$L_6$ spinal nerves. The left $L_5$ (or $L_5$ and $L_6$) spinal nerve(s) is isolated and tightly ligated with silk thread. A complete hemostasis is confirmed and the wound is sutured using non-absorbable sutures, such as nylon sutures or stainless steel staples. Sham-treated rats undergo an identical surgical procedure except that the spinal nerve(s) is not manipulated. Following surgery animals are weighed, administered a subcutaneous (s.c.) injection of saline or ringers lactate, the wound area is dusted with antibiotic powder and they are kept on a warm pad until they recover from the anesthesia. Animals are then returned to their home cages until behavioral testing begins. The animals are assessed for response to noxious mechanical stimuli by determining PWT, as described below, prior to surgery (baseline), then immediately prior to and 1, 3, and 5 hours after being administered a Phosphorus-Substituted Quinoxaline-Type Piperidine Compound for the left rear paw of the animal. The animal can also be assessed for response to noxious thermal stimuli or for tactile allodynia, as described below. The Chung model for neuropathic pain is described in Kim, "An Experimental Model for Peripheral Neuropathy Produced by Segmental Spinal Nerve Ligation in the Rat," *Pain* 50(3):355-363 (1992).

Response to Mechanical Stimuli as an Assessment of Mechanical Hyperalgesia: The paw pressure assay can be used to assess mechanical hyperalgesia. For this assay, hind paw withdrawal thresholds (PWT) to a noxious mechanical stimulus are determined using an analgesymeter (Model 7200, commercially available from Ugo Basile of Italy) as described in Stein, "Unilateral Inflammation of the Hindpaw in Rats as a Model of Prolonged Noxious Stimulation: Alterations in Behavior and Nociceptive Thresholds," *Pharmacol. Biochem. and Behavior* 31:451-455 (1988). The maximum weight that can be applied to the hind paw is set at 250 g and the end point is taken as complete withdrawal of the paw. PWT is determined once for each rat at each time point and either only the affected (ipsilateral) paw is tested, or both the ipsilateral and contralateral (non-injured) paw are tested.

Response to Thermal Stimuli as an Assessment of Thermal Hyperalgesia: The plantar test can be used to assess thermal hyperalgesia. For this test, hind paw withdrawal latencies to a noxious thermal stimulus are determined using a plantar test apparatus (commercially available from Ugo Basile of Italy) following the technique described by Hargreaves et al., "A New and Sensitive Method for Measuring Thermal Nociception in Cutaneous Hyperalgesia," *Pain* 32(1):77-88 (1988). The maximum exposure time is set at 32 seconds to avoid tissue damage and any directed paw withdrawal from the heat source is taken as the end point. Three latencies are determined at each time point and averaged. Either only the affected (ipsilateral) paw is tested, or both the ipsilateral and contralateral (non-injured) paw are tested.

Assessment of Tactile Allodynia: To assess tactile allodynia, rats are placed in clear, plexiglass compartments with a wire mesh floor and allowed to habituate for a period of at least 15 minutes. After habituation, a series of von Frey monofilaments are presented to the plantar surface of the left (operated) foot of each rat. The series of von Frey monofilaments consists of six monofilaments of increasing diameter, with the smallest diameter fiber presented first. Five trials are conducted with each filament with each trial separated by approximately 2 minutes. Each presentation lasts for a period of 4-8 seconds or until a nociceptive withdrawal behavior is observed. Flinching, paw withdrawal or licking of the paw are considered nociceptive behavioral responses.

The invention is not to be limited in scope by the specific embodiments disclosed in the examples that are intended as illustrations of a few aspects of the invention and any embodiments that are functionally equivalent are within the scope of this invention. Indeed, various modifications of the invention in addition to those shown and described herein will become apparent to those skilled in the art and are intended to fall within the scope of the appended claims. A number of references have been cited, the entire disclosures of which are incorporated herein by reference for all purposes.

What is claimed is:

1. A compound of Formula (I):

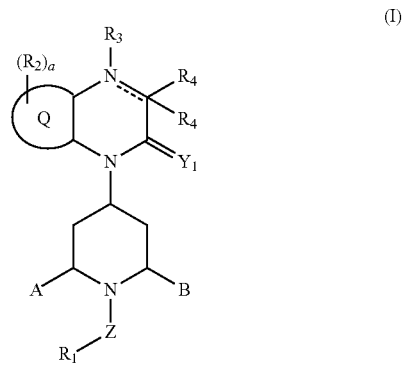

or a pharmaceutically acceptable salt thereof wherein:

$Y_1$ is O or S;

Q is benzo or (5- or 6-membered)heteroaryl;

each $R_2$ is independently selected from:

(a) -halo, —CN, —NO$_2$, -OT$_3$, —C(=O)T$_3$, —C(=O)OT$_3$, —C(=O)N(T$_1$)(T$_2$), —S(=O)$_2$OT$_3$, —S(=O)T$_3$, —S(=O)$_2$T$_3$, —S(=O)$_2$N(T$_1$)(T$_2$), —N(T$_1$)(T$_2$), —N(T$_3$)C(=O)T$_3$, —N(T$_3$)C(=O)N(T$_1$)(T$_2$), —N(T$_3$)S(=O)$_2$T$_3$, and —N(T$_3$)S(=O)$_2$N(T$_1$)(T$_2$); and (b) —(C$_1$-C$_6$)alkyl, —(C$_2$-C$_6$)alkenyl, —(C$_2$-C$_6$)alkynyl, —(C$_1$-C$_6$)alkoxy, —(C$_3$-C$_7$)cycloalkyl, —(C$_6$-C$_{14}$)bicycloalkyl, —(C$_8$-C$_{20}$)tricycloalkyl, —(C$_5$-C$_{10}$)cycloalkenyl, —(C$_7$-C$_{14}$)bicycloalkenyl, —(C$_8$-C$_{20}$)tricycloalkenyl, -(5- or 6-membered) heterocycle, and -(7- to 10-membered) bicycloheterocycle, each of which is unsubstituted or substituted with 1, 2, or 3 independently selected $R_8$ groups; and (c) -phenyl, -naphthalenyl, —(C$_{14}$)aryl, and -(5- or 6-membered)heteroaryl, each of which is unsubstituted or substituted with 1, 2, or 3 independently selected $R_7$ groups;

a is an integer selected from 0, 1, and 2;

the dashed line in the 6-membered, nitrogen-containing ring that is fused to the Q group denotes the presence or absence of a bond, and when that dashed line is present as a bond to provide one bond of a double bond then one $R_4$ group is absent, one $R_4$ group is present, and optionally $R_3$ is absent;

$R_3$ is selected from:

(a) —H; and (b) —(C$_1$-C$_4$)alkyl which is unsubstituted or substituted with 1, 2, or 3 groups independently selected from —OH, —(C$_1$-C$_4$)alkoxy, —N(R$_6$)$_2$, —C(=O)OR$_9$, and —C(=O)N(R$_6$)$_2$; and (c) —(C$_3$-C$_7$)cycloalkyl which is unsubstituted or substituted with 1, 2, or 3 groups independently selected from —OH, —(C$_1$-C$_4$)alkyl, —(C$_1$-C$_4$)alkoxy, —N(R$_6$)$_2$, —C(=O)OR$_9$, and —C(=O)N(R$_6$)$_2$;

each $R_4$ group is independently selected from —H and —U$_1$—U$_2$—U$_3$—U$_4$—U$_5$—U$_6$—U$_7$—U, wherein said compound of Formula (I) contains at least one $R_4$ group that is not hydrogen;

U is —P(=O)(OR$_9$)([O]$_x$R$_9$);

$U_1$, $U_3$, $U_5$, and $U_7$ are independently selected from:
(a) a single bond; and
(b) —$(C_1-C_6)$alkyl-, —$(C_2-C_6)$alkenyl-, —$(C_6-C_{12})$cycloalkyl-, —$(C_6-C_{14})$bicycloalkyl-, —$(C_5-C_{14})$cycloalkenyl-, —$(C_7-C_{14})$bicycloalkenyl-, -phenyl-, and -(5- or 6-membered)heterocycle-, each of which is unsubstituted or substituted with 1, 2, or 3 independently selected $R_7$ groups; and
(c) absent;

$U_2$, $U_4$, and $U_6$ are independently —Y—, —N($R_9$)—, —C(=Y)—, a single bond, or absent;

each Y is independently O or S;

A and B are independently selected from:
(a) —H, —CN, —C(=O)O$T_3$, and —C(=O)N($T_1$)($T_2$); and
(b) —$(C_3-C_{12})$cycloalkyl, —$(C_3-C_{12})$cycloalkoxy, —$(C_1-C_6)$alkyl, —$(C_2-C_6)$alkenyl, —$(C_2-C_6)$alkynyl, and —$(C_1-C_6)$alkoxy, each of which is unsubstituted or substituted with:
(1') 1 or 2 substituents independently selected from —OH, —S(=O)$_2$NH$_2$, —N($R_6$)$_2$, =N$R_6$, —C(=O)O$T_3$, —C(=O)N($R_6$)$_2$, —N($R_6$)C(=O)$R_9$, and -(5- or 6-membered)heterocycle, or
(2') 1, 2, or 3 independently selected -halo; or
(c) A-B can together form a $(C_2-C_6)$bridge, which is unsubstituted or substituted with 1, 2, 3, 4, 5, 6, 7, or 8 substituents independently selected from —OH, —$(C_1-C_4)$alkyl, -halo, and —C(halo)$_3$, and which bridge optionally contains —HC=CH— or —O— within the $(C_2-C_6)$bridge, wherein the 6-membered, nitrogen-containing ring that is fused to the Q group can be in the endo- or exo-configuration with respect to the A-B bridge; or
(d) A-B can together form a —CH$_2$—N($R_a$)—CH$_2$— bridge, a

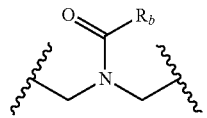

bridge, or a bridge,

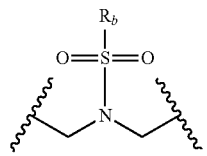

wherein the 6-membered, nitrogen-containing ring that is fused to the Q group can be in the endo- or exo-configuration with respect to the A-B bridge;

$R_a$ is —H, —$(C_1-C_6)$alkyl, —$(C_3-C_7)$cycloalkyl, —CH$_2$—C(=O)—$R_c$, —(CH$_2$)—C(=O)—O$R_c$, —(CH$_2$)—C(=O)—N($R_c$)$_2$, —(CH$_2$)$_2$—O—$R_c$, —(CH$_2$)$_2$—S(=O)$_2$—N($R_c$)$_2$, $R_c$, or —(CH$_2$)$_2$—N($R_c$)S(=O)$_2$—$R_c$;

$R_b$ is selected from:
(a) —H, —$(C_1-C_6)$alkyl, —$(C_3-C_7)$cycloalkyl, -(3- to 7-membered)heterocycle, —N($R_c$)$_2$, —N($R_c$)—$(C_3-C_2)$cycloalkyl, and —N($R_c$)-(3- to 7-membered)heterocycle; and (b) -phenyl, -naphthalenyl, and -(5- or 6-membered)heteroaryl, each of which is unsubstituted or substituted with 1, 2, or 3 independently selected $R_7$ groups; and
(c) —N($R_c$)-phenyl, —N($R_c$)-naphthalenyl, —N($R_c$)—$(C_{14})$aryl, and —N($R_c$)-(5- to 10-membered)heteroaryl, each of which is unsubstituted or substituted with 1, 2, or 3 independently selected $R_7$ groups;

each $R_c$ is independently —H or —$(C_1-C_4)$alkyl;

Z is —[$(C_1-C_{10})$alkyl optionally substituted by $R_1$]$_h$—, wherein h is 0 or 1; —$(C_2-C_{10})$alkenyl- optionally substituted by $R_1$; or —$(C_1-C_{10})$alkyl-N($R_6$)C(=Y)—;

each $R_1$ is independently selected from:
(a) —H, -halo, —CN, —OH, —CH$_2$OH, —CH$_2$CH$_2$OH, —NO$_2$, —N($R_6$)$_2$, —S(=O)NH$_2$, —S(=O)$_2$NH$_2$, —C(=O)O$V_1$, and —C(=O)CN; and
(b) —$(C_1-C_{10})$alkyl, —$(C_2-C_{10})$alkenyl, —$(C_2-C_{10})$alkynyl, —O$(C_1-C_6)$alkyl, —$(C_3-C_7)$cycloalkoxy, —$(C_6-C_{14})$bicycloalkyl, —$(C_8-C_{20})$tricycloalkyl, —$(C_5-C_{10})$cycloalkenyl, —$(C_7-C_{14})$bicycloalkenyl, —$(C_8-C_{20})$tricycloalkenyl, -(3- to 7-membered)heterocycle, and -(7- to 10-membered)bicycloheterocycle, each of which is unsubstituted or substituted with 1, 2, 3, or 4 independently selected $R_8$ groups; and
(c)

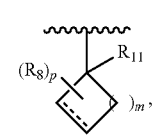

(i)

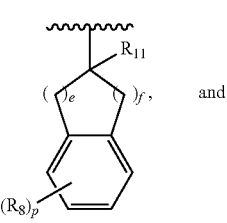

(ii)

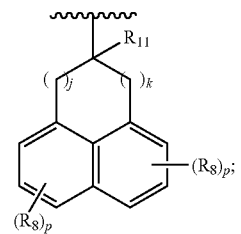

(iii)

and
(d) -phenyl, -naphthalenyl, —$(C_{14})$aryl, and -(5- to 10-membered)heteroaryl, each of which is unsubstituted or substituted with a $R_7$ group; or —Z—$R_1$ is 3,3-diphenylpropyl- optionally substituted at the 3 carbon of the propyl with —CN, —C(=O)N($R_6$)$_2$, —C(=O)O$V_1$, or -tetrazolyl; or —Z—$R_1$ is —$(C_1-C_4)$alkyl substituted with tetrazolyl;

each $R_6$ is independently —H, —$(C_1-C_6)$alkyl, or —$(C_3-C_7)$cycloalkyl, or two $R_6$ groups attached to the same nitrogen atom can together form a 5- to 8-membered ring, wherein the number of atoms in the ring includes the nitrogen atom, and in which one of the 5- to 8-membered ring carbon atoms is optionally replaced by O, S, or N($R_{12}$);

each $R_7$ is independently —($C_1$-$C_4$)alkyl, —($C_2$-$C_6$)alkenyl, —($C_2$-$C_6$)alkynyl, —$OR_9$, —$SR_9$, —C(halo)$_3$, —CH(halo)$_2$, —CH$_2$(halo), —CN, -halo, —$N_3$, —$NO_2$, —CH=N($R_9$), —N($R_9$)$_2$, —N($R_9$)OH, —N($R_9$)S(=O)$R_{12}$, —N($R_9$)S(=O)$_2R_{12}$, —N($R_9$)C(=O)$R_{12}$, —N($R_9$)C(=O)N($T_1$)($T_2$), —N($R_9$)C(=O)$OR_{12}$, —C(=O)N($T_1$)($T_2$), —C(=O)$OR_9$, —OC(=O)$R_9$, —OC(=O)N($T_1$)($T_2$), —OC(=O)$OR_9$, —S(=O)$R_9$, or —S(=O)$_2R_9$;

each $R_8$ is independently —($C_1$-$C_6$)alkyl, —($C_2$-$C_6$)alkenyl, —($C_2$-$C_6$)alkynyl, -(5- or 6-membered)heteroaryl, —($C_1$-$C_6$)alkyl-C(=O)$OR_9$, —$OR_9$, —$SR_9$, —C(halo)$_3$, —CH(halo)$_2$, —CH$_2$(halo), —CN, =O, -halo, —$N_3$, —$NO_2$, —CH=N($R_9$), —N($R_9$)($C_1$-$C_6$)alkyl-C(=O)$OR_9$, —N($R_9$)$_2$, —N($R_9$)OH, —N($R_9$)S(=O)$R_{12}$, —N($R_9$)S(=O)$_2R_{12}$, —N($R_9$)C(=O)$R_{12}$, —N($R_9$)C(=O)N($R_{12}$)($R_{12}$), —N($R_9$)C(=O)$OR_{12}$, —C(=O)$R_9$, —C(=O)N($R_{12}$)($R_{12}$), —C(=O)$OR_9$, —OC(=O)$R_9$, —OC(=O)N($R_{12}$)($R_{12}$), —OC(=O)$OR_9$, —S(=O)$R_9$, or —S(=O)$_2R_9$;

each $R_9$ is independently —H, —($C_1$-$C_6$)alkyl, —($C_2$-$C_6$)alkenyl, —($C_2$-$C_6$)alkynyl, —($C_3$-$C_8$)cycloalkyl, —($C_5$-$C_8$)cycloalkenyl, -phenyl, -benzyl, —CH$_2$—O—C(O)-phenyl, —CH$_2$—C(O)—O-phenyl, —CH$_2$—O—C(O)—O— phenyl, —C(halo)$_3$, —CH(halo)$_2$, or —CH$_2$(halo);

if h is 0, then $R_{11}$ can be selected from —H, —CN, —C(=O)$OR_9$, and —C(=O)N($R_6$)$_2$ or $R_{11}$ can be —($C_1$-$C_4$)alkyl which is unsubstituted or substituted with —OH, —($C_1$-$C_4$)alkoxy, —N($R_6$)$_2$, —C(=O)$OR_9$, or —C(=O)N($R_6$)$_2$;

if h is 1, then each $R_{11}$ can be independently selected from —H, —CN, —OH, -halo, —C(=O)$OR_9$, and —C(=O)N($R_6$)$_2$ and each $R_{11}$ can be independently selected from —($C_1$-$C_4$)alkyl which is unsubstituted or substituted with —OH, —($C_1$-$C_4$)alkoxy, —N($R_6$)$_2$, —C(=O)$OR_9$, or —C(=O)N($R_6$)$_2$;

otherwise, where Z is —($C_2$-$C_{10}$)alkenyl- optionally substituted by $R_1$ or —($C_1$-$C_{10}$)alkyl-N($R_6$)C(=Y), then each $R_{11}$ can be independently selected from —H, —CN, —C(=O)$OR_9$, and —C(=O)N($R_6$)$_2$ and each $R_{11}$ can be independently selected from —($C_1$-$C_4$)alkyl which is unsubstituted or substituted with —OH, —($C_1$-$C_4$)alkoxy, —N($R_6$)$_2$, —C(=O)$OR_9$, or —C(=O)N($R_6$)$_2$;

each $R_{12}$ is independently —H or —($C_1$-$C_6$)alkyl;

each m is an integer independently selected from 0, 1, 2, 3, 4, 5, 6, 7, 8, 9, 10, and 11;

each e and f are each an integer independently selected from 0, 1, 2, 3, 4, and 5 provided that 2≤(e+f)≤5;

each j and k are each an integer independently selected from 0, 1, 2, 3, and 4 provided that 1≤(j+k)≤4;

each p is an integer independently selected from 0, 1, 2, 3, and 4;

x is the integer 0 or 1 provided that when the x of $[O]_xR_9$ is 0, then the $R_9$ of that $[O]_xR_9$ is not —H;

each $T_1$, $T_2$, and $T_3$ is independently —H or —($C_1$-$C_{10}$)alkyl which is unsubstituted or substituted with 1, 2, or 3 independently selected $R_8$ groups and in which 0, 1, 2, or 3 independently selected —($C_1$-$C_{10}$)alkyl carbon atoms except the carbon atom bonded directly to the atom to which $T_1$, $T_2$, or $T_3$ is attached are independently replaced by O, S, or N($R_6$), or $T_1$ and $T_2$ can together form a 5- to 8-membered ring where the number of atoms in the ring includes the nitrogen atom to which $T_1$ and $T_2$ are bonded, said 5- to 8-membered ring is unsubstituted or substituted with 1, 2, or 3 independently selected $R_8$ groups and 0, 1, 2, or 3 independently selected carbon atoms in said 5- to 8-membered ring are independently replaced by O, S, or N($R_6$);

each $V_1$ is independently —H, —($C_1$-$C_6$)alkyl, —($C_3$-$C_7$) cycloalkyl, -phenyl, or -benzyl; and each halo is independently —F, —Cl, —Br, or —I.

2. The compound of claim 1 or a pharmaceutically acceptable salt thereof, wherein $Y_1$ is O.

3. The compound of claim 2 or a pharmaceutically acceptable salt thereof, wherein the dashed line is present as a bond to provide one bond of a double bond, one $R_4$ group is absent, one $R_4$ group is present, and $R_3$ is absent.

4. The compound of claim 3 or a pharmaceutically acceptable salt thereof, wherein Q is benzo or pyridino, wherein the 2- and 3-positions of the pyridino are fused to the 6-membered, nitrogen-containing ring.

5. The compound of claim 3 or a pharmaceutically acceptable salt thereof, wherein Q is benzo.

6. The compound of claim 5 or a pharmaceutically acceptable salt thereof, wherein a is 0.

7. The compound of claim 6, which is:

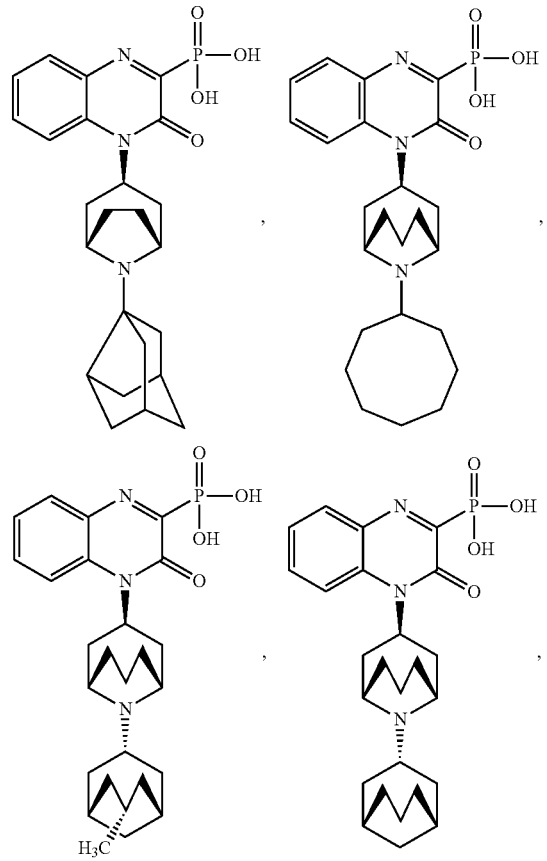

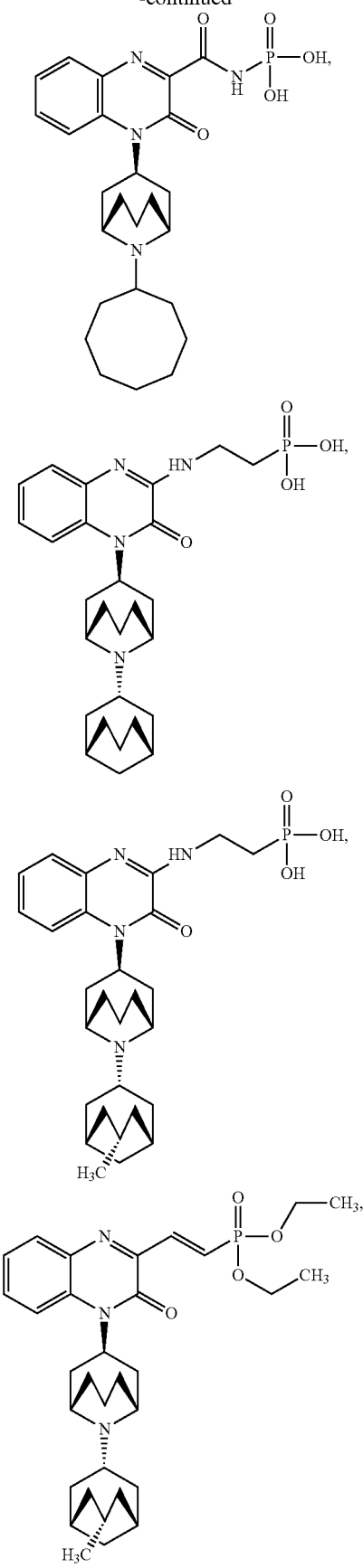
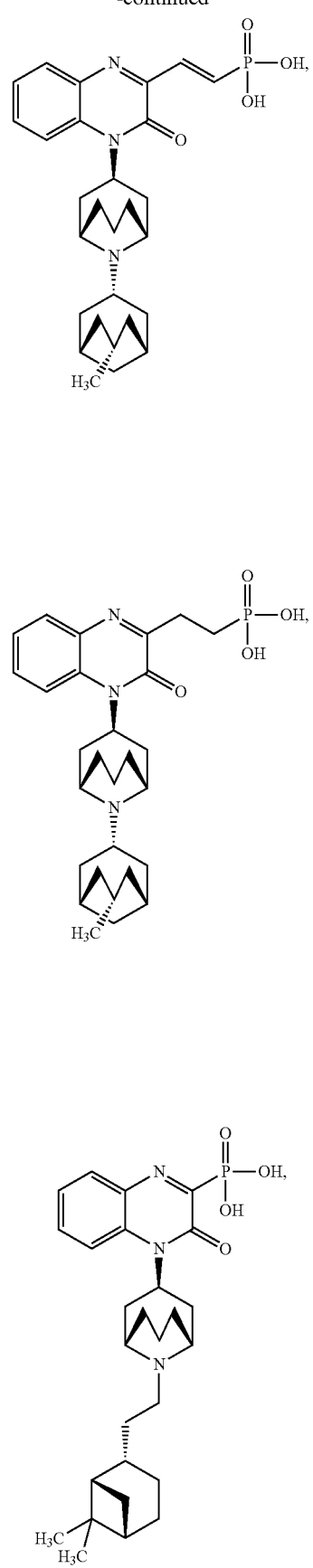

247
-continued
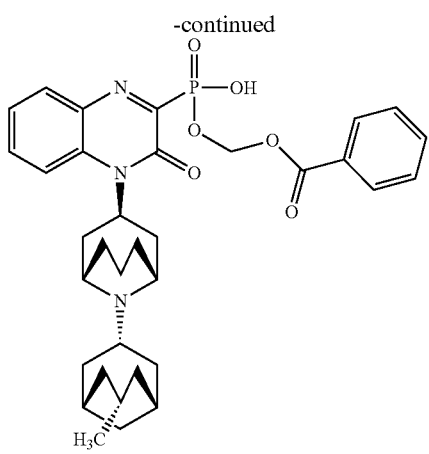
248
-continued
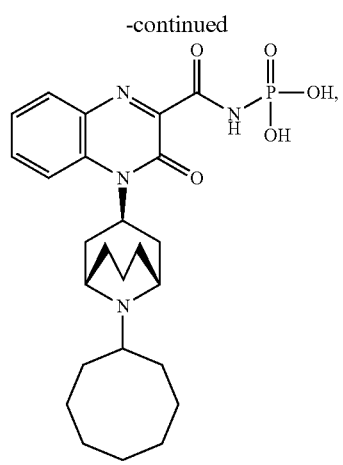
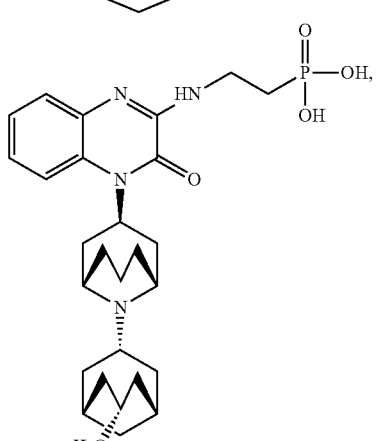
or a pharmaceutically acceptable salt thereof.
8. The compound of claim 7, which is:
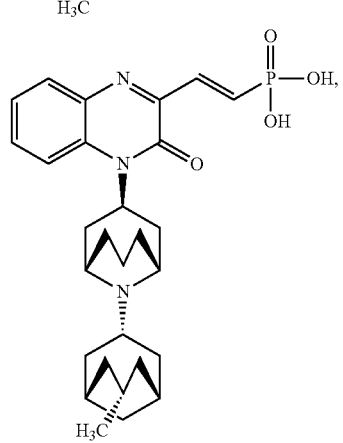
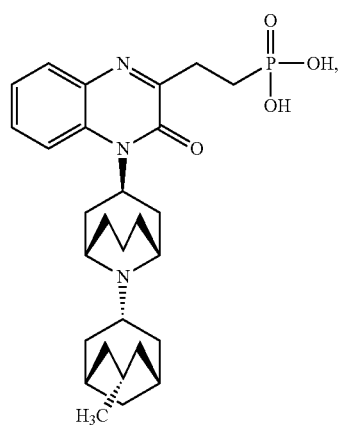

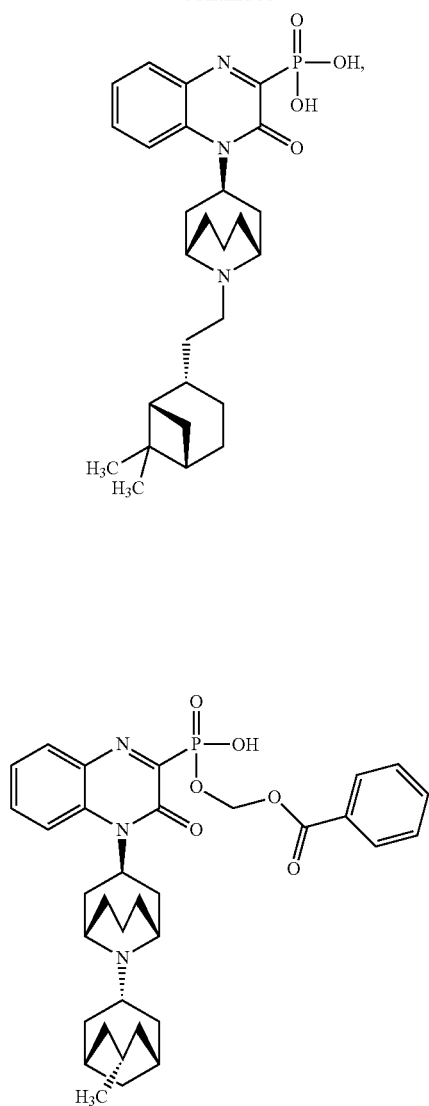

or a pharmaceutically acceptable salt thereof.

9. The compound of claim 8, which is:

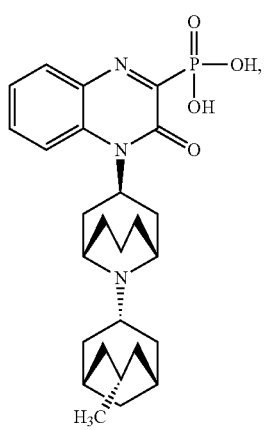

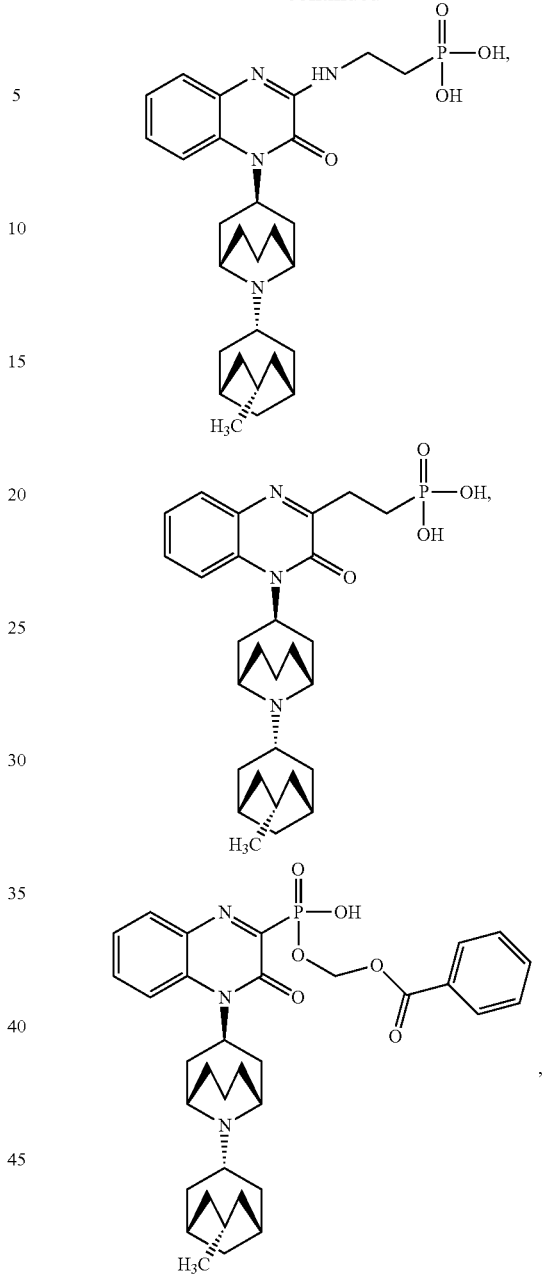

or a pharmaceutically acceptable salt thereof.

10. The compound of claim 4 or a pharmaceutically acceptable salt thereof, wherein
$U_5$, $U_6$, and $U_7$ are absent; and
the $R_4$ group is —$U_1$—$U_2$—$U_3$—$U_4$—U.

11. The compound of claim 10 or a pharmaceutically acceptable salt thereof, wherein U is —P(=O)(OR$_9$)$_2$.

12. The compound of claim 11 or a pharmaceutically acceptable salt thereof, wherein $U_1$ and $U_3$ are independently —(C$_1$-C$_6$)alkyl- or —(C$_2$-C$_6$)alkenyl-, which is unsubstituted or substituted with 1 or 2 independently selected $R_7$ groups, a single bond, or absent.

13. The compound of claim 12 or a pharmaceutically acceptable salt thereof, wherein $U_2$ and $U_4$ are independently —Y—, —N(R$_9$)—, —C(=Y)—, a single bond, or absent.

14. The compound of claim 13 or a pharmaceutically acceptable salt thereof, wherein each Y is O.

15. The compound of claim 14 or a pharmaceutically acceptable salt thereof, wherein U is —P(=O)(OH)$_2$, —P(=O)(OCH$_2$CH$_3$)$_2$ or —P(=O)(OH)(O—CH$_2$—O—C(O)-phenyl).

16. The compound of claim 15 or a pharmaceutically acceptable salt thereof, wherein U$_1$ is a bond and U$_2$, U$_3$, and U$_4$ are each absent.

17. The compound of claim 14 or a pharmaceutically acceptable salt thereof, wherein U$_1$ and U$_3$ are each a single bond, U$_2$ is —C(O)—, and U$_4$ is —NH—.

18. The compound of claim 14 or a pharmaceutically acceptable salt thereof, wherein U$_1$ and U$_4$ are each a single bond, U$_2$ is —NH—, and U$_3$ is —(C$_1$-C$_6$)alkyl- which is unsubstituted.

19. The compound of claim 14 or a pharmaceutically acceptable salt thereof, wherein U$_2$ is single bond, U$_3$, and U$_4$ are each absent, and U$_1$ is —(C$_1$-C$_6$)alkyl- which is unsubstituted.

20. The compound of claim 14 or a pharmaceutically acceptable salt thereof, wherein U$_2$ is single bond, U$_3$, and U$_4$ are each absent, and U$_1$ is —(C$_2$-C$_6$)alkenyl- which is unsubstituted.

21. The compound of claim 20 or a pharmaceutically acceptable salt thereof, wherein U is —P(=O)(OH)$_2$.

22. The compound of claim 20 or a pharmaceutically acceptable salt thereof, wherein U is —P(=O)(OH)(O—CH$_2$—O—C(O)-phenyl).

23. The compound of claim 20 or a pharmaceutically acceptable salt thereof, wherein U is —P(=O)(OCH$_2$CH$_3$)$_2$.

24. The compound of claim 23 or a pharmaceutically acceptable salt thereof, wherein U$_1$ is -(5 or 6-membered heterocycle).

25. The compound of claim 24 or a pharmaceutically acceptable salt thereof, wherein U$_1$ is tetrahydropyridinyl.

26. The compound of claim 24 or a pharmaceutically acceptable salt thereof, wherein
U$_3$, U$_4$, U$_5$, U$_6$, and U$_7$ are absent;
the R$_4$ group is —U$_1$—U$_2$—U;
U$_1$ is -phenyl- or -(5- or 6-membered)heterocycle-, which is unsubstituted or substituted with 1 or 2 independently selected R$_7$ groups;
U$_2$ is —Y—, —N(R$_9$)—, —C(=Y)—, a single bond, or absent; and
each Y is O.

27. The compound of claim 26 or a pharmaceutically acceptable salt thereof, wherein U is —P(=O)(OH)(CH$_3$), —P(=O)(OCH$_2$CH$_3$)(CH$_3$), —P(=O)(O—CH$_2$—O—C(O)-phenyl)(CH$_3$), —P(=O)(OH)(CH$_2$CH$_3$), —P(=O)(OCH$_2$CH$_3$)(CH$_2$CH$_3$), or —P(=O)(O—CH$_2$—O—C(O)-phenyl)(CH$_2$CH$_3$).

28. The compound of claim 27 or a pharmaceutically acceptable salt thereof, wherein U$_1$ is -(5- or 6-membered) heterocycle- which is unsubstituted or substituted with 1 or 2 independently selected R$_7$ groups and U$_2$ is absent.

29. The compound of claim 28 or a pharmaceutically acceptable salt thereof, wherein U$_1$ is 1,4-piperidinyl, 1,4-(1,2,3,6-tetrahydropyridinyl), or 1,4-piperazinyl which is unsubstituted or substituted with 1 or 2 independently selected R$_7$ groups and U$_2$ is absent.

30. The compound of claim 29 or a pharmaceutically acceptable salt thereof, wherein U$_1$ is 1,4-piperidinyl, 1,4-(1,2,3,6-tetrahydropyridinyl), or 1,4-piperazinyl which is unsubstituted and U$_2$ is absent.

31. The compound of claim 27 or a pharmaceutically acceptable salt thereof, wherein U$_1$ is -(5- or 6-membered) heterocycle- which is unsubstituted or substituted with 1 or 2 independently selected R$_7$ groups and U$_2$ is —O—.

32. The compound of claim 31 or a pharmaceutically acceptable salt thereof, wherein U$_1$ is 1,4-piperidinyl, 1,4-(1,2,3,6-tetrahydropyridinyl), or 1,4-piperazinyl which is unsubstituted or substituted with 1 or 2 independently selected R$_7$ groups and U$_2$ is —O—.

33. The compound of claim 32 or a pharmaceutically acceptable salt thereof, wherein U$_1$ is 1,4-piperidinyl, 1,4-(1,2,3,6-tetrahydropyridinyl), or 1,4-piperazinyl which is unsubstituted and U$_2$ is —O—.

34. The compound of claim 33 or a pharmaceutically acceptable salt thereof, wherein U is —P(=O)(OH)(CH$_3$).

35. The compound of claim 33 or a pharmaceutically acceptable salt thereof, wherein U is —P(=O)(OCH$_2$CH$_3$)(CH$_3$).

36. The compound of claim 6 or a pharmaceutically acceptable salt thereof, wherein A and B are independently —H or —(C$_1$-C$_6$)alkyl.

37. The compound of claim 6 or a pharmaceutically acceptable salt thereof, wherein A and B together form a bridge such that the bridged-piperidine is:

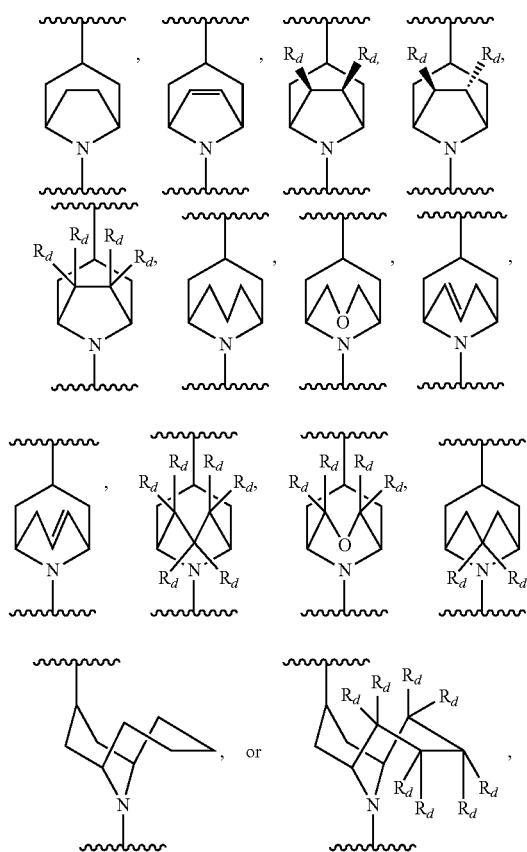

wherein each R$_d$ is independently —H, —(C$_1$-C$_4$)alkyl, -halo, or —C(halo)$_3$.

38. The compound of claim 37 or a pharmaceutically acceptable salt thereof, wherein A and B together form a bridge such that the bridged-piperidine is:

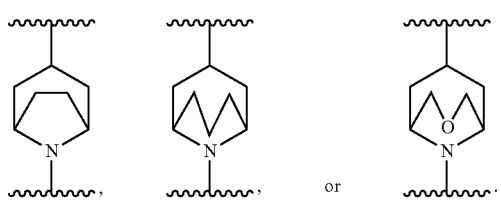 [SMILES: *C1CC2CCC(C1)N2* ; *C1CC2CCCC(C1)N2* ; *C1CC2COCC(C1)N2*]

39. The compound of claim 38 or a pharmaceutically acceptable salt thereof, wherein A and B together form a bridge such that the bridged-piperidine is:

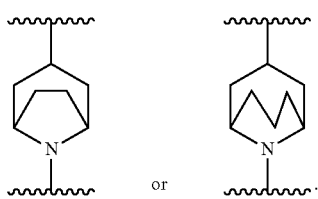 [SMILES: *C1CC2CCC(C1)N2* ; *C1CC2CCCC(C1)N2*]

40. The compound of claim 37 or a pharmaceutically acceptable salt thereof, wherein the 6-membered, nitrogen-containing ring that is fused to the Q group is in the endo configuration with respect to the A-B bridge of the bridged-piperidine.

41. The compound of claim 6 or a pharmaceutically acceptable salt thereof, wherein h is 0 and $R_1$ is —$(C_3$-$C_{14})$cycloalkyl, —$(C_5$-$C_{10})$cycloalkenyl, —$(C_3$-$C_{14})$cycloalkenyl, —$(C_6$-$C_{14})$bicycloalkyl, —$(C_7$-$C_{14})$bicycloalkenyl, or —$(C_8$-$C_{20})$tricycloalkyl, each of which is unsubstituted or substituted with 1, 2, 3, or 4 independently selected $R_8$ groups.

42. The compound of claim 41 or a pharmaceutically acceptable salt thereof, wherein $R_1$ is:

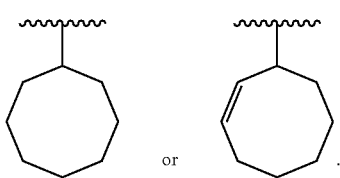 [SMILES: *C1CCCCCCC1 ; *C1/C=C\CCCCC1]

43. The compound of claim 41 or a pharmaceutically acceptable salt thereof, wherein —Z—$R_1$ is:

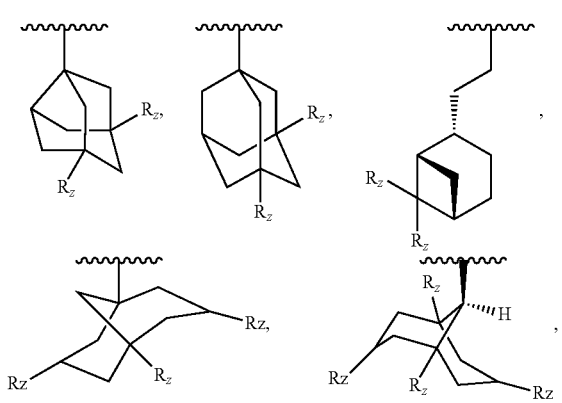

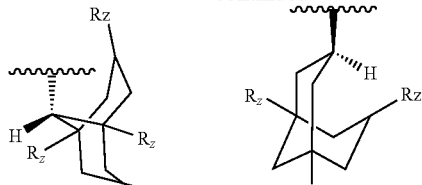

and each $R_z$ is independently —H, —$(C_1$-$C_4)$alkyl, —OH, or —CN.

44. The compound of claim 43 or a pharmaceutically acceptable salt thereof, wherein $R_1$ is:

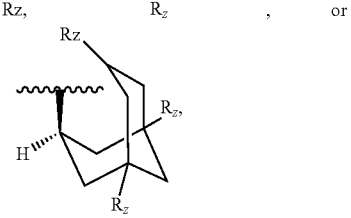

and each $R_z$ is independently —H, —$(C_1$-$C_4)$alkyl, —OH, or —CN.

45. The compound of claim 41 or a pharmaceutically acceptable salt thereof, wherein $R_1$ is:

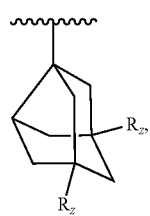

and each $R_z$ is —H.

46. The compound of claim 41 or a pharmaceutically acceptable salt thereof, wherein $R_1$ is:

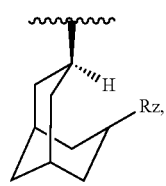

and $R_z$ is —H or —$CH_3$.

47. The compound of claim 5 or a pharmaceutically acceptable salt thereof, wherein a is 1 and $R_2$ is -halo.

48. The compound of claim 41 or a pharmaceutically acceptable salt thereof, wherein the $R_1$ group is in the exo-configuration with respect to the A-B bridge of the bridged piperidine.

49. The compound of claim 6 or a pharmaceutically acceptable salt thereof, wherein —$R_1$ is selected from:
(a) cyclooctyl, cyclononyl, cyclodecyl, cycloundecyl, or cyclododecyl; and
(b) cyclohexenyl, cycloheptenyl, or cyclooctenyl; and
(c)

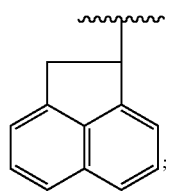 [SMILES: *C1Cc2cccc3cccc1c23]

and
(d) ($C_6$-$C_{12}$)cycloalkyl optionally substituted by one —($C_1$-$C_4$)alkyl.

50. The compound of claim 6, wherein the compound is:

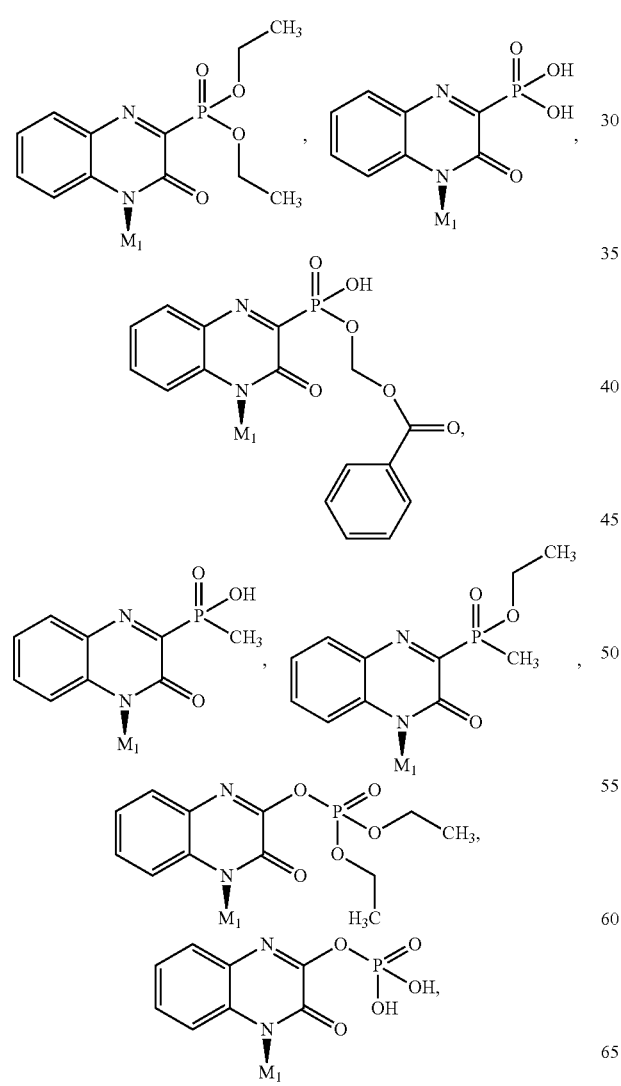

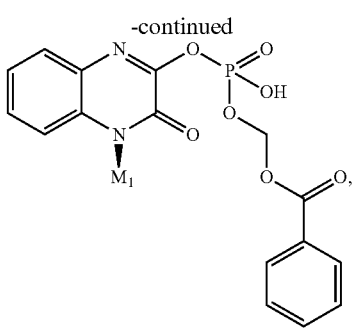

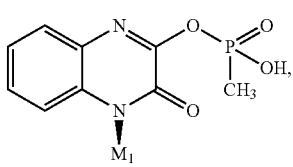

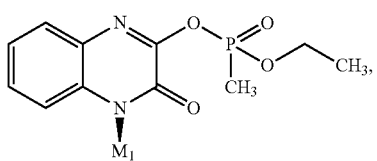

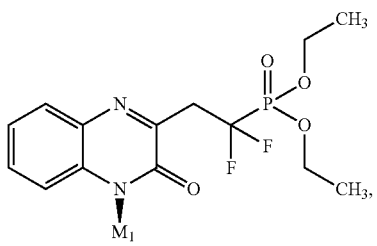

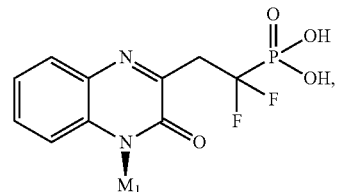

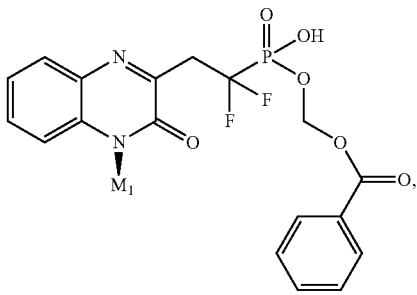

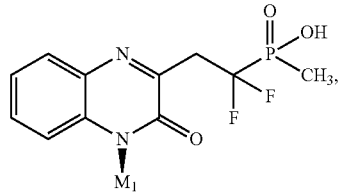

257
-continued
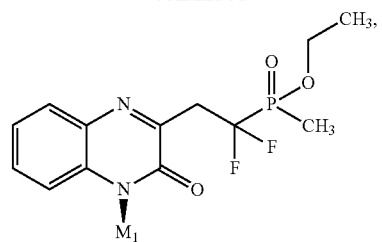
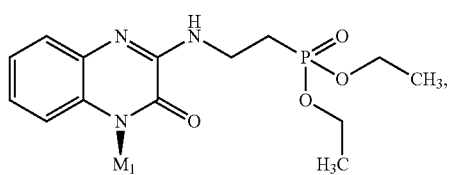
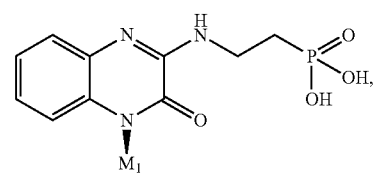
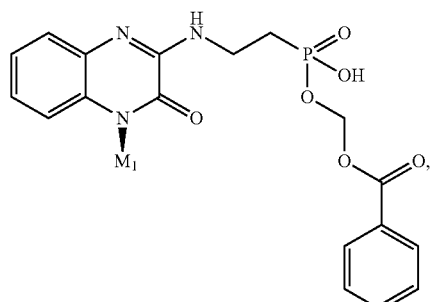
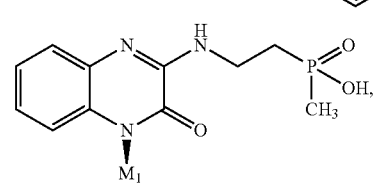
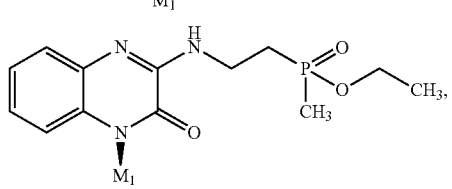
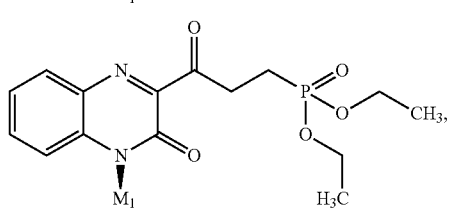
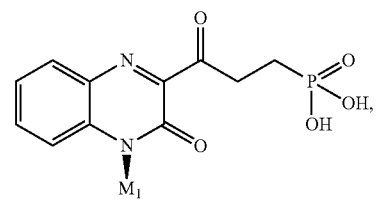
258
-continued
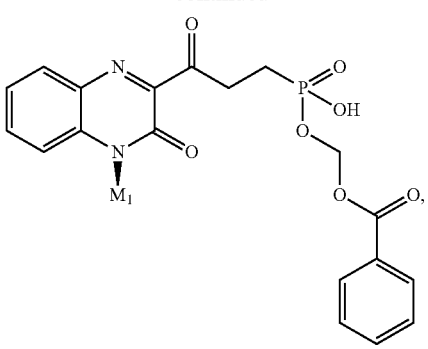

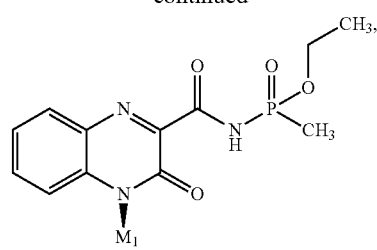
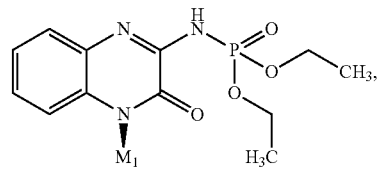
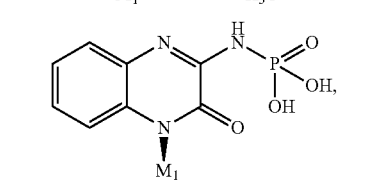
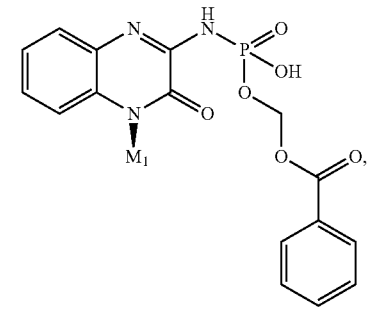
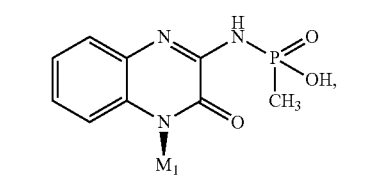
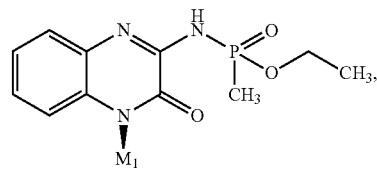
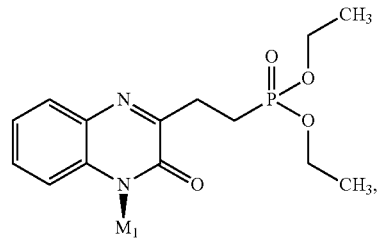
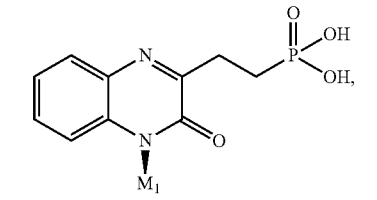
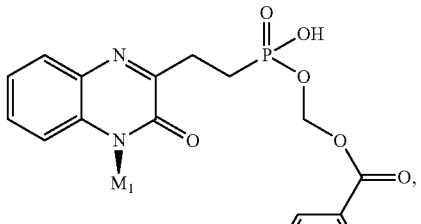
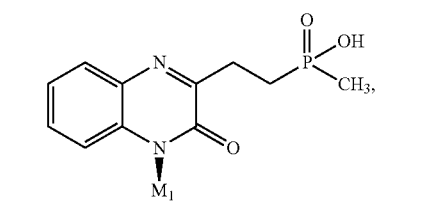
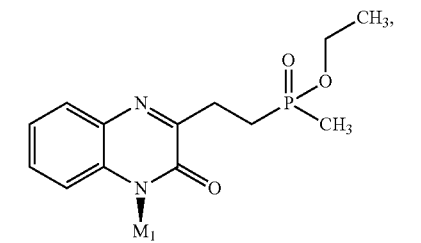
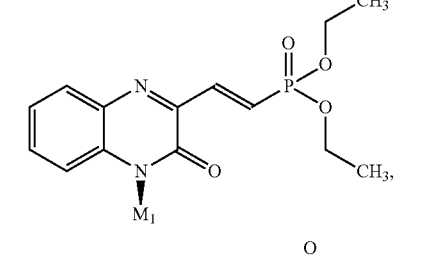
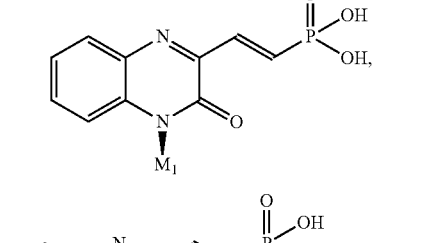
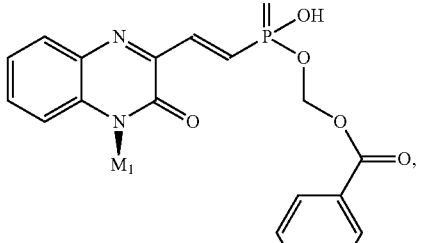
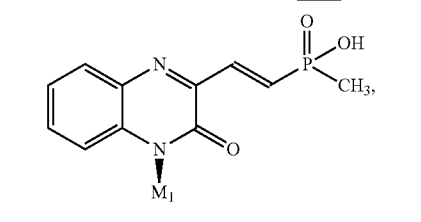

-continued
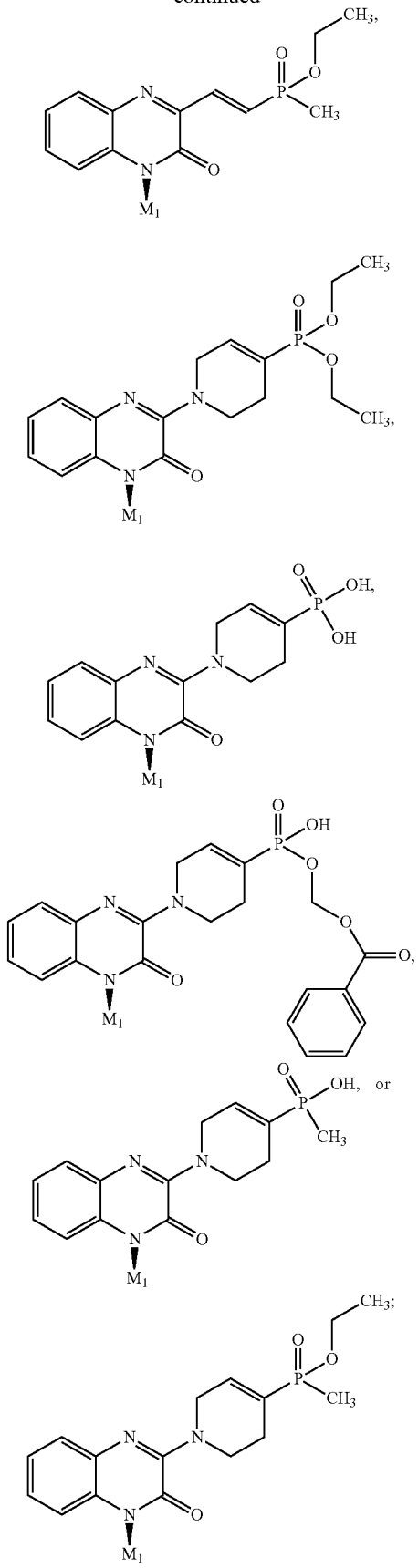
wherein $M_1$ is:
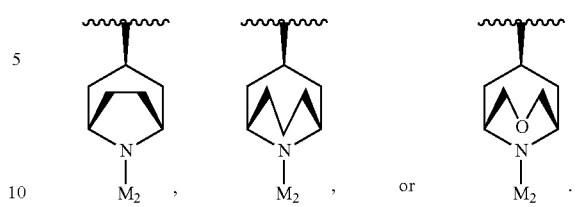
$M_2$ is:
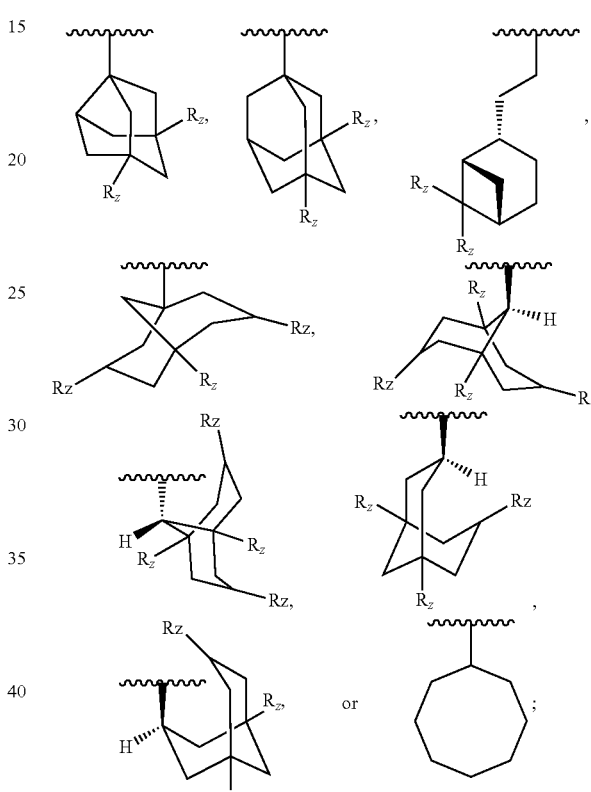
and
each $R_z$ is independently —H or —CH$_3$,
or a pharmaceutically acceptable salt thereof.
51. The compound of claim 6, wherein the compound is:
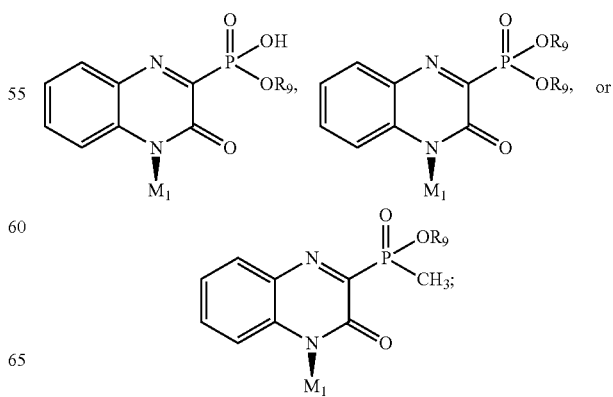

wherein each R₉ is independently —H, —(C₁-C₆)alkyl, —(C₂-C₆)alkenyl, -phenyl, -benzyl, or —CH₂—O—C(O)-phenyl;
M₁ is:
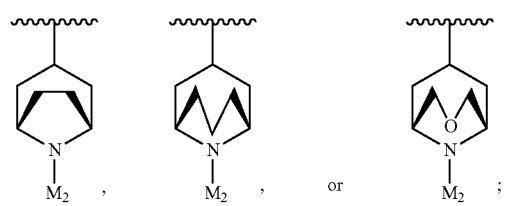
and
M₂ is:
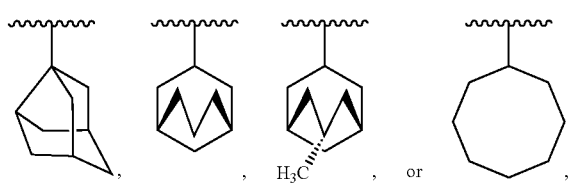
or a pharmaceutically acceptable salt thereof.
52. The compound of claim 51 or a pharmaceutically acceptable salt thereof, wherein the compound is:
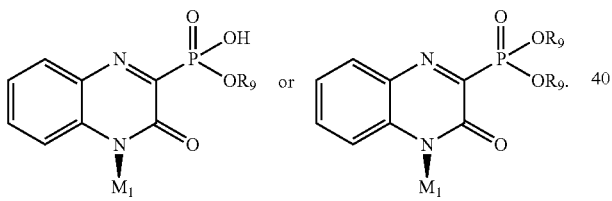
53. A compound which is:
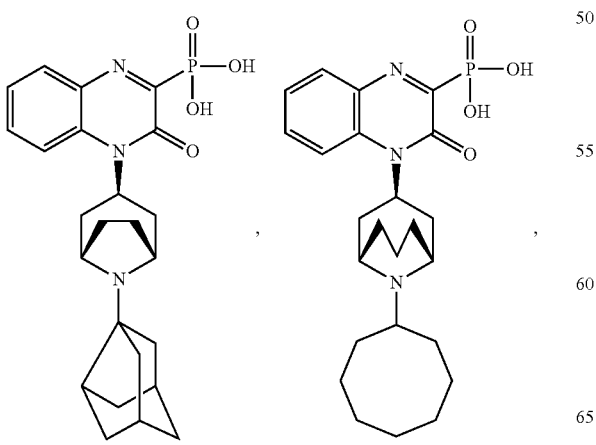
-continued
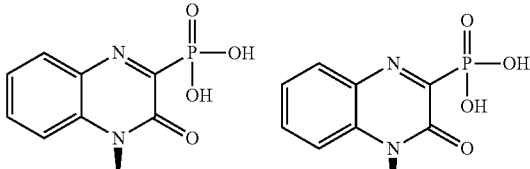
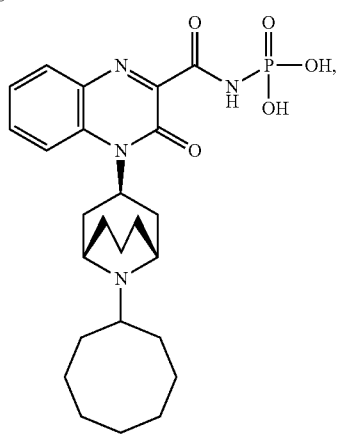
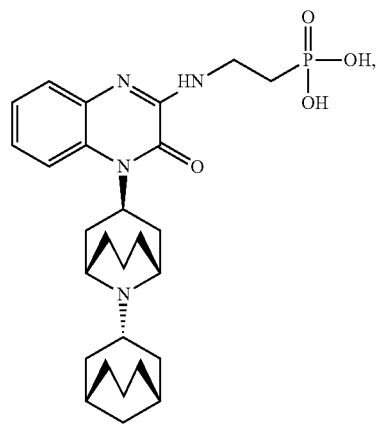
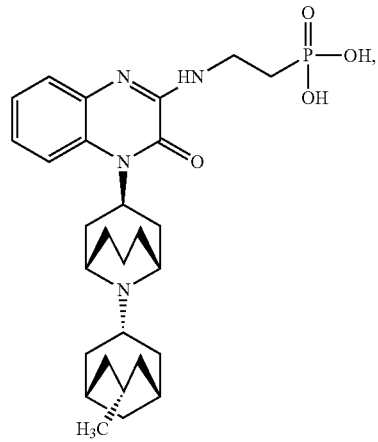

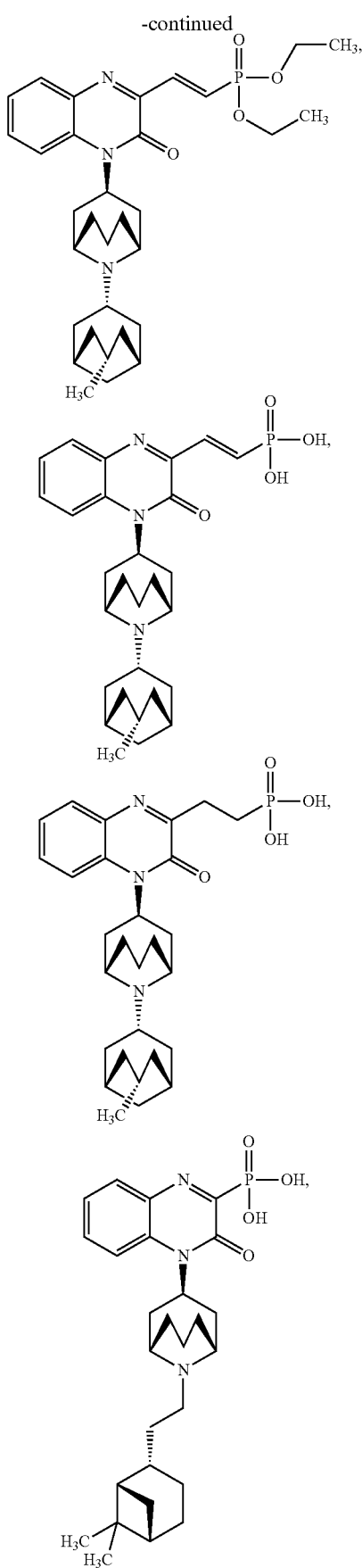

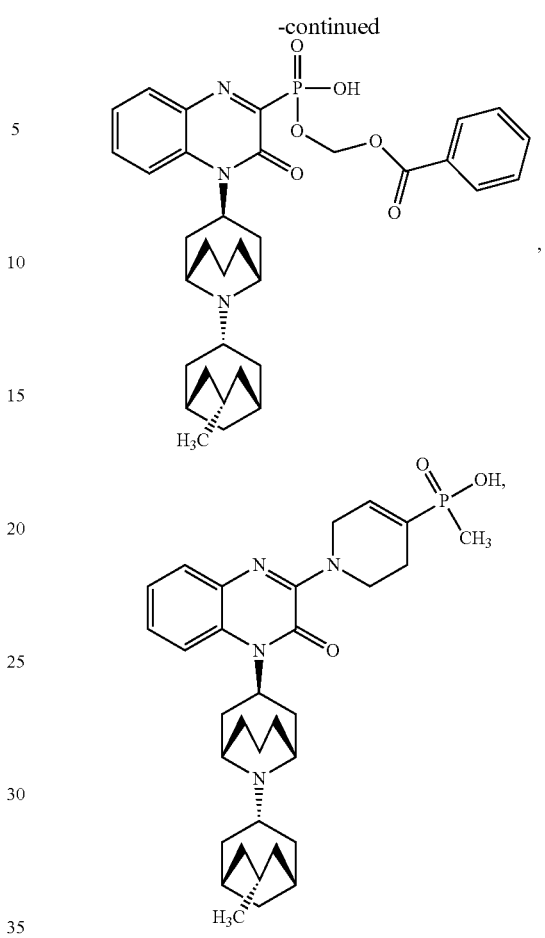

or a pharmaceutically acceptable salt thereof.

54. The compound of claim 1, wherein the pharmaceutically acceptable salt is a hydrochloride-salt, a sodium-salt, a potassium-salt, or a para-toluenesulfonic acid-salt.

55. A composition comprising an effective amount of the compound or a pharmaceutically acceptable salt of the compound of claim 1 and a pharmaceutically acceptable carrier or excipient.

56. A method for preparing a composition, comprising the step of admixing a compound or a pharmaceutically acceptable salt of the compound of claim 1 and a pharmaceutically acceptable carrier or excipient.

57. A method for modulating ORL-1 receptor function in a cell, comprising contacting a cell capable of expressing the ORL-1 receptor with an effective amount of the compound or a pharmaceutically acceptable salt of the compound of claim 1.

58. The method of claim 57, wherein the compound or the pharmaceutically acceptable salt of the compound acts as an agonist at the ORL-1 receptor.

59. The method of claim 57, wherein the compound or the pharmaceutically acceptable salt of the compound acts as a partial agonist at the ORL-1 receptor.

60. A method for treating pain in an animal, comprising administering to an animal in need thereof an effective amount of the compound or a pharmaceutically acceptable salt of the compound of claim 1.

* * * * *

UNITED STATES PATENT AND TRADEMARK OFFICE
CERTIFICATE OF CORRECTION

PATENT NO.       : 9,598,447 B2
APPLICATION NO.  : 13/996440
DATED            : March 21, 2017
INVENTOR(S)      : Dawit Tadesse et al.

It is certified that error appears in the above-identified patent and that said Letters Patent is hereby corrected as shown below:

In the Claims

In Column 243, Line 12, Claim 1, "-C(=O)N($T_1$)($T_2$)" should read -- -C(=O)$R_9$, -C(=O)N($T_1$)($T_2$) --.

In Column 243, Line 18, Claim 1, "=O," should read -- =O, =S, --.

In Column 243, Line 30, Claim 1, "-$CH_2$-O-C(O)-O- phenyl" should read -- -$CH_2$-O-C(O)-O-phenyl --.

Signed and Sealed this
Twenty-fourth Day of October, 2017

Joseph Matal
*Performing the Functions and Duties of the*
*Under Secretary of Commerce for Intellectual Property and*
*Director of the United States Patent and Trademark Office*